US011447532B2

(12) United States Patent
Breslauer et al.

(10) Patent No.: US 11,447,532 B2
(45) Date of Patent: Sep. 20, 2022

(54) LONG UNIFORM RECOMBINANT PROTEIN FIBERS

(71) Applicant: Bolt Threads, Inc., Emeryville, CA (US)

(72) Inventors: David Breslauer, San Francisco, CA (US); Joshua Kittleson, Pleasant Hill, CA (US); Loren Perelman, Oakland, CA (US); Lindsay Wray, Benicia, CA (US)

(73) Assignee: BOLT THREADS, INC., Emeryville, CA (US)

(*) Notice: Subject to any disclaimer, the term of this patent is extended or adjusted under 35 U.S.C. 154(b) by 945 days.

(21) Appl. No.: 15/705,185

(22) Filed: Sep. 14, 2017

(65) Prior Publication Data
US 2018/0111970 A1 Apr. 26, 2018

Related U.S. Application Data

(60) Provisional application No. 62/394,683, filed on Sep. 14, 2016.

(51) Int. Cl.
C07K 14/435 (2006.01)
D01F 4/00 (2006.01)
C12N 15/81 (2006.01)
D01B 7/00 (2006.01)
D02G 3/04 (2006.01)
D01D 5/06 (2006.01)
D06M 101/12 (2006.01)

(52) U.S. Cl.
CPC ........ C07K 14/43518 (2013.01); C12N 15/81 (2013.01); D01B 7/00 (2013.01); D01F 4/00 (2013.01); D02G 3/042 (2013.01); D01D 5/06 (2013.01); D06M 2101/12 (2013.01); D10B 2211/04 (2013.01)

(58) Field of Classification Search
CPC ....... C07K 14/43518; D01F 4/00; D01B 7/00; D06M 2101/12; D10B 2211/04
See application file for complete search history.

(56) References Cited

U.S. PATENT DOCUMENTS

| 5,171,505 A | 12/1992 | Lock |
| 5,273,548 A | 12/1993 | Lapierre et al. |
| 6,268,169 B1 | 7/2001 | Fahnestock |
| 7,057,023 B2 | 6/2006 | Islam et al. |
| 7,335,739 B2 | 2/2008 | Mello et al. |
| 7,868,146 B2 | 1/2011 | Scheibel et al. |
| 8,250,676 B2 | 8/2012 | Ramsey et al. |
| 8,623,398 B2 * | 1/2014 | Altman ........... A61L 27/227 424/426 |
| 9,051,383 B2 | 6/2015 | Hayashi et al. |
| 9,051,453 B2 | 6/2015 | Sugahara et al. |
| 9,074,302 B2 | 7/2015 | Lo et al. |
| 9,131,671 B2 | 9/2015 | Brigham |
| 9,963,554 B2 | 5/2018 | Widmaier et al. |
| 10,035,886 B2 | 7/2018 | Widmaier et al. |
| 10,435,516 B2 | 10/2019 | Widmaier et al. |
| 2003/0013154 A1 | 1/2003 | Crawford et al. |
| 2003/0201560 A1 | 10/2003 | Vollrath et al. |
| 2003/0203417 A1 | 10/2003 | Fowlkes et al. |
| 2003/0233675 A1 | 12/2003 | Cao et al. |
| 2004/0102614 A1 | 5/2004 | Islam et al. |
| 2004/0210956 A1 | 10/2004 | Roth et al. |
| 2004/0241672 A1 | 12/2004 | Goldsmith et al. |
| 2005/0010035 A1 | 1/2005 | Lewis et al. |
| 2005/0054830 A1 * | 3/2005 | Islam ............... C07K 14/43513 530/353 |
| 2005/0101209 A1 | 5/2005 | Li et al. |
| 2007/0178505 A1 | 8/2007 | Fischer et al. |
| 2007/0256250 A1 | 11/2007 | Knight |
| 2007/0260039 A1 | 11/2007 | Karatzas et al. |
| 2009/0018031 A1 | 1/2009 | Trinklein et al. |
| 2009/0053288 A1 | 2/2009 | Eskridge, Jr. et al. |
| 2010/0068517 A1 | 3/2010 | Liu et al. |
| 2010/0222553 A1 | 9/2010 | Hayashi et al. |
| 2011/0009960 A1 | 1/2011 | Altman et al. |
| 2011/0124046 A1 | 5/2011 | Linger et al. |
| 2011/0136669 A1 | 6/2011 | Liebmann et al. |
| 2011/0165681 A1 | 7/2011 | Boyden et al. |
| 2011/0230911 A1 | 9/2011 | Scheibel et al. |
| 2011/0297904 A1 | 12/2011 | Dhinojwala et al. |
| 2012/0004117 A1 | 1/2012 | Aburatani et al. |
| 2012/0041177 A1 | 2/2012 | Johansson et al. |
| 2013/0109762 A1 | 5/2013 | Lammel et al. |
| 2013/0212718 A1 | 8/2013 | Fraser et al. |

(Continued)

FOREIGN PATENT DOCUMENTS

| CN | 107059465 A * | 8/2017 | ............. C01B 33/42 |
| EP | 2258855 A1 | 12/2010 | |

(Continued)

OTHER PUBLICATIONS

English machine translation of CN 107059465 A (6 pages), obtained on May 5, 2022. (Year: 2022).*
European Extended Search Report, European Application No. 16765690.9, dated Sep. 14, 2018, 9 pages.
Elices, M. et al., "Bioinspired Fibers Follow the Track of Natural Spider Silk." Macromolecules, 2011, DD. 1166-1176, vol. 44.
Guerette, P.A. et al., "Silk Properties Determined by Gland-Specific Expression of a Spider Fibroin Gene Family." Science, Apr. 5, 1996, pp. 112-115, vol. 272, No. 5258.
Paal, M. et al., "A Novel Ecotin-Ubiquitin-Tag (ECUT) for Efficient, Soluble Peptide Production in the Periplasm of *Escherichia coli*," Microbial Cell Factories, Jan. 21, 2009, pp. 1-9, vol. 8, No. 7.

(Continued)

Primary Examiner — Neil P Hammell
(74) Attorney, Agent, or Firm — Marshall, Gerstein & Borun LLP

(57) ABSTRACT

The present disclosure provides improved long uniform recombinant protein fibers with desirable physical traits. The present disclosure also provides compositions derived from the long uniform recombinant protein fibers.

25 Claims, 4 Drawing Sheets
Specification includes a Sequence Listing.

(56) References Cited

U.S. PATENT DOCUMENTS

| | | |
|---|---|---|
| 2014/0058066 A1 | 2/2014 | Sekiyama et al. |
| 2014/0128991 A1 | 5/2014 | Atanasoska et al. |
| 2014/0194603 A1 | 7/2014 | Lehmann et al. |
| 2015/0047532 A1 | 2/2015 | Lewis et al. |
| 2015/0274789 A1 | 10/2015 | Guerette et al. |
| 2016/0047075 A1 | 2/2016 | Foley et al. |
| 2016/0222174 A1 | 8/2016 | Widmaier et al. |
| 2017/0088675 A1 | 3/2017 | Widmaier et al. |
| 2018/0298151 A1 | 10/2018 | Widmaier et al. |
| 2020/0055996 A1 | 2/2020 | Widmaier et al. |

FOREIGN PATENT DOCUMENTS

| | | | |
|---|---|---|---|
| EP | 2868782 A1 | 5/2015 | |
| EP | 3271471 A1 | 1/2018 | |
| JP | 2005-502347 A | 1/2005 | |
| JP | 2005-515309 | 5/2005 | |
| JP | 2009-521921 | 6/2009 | |
| JP | 2012-531889 | 12/2012 | |
| JP | 2013-528568 | 7/2013 | |
| WO | 02/099082 A2 | 12/2002 | |
| WO | 03/020916 A2 | 3/2003 | |
| WO | 03/060207 A1 | 7/2003 | |
| WO | 2003/057727 A1 | 7/2003 | |
| WO | 2010/015419 A2 | 2/2010 | |
| WO | 2010/123450 A1 | 10/2010 | |
| WO | WO 2011/039345 A1 | 4/2011 | |
| WO | 2011/113592 A1 | 9/2011 | |
| WO | 2012/050919 A2 | 4/2012 | |
| WO | 2012/055854 A1 | 5/2012 | |
| WO | 2012165476 A1 | 12/2012 | |
| WO | 2013/065650 | 5/2013 | |
| WO | 2013/180767 A2 | 12/2013 | |
| WO | WO 2014/002605 A1 | 1/2014 | |
| WO | 2014/037453 A1 | 3/2014 | |
| WO | 2014/066374 A1 | 5/2014 | |
| WO | WO 2015/042164 A2 | 3/2015 | |
| WO | WO-2015042164 A2 * | 3/2015 | ............ C12P 21/02 |
| WO | WO 2016/149414 A1 | 9/2016 | |
| WO | WO 2016/201369 A1 | 12/2016 | |

OTHER PUBLICATIONS

PCT Invitation to Pay Additional Fees, PCT Application No. PCT/US14/56117, dated Jan. 14, 2015, 3 pages.

PCT International Search Report and Written Opinion, PCT Application No. PCT/US14/56117, dated Mar. 10, 2015, 26 pages.

Bliven, S. et al., "Circular Permutation in Proteins," PLoS Computational Biology, Mar. 2012, pp. 1-5, vol. 8, Issue 3, e1002445.

United States Office Action, U.S. Appl. No. 15/073,514, filed Aug. 15, 2017, 11 pages.

Hayashi, C.Y. et al., "Evidence from Flagelliform Silk cDNA for the Structural Basis of Elasticity and Modular Nature of Spider Silks," J. Mol. Biol., 1998, pp. 773-784, vol. 275, No. 5.

Collins, T. et al., "Batch Production of a Silk-Elastin-Like Protein in E.coli BL21(DE3): Key Parameters for Optimisation," Microbial Cell Factories, Feb. 27, 2013, pp. 1-16, vol. 12, No. 21.

European Extended Search Report, European Application No. 14846179.1, dated Feb. 24, 2017, 11 pages.

Database Accession No. I6YNT3, "SubName: Full=Major Ampullate Silk Protein 2 {ECO:0000313IENBL: AFN54363.1}," Retrieved from EBI Accession No. UNIPROT:I6YNT3, Oct. 3, 2012, 1 page.

United States Office Action, U.S. Appl. No. 15/285,256, filed Dec. 27, 2017, 6 pages.

European Extended Search Report, European Application No. 16808475.4, Oct. 8, 2018, 8 pages.

PCT International Preliminary Report on Patentability, PCT Application No. PCT/US17/37013, dated Aug. 3, 2018, 9 pages.

PCT International Preliminary Reporton Patentability, PCT Application No. PCT/US16/37084, dated Jun. 1, 2018, 6 pages.

PCT Written Opinion of the International Preliminary Examining Authority, PCT Application No. PCT/US16/37084, dated Feb. 23, 2018, 5 pages.

PCT International Search Report, PCT Application No. PCT/US16/37084, Sep. 8, 2016, 12 pages.

PCT International Search Report and Written Opinion, PCT Application No. PCT/US17/37013, dated Sep. 1, 2017, 14 pages.

PCT International Search Report and Written Opinion, PCT Application No. PCT/US16/22707, dated Jul. 12, 2016, 17 pages.

Hopp, T.P. et al., "A Short Polypeptide Marker Sequence useful for Recombinant Protein Identification and Purification," Nature Biotechnology, Oct. 1988, pp. 1204-1210, vol. 6.

PCT International Search Report & Written Opinion, International Application No. PCT/US2017/037013, dated Sep. 1, 2017, 14 Pages.

Zhang, Y., et al., "The molecular structures of major ampullated silk proteins of the wasp spider, Argiope bruennichi: A second blueprint for synthesizing de nova silk," Comparative Biochemistry and Physiology, 2013, pp. 151-158, vol. 164, Part B.

PCT International Search Report and Written Opinion, PCT Application No. PCT/US18/21818, dated Jul. 26, 2018, 24 pages.

Blackledge, T.A. et al., Sequential Origin in the High Performance Properties of Orb Spider Dragline Silk Science Reports, Oct. 29, 2012, pp. 1-5, vol. 2, No. 782.

Gosline, J.M. et al., "The Mechanical Design of Spider Silks: from Fibroin Sequence to Mechanical Function," The Journal of Experimental Biology, Dec. 1999, pp. 3295-3303, vol. 202, No. 23.

Guinea, G.V. et al., "Stretching of Supercontacted Fibers: A Link Between Spinning and the Variability of Spider Silk," The Journal of Experimental Biology, Jan. 2005, pp. 25-30, vol. 208, No. 1.

Karaguzel, B., "Characterization and Role of Porosity in Knitted Fabrics," North Carolina State University, 2004, pages, [Online] [Retrieved on Jul. 17, 2018] Retrieved from the Internet<URL:https://repository.lib.ncsu.edu/handle/1840.16/1073>.

Mortimer, B. et al. "Linking Naturally and Unnaturally Spun Silks Through the Forced Reeling of Bombyx mori," Acta Biomaterialia, Sep. 19, 2015, pp. 247-255, vol. 11.

Qian, X. et al., "Prediction of Clothing Thermal Insulation and Moisture Vapour Resistance of the Clothed Body Walking in the Wind," The Annals of Occupational Hygiene, Jul. 20, 2006, oo. 833-842, vol. 50, No. 8.

Saravanan, D., "Spider Silk—Structure, Properties and Spinning," Journal of Textile and Apparel, Technoloay and Management, 2006, pp. 1-20, vol. 5, No. 1.

Shao, Z. et al., "Analysis of Spider Silk in Native and Supercontracted States Using Raman Spectroscoov," Polymer, May 1, 1999, pp. 2493-2500, vol. 40, No. 10.

Umair, M. et al., "Development and Characterization of Three-Dimensional Woven Shaped Preforms and Their Associated Composites," Journal of Reinforced Plastics and Composites, Dec. 2015, pp. 2018-2028, vol. 34, No. 24.

Gauthier et al., Increase in Xylanase Production by Streptomyces lividans through Simultaneous Use of the Sec- and Tat-Dependent Protein Export Systems, Appl. Environ. Microbial., 2005, 71, 3085-92.

La Grange et al., Degradation of Xylan to D-Xylose by Recombinant Saccharomyces cerevisiae Coexpressing the Aspergillus niger ?-Xylosidase (xlnD) and the Trichoderma reesei Xylanase II (xyn2) Genes, Appl. Environ. Microbial., 2001, 67, 5512-19.

La Grange, et al., Expression of a trichoderma reesei beta-xylanase gene (XYN2) in Saccharomyces cerevisiae, Appl. Environ. Microbial., 1996, 62, 1036-44.

Liang, et al., Endogenous signal peptides efficiently mediate the secretion of recombinant proteins in Pichia pastoris, Biotechnol. Lett., 2013, 35, 97-105.

Puseenam, et al., Co-expression of Endoxylanase and Endoglucanase in Scheffersomyces stipitis and its Application in Ethanol Production, Appl. Biochem. Biotechnol., 2015, 177, 1690-1700.

Romanos, et al., Foreign gene expression in yeast, Yeast, 1992, 8, 423-88.

(56) References Cited

OTHER PUBLICATIONS

Jelinski, Lynn W. et al., "Orientation, structure, wet-spinning, and molecular basis for supercontraction of spider dragline silk", International Journal of Biological Macromolecules, 24 (1999), pp. 197-201.

European Supplementary Partial Search Report, European Application No. 17851570.6, dated Feb. 5, 2020, 13 pages.

European Extended Search Report, European Application No. 17811154.8, dated Dec. 9, 2019, 7 pages.

PCT International Preliminary Reporton Patentability, PCT Application No. PCT/US2018/021818, dated Sep. 19, 2019, 15 pages.

PCT International Search Report and Written Opinion, PCT Application No. PCT/US2013/066159, dated Jan. 28, 2014, 18 pages.

Cereghino, J. L., et al., "Heterologous Protein Expression in the Methylotrophic Yeast *Pichia pastoris*," FEMS Microbiology Reviews, Jan. 2000, pp. 45-66, vol. 24, No. 1.

Mett et al., "Copper-controllable gene expression system for whole plants" 90 Proceedings of the National Academy of Sciences USA 4567-4571 (1993).

Hartner et al., "Promoter library designed for fine-tuned gene expression in Pichia pastoris" 36(12) Nucleic Acids Research e76 1-15 and incl. Supplementary Information (Jun. 6, 2008).

Fahnestock et al., "Microbial production of spider silk proteins" 74 Reviews in Molecular Biotechnology 105-119 (2000).

PCT International Preliminary Report on Patentability, PCT Application No. PCT/US13/66159, dated Oct. 21, 2014, 9 pages.

GenBank Acession No. AFN54363.1, "Major Amplullate Silk Protein 2 [Argiope bruennichi]", Jan. 22, 2013, 2 pages.

An, B. et al., "Reproducing Natural Spider Silks' Copolymer Behavior in Synthetic Silk Mimics," Biomacromolecules, 2012, pp. 3938-3948, vol. 13.

Lazaris, A. et al., "Spider Silk Fibers Spun from Soluble Recombinant Silk Produced in Mammalian Cells," Science, Jan. 18, 2002, 472-476, vol. 295.

PCT International Search Report and Written Opinion, PCT Application No. PCT/US17/51668, dated Jan. 5, 2018, 13 pages.

Xia, X.X. et al., "Native-Sized Recombinant Spider Silk Protein Produced in Metabolically Engineered *Escherichia coli* Results in a Strong Fiber," Proceedings of the National Academy of Sciences of the United States of America, Aug. 10, 2010, Epub Jul. 26, 2010, pp. 14059-14063, vol. 107, No. 32.

\* cited by examiner

LONG UNIFORM RECOMBINANT PROTEIN FIBERS

CROSS-REFERENCE TO RELATED APPLICATIONS

This application claims the benefit of U.S. Provisional Patent Application No. 62/394,683, filed Sep. 14, 2016, the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Dec. 28, 2017, is named 37838US_CRF_sequencelisting.txt and is 291,397 bytes in size.

TECHNICAL FIELD

The present disclosure relates generally to recombinant protein fibers. Specifically, the present disclosure relates to increased uniformity of physical, mechanical and chemical properties of recombinant protein fibers.

BACKGROUND

Recombinant protein fibers, such as those synthesized from the polypeptides in spider silks, are not commercially available due to the difficulty in commercial scale fabrication and the technical challenges in producing fibers that are manufacturable into threads, yarns, and textiles.

There are many types of recombinant protein fibers that could be produced, with various useful properties.

One example is a recombinant protein fiber made from proteins designed by modifying spider silk proteins and protein fragments. Spider silk cannot be commercially farmed and harvested using the same methods that are applied to silkworm silk. This is due, in part, to the aggressive and territorial nature of spiders. Therefore, synthetically produced spider silk is the most likely cost-effective and viable path to commercialization.

A single species of spider creates a variety of fibers, each of which are utilized for different functions. Examples of these different functions include draglines, web capture spirals, prey immobilization, and silks to protect an egg sac. Dragline silks have exceptional mechanical properties. They are very strong for their weight and diameters, and also exhibit a combination of high extensibility in conjunction with high ultimate tensile strength.

Amino acid composition and protein structure vary considerably between types of silks and species of spiders. For example, orb weaving spiders have six unique types of glands that produce different silk polypeptide sequences that are polymerized into fibers tailored to fit an environmental or lifecycle niche. The fibers are named for the gland they originate from and the polypeptides are labeled with the gland abbreviation, for example "Sp" for spidroin (short for spider fibroin). In orb weaver spiders, examples include Major Ampullate (MaSp, also called dragline), Minor Ampullate (MiSp), Flagelliform (Flag), Aciniform (AcSp), Tubuliform (TuSp), and Pyriform (PySp).

There is a common class of orb weaver MaSp dragline silks (e.g., Nephila clavipes MaSp1) where the repeat domains contain glycine-rich regions, which are associated with amorphous regions of the fiber (possibly containing alpha-helices and/or beta-turns), and poly-alanine regions, which are associated with the beta-sheet crystalline regions of the fiber. The amino acid composition and sequence, as well as the fiber formation details both affect the mechanical properties of the fiber.

Currently, recombinant silk fibers are not commercially available and, with a handful of exceptions, are not produced in microorganisms outside of Escherichia coli and other gram-negative prokaryotes. Recombinant silks produced to date have largely consisted either of polymerized short silk sequence motifs or fragments of native repeat domains, sometimes in combination with NTDs and/or CTDs. While these methods are able to produce small scales of recombinant silk polypeptides (milligrams at lab scale, kilograms at bioprocessing scale) using intracellular expression and purification by chromatography or bulk precipitation, they have not been scaled to volumes necessary for commercial manufacturing. Additional production hosts that have been utilized to make silk polypeptides include transgenic goats, transgenic silkworms, and plants. Similarly, these hosts have yet to enable commercial scale production of silk.

There are disclosures of continuous spinning methods for recombinant protein fibers. Several references generally disclose systems for continuous spinning of recombinant protein fibers, however none actually discloses working examples of fiber that are produced by continuous methods. See U.S. Pat. Nos. 7,868,146, 7,335,739, 8,979,992, 9,023, 142, 9,051,453, PCT/JP2013/062429, and U.S. patent Pub. Nos. 2003/0201560, 2007/0256250, 2005/0054830, incorporated by reference herein in their entirety. All working examples (such as in PCT/JP2013/062429, and in U.S. Pat. Pub. No. 20050054830) are produced using spin dope dispensed from a syringe, not a larger vessel capable of dispensing the volumes needed for long continuous fibers. As a result, the fibers suffer from poor uniformity, poor reproducibility, or both.

The syringe-based approaches at the lab scale produce fibers with highly variable mechanical properties. For instance, collaboration between University of Wyoming, Arizona State University, Sandia National Laboratories and Utah State University published work where 4 different spider silk derived proteins were produced at small scales using E. coli. An et al., Biomacromolecules 2012, 13, 3938-3948. The cell suspension volumes used for purification were approximately 800 mL, and the spinning apparatus utilized 1 mL syringes from which to spin the fibers. This approach resulted in fibers that were 2-3 m long. These fibers were then examined by eye to exclude visible large defects, and sections 2 cm long were selected for analysis. The mechanical properties of the as-spun fibers produced by these small-scale methods had average coefficient of variation (CV) of 40% for strength, 36% for extension, and 59% for toughness. The mechanical properties of the drawn (i.e. stretched) fibers produced by these small-scale methods had average coefficient of variation (CV) of 35% for strength, 88% for extension, and 97% for toughness. The average CV, in this instance, refers to the average CV of the 4 different proteins that were used in the spin dope. Furthermore, the average strength of these fibers was insufficient for commercial yarn and fabric production.

Another study, which produced spider silk derived proteins in small volumes using mammalian cells, also produced fibers with highly variable mechanical properties. Lazaris et al., Science 295, Jan. 18, 2002, 472-476. Seven fibers from the same production methods were tested and had an average toughness of 0.895 gpd, and a CV of 61%.

There are a variety of test methods that have been developed for fiber, yarns and fabrics. The American Association of Textile Chemists and Colorists (AATCC) has developed a series of tests for fibers and textiles. The standard AATCC tests are known to persons of ordinary skill in the textile arts and can be found at in the 2016 AATCC Technical Manual (ISBN 978-1-942323-01-3) and are incorporated by reference in their entirety.

In order to manufacture goods comprising recombinant protein fibers, methods are required to produce large quantities of uniform fibers at low cost. What is needed, therefore, are large-scale methods to produce recombinant protein fibers with uniform properties, wherein those properties are adequate for commercial yarn spinning and textile production.

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The reagents employed in the examples are generally commercially available or can be prepared using commercially available instrumentation, methods, or reagents known in the art. The foregoing examples illustrate various aspects described herein and practice of the methods described herein. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

SUMMARY

In some embodiments, provided herein is a long uniform recombinant protein fiber, comprising a continuous fiber length of at least 600 m, wherein the mean properties of the fiber comprise: a tenacity greater than or equal to 12 cN/tex; a linear density less than or equal to 6 dtex; a coefficient of variation of tenacity less than 15% along the length; and a coefficient of variation of linear density less than 20% along the length, wherein the tenacity is measured using ASTM D3822-14, and the linear density is measured using ASTM D1577.

In some embodiments, the length of the recombinant protein fiber is at least 50 m. In some embodiments, the length of the recombinant protein fiber is at least 650 m.

In some embodiments, the tenacity of the recombinant protein fiber has a coefficient of variation less than 10% along the length of the recombinant protein fiber. In some embodiments, the linear density of the recombinant protein fiber has a coefficient of variation less than 15% along the length of the recombinant protein fiber.

In some embodiments, the mean elongation at break of the recombinant protein fiber is greater than 25% and the elongation at break of the recombinant protein fiber has a coefficient of variation of less than 35% along the length of the recombinant protein fiber.

In some embodiments, the mean initial modulus of the recombinant protein fiber is greater than 480 cN/tex and the initial modulus of the recombinant protein fiber has a coefficient of variation of less than 5% along the length.

In some embodiments, the mean elongation of the recombinant protein fiber is greater than 24% and the elongation of the recombinant protein fiber has a coefficient of variation of less than 45% along the length of the recombinant protein fiber.

In some embodiments, the mean work of rupture of the recombinant protein fiber is greater than 3 cN*cm and the work of rupture of the recombinant protein fiber has a coefficient of variation of less than 50% along the length of the recombinant protein fiber.

In some embodiments, the mean force at rupture of the recombinant protein fiber is greater than 7 cN and the force at rupture of the recombinant protein fiber has a coefficient of variation less than 25% along the length of the recombinant protein fiber.

In some embodiments, the recombinant protein fiber is produced by wet spinning a dope comprising a recombinant protein powder. In some embodiments, the recombinant protein powder is less than 65% proteinaceous block copolymer by mass.

In some embodiments, the recombinant protein fiber comprises a protein sequence comprising repeat units, wherein each repeat unit has at least 95% sequence identity to a sequence that comprises from 2 to 20 quasi-repeat units, each quasi-repeat unit having a composition comprising {GGY-[GPG-$X_1$]$_{n1}$-GPS-(A)n2}, (SEQ ID NO: 111), wherein for each quasi-repeat unit: X1 is independently selected from the group consisting of SGGQQ (SEQ ID NO: 100), GAGQQ (SEQ ID NO: 101), GQGPY (SEQ ID NO: 102), AGQQ (SEQ ID NO: 103), and SQ; and n1 is from 4 to 8, and n2 is from 6 to 10. In some embodiments, n1 is from 4 to 5 for at least half of the quasi-repeat units. In some embodiments, n2 is from 5 to 8 for at least half of the quasi-repeat units.

In some embodiments, each quasi-repeat unit has at least 95% sequence identity to a MaSp2 dragline silk protein subsequence. In some embodiments, the repeat unit comprises SEQ ID NO: 1.

In some embodiments, the recombinant protein sequence comprises alanine-rich regions and glycine-rich regions, wherein: the alanine-rich regions form a plurality of nanocrystalline beta-sheets; and the glycine-rich regions form a plurality of beta-turn structures.

In some embodiments, the linear density and the tenacity of the recombinant protein fiber are measured using FAVIMAT fiber tensile test equipment model Favimat+ and Robot2.

In some embodiments, the recombinant fiber is not a MaSp2 dragline silk protein.

In some embodiments, also provided herein is a yarn comprising the recombinant protein fiber provided herein, wherein the yarn is a filament yarn. In some embodiments, the yarn is a spun yarn. In some embodiments, the yarn is a blended yarn.

In some embodiments, also provided herein is a textile comprising the yarn comprising the recombinant protein fiber provided herein, wherein the textile is a knitted textile. In some embodiments, the textile is a circular-knitted textile, a flat-knitted textile, or a warp-knitted textiles.

In some embodiments, also provided herein is a textile comprising the yarn comprising the recombinant protein fiber provided herein, wherein the textile is a woven textile. In some embodiments, the textile is a plain weave textile, a dobby weave textile, or a jacquard weave textile.

In some embodiments, also provided herein is a textile comprising the yarn comprising the recombinant protein fiber provided herein, wherein the textile is a non-woven textile. In some embodiments, the textile is a needle punched textile, a spunlace textile, a wet-laid textile, a dry-laid textile, a melt-blown textile, or a 3-D printed non-woven textile.

BRIEF DESCRIPTION OF THE DRAWINGS

FIG. 1 discloses SEQ ID NOS 109-110 and 99, respectively, in order of appearance.

Figure 1:
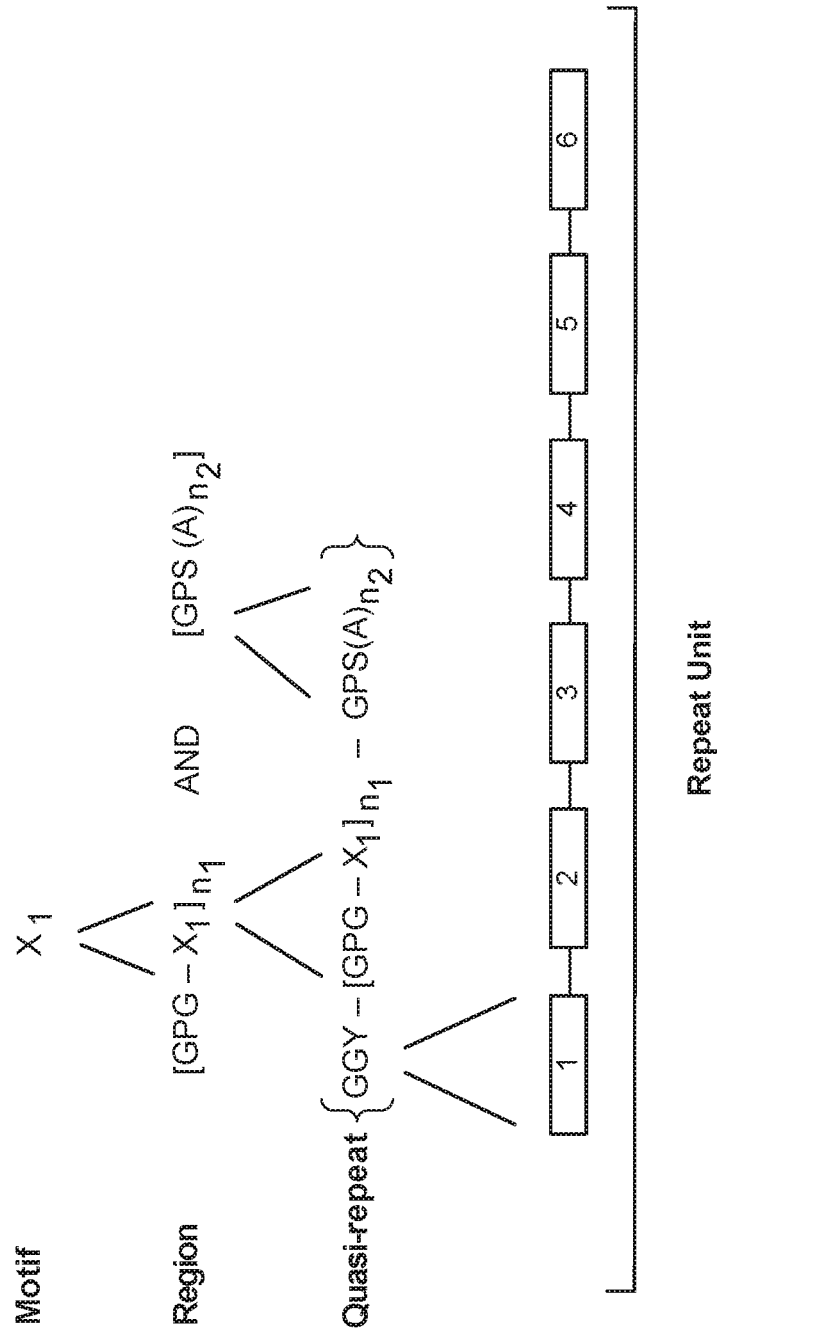
FIG. 1 schematically illustrates a molecular structure of a block copolymer of the present disclosure, in an embodiment.

The figures depict various embodiments of the present disclosure for purposes of illustration only. One skilled in the art will readily recognize from the following discussion that alternative embodiments of the structures and methods illustrated herein may be employed without departing from the principles described herein.

Definitions

Recombinant protein fibers (RPFs) are fibers that are produced from recombinant proteins. In some cases, the proteins making up the RPFs can contain concatenated repeat units and quasi-repeat units. Repeat units are defined as amino acid sequences that are repeated exactly within the polypeptide. Quasi-repeats are inexact repeats, i.e., there is some sequence variation from quasi-repeat to quasi-repeat. Each repeat can be made up of concatenated quasi-repeats.

Amino acids can be referred to by their single-letter codes or by their three-letter codes. The single-letter codes, amino acid names, and three-letter codes are as follows: G—Glycine (Gly), P—Proline (Pro), A—Alanine (Ala), V—Valine (Val), L—Leucine (Leu), I—Isoleucine (Ile), M—Methionine (Met), C—Cysteine (Cys), F—Phenylalanine (Phe), Y—Tyrosine (Tyr), W—Tryptophan (Trp), H—Histidine (His), K—Lysine (Lys), R—Arginine (Arg), Q—Glutamine (Gln), N—Asparagine (Asn), E—Glutamic Acid (Glu), D—Aspartic Acid (Asp), S—Serine (Ser), T—Threonine (Thr).

Filament yarns are yarns that are composed of more than one fiber filaments that run the whole length of the yarn. Filament yarns can also be referred to as multi-filament yarns. The structure of a filament yarn is influenced by the amount of twist, and in some cases the fiber texturing. The properties of the filament yarn can be influenced by the structure of the yarn, fiber to fiber friction of the constituent fibers, and the properties of the constituent fibers. In some embodiments, the yarn structure and the RPF properties are chosen to impart various characteristics to the resulting yarns. The properties of the yarn can also be influenced by the number of fibers (i.e., filaments) in the yarn. The filament yarns in this application can be multifilament yarns. Throughout this disclosure "filament yarns" can refer to flat filament yarns, textured filament yarns, drawn filament yarns, undrawn filament yarns, or filament yarns of any structure.

Spun yarn is made by twisting staple fibers together to make a cohesive yarn (or thread, or "single"). The structure of a spun yarn is influenced by the spinning methods parameters. The properties of the spun yarn are influenced by parameters such as the structure of the yarn, fiber to fiber friction, and the properties of the constituent fibers.

Blended yarns are a type of yarn comprising various fibers being blended together. In different embodiments, the RPFs can be blended with cotton, wool, other animal fibers, polyamide, acrylic, nylon, linen, polyester, and/or combinations thereof. RPFs can be blended with non-recombinant protein fibers, or with more than one other type of non-recombinant protein fibers. RPFs can also be blended with a second type of RPF with different properties than the first type of RPFs. In this disclosure, blended yarns specifically refer to RPFs blended with non-RPFs or a second type of RPFs into a yarn. Even though spandex is generally incorporated into a yarn using somewhat different methods and structures than the other blended yarns described above (e.g., a wrapped RPF/spandex yarn has spandex core wrapped with RPF in order to hide the spandex from view in the textile), a composite RPF/spandex yarn therefore is another example of a blended yarn.

"Textured" fibers or yarns are fibers or yarns that have been subjected to processes that arrange the straight filaments into crimped, coiled or looped filaments. Some examples of methods used for processing textured fibers and yarns are air jet texturing, false twist texturing, or stuffer box texturing.

The standard test method for measuring tensile properties of single fibers is ASTM D3822-14. The standard test method for measuring tensile properties of yarns (or multiple fibers in a tow) by the single-strand method is ASTM D2256-10. All fiber and yarn mechanical properties measured in this disclosure are measured using one of these standards.

Some of the mechanical properties of the fibers in this disclosure are reported in units of MPa (i.e. $10^6$ N/m$^2$, or force per unit area), and some are reported in units of cN/tex (force per linear density). The measurements of fibers mechanical properties reported in MPa were obtained using a custom instrument, which includes a linear actuator and calibrated load cell, and the fiber diameter was measured by light microscopy. The measurements of fibers mechanical properties reported in cN/tex were obtained using FAVIMAT testing equipment (specifically, the Favimat+ and Robot2 models), which includes a measurement of the fiber linear density using a vibration method (e.g., according to ASTM D1577). To accurately convert measurements from MPa to cN/tex, an estimate of the bulk density (e.g. in g/cm$^3$) of the fiber is used. An expression that can be used to convert a force per unit area in MPa, "FA", to a force per linear density in cN/tex, "FLD", using the bulk density in g/cm$^3$, "BD", is FLD=FA/(10*BD). Since the bulk density of recombinant silk can vary, a given value of fiber tenacity in MPa does not translate to a given value of fiber tenacity in cN/tex. However, if the bulk density of the recombinant silk is assumed to be from 1.1 to 1.4 g/cm$^3$, then mechanical property values can be converted from one set of units into the other within a certain range of error. For example, a maximum tensile stress of 100 MPa is equivalent to about 9.1 cN/tex if the mass density of the fiber is 1.1 g/cm$^3$, and a maximum tensile stress of 100 MPa is equivalent to about 7.1 cN/tex if the mass density of the fiber is 1.4 g/cm$^3$.

The "work of rupture" of a fiber or yarn is the work done from the point of the pretension load to the point of the breaking load. The energy required to bring a fiber or yarn to the breaking load can be obtained from the area under the load-elongation curve. The units of work of rupture can therefore be cN*cm. The "toughness" of a fiber or yarn is the energy per unit mass required to rupture the fiber or yarn.

The toughness is the integral of the stress-strain curve, and can be calculated by dividing the work of rupture by the mass of the sample of fiber or yarn being tested. The units of toughness can therefore be cN/tex.

Throughout this disclosure, and in the claims, when percentages of amino acids are recited, that percentage indicates a mole fraction percentage (not a weight fraction percentage).

Throughout this disclosure, and in the claims, where method steps are recited, the order in which the steps are carried out can be varied from the order in which they are described, so long as an operable method results.

Throughout this disclosure, "along the length of the fiber" refers to samples taken along the length of the fiber at certain intervals. In some embodiments, "along the length of the fiber" can refer to a samples taken at an interval of, e.g., 1 per meter, 1 per 2 meters, 1 per 5 meters, 1 per 20 meters, 1 per 50 meters, or 1 per 100 meters. If the fibers are sampled from a textile or garment, then "along the length of the fiber" can also refer to samples taken from different areas of a textile or garment at an interval of, e.g., 1 per 1 cm$^2$, or 1 per 2 cm$^2$, or 1 per 5 cm$^2$, or 1 per 10 cm$^2$, or 1 per 20 cm$^2$, or 1 per 50 cm$^2$, or 1 per 100 cm$^2$, or 1 per 200 cm$^2$, or 1 per 500 cm$^2$.

The coefficient of variation of a quantitative property of a population is known to those skilled in the art as the standard deviation of the property of the population divided by the mean of the property of the population. When discussing coefficient of variation, enough samples are taken from a fiber, yarn, or textile to sufficiently mitigate low sample bias towards an artificially low CV. In all embodiments described in this disclosure the total number of samples used to calculate the CV is greater than or equal to 20. In some embodiments, the total number of samples is 20, or 40, or 60, or 80, or 100, or more than 100.

When a range of values is recited in this disclosure, e.g., "from X to Y," the range includes the extremes of the range, i.e., the range includes X and Y.

DETAILED DESCRIPTION

Recombinant Protein Fiber Engineering

Recombinant protein fibers (i.e., RPFs) can be engineered to have different mechanical, structural, chemical, and biological properties. Some methods to engineer long uniform RPFs for different properties are protein sequence design (e.g., higher ratio of GPG to poly-alanine to improve elasticity, where glycine is between 25-50% of the polypeptide), and/or microorganism strain design and/or growth conditions and/or protein purification, and/or fiber spinning conditions (e.g., changing spinneret diameter to tune fiber diameter).

Embodiments of the present disclosure include long uniform RPFs. In some embodiments, a "long uniform RPF" has a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, and physical (e.g., linear density, diameter), mechanical (e.g., maximum tenacity, initial modulus, extensibility, toughness), chemical (e.g., moisture absorption, moisture regain) and/or biological (e.g., antimicrobial) properties that are uniform along the length of the fiber, wherein the physical, mechanical and/or chemical property has a CV along the length of the fiber less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%. In many embodiments, the long uniform RPFs are engineered to comprise various improved mechanical, structural, chemical and biological properties. In some embodiments, long uniform RPFs are used to create yarns, textiles and/or products. In embodiments, the yarn, textile and/or product structure and the long uniform RPF properties are chosen to impart various characteristics to the resulting yarns, textiles and/or products fabricated from the long uniform RPFs.

In some embodiments, the hydrophilicity and/or moisture absorption of the long uniform RPFs can be engineered by changing the protein sequence. In some embodiments, the RPF hydrophilicity and/or moisture absorptivity is increased by increasing the ratio of substantially hydrophilic to substantially hydrophobic amino acids in the sequence, without disrupting fiber forming features such as poly-alanine stretches. Examples of relatively polar (relatively hydrophilic) amino acids in recombinant spider silk polypeptide sequences are glutamine, serine and tyrosine, while glycine and alanine are relatively hydrophobic. In some embodiments, a long uniform RPF comprising hydrophilic RPFs comprises greater than 25% glycine, or greater than 30% glycine, or greater than 35% glycine, or greater than 40% glycine, or greater than 45% glycine, or between 25% and 45% or between 25% and 40% or between 25% and 35% glycine, or between 35% and 45% glycine, or between 35% and 40% glycine, or between 40% and 45% glycine. In some embodiments, a long uniform RPF comprising hydrophilic RPFs comprises greater than 5% glutamine, or greater than 10% glutamine, or greater than 15% glutamine, or greater than 20% glutamine, or greater than 25% glutamine, or between 5% and 10% glutamine, or between 10% and 15% glutamine, or between 15% and 20% glutamine, or between 20% and 25% glutamine. In some embodiments, a long uniform RPF comprising highly moisture absorbing RPFs comprises greater than 25% glycine, or greater than 30% glycine, or greater than 35% glycine, or greater than 40% glycine, or greater than 45% glycine, or between 25% and 45% or between 25% and 40% or between 25% and 35% glycine, or between 35% and 45% glycine, or between 35% and 40% glycine, or between 40% and 45% glycine. In some embodiments, a long uniform RPF comprising highly moisture absorbing RPFs comprises greater than 5% glutamine, or greater than 10% glutamine, or greater than 15% glutamine, or greater than 20% glutamine, or greater than 25% glutamine, or between 5% and 10% glutamine, or between 10% and 15% glutamine, or between 15% and 20% glutamine, or between 20% and 25% glutamine. In some embodiments, a highly moisture absorbing RPF, upon being submerged in water at a temperature of 21° C.+/−1° C., can have a median or mean diameter change greater than 10%, or greater than 15%, or greater than 20%, or greater than 25%, or greater than 30%, or greater than 35%, or greater than 40%, or greater than 45%, or greater than 50%, or greater than 60%, or greater than 70%, or greater than 80%, or greater than 90%, or from 10% to 20%, or from 20% to 30%, or from 30% to 40%, or from 40% to 50%, or from 50% to 60%, or from 60% to 70%, or from 70% to 80%, or from 80% and 90%, or from 90% to 100%, or from 20% to 35%, or from 15% to 40%, or from 15% to 35%.

In some embodiments, the wickability of textiles can be engineered by changing the spinning parameters of the fibers making up the textile. In some embodiments, the fiber cross-section shape can be changed by changing the residence time in the coagulation bath, or by changing the ratio of protein solvent to protein non-solvent in the coagulation bath. The long uniform RPFs of the present disclosure processed with residence times in coagulation baths at the longer end of the disclosed range (such as greater than 60 seconds) produce corrugated cross sections. That is, each fiber has a plurality of corrugations (or alternatively "grooves") disposed at an outer surface of a fiber. Each of these corrugations is parallel to a longitudinal axis of the corresponding fiber on which the corrugations are disposed. These corrugations can act as channels to assist in the wicking of liquids including water. Theses long uniform RPFs with tailored cross-sections can also be formed into filament yarns, or spun yarns, or blended yarns. Filament yarn, or spun yarn, or blended yarn containing long uniform RPFs with tailored cross-sections can be used to make textiles with tailored moisture transport properties, such as higher wicking rates.

In some embodiments, antimicrobial protein motifs are added to the protein sequence to impart antimicrobial properties to the resulting long uniform RPFs, as well as improve the antimicrobial properties of filament yarns, or spun yarns, or blended yarns, and fabrics comprising the long uniform RPFs. Some examples of antimicrobial protein sequence motifs are the human antimicrobial peptides human neutrophil defensin 2 (HNP-2), human neutrophil defensins 4 (HNP-4) and hepcidin. These antimicrobial amino acid sequences can be added to the spider silk-derived polypeptide sequence after every quasi-repeat unit, or every 2 quasi-repeat units, or every 3 quasi-repeat units, or every 4 quasi-repeat units, or every 5 quasi-repeat units, or every 6 quasi-repeat units, or every 7 quasi-repeat units, or every 8 quasi-repeat units, or every 9 quasi-repeat units, or every 10 quasi-repeat units, or every 12 quasi-repeat units, or every 14 quasi-repeat units, or every 16 quasi-repeat units, or every 18 quasi-repeat units, or every 20 quasi-repeat units, or every 30 quasi-repeat units, or every 40 quasi-repeat units, or every 50 quasi-repeat units, or every 60 quasi-repeat units, or every 70 quasi-repeat units, or every 80 quasi-repeat units, or every 90 quasi-repeat units, or every 100 quasi-repeat units. In some embodiments, a textile, comprising filament yarn, or spun yarn, or blended yarn, comprising long uniform RPFs with such antimicrobial amino acid sequences, is tested using AATCC test method 100-2012, and has an increase in colony forming units less than 100 times in 24 hours, or has an increase in colony forming units less than 500 times in 24 hours, or has an increase in colony forming units less than 1000 times in 24 hours, or has a change in colony forming units from a 100 times reduction to a 1000 times increase in 24 hours.

In some embodiments, the extensibility of the long uniform RPFs is increased by increasing the ratio of GPG to poly-alanine in the protein sequence. In some embodiments, a long uniform RPF with a high degree of extensibility (such as extensibility greater than 3%, or greater than 10%, or greater than 20%, or greater than 30%, or from 3 to 30%, or from 3 to 100%), comprises greater than 25% glycine, or greater than 30% glycine, or greater than 35% glycine, or greater than 40% glycine, or greater than 45% glycine, or from 25% and 45% glycine, or from 25% to 40% glycine, or from 25% to 35% glycine, or from 35% to 45% glycine, or from 35% to 40% glycine, or from 40% to 45% glycine.

In some embodiments, the maximum tensile strength of the long uniform RPFs is increased by increasing the monodispersity of the protein comprising the long uniform RPFs. In some embodiments, the monodispersity of the protein comprising the long uniform RPFs is improved by engineering the strain of the microorganism used to produce the recombinant protein to secrete the protein. In turn, improved monodispersity improves the maximum tensile strength of the long uniform RPFs. In some embodiments, the proteins of the spin dope (the synthesis of which is described in WO2015042164 A2, especially at paragraphs 114-134, which are incorporated by reference herein) composed of any of the polypeptides of the present disclosure, that are used to produce the long uniform RPFs with a high tensile strength (such as greater than 10 cN/tex), are substantially monodisperse. In this disclosure, "substantially monodisperse" can be >50%, or >55%, or >60%, or >65%, or >70%, or >75%, or >80%, or >85%, or >90%, or >95%, or >99% of the protein in the spin dope (percentages here are mass percentages) having molecular weight >50%, or >55%, or >60%, or >65%, or >70%, or >75%, or >80%, or >85%, or >90%, or >95%, or >99% of the full-length molecular weight of the encoded protein. In this disclosure "substantially monodisperse" also encompasses spin dope mixtures in which from 50% to 100%, or from 60% to 100%, or from 70% to 100%, or from 80% to 100%, or from 90% to 100%, or from 50% to 99%, or from 60% to 99%, or from 70% to 99%, or from 80% to 99%, or from 90% to 99% of the protein in the spin dope (percentages here are mass percentages) having molecular weight from 50% to 100%, or from 60% to 100%, or from 70% to 100%, or from 80% to 100%, or from 90% to 100%, or from 50% to 99%, or from 60% to 99%, or from 70% to 99%, or from 80% to 99%, or from 90% to 99% of the full-length molecular weight of the encoded protein.

Work of rupture is a measure of toughness and combines elasticity and tenacity. Therefore, in some embodiments, the toughness of the long uniform RPFs is increased by combining protein sequence engineering and strain engineering to simultaneously increase the elasticity and the tenacity, as described in this disclosure. In some embodiments, long uniform RPFs with a high degree of toughness (such as greater than 100 cN/tex measured using ASTM D3822-14), comprise greater than 25% glycine, or greater than 30% glycine, or greater than 35% glycine, or greater than 40% glycine, or greater than 45% glycine, or from 25% to 45% or from 25% to 40% or from 25% to 35% glycine, or from 35% to 45% glycine, or from 35% to 40% glycine, or from 40% to 45% glycine. In some embodiments, the long uniform RPFs with a high work of rupture (such as greater than 0.5 cN*cm measured using ASTM D3822-14), comprises greater than 25% glycine, or greater than 30% glycine, or greater than 35% glycine, or greater than 40% glycine, or greater than 45% glycine, or between 25% and 45% or from 25% to 40% or from 25% to 35% glycine, or from 35% to 45% glycine, or from 35% to 40% glycine, or from 40% to 45% glycine. In some embodiments, the proteins of the spin dope (the synthesis of which is described in WO2015042164 A2, especially at paragraphs 114-134, which are incorporated by reference herein), expressed from any of the polypeptides of the present disclosure, comprising the RPFs with a high degree of toughness (such as greater than 100 cN/tex measured using ASTM D3822-14) or a high work of rupture (such as greater than 0.5 cN*cm measured using ASTM D3822-14), are substantially monodisperse.

In some embodiments, the initial modulus of the long uniform RPFs is increased by engineering the proteins to have better intermolecular forces. In some embodiments, intermolecular forces are increased by adding protein blocks that provide hydrogen bonding and cross-linking bonds between the molecules that comprise the fiber. One example of a protein motif that improves the intermolecular forces is by increasing the number of polyalanine segments for intermolecular crystallization. Another example of polypeptide engineering to increase intermolecular forces is through the addition of amino acids that are capable of covalently cross-linking such as the disulfide bridges of cysteine. A long uniform RPFs with tailored intermolecular forces can have high initial modulus. In some embodiments long uniform RPFs with engineered polypeptides described above can have a high initial modulus greater than 50 cN/tex, or greater than 115 cN/tex, or greater than 200 cN/tex, or greater than 400 cN/tex, or greater than 550 cN/tex, or greater than 600 cN/tex, or greater than 800 cN/tex, or greater than 1000 cN/tex, or greater than 2000 cN/tex, or greater than 3000 cN/tex, or greater than 4000 cN/tex, or greater than 5000 cN/tex, or from 200 to 900 cN/tex, or from 100 to 7000 cN/tex, or from 500 to 7000 cN/tex, or from 50 to 7000 cN/tex, or from 100 to 5000 cN/tex, or from 500 to 5000 cN/tex, or from 50 to 5000 cN/tex, or from 100 to 2000 cN/tex, or from 500 to 2000 cN/tex, or from 50 to 2000 cN/tex, or from 100 to 1000 cN/tex, or from 500 to 1000 cN/tex, or from 50 to 1000 cN/tex, or from 50 to 500 cN/tex, or from 100 to 1000 cN/tex, or from 500 to 1000 cN/tex, or from 100 to 700 cN/tex (measured using ASTM D3822-14).

In some embodiments, the initial modulus of the long uniform RPFs is increased by increasing the draw ratio of the fiber during spinning. In some embodiments, long uniform RPFs with a high initial modulus has a draw ratio of greater than 1.5×, or greater than 2×, or greater than 3×, or greater than 4×, or greater than 5×, or greater than 6×, or greater than 8×, or greater than 10×, or greater than 15×, or greater than 20×, or greater than 25×, or greater than 30×, or from 1.5× to 30×, or from 1.5× to 20×, or from 1.5× to 15×, or from 1.5× to 10×, or from 1.5× to 6×, or 1.5× to 4×, or from 2× to 30×, or from 2× to 20×, or from 2× to 15×, or from 2× to 10×, or from 2× to 6×, or from 2× to 4×, or from 4× to 30×, or from 4× to 20×, or from 4× to 15×, or from 4× to 10×, or from 4× to 6×, or from 6× to 30×, or from 6× to 20×, or from 6× to 15×, or from 6× to 10×, or from 10× to 30×, or from 10× to 20×, or from 10× to 15×.

In some embodiments the long uniform RPF cross-section shape is changed by changing the spinneret orifice shapes. In some embodiments, the long uniform RPF diameter or linear density is increased or decreased by increasing or decreasing the spinneret orifice diameter. The softness of a fiber is highly influenced by the diameter or linear density, and in some embodiments, the spinneret diameter can also be used to tune the softness of the long uniform RPFs by decreasing the fineness of the fibers. In some embodiments, the linear density of the long uniform RPFs can be tuned from less than 10 decitex (i.e., dtex), or less than 5 dtex, or less than 1 dtex, or from 1 to 20 dtex, or from 1 to 10 dtex by using a draw ratio during spinning of greater than 1.5×, or greater than 2×, or greater than 3×, or greater than 4×, or greater than 5×, or greater than 6×, or greater than 8×, or greater than 10×, or greater than 15×, or greater than 20×, or greater than 25×, or greater than 30×, or from 1.5× to 30×, or from 1.5× to 20×, or from 1.5× to 15×, or from 1.5× to 10×, or from 1.5× to 6×, or 1.5× to 4×, or from 2× to 30×, or from 2× to 20×, or from 2× to 15×, or from 2× to 10×, or from 2× to 6×, or from 2× to 4×, or from 4× to 30×, or from 4× to 20×, or from 4× to 15×, or from 4× to 10×, or from 4× to 6×, or from 6× to 30×, or from 6× to 20×, or from 6× to 15×, or from 6× to 10×, or from 10× to 30×, or from 10× to 20×, or from 10× to 15×. In some embodiments, a textile with good softness contains long uniform RPFs with fiber linear density less than 10 dtex, or less than 5 dtex, or less than 1 dtex, or from 1 to 20 dtex, or from 1 to 10 dtex. The drape of a fabric is highly influenced by the linear density or diameter of the fibers comprising the fabric, and in some embodiments, the spinneret diameter or the draw ratio can also be used to tune the drape of a fabric by increasing or decreasing the fineness of the long uniform RPFs comprising the fabric. In some embodiments, a textile with desirable drape contains filament yarn, or spun yarn, or blended yarn comprising long uniform RPFs with fiber linear density less than 10 dtex, or less than 5 dtex, or less than 1 dtex, or from 1 to 20 dtex, or from 1 to 10 dtex.

In some embodiments, the long uniform RPF cross-section shape can be changed by changing the residence time in the coagulation bath, or by changing the ratio of protein solvent to protein non-solvent in the coagulation bath. The long uniform RPFs of the present disclosure processed with residence times in coagulation baths at the longer end of the disclosed range produce corrugated cross sections. That is, each long uniform RPFs has a plurality of corrugations (or alternatively "grooves") disposed at an outer surface of a fiber. Each of these corrugations is parallel to a longitudinal axis of the corresponding fiber on which the corrugations are disposed. The luster of a fiber is also highly influenced by the smoothness of the surface. A long uniform RPF with a smoother surface has a higher luster, and in some embodiments, the luster of the fiber can also be tuned by changing the coagulation bath residence time or chemistry. A filament yarn, or spun yarn, or blended yarn can also contain long uniform RPFs with tailored cross-sections to create a yarn with low or high luster.

Recombinant Protein Fiber Protein Design

Long uniform RPFs can be produced using the following proteins and methods.

Embodiments of the present disclosure include fibers synthesized from synthetic proteinaceous copolymers based on recombinant spider silk protein fragment sequences derived from MaSp2, such as from the species *Argiope bruennichi*. Each synthesized fiber contains protein molecules that include two to twenty repeat units, in which a molecular weight of each repeat unit is greater than about 20 kDal. Within each repeat unit of the copolymer are more than about 60 amino acid residues that are organized into a number of "quasi-repeat units." In some embodiments, the repeat unit of a polypeptide described in this disclosure has at least 95% sequence identity to a MaSp2 dragline silk protein sequence.

Utilizing long polypeptides with fewer long exact repeat units has many advantages over utilizing polypeptides with a greater number of shorter exact repeat units to create a recombinant spider silk fiber. An important distinction is that a "long exact repeat" is defined as an amino acid sequence without shorter exact repeats concatenated within it. Long polypeptides with long exact repeats are more easily processed than long polypeptides with a greater number of short repeats because they suffer less from homologous recombination causing DNA fragmentation, they provide more control over the composition of amorphous versus crystalline domains, as well as the average size and size distribution of the nano-crystalline domains, and they do not suffer from unwanted crystallization during intermediate processing steps prior to fiber formation. Throughout this disclosure the term "repeat unit" refers to a subsequence that is exactly repeated within a larger sequence.

Throughout this disclosure, wherever a range of values is recited, that range includes every value falling within the range, as if written out explicitly, and further includes the values bounding the range. Thus, a range of "from X to Y" includes every value falling between X and Y, and includes X and Y.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared (i.e., subsequence), e.g., over a functional domain, or, alternatively, exist over the full length of the two sequences to be compared. Within this disclosure, a "region" is considered to be 6 or more amino acids in a continuous stretch within a polypeptide.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. Such software also can be used to determine the mole percentage of any specified amino acid found within a polypeptide sequence or within a domain of such a sequence. As the person of ordinary skill will recognize such percentages also can be determined through inspection and manual calculation.

FIG. 1 schematically illustrates an example copolymer molecule of the present disclosure, in an embodiment. A block copolymer molecule of the present disclosure includes in each repeat unit more than 60, or more than 100, or more than 150, or more than 200, or more than 250, or more than 300, or more than 350, or more than 400, or more than 450, or more than 500, or more than 600, or more than 700, or more than 800, or more than 900, or more than 1000 amino acid residues, or from 60 to 1000, or from 100 to 1000, or from 200 to 1000, or from 300 to 1000, or from 400 to 1000, or from 500 to 1000, or from 150 to 1000, or from 150 to 400, or from 150 to 500, or from 150 to 750, or from 200 to 400, or from 200 to 500, or from 200 to 750, or from 250 to 350, or from 250 to 400, or from 250 to 500, or from 250 to 750, or from 250 to 1000, or from 300 to 500, or from 300 to 750 amino acid residues. Each repeat unit of the polypeptide molecules of this disclosure can have a molecular weight from 20 kDal to 100 kDal, or greater than 20 kDal, or greater than 10 kDal, or greater than 5 kDal, or from 5 to 60 kDal, or from 5 to 40 kDal, or from 5 to 20 kDal, or from 5 to 100 kDal, or from 5 to 50 kDal, or from 10 to 20 kDal, or from 10 to 40 kDal, or from 10 to 60 kDal, or from 10 to 100 kDal, or from 10 to 50 kDal, or from 20 to 100 kDal, or from 20 to 80 kDal, or from 20 to 60 kDal, or from 20 to 40 kDal, or from 20 to 30 kDal. A copolymer molecule of the present disclosure can include in each repeat unit more than 300 amino acid residues. A copolymer molecule of the present disclosure can include in each repeat unit about 315 amino acid residues. These amino acid residues are organized within the molecule at several different levels. A copolymer molecule of the present disclosure includes from 2 to 20 occurrences of a repeat unit. After concatenating the repeat unit, the polypeptide molecules of this disclosure can be from 20 kDal to 2000 kDal, or greater than 20 kDal, or greater than 10 kDal, or greater than 5 kDal, or from 5 to 400 kDal, or from 5 to 300 kDal, or from 5 to 200 kDal, or from 5 to 100 kDal, or from 5 to 50 kDal, or from 5 to 500 kDal, or from 5 to 1000 kDal, or from 5 to 2000 kDal, or from 10 to 400 kDal, or from 10 to 300 kDal, or from 10 to 200 kDal, or from 10 to 100 kDal, or from 10 to 50 kDal, or from 10 to 500 kDal, or from 10 to 1000 kDal, or from 10 to 2000 kDal, or from 20 to 400 kDal, or from 20 to 300 kDal, or from 20 to 200 kDal, or from 40 to 300 kDal, or from 40 to 500 kDal, or from 20 to 100 kDal, or from 20 to 50 kDal, or from 20 to 500 kDal, or from 20 to 1000 kDal, or from 20 to 2000 kDal. As shown in FIG. 1, each "repeat unit" of a copolymer fiber comprises from two to twenty "quasi-repeat" units (i.e., n3 is from 2 to 20). Quasi-repeats do not have to be exact repeats. Each repeat can be made up of concatenated quasi-repeats. Equation 1 shows the composition of a quasi-repeat unit according the present disclosure.

$$\{GGY\text{-}[GPG\text{-}X_1]_{n1}\text{-}GPS\text{-}(A)_{n2}\}_{n3}(SEQ\ ID\ NO:\ 99). \quad \text{(Equation 1)}$$

The variable compositional element $X_1$ (termed a "motif") is according to any one of the following amino acid sequences shown in Equation 2 and $X_1$ varies randomly within each quasi-repeat unit.

$$X_1\text{=SGGQQ}(SEQ\ ID\ NO:\ 100)\ \text{or GAGQQ}(SEQ\ ID\ NO:\ 101)\ \text{or GQGPY}(SEQ\ ID\ NO:\ 102)\ \text{or}$$
$$\text{AGQQ}(SEQ\ ID\ NO:\ 103)\ \text{or SQ} \quad \text{(Equation 2)}$$

Referring again to Equation 1, the compositional element of a quasi-repeat unit represented by "GGY-[GPG-$X_1]_{n1}$-GPS" (SEQ ID NO: 104) in Equation 1 is referred to a "first region." A quasi-repeat unit is formed, in part by repeating from 4 to 8 times the first region within the quasi-repeat unit. That is, the value of $n_1$ indicates the number of first region units that are repeated within a single quasi-repeat unit, the value of $n_1$ being any one of 4, 5, 6, 7 or 8. The compositional element represented by "$(A)_{n2}$" (SEQ ID NO: 105) is referred to a "second region" and is formed by repeating within each quasi-repeat unit the amino acid sequence "A" $n_2$ times (SEQ ID NO: 105). That is, the value of $n_2$ indicates the number of second region units that are repeated within a single quasi-repeat unit, the value of $n_2$ being any one of 6, 7, 8, 9, 10, 11, 12, 13, 14, 15, 16, 17, 18, 19, or 20. In some embodiments, the repeat unit of a polypeptide of this disclosure has at least 95% sequence identity to a sequence containing quasi-repeats described by Equations 1 and 2. In some embodiments, the repeat unit of a polypeptide of this disclosure has at least 80%, or at least 90%, or at least 95%, or at least 99% sequence identity to a sequence containing quasi-repeats described by Equations 1 and 2.

The first region described in Equation 1 is considered a glycine-rich region. A region can be glycine-rich if 6 or more consecutive amino acids within a sequence are more than 45% glycine. A region can be glycine-rich if 12 or more consecutive amino acids within a sequence are more than 45% glycine. A region can be glycine-rich if 18 or more consecutive amino acids within a sequence are more than 45% glycine. A region can be glycine-rich if 4 or more, or 6 or more, or 10 or more, or 12 or more, or 15 or more, or 20 or more, or 25 or more, or 30 or more, or 40 or more, or 50 or more, or 60 or more, or 70 or more, or 80 or more, or 100 or more, or 150 or more consecutive amino acids within a sequence are more than 30%, or more than 40%, or more than 45%, or more than 50%, or more than 55% glycine, or more than 60% glycine, or more than 70% glycine, or more than 80% glycine, or from 30% to 80%, or from 40% to 80%, or from 45% to 80%, or from 30% to 55%, or from 30% to 50%, or from 30% to 45%, or from 30% to 40%, or from 40% to 50%, or 40% to 55%, or 40% to 60% glycine. A region can be glycine-rich if from 5 to 150, or from 10 to 150, or from 12 to 150, or from 12 to 100, or from 12 to 80, or from 12 to 60, or from 20 to 60 consecutive amino acids within a sequence are more than 30%, or more than 40%, or more than 45%, or more than 50%, or more than 55% glycine, or more than 60% glycine, or more than 70% glycine, or more than 80% glycine, or from 30% to 80%, or from 40% to 80%, or from 45% to 80%, or from 30% to 55%, or from 30% to 50%, or from 30% to 45%, or from 30% to 40%, or from 40% to 50%, or 40% to 55%, or 40% to 60% glycine. In addition, a glycine-rich region can have less than 10%, or less than 20%, or less than 30%, or less than 40% alanine, or from about 0% to 10%, or from about 0% to 20%, or from about 0% to 30%, or from about 0% to 40%, or alanine. A region can be alanine-rich if 4 or more, or 6 or more, or 8 or more, or 10 or more consecutive amino acids within a sequence are more than 70%, or more than 75%, or more than 80%, or more than 85%, or more than 90% alanine, or from 70% to about 100%, or from 75% to about 100%, or from 80% to about 100%, or from 85% to about 100%, or from 90% to about 100% alanine. A region can be alanine-rich if from 4 to 10, or from 4 to 12, or from 4 to 15, or from 6 to 10, or from 6 to 12, or from 6 to 15, or from 4 to 20, or from 6 to 20 consecutive amino acids within a sequence are more than 70%, or more than 75%, or more than 80%, or more than 85%, or more than 90% alanine, or from 70% to about 100%, or from 75% to about 100%, or from 80% to about 100%, or from 85% to about 100%, or from 90% to about 100% alanine. The repeats described in this disclosure can have 6, or more than 2, or more than 4 or more than 6, or more than 8, or more than 10, or more than 15, or more than 20, or from 2 to 25, or from 2 to 10, or from 4 to 10, or from 2 to 8, or from 4 to 8 alanine-rich regions. The repeats described in this disclosure can have 6, or more than 2, or more than 4 or more than 6, or more than 8, or more than 10, or more than 15, or more than 20, or from 2 to 25, or from 2 to 10, or from 4 to 10, or from 2 to 8, or from 4 to 8 glycine-rich regions.

In some embodiments, long uniform RPFs comprise proteins containing SEQ described by Equation 1 and Equation 2. In some embodiments, long uniform RPFs comprise proteins with repeat units, where each repeat unit has at least 95% sequence identity to a sequence that comprises from 2 to 20 quasi-repeat units, and each quasi-repeat unit has a composition of $\{GGY\text{-}[GPG\text{-}X_1]_{n1}\text{-}GPS\text{-}(A)_{n2}\}$ (SEQ ID NO: 111), and for each quasi-repeat unit $X_1$ is independently selected from the group consisting of SGGQQ (SEQ ID NO: 100), GAGQQ (SEQ ID NO: 101), GQGPY (SEQ ID NO: 102), AGQQ (SEQ ID NO: 103), and SQ, and n1 is from 4 to 8, and n2 is from 6 to 10.

As further described below, one example of a copolymer molecule includes three "long" quasi-repeats followed by three "short" quasi-repeat units. A "long" quasi-repeat unit is comprised of quasi-repeat units that do not use the same $X_1$ constituent (as shown in Equation 2) more than twice in a row, or more than two times in a repeat unit. Each "short" quasi-repeat unit includes any of the amino acid sequences identified in Equation 2, but regardless of the amino acid sequences used, the same sequences are in the same location within the molecule. Furthermore, in this example copolymer molecule, no more than 3 quasi-repeats out of 6 share the same $X_1$. "Short" quasi-repeat units are those in which n1=4 or 5 (as shown in Equation 1). Long quasi-repeat units are defined as those in which n1=6, 7 or 8 (as shown in Equation 1).

In some embodiments, the repeat unit of the copolymer is composed of $X_{qr}$ quasi-repeat units, where $X_{qr}$ is a number from 2 to 20, and the number of short quasi-repeat units is $X_{sqr}$ and the number of long quasi-repeat units is $X_{lqr}$, where $$X_{sqr}+X_{lqr}=X_{qr} \quad \text{(Equation 3)}$$

and $X_{sqr}$ is a number from 1 to ($X_{qr}$−1) and $X_{lqr}$ is a number from 1 to ($X_{qr}$−1).

In another embodiment, n1 is from 4 to 5 for at least half of the quasi-repeat units. In yet another embodiment, n2 is from 5 to 8 for at least half of the quasi-repeat units.

One feature of copolymer molecules of the present disclosure is the formation of nano-crystalline regions that, while not wishing to be bound by theory, are believed to form from the stacking of beta-sheet regions, and amorphous regions composed of alpha-helix structures, beta-turn structures, or both. Poly-alanine regions (or in some species $(GA)_n$ regions) in a molecule form crystalline beta-sheets within major ampullate (MA) fibers. Other regions within a repeat unit of major ampullate and flagelliform spider silks (for example containing GPGGX (SEQ ID NO: 106), GPGQQ (SEQ ID NO: 107), GGX where X=A, S or Y, GPG, SGGQQ (SEQ ID NO: 100), GAGQQ (SEQ ID NO: 101), GQGPY (SEQ ID NO: 102), AGQQ (SEQ ID NO: 103), and SQ, can form amorphous rubber-like structures that include alpha-helices and beta-turn containing structures. Furthermore, secondary, tertiary and quaternary structure is imparted to the morphology of the fibers via amino acid sequence and length, as well as the conditions by which the fibers are formed, processed and post-processed. Materials characterization techniques (such as NMR, FTIR and x-ray diffraction) have suggested that the poly-alanine crystalline domains within natural MA spider silks and recombinant silk derived from MA spider silk sequences are typically very small (<10 nm). Fibers can be highly crystalline or highly amorphous, or a blend of both crystalline and amorphous regions, but fibers with optimal mechanical properties have been speculated to be composed of 10-40% crystalline material by volume. In some embodiments, the repeat unit of a polypeptide described in this disclosure has at least 80%, or at least 90%, or at least 95%, or at least 99% sequence identity to a MA dragline silk protein sequence. In some embodiments, the repeat unit of a polypeptide described in this disclosure has at least 80%, or at least 90%, or at least 95%, or at least 99% sequence identity to a MaSp2 dragline silk protein sequence. In some embodiments, the repeat unit of a polypeptide described in this disclosure has at least 80%, or at least 90%, or at least 95%, or at least 99% sequence identity to a spider dragline silk protein sequence. In some embodiments, a quasi-repeat unit of a polypeptide described in this disclosure has at least 80%, or at least 90%, or at least 95%, or at least 99% sequence identity to a MA dragline silk protein sequence. In some embodiments, a quasi-repeat unit of a polypeptide described in this disclosure has at least 80%, or at least 90%, or at least 95%, or at least 99% sequence identity to a MaSp2 dragline silk protein sequence. In some embodiments, a quasi-repeat unit of a polypeptide described in this disclosure has at least 80%, or at least 90%, or at least 95%, or at least 99% sequence identity to a spider dragline silk protein sequence.

While not wishing to be bound by theory, the structural properties of the proteins within the spider silk are theorized to be related to fiber mechanical properties. Crystalline regions in a fiber have been linked with the tensile strength of a fiber, while the amorphous regions have been linked to the extensibility of a fiber. The major ampullate (MA) silks tend to have higher strengths and less extensibility than the flagelliform silks, and likewise the MA silks have higher volume fraction of crystalline regions compared with flagelliform silks. Furthermore, theoretical models based on the molecular dynamics of crystalline and amorphous regions of spider silk proteins, support the assertion that the crystalline regions have been linked with the tensile strength of a fiber, while the amorphous regions have been linked to the extensibility of a fiber. Additionally, the theoretical modeling supports the importance of the secondary, tertiary and quaternary structure on the mechanical properties of RPFs. For instance, both the assembly of nano-crystal domains in a random, parallel and serial spatial distributions, and the strength of the interaction forces between entangled chains within the amorphous regions, and between the amorphous regions and the nano-crystalline regions, influenced the theoretical mechanical properties of the resulting fibers.

The repeat unit of the proteinaceous block copolymer that forms fibers with good mechanical properties can be synthesized using a portion of a silk polypeptide. Some exemplary sequences that can be used as repeats in the proteinaceous block copolymers of this disclosure are shown in Table 1. These polypeptide repeat units contain alanine-rich regions and glycine-rich regions, and are 150 amino acids in length or longer. These exemplary sequences were demonstrated to express using a *Pichia* expression system as taught in co-owned PCT Publication WO 2015042164.

TABLE 1

Exemplary sequences that can be used as repeat units

| Seq. ID No. | AA |
|---|---|
| 1 | GGYGPGAGQQGPGSGGQQGPGGQPGYGSGQQGPGGAGQQGPGGQGPYGPGAAAAAAAA AGGYGPGAGQQGPGGAGQQGPGSQGPGGQGPYGPGAGQQGPGSQGPGSGGQQGPGGQG PYGPSAAAAAAAAAGGYGPGAGQRSQGPGGQGPYGPGAGQQGPGSQGPGSGGQQGPGG QGPYGPSAAAAAAAAGGYGPGAGQQGPGSQGPGSGGQQGPGGQGPYGPGAAAAAAAVG GYGPGAGQQGPGSQGPGSGGQQGPGGQGPYGPSAAAAAAAAGGYGPGAGQQGPGSQGP GSGGQQGPGGQGPYGPSAAAAAAAA |
| 2 | GGQGGRGGFGGLGSQGAGGAGQGGAGAAAAAAAAGGDGGSGLGGYGAGRGHGVGLGGA GGAGAASAAAAAGGQGGRGGFGGLGSQGAGGAGQGGAGAAAAAAAAAGGDGGSGLGGYG AGRGHGAGLGGAGGAGAASAAAAAGGQGGRGGFGGLGSQGSGGAGQGGSGAAAAAAAA GGDGGSGLGGYGAGRGYGAGLGGAGGAGAASAAAAAGGQGGRGGFGGLGSQGAGGAGQ GGSGAAAAAAAAVADGGSGLGGYGAGRGYGAGLGGAGGAGAASAAAAT |
| 3 | GSAPQGAGGPAPQGPSQQGPVSQGPYGPGAAAAAAAAGGYGPGAGQQGPGSQGPGSGG QQGPGSQGPGSGGQQGPGGQGPYGPSAAAAAAAAAGGYGPGAGQQGPGSQGPGSGGQQ GPGGQGPYGPGAAAAAAAVGGYGPGAGQQGPGSQGPGSGGQQGPGGQGPYGPSAAAAA AAAGGYGPGAGQQGPGSQGPGSGGQQGPGGQGPYGPSAAAAAAAAAGGYGPGAGQQGPG SGGQQGPGGQGPYGSGQQGPGGAGQQGPGGQGPYGPGAAAAAAAA |
| 4 | GGYGPGAGQQGPGSGGQQGPGGQGPYGSGQQGPGGAGQQGPGGQGPYGPGAAAAAAAA AGGYGPGAGQQGPGGAGQQGPGSQGPGGQGPYGPGAGQQGPGSQGPGSGGQQGPGGQG PYGPSAAAAAAAAGGYGPGAGQQGPGSQGPGSGGQQGPGGQGPYGPSAAAAAAAAGGY GPGAGQQGPGSGGQQGPGGQGPYGSGQQGPGGAGQQGPGGQGPYGGGYGPGAGQQGPG SQGPGSGGQQGPGGQGPYGPSAAAAAAAA |
| 5 | GPGARRQGPGSQGPGSGGQQGPGGQGPYGSGQQGPGGAGQQGPGGQGPYGPGAAAAAA AAAGGYGPGAGQQGPGGAGQQGPGSQGPGGQGPYGPGAGQQGPGSQGPGSGGQQGPGG QGPYGPSAAAAAAAAGGYGPGAGQQGPGSQGPGSGGQQGPGGQGPYGPGAAAAAAAAV GGYGPGAGQQGPGSQGPGSGGQQGPGGQGPYGPSAAAAAAAAGGYGPGAGQQGPGSQG PGSGGQQGPGGQGPYGPSAAAAAAAA |
| 6 | GPGARRQGPGSQGPGSGGQQGPGGQGPYGSGQQGPGGAGQQGPGGQGPYGPGAAAAAA AAAGGYGPGAGQQGPGGAGQQGPGSQGPGGQGPYGPGAGQQGPGSQGPGSGGQQGPGG QGPYGPSAAAAAAAAGGYGPGAGQQGPGSQGPGSGGQQGPGGQGPYGPGAAAAAAAVG GYGPGAGQQGPGSQGPGSGGQQGPGGQGPYGPSAAAAAAAAGGYGPGAGQQGPGSQGP GSGGQQGPGGQGPYGPSAAAAAAAA |
| 7 | GGYGPGAGQQGPGSGGQQGPGGQGPYGSGQQGPGGAGQQGPGGQGPYGPGAAAAAAAA AGGYGPGAGQQGPGGAGQQGPEGPGSQGPGSGGQQGPGGQGPYGPGAAAAAAAVGGYG PGAGQQGPGSQGPGSGGQQGPGGQGPYGPSAAAAAAAAGGYGPGAGQQGPGSQGPGSG GQQGPGGQGPYGPSAAAAAAAAGGYGPGAGQQGPGSGGQQGPGGQGPYGSGQQGPGGA GQGPGGQGPYGPGAAAAAAAA |

TABLE 1-continued

Exemplary sequences that can be used as repeat units

| Seq. ID No. | AA |
|---|---|
| 8 | GVFSAGQGATPWENSQLAESFISRFLRFIGQSGAFSPNQLDDMSSIGDTLKTAIEKMA QSRKSSKSKLQALNMAFASSMAEIAVAEQGGLSLEAKTNAIASALSAAFLETTGYVNQ QFVNEIKTLIFMIAQASSNEISGSAAAAGGSSGGGGGSGQGGYGQGAYASASAAAAYG SAPQGTGGPASQGPSQQGPVSQPSYGPSATVAVTAVGGRPQGPSAPRQQGPSQQGPGQ QGPGGRGPYGPSAAAAAAAA |
| 9 | GAGAGAGAGAGAGAGAGSGASTSVSTSSSSGSGAGAGAGSGAGSGAGAGSGAGAGAGA GGAGAGFGSGLGLGYGVGLSSAQAQAQAQAAAQAQAQAQAQAYAAAQAQAQAQAQAQA AAAAAAAAAAGAGAGAGAGAGAGAGSGASTSVSTSSSSGSGAGAGAGSGAGSGAGA GSGAGAGAGAGGAGAGFGSGLGLGYGVGLSSAQAQAQAQAAAQAQAQAQAQAYAAAQA QAQAQAQAQAAAAAAAAAAA |
| 10 | GAGAGAGAGAGAGAGSGASTSVSTSSSSGSGAGAGAGSGAGSGAGAGSGAGAGAGA GGAGAAFGSGLGLGYGVGLSSAQAQAQAQAAAQAQADAQAQAYAAAQAQAQAQAQA AAAAAAAAAAGAGAGAGAGSGAGAGAGSGAGAGAGSGASTSVSTSSSSGSGAGAGAGSGAGSGAGA GSGAGAGAGAGGAGAGFGSGLGLGYGVGLSSAQAQAQAQAAAQAQADAQAQAYAAAQA QAQAQAQAQAAAAAAAAAAA |
| 11 | GAGAGAGAGSGAGAGAGSGASTSVSTSSSSGSGAGAGAGSGAGSGAGAGSGAGAGAGA GGAGAGFGSGLGLGYGVGLSSAQAQAQSAAAARAQADAQAQAYAAAQAQAQAQAQAQA AAAAAAAAAAGAGAGAGAGAGAGAGSGASTSVSTSSSASGAGAGAGSGAGSGAGA GSGAGAGAGAGGAGAGFGSGLGLGYGVGLSSAQAQAQAQAAAQAQAQAQAQALAAAQA QAQAQAQAQAAAATAAAAAA |
| 12 | GGYGPGAGQQGPGGAGQQGPGSQGPGGQGPYGPGAGQQGPGSQGPGSGGQQGPGGQGP YGPSAAAAAAAAGGYGPGAGQQGPGSQGPGSGGQQGPGSQGPGSGGQQGPGGQGPYGP SAAAAAAAAAGGYGPGAGQQGPGSQGPGSGGQQGPGGQGPYGPGAAAAAAAVGGYGPG AGQQGPGSQGPGSGGQQGPGGQGPYGPSAAAAAAAAAGGYGPGAGQQGPGSQGPGSGGQ QGPGGQGPYGPSAAAAAAAA |
| 13 | GGYGPGAGQQGPGGAGQQGPGSQGPGGQGPYGPGAGQQGPGSQGPGSGGQQGPGGQGP YGPSAAAAAAAAAGGYGPGAGQQGPGSQGPGSGGQQGPGSQGPGSGGQQGPGGQGPYGP SAAAAAAAAAGGYGPGAGQQGPGSQGPGSGGQQGPGGQGPYGPGAAAAAAAVGGYGPGA GQQGPGSQGPGSGGQQGPGGQGPYGPSAAAAAAAAAGGYGPGAGQQGPGSQGPGSGGQQ GPGGQGPYGPSAAAAAAAA |
| 14 | GHQGPHRKTPWETPEMAENFMNNVRENLEASRIFPDELMKDMEAITNTMIAAVDGLEA QHRSSYASLQAMNTAFASSMAQLFATEQDYVDTEVIAGAIGKAYQQITGYENPHLASE VTRLIQLFREEDDLENEVEISFADTDNAIARAAAGAAAGSAAASSSADASATAEGASG DSGFLFSTGTFGRGGAGAGAGAAAASAAAASAAAAGAEGDRGLFFSTGDFGRGGAGAG AGAAAASAAAASAAAA |
| 15 | GGAQKHPSGEYSVATASAAATSVTSGGAPVGKPGVPAPIFYPQGPLQQGPAPGPSNVQ PGTSQQGPIGGVGESNTFSSSFASALGGNRGFSGVISSASATAVASAFQKGLAPYGTA FALSAASAAADAYNSIGSGASASAYAQAFARVLYPLLQQYGLSSSADASAFASAIASS FSTGVAGQGPSVPYVGQQQPSIMVSAASASAAASAAAVGGGPVVQGPYDGGQPQQPNI AASAAAAATATSSAAAA |
| 16 | GGQGGRGGFGGLGSQGEGGAGQGGAGAAAAAAAAGADGGFGLGGYGAGRGYGAGLGGA GGAGASAAAAAGGQGGRSGFGGLGSQGAGGAGQGGAGAAAAAAAAAGADGGSGLGGYG AGRGYGASLGGADGAGAASAAAAAGGAGGRGGFGGLGSQGAGGAGQGGAGQGGAGAAA SGDGGSGLGGYGAGRGYGAGLGGAGGAGAASAAAAAGGEGGRGGFGGLGSQGAGGAGQ GGSLAAAAAAAA |
| 17 | GPGGYGGPGQPGPGQGQYGPGPGQQGPRQGGQQGPASAAAAAAAAGPGGYGGPGQQGPR QGQQQGPASAAAAAAAAAAGPRGYGGPGQQGPVQGGQQGPASAAAAAAAAAGVGGYGGP GQQGPGQGQYGPGTGQQGQPSGQQGPAGAAAAAAAGGAAGPGGYGGPGQQGPGQGQYG PGTGQQGQPSGQQGPAGAAAAAAAAGPGGYGGPGQQGPGQGYGPGAGQQGQPGS QQGPASAAAAAA |
| 18 | GSGAGQGTGAGAGAAAAAAGAAGSGAGQGAGSGAGAAAAAAAAAASAAGAGQGAGSGSGA GAAAAAAAAAAGAGQGAGSGSGAGAAAAAAAAAAAAQQQQQQQAAAAAAAAAAAAAGSG QGASFGVTQQFGAPSGAASSAAAAAAAAAAAAAGSGAGQEAGTGAGAAAAAAAAAGAAG SGAGQGAGSGAGAAAAAAAAAAAASAAGAGQGAGSGSGAGAAAAAAAAAAAAQQQQQQAA AAAAAAAAAA |
| 19 | GGAQKQPSGESSVATASAAATSVTSAGAPVGKPGVPAPIFYPQGPLQQGPAPGPSYVQ PATSQQGPIGGAGRSNAFSSSFASALSGNRGFSEVISSASATAVASAFQKGLAPYGTA FALSAASAAADAYNSIGSGANAFAYAQAFARVLYPLVQQYGLSSSAKASAFASAIASS FSSGAAGQGQSIPYGGQQQPPMTISAASASAGASAAAVKGGQVGQGPYGGQQQSTAS ASAAATTATA |

TABLE 1-continued

Exemplary sequences that can be used as repeat units

| Seq. ID No. | AA |
|---|---|
| 20 | GADGGSGLGGYGAGRGYGAGLGGADGAGAASAAAAAGGQGGRGGFGRLGSQGAGGAGQ GGAGAAAAVAAAGGDGGSGLGGYGAGRGYGAGLGGAGGAGAASAAAAAGGQGGRGGFG GLGSQGAGGAGQGGAGAAASGDGGSGLGGYGAGRGYGAGLGGADGAGAASAASAAGGQ GGRGGFGGLGSQGAGGAGQGGAGAAAAAATAGGDGGSGLGGYGAGRGYGAGLGGAGGA GASAAAAA |
| 21 | GAGAGQGGRGGYGQGGFGGQGSGAGAGAGASAAAGAGAGQGGRGGYGQGGFGGQGSGAGA GASAAAAGAGAGQGGRGGYGQGGFGGQGSGAGAGASAAAAAGAGQGGRGGYGQGGLGGS GSGAGAGAGAAAAAAGAGGYGQGGLGGYGQGAGAGQGGLGGYGSGAGAGASAAAAAG AGGAGQGGLGGYGQGAGAGQGGLGGYGSGAGAGAAAAAAAGAGGSGQGGLGGYGSGGG AGGASAAAA |
| 22 | GAYAYAYAIANAFASILANTGLLSVSSAASVASSVASAIATSVSSSSAAAAASASAAA AASAGASAASSASASSSASAAAGAGAGAGASGASGAAGGSGGFGLSSGFGAGIGGL GGYPSGALGGLGIPSGLLSSGLLSPAANQRIASLIPLILSAISPNGVNFGVIGSNIAS LASQISQSGGGIAASQAFTQALLELVAAFIQVLSSAQIGAVSSSSASAGATANAFAQS LSSAFAG |
| 23 | GAAQKQPSGESSVATASAAATSVTSGGAPVGKPGVPAPIFYPQGPLQQGPAPGPSNVQ PGTSQQGPIGGVGGSNAFSSSFASALSLNRGFTEVISSASATAVASAFQKGLAPYGTA FALSAASAAADAYNSIGSGANAFAYAQAFARVLYPLVRQYGLSSSGKASAFASAIASS FSSGTSGQGPSIGQQQPPVTISAASASAGASAAAVGGGQVGQGPYGGQQQSTAASASA AAATATS |
| 24 | GAAQKQPSGESSVATASAAATSVTSGGAPVGKPGVPAPIFYPQGPLQQGPAPGPSNVQ PGTSQQGPIGGVGGSNAFSSSFASALSLNRGFTEVISSASATAVASAFQKGLAPYGTA FALSAASAAADAYNSIGSGANAFAYAQAFARVLYPLVRQYGLSSSGKASAFASAIASS FSSGTSGQGPSIGQQQPPVTISAASASAGASAAAVGGGQVGQGPYGGQQQSTAASASA AAATATS |
| 25 | GAAQKQPSGESSVATASAAATSVTSGGAPVGKPGVPAPIFYPQGPLQQGPAPGPSNVQ PGTSQQGPIGGVGGSNAFSSSFASALSLNRGFTEVISSASATAVASAFQKGLAPYGTA FALSAASAAADAYNSIGSGANAFAYAQAFARVLYPLVQQYGLSSSAKASAFASAIASS FSSGTSGQGPSIGQQQPPVTISAASASAGASAAAVGGGQVGQGPYGGQQQSTAASASA AAATATS |
| 26 | GGAQKQPSGESSVATASAAATSVTSAGAPVGKPGVPAPIFYPQGPLQQGPAPGPSNVQ PGTSQQGPIGGVGGSNAFSSSFASALSLNRGFTEVISSASATAVASAFQKGLAPYGTA FALSAASAAADAYNSIGSGANAFAYAQAFARVLYPLVQQYGLSSSAKASAFASAIASS FSSGTSGQGPSNGQQQPPVTISAASASAGASAAAVGGGQVSQGPYGGQQQSTAASASA AAATATS |
| 27 | GGAQKQPSGESSVATASAAATSVTSAGAPGGKPGVPAPIFYPQGPLQQGPAPGPSNVQ PGTSQQGPIGGVGGSNAFSSSFASALSLNRGFTEVISSASATAVASAFQKGLAPYGTA FALSAASAAADAYNSIGSGANAFAYAQAFARVLYPLVQQYGLSSSAKASAFASAIASS FSSGTSGQGPSIGQQQPPVTISAASASAGASAAAVGGGQVGQGPYGGQQQSTAASASA AAATATS |
| 28 | GPGGYGGPGQQGPGQGQQQGPASAAAAAAAAGPGGYGGPGQQGPGQGQQQGPASAAAA AAAAAGPGGYGGPGQQRPGQAQYGRGTGQQGQGPGAQQQGPASAAAAAAAAGAGLYGGPG QQGPGQGQQQGPASAAAAAAAAAAGPGGYGGPGQQGPGQAQQQGPASAAAAAAAAGPG GYSGPGQQGPGQAQQQGPASAAAAAAAAAGPGGYGGPGQQGPGQGQQQGPASAAAAAA ATAA |
| 29 | GAGGDGGLFLSSGDFGRGGAGAGAGAAAASAAAASSAAAGARGGSGFGVGTGGFGRGG AGDGASAAAASAAAASAAAAGAGGDSGLFLSSGDFGRGGAGAGAGAAAASAAAASAAA AGTGGVGGLFLSSGDFGRGGAGAGAGAAAASAAAASSAAAGARGGSGFGVGTGGFGRG GPGAGTGAAAASAAAASAAAAGAGGDSGLFLSSEDFGRGGAGAGTGAAAASAAAASAA AA |
| 30 | GAGRGYGGGYGGGAAAGAGAGAGAGRGYGGGYGGGAGSGAGSGAGAGGGSGYGRGAGA GAGAGAAAAGAGAGGAGGYGGGAGAGAGAAAAGAGAGAGGGYGGGYGGGAGAGA GAGAAAAAGAGAGAGAGRGYGGGFGGGAGSGAGAGAGAGGGSGYGRGAGGYGGGYGGG AGTGAGAAAATGAGAGAGAGRGYGGGYGGGAGAGAGAGAGGGSGYGRGAGAGASVA A |
| 31 | GALGQGASVWSSPQMAENFMNGFSMALSQAGAFSGQEMKDFDDVRDIMNSAMDKMIRS GKSGRGAMRAMNAAFGSAIAEIVAANGGKEYQIGAVLDAVTNTLLQLTGNADNGFLNE ISRLITLFSSVEANDVSASAGADASGSSGPVGGYSSGAGAAVGQGTAQAVGYGGGAQG VASSAAAGATNYAQGVSTGSTQNVATSTVTTTTNVAGSTATGYNTGYGIGAAAGAAA |
| 32 | GGQGGQGGYDGLGSQGAGQGGYGQGGAAAAAAASGAGSAQRGGLGAGGAGQGYGAGS GGQGGAGQGGAAAATAAAAGGQGGQGGYGGLGSQGSGQGGYGQGGAAAAAAAASGDGG AGQEGLGAGGAGQGYGAGLGGQGGAGQGGAAAAAAAAAAGGQGGQGGYGGLGSQGAGQG GYGQGGAAAAAAAAS GAGGAGQGGLGAAGAGQGYGAGSGGQGGAGQGGAAAAAAAAA |

TABLE 1-continued

Exemplary sequences that can be used as repeat units

| Seq. ID No. | AA |
|---|---|
| 33 | GGQGGQGGYGGLGSQGAGQGGYGQGGVAAAAAAASGAGGAGRGGLGAGGAGQEYGAVS GGQGGAGQGGEAAAAAAAAGGQGGQGGYGGLGSQGAGQGGYGQGGAAAAAAAASGAGG ARRGGLGAGGAGQGYGAGLGGQGGAGQGSASAAAAAAAAGGQGGQGGYGGLGSQGSGQG GYGQGGAAAAAAAASGAGGAGRGSLGAGGAGQGYGAGLGGQGGAGQGGAAAAASAAA |
| 34 | GPGGYGGPGQQGPGQGQYGPGTGQQGQGPGGQQGPVGAAAAAAAAAVSSGGYGSQGAGQ GGQQGSGQRGPAAAGPGGYSGPGQQGPGQGQQGPASAAAAAAAAAGPGGYGGSGQQG PGQQGRGTGQQGQGPGGQQGPASAAAAAAAAGPGGYGGPGQQGPGQGQYGPGTGQQGQGP ASAAAAAAAAGPGGYGGPGQQGPGQGQYGPGTGQQGQGPGGQQGPGGASAAAAAAA |
| 35 | GGYGPGAGQQGPGSGQQGPGGQGPYGSGQQGPGQQGPGGAGQQGPGGQGPYGPGAAA AGGYGPGAGQQGPGGAGQQGPGSQGPGGQGPYGPGAGQQGPGSQGPGSGQQGPGGQG PYGPSAAAAAAAAGGYGPGAGQRSQGPGGQGPYGPGAGQQGPGSQGPGSGQQGPGG QGPYGPSAAAAAAAGPGAGRQGPGSQGPGSGQQGPGGQGPYGPSAAAAAAA |
| 36 | GQGGQGQGGLGQGGYGQGAGSSAAAAAAAAAAAAAAGRQGGYGQGSGGNAAAAAAAA AAAAASGQGSQGGQGGGQGQGGYGQGAGSSAAAAAAAAAAAAASGRGQGGYGQGAGGNA AAAAAAAAAAAAGQGGQGGYGGLGQGGYGQGAGSSAAAAAAAAAAAAGGQGGQGQGG YGQGSGGSAAAAAAAAAAAAAAAGRQGGYGQGSGGNAAAAAAAAAAAAAA |
| 37 | GRGPGGYGPGQQGPGGPGAAAAAAAGPGGYGPGGYGPGQQGPGGPGAAAAAAAGRGPGG YGPGQQGPGQQGPGGSGAAAAAAAGRGPGGYGPGQQGPGGPGAAAAAAAGPGGYGPGQQG PGAAAAAAAAGRGPGGYGPGQQGPGGPGAAAAAAAGRGPGGYGPGQQGPGQQGPGGSG AAAAAAAGRGPGGYGPGQQGPGGPGAAAAAAAGPGGYGPGQQGPGAAAAAAAA |
| 38 | GRGPGGYGPGQQGPGGSGAAAAAAAGRGPGGYGPGQQGPGGPGAAAAAAAGPGGYGPGQQ GTGAAAAAAAAGSGAGGYGPGQQGPGGPGAAAAAAAGPGGYGPGQQGPGAAAAAAAAGSGP GGYGPGQQGPGGSSAAAAAAAGPGRYGPGQQGPGAAAAASAGRGPGGYGPGQQGPGGPG AAAAAAAAGPGGYGPGQQGPGAAAAAAAAGSGPGGYGPGQQGPGGPGAAAAAAAA |
| 39 | GAAATAGAGASVAGGYGGGAGAAAGAGAGGYGGGYGAVAGSGAGAAAAASSGAGGAAG YGRGYGAGSGAGAGAGTVAAYGGAGGVATSSSSATASGSRIVTSGGYGYGTSAAAGAG VAAGSYAGAVNRLSSAEAASRVSSNIAAIASGGASALPSVISNIYSGVVASGVSSNEA LIQALLELLSALVHVLSSASIGNVSSVGVDSTLNVVQDSVGQYVG |
| 40 | GGQGGFSGQGQGGFGPGAGSSAAAAAAAAAAAARQGGQGQGGFGQGAGGNAAAAAAAAA AAAAAQGGQGGFSGRGQGGFGPGAGSSAAAAAAGQGGQGQGGFGQGAGGNAAAAAAAAA AAAAAAGQGGQGRGGFGQGAGGNAAAAAAAAAAAAAAQGGQGGFGGRGQGGFGP GAGSSAAAAAAGQGGQGRGGFGQGAGGNAAAASAAAAASAAAAGQ |
| 41 | GGYGPGAGQQGPGGAGQQGPGSQGPGGAGQQGPGGQGPYGPGAAAAAAAVGGYGPGAG QQGPGSQGPGSGQQGPGGQGPYGPSAAAAAAAAGGYGPGAGQQGPGSQGPGSGGQQG PGGLGPYGPSAAAAAAAAGGYGPGAGQQGPGSQGPGSGGQQRPGGLGPYGPSAAAAAA AAGGYGPGAGQQGPGSQGPGSGGQQRPGGLGPYGPSAAAAAAAA |
| 42 | GAGAGGGYGGGYSAGGGAGAGSGAAAGAGAGRGGAGGYSAGAGTGAGAAAGAGTAGGY SGGYGAGASSSAGSSFISSSSMSSSQATGYSSSSGYGGGAASAAAGAGAAAGGYGGGY GAGAGAGAAAASGATGRVANSLGAMASGGINALPGVFSNIFSQVSAASGGASGGAVLV QALTEVIALLLHILSSASIGNVSSQGLEGSMAIAQQAIGAYAG |
| 43 | GAGAGGAGGYAQGYGAGAGAGAGAGTGAGGAGGYGQGYGAGSGAGAGGAGGYGAGAGA GAGAGDASGYGQGYGDGAGAGAGAAAAAGAAAGARGAGGYGGGAGAGAGAGAAGGY GQGYGAGAGEGAGAGAGAGAVAGAGAAAAAGAGAGAGAAEGYGAGAGAGGAGGYGQSY GDGAAAAAGSGAGAGGSGGYGAGAGAGSGAGAAGGYGGGAGA |
| 44 | GPGGYGPGQQGPGGYGPGQQGPGRYGPGQQGPSGPGSAAAAAAGSGQQGPGGYGPRQQ GPGGYGQGQQGPSGPGSAAAASAAASAESGQQGPGGYGPGQQGPGGYGPGQQGPGGYG PGQQGPSGPGSAAAAAAAASGPGQQGPGGYGPGQQGPGGYGPGQQGPSGPGSAAAAAA AASGPGQQGPGGYGPGQQGPGGYGPGQQGLSGPGSAAAAAAA |
| 45 | GRGPGGYGQGQQGPGGPGAAAAAAAGPGGYGPGQQGPGAAAAAAAAGSGPGGYGPGQQGP GRSGAAAAAAAAAGRGPGGYGPGQQGPGGPGAAAAAAAGPGGYGPGQQGPGAAAAASAGR GPGGYGPGQQGPGGSGAAAAAAAGRGPGGYGPGQQGPGGPGAAAAAAAAGRGPGGYGPGQ QGPGQQGPGGSGAAAAAAAGRGPGGYGPGQQGPGGPGAAAAAA |
| 46 | GVGAGGEGGYDQGYGAGAGAGSGGGAGGAGGYGGGAGAGSGGGAGGAGGYGGGAGAGA GAGAGGAGGYGGGAGAGTGARAGAGGVGGYGQSYGAGASAAAAGAGVGAGGAGAGGAGG YGQGYGAGAGIGAGDAGGYGGGAGAGASAGAGGYGGGAGAGAGGVGGYGKGYGAGSGA GAAAAAGAGAGSAGGYGRGDGAGAGGASGYGQGYGAGAAA |
| 47 | GYGAGAGRGYGAGAGAGAGAVAASGAGAGAGAGYGAGAGAGAGAGYGAGAGRGYGAGAGA GAGSGAASGAGAGAGYGAGAGAGAGYGAGAGSGYGTGAGAGAGAAAAGGAGAGAGYGA GAGRGYGAGAGAGAASGAGAGAGAGAASGAGAGSGYGAGAAAAGGAGAGAGGGYGAGA GRGYGAGAGAGAGAGSGSGSAAGYGQGYGSGSGAGAAA |

TABLE 1-continued

Exemplary sequences that can be used as repeat units

| Seq. ID No. | AA |
|---|---|
| 48 | GQGTDSSASSVSTSTSVSSSATGPDTGYPVGYYGAGQAEAAASAAAAAAASAAEEAATI AGLGYGRQGQGTDSSASSVSISTSVSSSATGPDMGYPVGNYGAGQAEAAASAAAAAAA SAAEAATIASLGYGRQGQGTDSSASSVSTSTSVSSSATGPGSRYPVRDYGADQAEAAA SAAAASAEEIASLGYGRQ |
| 49 | GQGTDSVASSASSSASASSSATGPDTGYPVGYYGAGQAEAAASAAAAAAASAAEEAATI AGLGYGRQGQGTDSSASSVSISTSVSSSATGPGSRYPVRDYGADQAEAAASATAAAAA AASAAEEIASLGYGRQGQGTDSVASSASSSASASSSATGPDTGYPVGYYGAGQAEAAA SAAAAAAASAAEAATIAGLGYGRQ |
| 50 | GQGGQGGYGGLGQGGYGQGAGSSAAAAAAAAAAAAGGQGGQGGQGRYGQGAGSSAAAA AAAAAAAAAGRGQGGYGQGSGGNAAAAAAAAAAAASGQGSQGGQGGQGGGYGQGAG SSAAAAAAAAAAAAASGRGQGGYGQGAGGNAAAAAAAAAAAAAAGQGGQGGYGGLGQG GYGQGAGSSAAA |
| 51 | GGLGGQGGLGGLGSQGAGLGGYGQGGAGQGGAAAAAAAAGGLGGQGGRGGLGSQGAGQ GGYGQGGAGQGGAAAAAAAAGGLGGQGGLGALGSQGAGQGGAGQGGYGQGGAAAAAAG GLGGQGGLGGLGSQGAGQGGYGQGGAGQGGAAAAAAAAGGLGGQGGLGGLGSQGAGPG GYGQGGAGQGGAAAAAAA |
| 52 | GGQGRGGFGQGAGGNAAAAAAAAAAAAAAAQQVGQFGFGGRGQGGFGPFAGSSAAAAAA ASAAAAGQGGQGGFGQGAGGNAAAAAAAAAAAARQGGQGQGGFSQGAGGNAAAAAAAA AAAAAAAAQQGGQGGFGGRGQGGFGPGAGSSAAAAAAATAAAGQGGQGRGGFGQGAGS NAAAAAAAAAAAAGQ |
| 53 | GGQGGQGGYGGLGSQGAGQGGYGAGQGAAAAAAAAGGAGGAGRGGLGAGGAGQGYGAG LGGQGGAGQAAAAAAAGGAGGARQGGLGAGGAGQGYGAGLGGQGGAGQGGAAAAAAAA GGQGGQGGYGGLGSQGAGQGGYGAGQGGAAAAAAAAGGQGGQGGYGGLGSQGAGQGGY GGRQGGAGAAAAAAAA |
| 54 | GGAGQRGYGGLGNQGAGRGGLGGQGAGAAAAAAAAGGAGQGGYGGLGNQGAGRGGQGAA AAAGGAGQGGYGGLGSQGAGRGGQGAGAAAAAAAVGAGQEGIRGQGAGQGGYGGLGSQG SGRGGLGGQGAGAAAAAAGGAGQGGLGGQGAGQGAGAAAAAAAGGVRQGGYGGLGSQGA GRGGQGAGAAAAAA |
| 55 | GGAGQGGLGGQGAGQGAGASAAAAGGAGQGGYGGLGSQGAGRGGEGAGAAAAAAAGGAG QGGYGGLGGQGAGQGGYGGLGSQGAGRGGLGGQGAGAAAAGGAGQGGLGGQGAGQGAG AAAAAAGGAGQGGYGGLGSQGAGRGGLGGQGAGAVAAAAAGGAGQGGYGGLGSQGAGR GGQGAGAAAAAA |
| 56 | GAGAGAGAGSGAGAAGGYGGGAGAGAGVGAGGAGGYDQGYGAGAGAGSGAGAGGAGGYGG GAGAGADAGGAGGYGGGAGAGARAGAGGVGGYGQSYGAGAGAGAGVGAGGAGAG GADGYGQGYGAGAGTGAGDAGGYGGGAGAGASAGAGGYGGGAGAGGVGVYGKGYGSGS GAGAAAAA |
| 57 | GGAGGYGVGQGYGAGAGAGAAAGAGAGGAGGYGAGQGYGAGAGVGAAAAAGAGAGVGG AGGYGRGAGAGAGAGAAAGAGAGAAAGAGAGGAGGYGAGQGYGAGAGVGAAAAAGA GAGVGGAGGYGRGAGAGAGAGGAGGYGRGAGAGAGAGAGGAGGYGAGQGYGAGA GAGAAAAA |
| 58 | GEAFSASSASSAVVFESAGPGEEAGSSGDGASAAASAAAAAGAGSGRRGPGGARSRGG AGAGAGAGSGVGGYGSGSGAGAGAGAGAGAGGEGGFGEGQGYGAGAGAGFGSGAGAGA GAGSGAGAGEGVGSGAGAGAGAGFGVGAGAGAGAGAGFGSGAGAGSGAGAGYGAGRAG GRGRGGRG |
| 59 | GEAFSASSASSAVVFESAGPGEEAGSSGGGASAAASAAAAAGAGSGRRGPGGARSRGG AGAGAGAGSGVGGYGSGSGAGAGAGAGAGAGGEGGFGEGQGYGAGAGAGFGSGAGAGA GAGSGAGAGEGVGSGAGAGAGAGFGVGAGAGAGAGAGFGSGAGAGSGAGAGYGAGRAG GRGRGGRG |
| 60 | GNGLGQALLANGVLNSGNYLQLANSLAYSFGSSLSQYSSSAAGASAAGAASGAAGAGA GAASSGGSSGSASSSTTTTTTTSTSSAAAAAAAAAAAAAAASTSASASASASASASAF SQTFVQTVLQSAAFGSYFGGNLSLQSAQAAASAAAQAAAQQIGLGSYGYALANAVASA FASAGANA |
| 61 | GNGLGQALLANGVLNSGNYLQLANSLAYSFGSSLSQYSSSAAGASAAGAASGAAGAGA GAASSGGSSGSASSSTTTTTTTSTSSAAAAAAAAAAAAAAASTSASASASASASASAF SQTFVQTVLQSAAFGSYFGGNLSLQSAQAAASAAAQAAAQQIGLGSYGYALANAVASA FASAGANA |
| 62 | GNGLGQALLANGVLNSGNYLQLANSLAYSFGSSLSQYSSSAAGASAAGAASGAAGAGA GAASSGGSSGSASSSTTTTTTTSTSSAAAAAAAAAAAAAAASTSASASASASASASAF SQTFVQTVLQSAAFGSYFGGNLSLQSAQAAASAAAQAAAQQIGLGSYGYALANAVASA FASAGANA |

TABLE 1-continued

Exemplary sequences that can be used as repeat units

| Seq. ID No. | AA |
|---|---|
| 63 | GASGAGQGQGYGQQGQGGSSAAAAAAAAAAAAAAAAQGQGQGYGQQGQGSAAAAAAAAA<br>AGASGAGQGQGYGQQGQGSAAAAAAAAAAGASGAGQGQGYGQQGQGGSAAAAAAAAAA<br>AAAAAAQGQGYGQQGQGSAAAAAAAAAAGASGAGQGQGYGQQGQGGSAAAAAAAAAA<br>AAAAAA |
| 64 | GRGQGGYGQGSGGNAAAAAAAGQGGFGGQEGNGQGAGSAAAAAAAAAAAAAGGSGQGRY<br>GGRGQGGYGQGAGAAASAAAAAAAAAAGQGGFGGQEGNGQGAGSAAAAAAAAAAAAGG<br>SGQGGYGGRGQGGYGQGAGAAAAAAAAAAAAAAAGQGGQGGFGSQGGNGQGAGSAAAAA<br>AAAAA |
| 65 | GQNTPWSSTELADAFINAFMNEAGRTGAFTADQLDDMSTIGDTIKTAMDKMARSNKSS<br>KGKLQALNMAFASSMAEIAAVEQGGLSVDAKTNAIADSLNSAFYQTTGAANPQFVNEI<br>RSLINMFAQSSANEVSYGGGYGGQSAGAAASAAAAGGGGQGGYGNLGGQGAGAAAAAA<br>ASAA |
| 66 | GQNTPWSSTELADAFINAFLNEAGRTGAFTADQLDDMSTIGDTLKTAMDKMARSNKSS<br>QSKLQALNMAFASSMAEIAAVEQGGLSVAEKTNAIADSLNSAFYQTTGAVNVQFVNEI<br>RSLISMFAQASANEVSYGGGYGGQGGQSAGAAAAAASAGAGQGGYGGLGGQGAGSAA<br>AAAA |
| 67 | GGQGGQGGYGGLGSQGAGQGGYGQGGAAAAAASAGGQGGQGGYGGLGSQGAGQGGYGG<br>GAFSGQQGGAASVATASAAASRLSSPGAASRVSSAVTSLVSSGGPTNSAALSNTISNV<br>VSQISSSNPGLSGCDVLVQALLEIVSALVHILGSANIGQVNSSGVGRSASIVGQSINQ<br>AFS |
| 68 | GGAGQGGYGGLGGQGAGAAAAAAGGAGQGGYGGQGAGQGAAAAAASGAGQGGYEGPGA<br>GQGAGAAAAAAGGAGQGGYGGLGGQGAGQGAGAAAAAAGGAGQGGYGGLGGQGAGQGA<br>GAAAAAAGGAGQGGYGGQGAGQGAAAAAAGGAGQGGYGGLGSGQGGYGRQGAGAAAAA<br>AAA |
| 69 | GASSAAAAAAATATSGGAPGGYGGYGPGIGGAFVPASTTGTGSGSGSGAGAAGSGGLG<br>GLGSSGGSGGLGGGNGGSGASAAASAAAASSSPGSGGYGPGQGVGSGSGSGAAGGSGT<br>GSGAGGPGSGGYGGPQFFASAYGGQGLLGTSGYGNGQGGASGTGSGGVGGSGSGAGSN<br>S |
| 70 | GQPIWTNPNAAMTMTNNLVQCASRSGVLTADQMDDMGMMADSVNSQMQKMGPNPPQHR<br>LRAMNTAMAAEVAEVVATSPPQSYSAVLNTIGACLRESMMQATGSVDNAFTNEVMQLV<br>KMLSADSANEVSTASASGASYATSISSAVSSSQATGYSTAAGYGNAAGAGAGAAAAVS |
| 71 | GQKIWTNPDAAMAMTNNLVQCAGRSGALTADQMDDLGMVSDSVNSQVRKMGANAPPHK<br>IKAMSTAVAAGVAEVVASSPPQSYSAVLNTIGGCLRESMMQVTGSVDNTFTTEMMQMV<br>NMFAADNANEVSASASGSGASYATGTSSAVSISQATGYSTAGGYGTAAGAGAGAAAAA |
| 72 | GSGYGAGAGAGAGSGYGAGAGAGSGYGAGAGAGAGSGYVAGAGAGAGSGYGAGAGA<br>GAGSSYSAGAGAGAGSGYGAGSSASAGSAVSTQTVSSSATISSQSAAAATGAAYGTRA<br>STGSGASAGAAASGAGAGYGGQAGYGQGGAAAYRAGAGSQAAYGQGASGSSGAAAAA |
| 73 | GGQGRGGFGGLSSQGAGGAGQGGSAAAAAAAAGGDGGSGLGDYGAGRGYGAGLGGA<br>GGAGVASAAASAAASRLSSPSAASRVSSAVTSLISGGGPTNPAALSNTFSNVVYQISV<br>SSPGLSGCDVLIQALLELVSALVHILGSAIIGQVNSSAAGESASLVGQSVYQAFS |
| 74 | GVGQAATPWENSQLAEDFINSFLRFIAQSGAFSPNQLDDMSSIGDTLKTAIEKMAQSR<br>KSSKSKLQALNMAFASSMAEIAVAEQGGLSLEAKTNAIANALASAFLETTGFVNQQFV<br>SEIKSLIYMIAQASSNEISGSAAAAGGGSGGGGGSGQGGYGQGASASASAAAA |
| 75 | GGGDGYGQGGYGNQRGVGSYGQGAGAGAAATSAAGGAGSGRGGYGEQGGLGGYGQGAG<br>AGAASTAAGGGDGYGQGGYGNQGGRGSYGQGSGAGAGAAVAAAAGGAVSGQGGYDGEG<br>GQGGYGQGSGAGAAVAAASGGTGAGQGGYGSQGSQAGYGQGAGFRAAAATAAA |
| 76 | GAGAGYGGQVGYGQGAGASAGAAAAGAGAGYGGQAGYGQGAGGSAGAAAAGAGAGRQA<br>GYGQGAGASARAAAAGAGTGYGQGAGASAGAAAAGAGAGSQVGYGQGAGSSGAAAAA<br>GAGAGYGGQVGYEQGAGASAGAEAAASSAGAGYGGQAGYGQGAGASAGAAAA |
| 77 | GGAGQGGYGGLGGQGAGQGGLGGQRAGAAAAAAGGAGQGGYGGLGSQGAGRGGYGGVG<br>SGASAASAAASRLSSPEASSRVSSAVSNLVSSGPTNSAALSSTISNVVSQISASNPGL<br>SGCDVLVQALLEVVSALIQILGSSSIGQVNYGTAGQAAQIVGQSVYQALG |
| 78 | GGYGPGSGQQGPGGAGQQGPGGQGPYGPGSSSAAAVGGYGPSSGLQGPAGQGPYGPGA<br>AASAAAAAGASRLSSPQASSRVSSAVSSLVSSGPTNSAALTNTISSVVSQISASNPGL<br>SGCDVLIQALLEIVSALVHILGYSSIGQINYDAAAQYASLVGQSVAQALA |
| 79 | GGAGAGQGSYGGQGGYGQGGAGAATATAAAAGGAGSGQGGYGGQGGLGGYGQGAGAGA<br>AAAAAAAAGGAGAGQGGYGGQGGQGGYGQGAGAGAAAAAAGGAGAGQGGYGGQGGYGQ<br>GGGAGAAAAAAAASGGSGSGQGGYGGQGGLGGYGQGAGAGAGAAASAAAA |

TABLE 1-continued

Exemplary sequences that can be used as repeat units

| Seq. ID No. | AA |
|---|---|
| 80 | GQGGQGGYGRQSQGAGSAAAAAAAAAAAAAAAGSGQGGYGGQQGGYGQSSASASAAAS AASTVANSVSRLSSPSAVSRVSSAVSSLVSNGQVNMAALPNIISNISSSVSASAPGAS GCEVIVQALLEVITALVQIVSSSSVGYINPSAVNQITNVVANAMAQVMG |
| 81 | GGAGQGGYGGLGGQGSAAAAGTGQGGYGSLGGQGAGAAGAAAAAVGGAGQGGYGGVG SAAASAAASRLSSPEASSRVSSAVSNLVSSGPTNSAALSNTISNVVSQISSSNPGLSG CDVLVQALLEVVSALIHILGSSSIGQVNYGSAGQATQIVGQSVYQALG |
| 82 | GAGAGGAGGYGAGQGYGAGAGAGAAAGAGAGGARGYGARQGYGSGAGAGAGARAGGAG GYGRGAGAGAAAASGAGAGGYGAGQGYGAGAGAVASAAAGAGSGAGGAGGYGRGAGAV AGAGAGGAGGYGAGAGAAAGVGAGGSGGYGGRQGGYSAGAGAGAAAA |
| 83 | GQGGQGGYGGLGQGGYGQGAGSSAAAAAAAAAAAGRGQGGYGQGSGGNAAAAAAAAAA AASGQGGQGGQGGQGQGGYGQGAGSSAAAAAAAAAAAAAAAAGRGQGGYGQGAGGNAA AAAAAAAASGQGGQGGQGGQGQGGYGQGAGSSAAAAAAAAAAAAAAA |
| 84 | GGYGPGSGQQGPGQQGPGQQGPGQQGPYGAGASAAAAAAGGYGPGSGQQGPGVRVAAP VASAAASRLSSSAASSRVSSAVSSLVSSGPTTPAALSNTISSAVSQISASNPGLSGCD VLVQALLEVVSALVHILGSSSVGQINYGASAQYAQMVGQSVTQALV |
| 85 | GAGAGGAGYGRGAGAGAGAAAGAGAGAAAGAGAGAGGYGGQGGYGAGAGAGAAAAAGA GAGGAAGYSRGGRAGAAGAGAGAAAGAGAGAGGYGGQGGYGAGAGAGAAAAAGAGSGG AGGYGRGAGAGAAAGAGAAAGAGAGAGGYGGQGGYGAGAGAAAAA |
| 86 | GAGAGRGGYGRGAGAGGYGGQGGYGAGAGAGAAAAAGAGAGGYGDKEIACWSRCRYTV ASTTSRLSSAEASSRISSAASTLVSGGYLNTAALPSVISDLFAQVGASSPGVSDSEVL IQVLLEIVSSLIHILSSSSVGQVDFSSVGSSAAAVGQSMQVVMG |
| 87 | GAGAGAGGAGGYGRGAGAGAGAGAAAAGQGYGSGAGAGAGASAGGAGSYGRGAGAGA AAASGAGAGGYGAGQGYGAGAGAVASAAAGAGSGAGGAGGYGRGAVAGSGAGAGAGAG GAGGYGAGAGAGAAAGAVAGGSGGYGGRQGGYSAGAGAGAAAAA |
| 88 | GPGGYGPVQQGPSGPGSAGPGGYGPAQQGPARYGPGSAAAAAAAAAAGSAGYGPGPQAS AAASRLASPDSGARVASAVSNLVSSGPTSSAALSSVISNAVSQIGASNPGLSGCDVLI QALLEIVSACVTILSSSSIGQVNYGAASQFAQVVGQSVLSAFS |
| 89 | GTGGVGGLFLSSGDFGRGGAGAGAGAAAASAAAASSAAAGARGGSGFGVGTGGFGRGG AGAGTGAAAASAAAASAAAAGAGGDGGLFLSSGDFGRGGAGAGAGAAAASAAAASSAA AGARGGSGFGVGTGGFGRGGAGDGASAAAASAAAASAAAA |
| 90 | GGYGPGAGQQGPGGAGQQGPGGQGPYGPSVAAAASAAGGYGPGAGQQGPVASAAVSRL SSPQASSRVSSAVSSLVSSGPTNPAALSNAMSSVVSQVSASNPGLSGCDVLVQALLEI VSALVHILGSSSIGQINYAASSQYAQMVGQSVAQALA |
| 91 | GGAGQGGYGGLGSQGAGRGGYGGQGAGAAAAATGGAGQGGYGGVGSGASAASAAASRL SSPQASSRVSSAVSNLVASGPTNSAALSSTISNAVSQIGASNPGLSGCDVLIQALLEV VSALIHILGSSSIGQVNYGSAGQATQIVGQSVYQALG |
| 92 | GGAGQGGYGGLGSQGAGRGGYGGQGAGAAVAAIGGVGQGGYGGVGSGASAASAAASRL SSPEASSRVSSAVSNLVSSGPTNSAALSSTISNVVSQIGASNPGLSGCDVLIQALLEV VSALVHILGSSSIGQVNYGSAGQATQIVGQSVYQALG |
| 93 | GASGGYGGGAGEGAGAAAAAGAGAGGAGGYGGGAGSGAGAVARAGAGGAGGYGSGIGG GYGSGAGAAAGAGAGGAGAYGGGYGTGAGAGARGADSAGAAAGYGGGVGTGTGSSAGY GRGAGAGAGAAAGSGAGAAGGYGGGYGAGAGAGA |
| 94 | GAGSGQGGYGGQGGLGGYGQGAGAGAAAGASGSGSGGAGQGGLGGYGQGAGAGAAAA AGASGAGQGGFGPYGSSYQSSTSYSVTSQGAAGGLGGYGQGSGAGAAAAGAAGQGGQG GYGQGAGAGAGAGAGQGGLGGYGQGAGSSAASAAAA |
| 95 | GGAGQGGYGGLGGQGVGRGGLGGQGAGAAAAGGAGQGGYGGVGSGASAASAAASRLSS PQASSRLSSAVSNLVATGPTNSAALSSTISNVVSQIGASNPGLSGCDVLIQALLEVVS ALIQILGSSSIGQVNYGSAGQATQIVGQSVYQALG |
| 96 | GAGSGGAGGYGRGAGAGAGAAAGAGAGAGSYGGQGGYGAGAGAGAAAAAGAGAGAGGY GRGAGAGAGAGAAAARAGAGGAGGYGGQGGYGAGAGAGAAAAAGAGAGGAGGYGRG AGAGAGAAAGAGAGAGGYGGQGSGYGAGAGAAAAA |
| 97 | GASGAGGQGGYGQQGQGGSSAAAAAAAAAAQGQGQGYGQQGQGYGQQGQGGSSAAAA AAAAAAAAQGQGQGYGQQGQGSAAAAAAAAAAAGASGAGGQGGYGQQGQGGSSAAAAAA AAAAAAAAAQGQGYGQQGQGSAAAAAAAAAAAAAAA |

In an embodiment a block copolymer polypeptide repeat unit that forms fibers with good mechanical properties is synthesized using SEQ ID NO. 1. This repeat unit contains 6 quasi-repeats, each of which includes motifs that vary in composition, as described herein. This repeat unit can be concatenated 1, 2, 3, 4, 5, 6, 7, 8, 9, 10, 11, 12, 13, 14, 15, 16, 17, 18, 19 or 20 times to form polypeptide molecules from 20 kDal to 535 kDal, or greater than 20 kDal, or greater than 10 kDal, or greater than 5 kDal, or from 5 to 400 kDal, or from 5 to 300 kDal, or from 5 to 200 kDal, or from 5 to 100 kDal, or from 5 to 50 kDal, or from 5 to 600 kDal, or from 5 to 800 kDal, or from 5 to 1000 kDal, or from 10 to 400 kDal, or from 10 to 300 kDal, or from 10 to 200 kDal, or from 10 to 100 kDal, or from 10 to 50 kDal, or from 10 to 600 kDal, or from 10 to 800 kDal, or from 10 to 1000 kDal, or from 20 to 400 kDal, or from 20 to 300 kDal, or from 20 to 200 kDal, or from 20 to 100 kDal, or from 20 to 50 kDal, or from 40 to 300 kDal, or from 40 to 500 kDal, or from 20 to 600 kDal, or from 20 to 800 kDal, or from 20 to 1000 kDal. This polypeptide repeat unit also contains poly-alanine regions related to nanocrystalline regions, and glycine-rich regions related to beta-turn containing less-crystalline regions. In other embodiments the repeat is selected from any of the sequences listed as SEQ ID Nos: 2-97.

In some embodiments, a long uniform RPFs comprises proteins containing one or more sequences from the list of SEQ ID Nos: 1-97.

In some embodiments, the quasi-repeat unit of the polypeptide can be described by the formula $\{GGY\text{-}[GPG\text{-}X_1]_{n1}\text{-}GPS\text{-}(A)_{n2}\}$ (SEQ ID NO: 108), where $X_1$ is independently selected from the group consisting of SGGQQ (SEQ ID NO: 100), GAGQQ (SEQ ID NO: 101), GQGPY (SEQ ID NO: 102), AGQQ (SEQ ID NO: 103) and SQ, n1 is a number from 4 to 8, and n2 is a number from 6 to 20. The repeat unit is composed of multiple quasi-repeat units. In additional embodiments, 3 "long" quasi repeats are followed by 3 "short" quasi-repeat units. As mentioned above, short quasi-repeat units are those in which n1=4 or 5. Long quasi-repeat units are defined as those in which n1=6, 7 or 8. In some embodiments, all of the short quasi-repeats have the same $X_1$ motifs in the same positions within each quasi-repeat unit of a repeat unit. In some embodiments, no more than 3 quasi-repeat units out of 6 share the same $X_1$ motifs.

In additional embodiments, a repeat unit is composed of quasi-repeat units that do not use the same $X_1$ more than two occurrences in a row within a repeat unit. In additional embodiments, a repeat unit is composed of quasi-repeat units where at least 1, 2, 3, 4, 5, 6, 7, 8, 9, 10, 11, 12, 13, 14, 15, 16, 17, 18, 19 or 20 of the quasi-repeats do not use the same $X_1$ more than 2 times in a single quasi-repeat unit of the repeat unit.

In some embodiments, the structure of fibers formed from the described polypeptides form beta-sheet structures, beta-turn structures, or alpha-helix structures. In some embodiments, the secondary, tertiary and quaternary protein structures of the formed fibers are described as having nanocrystalline beta-sheet regions, amorphous beta-turn regions, amorphous alpha helix regions, randomly spatially distributed nanocrystalline regions embedded in a non-crystalline matrix, or randomly oriented nanocrystalline regions embedded in a non-crystalline matrix.

In some embodiments, the polypeptides utilized to form fibers with mechanical properties as described herein include glycine-rich regions from 20 to 100 amino acids long concatenated with poly-alanine regions from 4 to 20 amino acids long. In some embodiments, polypeptides utilized to form fibers with good mechanical properties comprise 5-25% poly-alanine regions (from 4 to 20 poly-alanine residues). In some embodiments, polypeptides utilized to form fibers with good mechanical properties comprise 25-50% glycine. In some embodiments, polypeptides utilized to form fibers with good mechanical properties comprise 15-35% GGX, where X is any amino acid. In some embodiments, polypeptides utilized to form fibers with good mechanical properties comprise 15-60% GPG. In some embodiments, polypeptides utilized to form fibers with good mechanical properties comprise 10-40% alanine. In some embodiments, polypeptides utilized to form fibers with good mechanical properties comprise 0-20% proline. In some embodiments, polypeptides utilized to form fibers with good mechanical properties comprise 10-50% beta-turns. In some embodiments, polypeptides utilized to form fibers with good mechanical properties comprise 10-50% alpha-helix composition. In some embodiments all of these compositional ranges will apply to the same polypeptide. In some embodiments two or more of these compositional ranges will apply to the same polypeptide.

Recombinant Protein Fiber Spin Dope and Spinning Parameters

Long uniform RPFs can be produced using the following processing conditions and methods.

In some embodiments, a spin dope is synthesized containing proteins expressed from any of the polypeptides of the present disclosure. The spin dope is prepared using published techniques such as those found in WO2015042164 A2, especially at paragraphs 114-134. In some embodiments, a fiber spinning solution was prepared by dissolving a powder comprising the purified and dried block copolymer polypeptide (hereinafter "recombinant polypeptide powder") in a formic acid-based spinning solution, using standard mixing techniques. Depending on the embodiment, the recombinant polypeptide powder can comprise various impurities and the purity of the recombinant protein powder as expressed by the amount of recombinant protein (i.e., proteinaceous block copolymer that forms protein fibers) by mass can range from 30-100%, 40-90%, 50-90%, 60-90%, 30-70%, 30-40% and/or 30-65%. Spin dopes were mixed until the polypeptide was completely dissolved as determined by visual inspection. Spin dopes were degassed and undissolved particulates were removed by centrifugation.

In an embodiment the fraction of protein that is at least some percentage (e.g., 80%) of the intended length is determined through quantitative analysis of the results of a size-separation process. In an embodiment, the size-separation process can include size-exclusion chromatography. In an embodiment, the size-separation process can include gel electrophoresis. The quantitative analysis can include determining the fraction of total protein falling within a designated size range by integrating the area of a chromatogram or densitometric scan peak. For example, if a sample is run through a size-separation process, and the relative areas under the peaks corresponding to full-length, 60% full-length and 20% full length are 3:2:1, then the fraction that is full length corresponds to 3 parts out of a total of 6 parts by mass =50% mass ratio.

In some embodiments, the proteins of the spin dope, expressed from any of the polypeptides of the present disclosure, are substantially monodisperse. In some embodiments, the proteins of the spin dope, expressed from any of the polypeptides of the present disclosure, have from 5% to 99%, or from 5% to 50%, or from 50% to 99%, or from 20% to 80%, or from 40% to 60%, or from 5% to 30%, or from 70% to 99%, or from 5% to 20%, or from 5% to 10%, or from 80% to 99%, or from 90% to 99% of the protein in the spin dope having molecular weight from 5% to 99%, or from 5% to 50%, or from 50% to 99%, or from 20% to 80%, or from 40% to 60%, or from 5% to 30%, or from 70% to 99%, or from 5% to 20%, or from 5% to 10%, or from 80% to 99%, or from 90% to 99% of the molecular weight of the encoded proteins. The "encoded proteins" are defined as the polypeptide amino acid sequences that are encoded by the DNA utilized in protein expression. In other words, the "encoded proteins" are the polypeptides that would be produced if there were no imperfect processes (e.g., transcription errors, protein degradation, homologous recombination, truncation, protein fragmentation, protein agglomeration) at any stage during protein production. A higher monodispersity of proteins in the spin dopes, in other words a higher purity, can have the advantage of producing fibers with better mechanical properties, such as higher initial modulus, higher extensibility, higher ultimate tensile strength, and higher maximum tensile strength.

In other embodiments, fibers with low monodispersity, <10%, or <15%, or <20%, or <25%, or <30%, or <35%, or <40%, or <45%, or <50% of the protein in the spin dope having molecular weight >50%, or >55%, or >60%, or >65%, or >70%, or >75%, or >80%, or >85%, or >90%, or >95%, or >99% of the molecular weight of the proteins encoded by the DNA utilized in protein expression, were still able to create fibers with good mechanical properties. The mechanical properties described herein (e.g., high initial modulus and/or extensibility), from fibers formed from low purity spin dopes was achieved through the use of the long polypeptide repeat units, suitable polypeptide compositions and spin dope and fiber spinning parameters described elsewhere in the present disclosure.

In other embodiments, the proteins are produced via secretion from a microorganism such as *Pichia pastoris, Escherichia coli, Bacillus subtilis,* or mammalian cells. Optionally, the secretion rate is at least 20 mg/g DCW/hr (DCW=dry cell weight). Optionally, the proteins are then recovered, separated, and spun into fibers using spin dopes containing solvents. Some examples of the classes of solvents that can be used in spin dopes are aqueous, inorganic or organic, including but not limited to ethanol, methanol, isopropanol, t-butyl alcohol, ethyl acetate, and ethylene glycol. Various methods for synthesizing recombinant proteinaceous block copolymers have been published such as those found in WO2015042164 A2, especially at paragraphs 114-134.

In some embodiments, the fibers are extruded through a spinneret to form long uniform RPFs, for example greater than 20 m long. Continuous fiber manufacturing includes the following processes: pumping, filtration, fiber forming, and optionally, fiber treatment. The spin dope is pumped through a filter and subsequently through the spinneret, which contains small holes. Resistance in the fluid paths through the filter and the spinneret produces a pressure drop across each of these elements. The pumping pressure and type of pump required is dictated by the system elements' intrinsic fluid dynamic properties, the pathways used to interconnect them, and the viscosity of the spin dope liquid. Filtration is used to screen out particles that would lead to defects in the fiber, or lead to an obstruction of one of the spinneret holes. In some embodiments, screen filtration or deep bed type filtration systems is used. RPFs are formed using wet spinning, and the spin dope coagulates in a coagulation bath upon leaving the spinneret holes. Due to the friction between the coagulated fiber and the coagulant, continuous fiber manufacture employs lower spinning speeds than those used for other spinning processes (such as melt spinning or dry spinning). In some embodiments post-spinning fiber treatments, such as cold drawing or hot drawing are used. Drawing imparts a higher degree of polymer orientation in the fiber, which leads to improved mechanical properties.

In some embodiments, a solution of polypeptide is spun into fibers using elements of processes known in the art. These processes include, for example, wet spinning, dry jet wet spinning, and dry spinning. In preferred wet-spinning embodiments, the filament is extruded through an orifice into a liquid coagulation bath. In one embodiment, the filament can be extruded through an air gap prior to contacting the coagulation bath. In a dry-jet wet spinning process, the spinning solution is attenuated and stretched in an inert, non-coagulating fluid, e.g., air, before entering the coagulating bath. Suitable coagulating fluids are the same as those used in a wet-spinning process.

In other embodiments, the coagulation bath conditions for wet spinning are chosen to promote fiber formation with certain mechanical properties. Optionally, the coagulation bath is maintained at temperatures of 0-90° C., more preferably 20-60° C. Optionally, the coagulation bath comprises about 60%, 70%, 80%, 90%, or even 100% alcohol, preferably isopropanol, ethanol, or methanol. Optionally, the coagulation bath is 95:5, 90:10, 85:15, 80:20, 75:25, 70:30, 65:35, 60:40, 55:45 or 50:50 by volume methanol:water. Optionally, the coagulation bath contains additives to enhance the fiber mechanical properties, such as additives comprising ammonium sulfate, sodium chloride, sodium sulfate, or other protein precipitating salts at temperature from 20 to 60° C.

In some embodiments, the extruded filament or fiber is passed through more than one bath. For embodiments in which more than one bath is used, the different baths have either different or same chemical compositions. In some embodiments, the extruded filament or fiber is passed through more than one coagulation bath. For embodiments in which more than one coagulation bath is used, the different coagulation baths have either different or same chemical compositions. The residence time can be tuned to improve mechanical properties, such as from 2 seconds to 100 minutes in the coagulant bath. The reeling/drawing rate can be tuned to improve fiber mechanical properties, such as a rate from 0.1 to 100 meters/minute.

Optionally, the filament or fiber is also passed through one or more rinse baths to remove residual solvent and/or coagulant. Rinse baths of decreasing salt or alcohol concentration up to, preferably, an ultimate water bath, preferably follow salt or alcohol baths.

Following extrusion, the filament or fiber can be drawn. Drawing can improve the consistency, axial orientation and toughness of the filament. Drawing can be enhanced by the composition of a coagulation bath. Drawing may also be performed in a drawing bath containing a plasticizer such as water, glycerol or a salt solution. Drawing can also be performed in a drawing bath containing a crosslinker such as gluteraldehyde or formaldehyde. Drawing can be performed at temperature from 25-100° C. to alter fiber properties, preferably at 60° C. As is common in a continuous process, drawing can be performed simultaneously during the coagulation, wash, plasticizing, and/or crosslinking procedures described previously. Drawing ratio depends on the filament being processed. In some embodiments, the drawing rate is about 4×, or 5×, or 6×, or 7×, or 8×, or 9×, or 10×, or 11×, or 12×, or 13×, or 14×, or 15× the rate of reeling from the coagulation bath.

In certain embodiments of the invention, the filament is wound onto a spool after extrusion or after drawing. Winding rates are generally 1 to 500 m/min, preferably 10 to 50 m/min.

The draw ratio can also be tuned to improve fiber mechanical properties. In different embodiments the draw ratio was 1.5× to 6×. In one embodiment, lower draw ratios improved the fiber extensibility. In one embodiment, higher draw ratios improved the fiber maximum tensile strength. Drawing can also be done in different environments, such as in solution, in humid air, or at elevated temperatures.

The fibers of the present disclosure processed with residence times in coagulation baths at the longer end of the disclosed range produce corrugated cross sections. That is, each fiber has a plurality of corrugations (or alternatively "grooves") disposed at an outer surface of a fiber. Each of these corrugations is parallel to a longitudinal axis of the corresponding fiber on which the corrugations are disposed. The fibers of the present disclosure processed with higher ethanol content in the coagulation bath produce hollow core fibers. That is, the fiber includes an inner surface and an outer surface. The inner surface defines a hollow core parallel to the longitudinal axis of the fiber.

In some embodiments a coagulation bath or the first coagulation bath is prepared using combinations of one or more of water, acids, solvents and salts, including but not limited to the following classes of chemicals of Brønsted-Lowry acids, Lewis acids, binary hydride acids, organic acids, metal cation acids, organic solvents, inorganic solvents, alkali metal salts, and alkaline earth metal salts. Some examples of acids used in the preparation of a coagulation bath or the first coagulation bath are dilute hydrochloric acid, dilute sulfuric acid, formic acid and acetic acid. Some examples of solvents that are used in the preparation of the first coagulation bath are ethanol, methanol, isopropanol, t-butyl alcohol, ethyl acetate, and ethylene glycol. Examples of salts used in the preparation of a coagulation bath or the first coagulation bath include LiCl, KCl, BeCl$_2$, MgCl$_2$, CaCl$_2$, NaCl, ammonium sulfate, sodium sulfate, and other salts of nitrates, sulfates or phosphates.

In some embodiments, the chemical composition and extrusion parameters of a coagulation bath or the first coagulation bath are chosen so that the fiber remains translucent in a coagulation bath or the first coagulation bath. In some embodiments the chemical composition and extrusion parameters of a coagulation bath or the first coagulation bath are chosen to slow down the rate of coagulation of the fiber in a coagulation bath or the first coagulation bath, which improves the ability to draw the resulting fiber in subsequent drawing steps. In various embodiments, these subsequent drawing steps are done in different environments, including wet, dry, and humid air environments. Examples of wet environments include one or more additional baths or coagulation baths. In some embodiments, the fiber travels through one or more baths after the first coagulation bath. The one or more additional baths, or coagulation baths, are prepared, in embodiments, using combinations of one or more of water, acids, solvents and salts, including but not limited to the following classes of chemicals of Brønsted-Lowry acids, Lewis acids, binary hydride acids, organic acids, metal cation acids, organic solvents, inorganic solvents, alkali metal salts, and alkaline earth metal salts. Some examples of acids that are used in the preparation of the second baths or coagulant baths are dilute hydrochloric acid, dilute sulfuric acid, formic acid and acetic acid. Some examples of solvents that are used in the preparation of the second coagulant baths are ethanol, methanol, isopropanol, t-butyl alcohol, ethyl acetate, and ethylene glycol. Some examples of salts used in the preparation of a second bath or coagulation bath include LiCl, KCl, MgCl$_2$, CaCl$_2$, NaCl, ammonium sulfate, sodium sulfate, and other salts of nitrates, sulfates, or phosphates. In some embodiments, there are two coagulation baths, where the first coagulation bath has a different chemical composition than the second coagulation bath, and the second coagulation bath has a higher concentration of solvents than the first coagulation bath. In some embodiments, there are more than two coagulation baths, and the first coagulation bath has a different chemical composition than the second coagulation bath, and the second coagulation bath has a lower concentration of solvents than the first coagulation bath. In some embodiments, there are two baths, the first being a coagulation bath and the second being a wash bath. In some embodiments, the first coagulation bath has a different chemical composition than the second wash bath, and the second wash bath has a higher concentration of solvents than the first bath. In some embodiments, there are more than two baths, and the first bath has a different chemical composition than the second bath, and the second bath has a lower concentration of solvents than the first bath.

In some embodiments a spin dope is further prepared using combinations of one or more of water, acids, solvents and salts, including but not limited to the following classes of chemicals of Brønsted-Lowry acids, Lewis acids, binary hydride acids, organic acids, metal cation acids, organic solvents, inorganic solvents, alkali metal salts, and alkaline earth metal salts. Some examples of acids that are used in the preparation of spin dopes are dilute hydrochloric acid, dilute sulfuric acid, formic acid and acetic acid. Some examples of solvents that are used in the preparation of spin dopes are ethanol, methanol, isopropanol, t-butyl alcohol, ethyl acetate, and ethylene glycol. Some examples of salts that are used in the preparation of spin dopes are LiCl, KCl, MgCl$_2$, CaCl$_2$, NaCl, ammonium sulfate, sodium sulfate, and other salts of nitrates, sulfates or phosphates.

In some embodiments, a spinneret is chosen to enhance the fiber mechanical properties. The dimensions of the spinneret can be from 0.001 cm to 5 cm long, and from 25 to 200 urn in diameter. In some embodiments, a spinneret includes multiple orifices to spin multiple fibers simultaneously. In some embodiments, the cross-section of a spinneret gradually tapers to the smallest diameter at the orifice, is straight-walled and then quickly tapers to the orifice, or includes multiple constrictions. An extrusion pressure of a spin dope from a spinneret can also be varied to affect the fiber mechanical properties in a range from 10 to 1000 psi. The interaction between fiber properties and extrusion pressure can be affected by spin dope viscosity, drawing/reeling rate, and coagulation bath chemistry.

The concentration of protein to solvent in the spin dope is also an important parameter. In some embodiments, the concentration of protein weight for weight is 20%, or 25%, or 30%, or 35%, or 40%, or 45% or 50%, or 55%, or from 20% to 55%, or from 20% to 40%, or from 30% to 40%, or from 30% to 55%, or from 30% to 50% in solution with solvents and other additives making up the remainder.

Long Uniform Recombinant Protein Fiber Spin Dope and Spinning Parameters

Methods to process long uniform RPFs are described. In some embodiments, the long uniform RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, and physical, mechanical and/or chemical properties that are uniform along the length of the fiber. In some embodiments, the physical, mechanical and/or chemical property has a CV along the length of the fiber less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%. When spinning long uniform RPFs, the following process parameters and conditions are useful guidelines. The spin dope should be mixed to minimize viscosity gradients/inhomogeneities. Spin dope viscosity changes should be minimized so as to not vary significantly during the duration of the spinning event. The spin dope should be devoid of bubbles and particulates that blind the filter over time, clog the spinneret orifice, or introduce defects into the fiber that become breaking points during subsequent processing steps (e.g., during the drawing steps). The extrusion pressure should be consistent for the duration of the spinning event (e.g., the extrusion pressure should be non-pulsatile). The coagulation bath formulation also should not change appreciably during the spinning event (e.g., due to preferential evaporation of one of the bath components, water absorption, or chemical reactions between bath components).

The spin dope can be mixed to minimize viscosity gradients/inhomogeneities using elevated temperatures as well as high shear mixing approaches (as opposed to gentle agitation). Elevated temperatures include those above 22° C. and below the flash point of the dope solvent. Some high shear mixing methods include impeller-based mixing, homogenization, sonic mixing, and planetary mixing.

Spin dope viscosity changes can be minimized so as to not vary significantly during the duration of the spinning event by using methods such as continual and/or in-line agitation, temperature control of the dope to reduce the molecular chain mobility (e.g., from 4° C. to 22° C., or at approximately 15° C., or at approximately 7° C.), and the addition of one or more chaotropic additive that disrupts the silk chain hydrogen bonding (e.g., urea, $MgCl_2$, LiCl, LiBr, and/or sodium dodecyl sulfate). In some embodiments, one or more chaotropic additive can be added to the spin dope in a concentration of less than 15 wt % (i.e., percentage by weight), less than 10 wt %, less than 5 wt %, less than 4 wt %, less than 3 wt %, less than 2 wt %, or less than 1 wt %, or from 0.1 wt % to 15 wt %, from 0.1 wt % to 10 wt %, from 0.1 wt % to 5 wt %, from 0.1 wt % to 2 wt %, or from 0.1 wt % to 1 wt %.

Various methods can be used to avoid bubbles and particulates that blind the filter over time, clog the spinneret orifice, or introduce defects into the fiber that become breaking points during subsequent processing steps (e.g., during the drawing steps). Bubbles can be removed using methods such as degassing the spin dope under vacuum, spin dope centrifugation, and spin dope sonication. Some methods to minimize the creation of bubbles in the first place include minimizing the introduction of bubbles by subsurface addition of powder, and removal of the overhead air gap over the spin dope during mixing. Particulates (non-silk particulates, undissolved silk powder) can be removed using methods such as filtering, and centrifugation at high relative centrifugal force (RCF). In some embodiments, the centrifugation is performed from 5000 to 20000 RCF, for a duration from 15 min to 30 min, at a temperature from 4° C. to 22° C. In some embodiments, the centrifugation is performed at 16000 RCF for a duration greater than 15 min at a temperature from 4° C. to 22° C., or at 7000 RCF for a duration greater than 15 min at a temperature from 4° C. to 22° C.

The flow of dope through the spinneret can be made continuous (i.e., non-pulsatile) for the duration of the spinning event by using a positive displacement pump, rather than a pump that is pulsatile (e.g., a peristaltic pump). Some example of positive displacement pumps are screw pumps, gear pumps, and piston pumps.

The coagulation bath formulation can be held appreciably constant during the spinning event (e.g., due to preferential evaporation of one of the bath components, water absorption, or chemical reactions between bath components) using methods such as monitoring the bath components with quantitative techniques such as chromatography or spectroscopic techniques, and compensating changes in coagulation bath components using inline adjustment of the coagulation bath formulation. In some embodiments, the tolerable variation of the concentrations of the components of the coagulation bath formulation are +/−10% absolute concentration, or +/−5% absolute concentration. In an example embodiment, for a coagulation bath with a target concentration of 20% formic acid and 80% ethanol, the tolerable range of formic acid concentration can be from 10% to 40% with the remainder of the formulation comprising ethanol, or be from 15% to 25% with the remainder of the formulation comprising ethanol. In some embodiments, the tolerable concentration of absorbed water can be less than 10%, or less than 5%, or less than 2%, or less than 1%.

Long Uniform Recombinant Protein Fibers

Embodiments of the present disclosure include RPFs with lengths greater than 20 m. In some embodiments, the RPFs are engineered to comprise various improved mechanical, physical, chemical, and biological properties, as compared to prior art fibers. The long fibers can have uniform mechanical properties, as described by low coefficient of variation (CV) of the mechanical properties along the length of the fibers. Some examples of physical properties of long uniform RPFs are linear density, cross-sectional shape and diameter. Some examples of mechanical properties of long uniform RPFs are maximum tenacity, initial modulus, extensibility, toughness and work of rupture. Some examples of chemical properties of long uniform RPFs are moisture absorption, moisture regain and moisture content. An example of biological properties of long uniform RPFs is antimicrobial action.

When discussing coefficient of variation, enough samples are taken from a fiber, yarn, or textile to sufficiently mitigate low sample bias towards an artificially low CV. In some embodiments, the samples are taken are regular intervals along the length of a fiber, or length of a yarn, or across the area of a textile, in a sufficient quantity to eliminate low sample bias towards an artificially low CV. In some embodiments, the total number of samples is 10, or 20, or 40, or 60, or 80, or 100, or more than 100.

In some embodiments, a RPF has improved mechanical properties such as high initial modulus, high extensibility, high tenacity, and high toughness, and one or more of these properties are uniform along the length of the fiber (e.g., with coefficient of variation less than 30%). In some embodiments the RPFs with improved mechanical properties, which are uniform along the length have improved physical properties such as low linear density (low dtex), small diameter, engineered cross-section shapes and low porosity. In some embodiments, the RPFs with improved mechanical properties, which are uniform along the length, have improved chemical properties such as hydrophilicity. In some embodiments, the RPFs with improved mechanical properties, which are uniform along the length have improved biological properties such as being antimicrobial.

In some embodiments, a long RPF (e.g., with length greater than 20 m) has improved mechanical properties, such as high initial modulus, high extensibility, high tenacity, and high toughness, which are uniform along the length of the fiber (e.g., with coefficient of variation less than 30%). In some embodiments the long RPF (e.g., with lengths greater than 20 m) has improved physical properties, such as high fineness (low dtex), engineered cross-section shapes and porosity, which are uniform along the length of the fiber (e.g., with coefficient of variation less than 30%). In some embodiments, the long RPFs (e.g., with lengths greater than 20 m) have improved chemical properties, such as absorbing moisture effectively (e.g., with a diameter change greater than 10% upon being submerged in water), which are uniform along the length of the fiber (e.g., with coefficient of variation less than 30%). In some embodiments, the long RPFs (e.g., with lengths greater than 20 m) have improved biological properties, such as being antimicrobial, which are uniform along the length of the fiber (e.g., with coefficient of variation less than 30%).

In some embodiments, a long RPF has a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m.

Engineering Long Uniform RPF Physical Properties

In some embodiments, the long uniform RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, and have a mean or median linear density less than 20 dtex, or less than 15 dtex, or less than 10 dtex, or less than 5 dtex, or less than 3 dtex, or less than 2 dtex, or less than 1.5 dtex, or greater than 1.5 dtex, or greater than 1.7 dtex, or greater than 2 dtex, or from 1 to 30 dtex, or from 1 to 20 dtex, or from 1 to 15 dtex, or from 1 to 10 dtex, or from 1 to 5 dtex, or from 1 to 3 dtex, or from 1.5 to 2 dtex, or from 1.5 to 2.5 dtex, or from 0.1 to 30 dtex, or from 0.1 to 20 dtex, or from 0.1 to 10 dtex, or from 0.1 to 5 dtex, or from 0.1 to 3 dtex, or from 0.1 to 2 dtex, and the linear density has a CV along the length of the fiber less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%. Yarns produced from long uniform RPFs are useful in a myriad of applications, such as construction into ropes, textiles and garments, upholstery or linens.

In some embodiments, the long uniform RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, and have a mean or median diameter less than 100 microns, or less than 75 microns, or less than 50 microns, or less than 25 microns, or less than 20 microns, or less than 15 microns, or less than 10 microns, or less than 5 microns, or less than 2 microns, or greater than 100 microns, or greater than 75 microns, or greater than 50 microns, or greater than 25 microns, or greater than 20 microns, or greater than 15 microns, or greater than 10 microns, or greater than 5 microns, or greater than 1 micron, or from 1 to 100 microns, or from 1 to 75 microns, or from 1 to 50 microns, or from 1 to 25 microns, or from 1 to 20 microns, or from 1 to 15 microns, or from 1 to 10 microns, or from 1 to 5 microns, or from 5 to 100 microns, or from 5 to 75 microns, or from 5 to 50 microns, or from 5 to 25 microns, or from 5 to 20 microns, or from 5 to 15 microns, or from 5 to 10 microns, and the diameter has a CV along the length of the fiber less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%.

Microfibers are a classification of fibers having a fineness of less than about 1 dtex (i.e., about 10 µm in diameter). H. K., Kaynak and O. Babaarslan, Woven Fabrics, Croatia: InTech, 2012. In some embodiments, the median or mean linear density of the long uniform RPFs with one or more of the long lengths, mechanical properties, linear density, and low coefficient of variation discussed herein is less than 1 dtex (i.e., about 15 microns in diameter). In some embodiments, the median or mean linear density of the RPFs comprising the filament yarn, or spun yarn, or blended yarn is less than about 0.5 dtex (about 10 microns in diameter). The small diameter of microfibers imparts a range of qualities and characteristics to microfiber yarns and fabrics that are desirable to consumers. Microfibers are inherently more flexible (bending is inversely proportional to fiber diameter) and thus have a soft feel, low stiffness, and high drapeability. Microfibers can also be formed into filament yarns having high fiber density (greater fibers per yarn cross-sectional area), giving microfiber yarns a higher strength compared to other yarns of similar dimensions. Microfibers also contribute to discrete stress relief within the yarn, resulting in anti-wrinkle fabrics. Furthermore, microfibers have high compaction efficiency within the yarn, which improves fabric waterproofness and windproofness while maintaining breathability compared to other waterproofing and windproofing techniques (such as polyvinyl coatings). The high density of fibers within microfiber fabrics results in microchannel structures between fibers, which promotes the capillary effect and imparts a wicking and quick drying characteristic. The high surface area to volume of microfiber yarns allows for brighter and sharper dyeing, and printed fabrics have clearer and sharper pattern retention as well. Currently, recombinant silk fibers do not have a fineness that is small enough to result in silks having microfiber type characteristics. U.S. Pat. App. Pub. No. 2014/0058066 generally discloses fiber diameters between 5-100 μm, but does not actually disclose any working examples of any fiber having a diameter as small as 5 μm.

In some embodiments, the long uniform RPFs have a longitudinal axis, an inner surface and an outer surface, the inner surface defining a hollow core parallel to the longitudinal axis of the fiber. In some embodiments, the long uniform RPFs have a longitudinal axis and an outer surface, the outer surface including a plurality of corrugations, each corrugation of the plurality parallel or substantially parallel to the longitudinal axis of the fiber. By substantially parallel, we mean an angular deviation between a line defining the longitudinal fiber axis and a line defining the axis of corrugation of less than 25° or less than 20° or less than 15° or less than 10° or less than 5°. In some embodiments, the long uniform RPFs have a longitudinal axis and cross-sectional shape transverse to the longitudinal axis that is substantially circular, or that is substantially triangular, or that is substantially bilobal, or that is substantially trilobal, or that is substantially ovular, or that is substantially c-shaped.

Surface area to volume ratios are relatively small when the fiber has a smooth surface and a circular cross-section. In some embodiments, the long uniform RPFs have a surface area to volume ratio greater than 1000 cm$^{-1}$, or from 1000 to $3\times10^5$ cm$^{-1}$, or greater than $1\times10^4$ cm$^{-1}$, or greater than $1\times10^5$ cm$^{-1}$. Surface area to volume ratios can be substantially larger when the fiber has a rough surface and/or a non-circular cross-section, for instance if the fiber is striated. In some embodiments, the long uniform RPFs have a surface area to volume ratio from 1000 to $3\times10^7$ cm$^{-1}$, or greater than $1\times10^6$ cm$^{-1}$, or greater than $1\times10^7$ cm$^{-1}$. Fibers with high surface area to volume ratios could be useful in biomedical applications, filters, and garments.

Engineering Long Uniform RPF Mechanical Properties

In some embodiments, RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, wherein the mean or median properties of the fibers comprise an initial modulus greater than 50 cN/tex, or greater than 115 cN/tex, or greater than 200 cN/tex, or greater than 400 cN/tex, or greater than 550 cN/tex, or greater than 600 cN/tex, or greater than 800 cN/tex, or greater than 1000 cN/tex, or greater than 2000 cN/tex, or greater than 3000 cN/tex, or greater than 4000 cN/tex, or greater than 5000 cN/tex, or from 200 to 900 cN/tex, or from 100 to 7000 cN/tex, or from 500 to 7000 cN/tex, or from 50 to 7000 cN/tex, or from 100 to 5000 cN/tex, or from 500 to 5000 cN/tex, or from 50 to 5000 cN/tex, or from 100 to 2000 cN/tex, or from 500 to 2000 cN/tex, or from 50 to 2000 cN/tex, or from 100 to 1000 cN/tex, or from 500 to 1000 cN/tex, or from 50 to 1000 cN/tex, or from 50 to 500 cN/tex, or from 100 to 1000 cN/tex, or from 500 to 1000 cN/tex, or from 100 to 700 cN/tex, and/or a maximum tensile strength greater than 0.5 cN/tex, or greater than 1 cN/tex, or greater than 2 cN/tex, or greater than 4 cN/tex, or greater than 6 cN/tex, or greater than 7.7 cN/tex, or greater than 8 cN/tex, or a greater than 10 cN/tex, or greater than 15 cN/tex, or greater than 20 cN/tex, or greater than 25 cN/tex, or greater than 30 cN/tex, or greater than 40 cN/tex, or greater than 50 cN/tex, or greater than 60 cN/tex, or greater than 70 cN/tex, or greater than 80 cN/tex, or greater than 90 cN/tex, or greater than 100 cN/tex, or from 0.5 cN/tex to 120 cN/tex, or from 1 cN/tex to 120 cN/tex, or from 6 cN/tex to 120 cN/tex, or from 6 cN/tex to 50 cN/tex, or from 6 cN/tex to 30 cN/tex, or from 6 cN/tex to 20 cN/tex, and/or an extensibility greater than 1%, or greater than 3%, or greater than 5%, or greater than 10%, or greater than 20%, or greater than 30%, or greater than 100%, or greater than 200%, or greater than 300%, or greater than 400%, or from 1% to 400%, or from 1 to 200%, or from 1 to 100%, or from 1 to 20%, or from 1 to 30%, or from 1 to 40%, or from 10 to 200%, or from 10 to 100%, or from 10 to 50%, or from 10 to 20%, or from 10% to 20%, or from 50% to 150%, or from 100% to 150%, or from 300% to 400%, and the CV of the initial modulus, maximum tensile strength and/or extensibility along the length of the fiber is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%. The standard test method for measuring tensile properties of single fibers is ASTM D3822-14. These fiber mechanical properties also enable use of the fibers in industrial fiber drawing and yarn forming methods. Yarns produced from long uniform RPFs are useful in a myriad of applications, such as construction into ropes, textiles and garments, upholstery or linens. Filament yarns, or spun yarns, or blended yarns comprising long uniform RPFs with high modulus, maximum tenacity, and/or extensibility can be used in many applications, including: carpeting and carpet backing, industrial textile products (such as tire cord and tire fabric, seat belts, industrial webbing and tape, tents, fishing line and nets, rope, and tape reinforcement), apparel fabrics (such as women's sheer hosiery, underwear, nightwear, anklets and socks, and a variety of apparel fabrics), and interior and household products (such as bed ticking, furniture upholstery, curtains, bedspreads, sheets, and draperies).

In some embodiments, the long uniform RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, wherein the mean or median properties of the fibers comprise a linear density less than 10 dtex, or less than 5 dtex, or less than 3 dtex, or less than 2 dtex, or less than 1.5 dtex, or greater than 1.5 dtex, or greater than 1.7 dtex, or greater than 2 dtex, or from 1 to 15 dtex, or from 1 to 10 dtex, or from 1 to 5 dtex, or from 1 to 3 dtex, or from 1.5 to 2 dtex, or from 1.5 to 2.5 dtex, and a maximum tensile strength greater than 0.5 cN/tex, or greater than 1 cN/tex, or greater than 2 cN/tex, or greater than 4 cN/tex, or greater than 6 cN/tex, or greater than 7.7 cN/tex, or greater than 8 cN/tex, or a greater than 10 cN/tex, or greater than 15 cN/tex, or greater than 20 cN/tex, or greater than 25 cN/tex, or greater than 30 cN/tex, or greater than 40 cN/tex, or greater than 50 cN/tex, or greater than 60 cN/tex, or greater than 70 cN/tex, or greater than 80 cN/tex, or greater than 90 cN/tex, or greater than 100 cN/tex, or from 0.5 cN/tex to 120 cN/tex, or from 1 cN/tex to 120 cN/tex, or from 6 cN/tex to 120 cN/tex, or from 6 cN/tex to 50 cN/tex, or from 6 cN/tex to 30 cN/tex, or from 6 cN/tex to 20 cN/tex, and the CV of the linear density and/or the maximum tensile strength along the length of the fiber is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%.

In some embodiments, RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, wherein the mean or median properties of the fibers comprise a work of rupture greater than 0.1 cN*cm, or greater than 0.2 cN*cm, or greater than 0.3 cN*cm, or greater than 0.4 cN*cm, or greater than 0.5 cN*cm, or greater than 0.6 cN*cm, or greater than 0.7 cN*cm, or greater than 0.8 cN*cm, or greater than 0.9 cN*cm, or greater than 1 cN*cm, or greater than 1.3 cN*cm, or greater than 2 cN*cm, or greater than 5 cN*cm, or greater than 10 cN*cm, or from 0.1 to 10 cN*cm, or from 0.1 to 5 cN*cm, or from 0.1 to 2 cN*cm, or from 0.2 to 5 cN*cm, or from 0.2 to 10 cN*cm, or from 0.2 to 2 cN*cm, or from 0.3 to 2 cN*cm, or from 0.4 to 10 cN*cm, or from 0.4 to 5 cN*cm, or from 0.4 to 2 cN*cm, or from 0.4 to 1 cN*cm, or from 0.5 to 2 cN*cm, or from 0.5 to 1.3 cN*cm, 0.6 to 2 cN*cm, or from 0.7 to 1.1 cN*cm, and the CV of the work or rupture along the length of the fiber is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%.

In some embodiments, RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, wherein the mean or median properties of the fibers comprise a toughness greater than 2 cN/tex, or from 0.5 to 70 cN/tex, or greater than 3 cN/tex, or greater than 4 cN/tex, or greater than 5 cN/tex, or greater than 7.5 cN/tex, or greater than 10 cN/tex, or greater than 20 cN/tex, or greater than 30 cN/tex, or greater than 40 cN/tex, or greater than 50 cN/tex, greater than 60 cN/tex, or greater than 70 cN/tex, or from 2 to 3 cN/tex, or from 3 to 4 cN/tex, or from 4 to 5 cN/tex, or from 5 to 7.5 cN/tex, or from 7.5 to 10 cN/tex, or from 10 to 20 cN/tex, or from 20 to 30 cN/tex, or from 30 to 40 cN/tex, or from 40 to 50 cN/tex, or from 50 to 60 cN/tex, or from 60 to 70 cN/tex, and the CV of the toughness along the length of the fiber is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%. Filament yarns, or spun yarns, or blended yarns comprising long uniform RPFs with high toughness can be used in many applications, including: carpeting and carpet backing, industrial textile products (such as tire cord and tire fabric, seat belts, industrial webbing and tape, tents, fishing line and nets, rope, and tape reinforcement), apparel fabrics (such as women's sheer hosiery, underwear, nightwear, anklets and socks, and a variety of apparel fabrics), interior and household products (such as bed ticking, furniture upholstery, curtains, bedspreads, sheets, and draperies).

Engineering Long Uniform RPF Moisture Properties

Another moisture-related characteristic of a fiber is the degree of swelling when submerged in water. In some embodiments, the long uniform RPF have high moisture absorption properties. In some embodiments, RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, wherein the mean or median properties of the fibers comprise diameter change upon being submerged in water at a temperature of 21° C.+/−1° C. of greater than 5%, or from 0.1% to 100%, or greater than 1%, or greater than 2%, or greater than 4%, or greater than 6%, or greater than 8%, or greater than 10%, or greater than 15%, or greater than 20%, or greater than 25%, or greater than 30%, or greater than 35%, or greater than 40%, or greater than 45%, or greater than 50%, or greater than 60%, or greater than 70%, or greater than 80%, or greater than 90%, or from 5% to 10%, or from 10% to 20%, or from 20% to 30%, or from 30% to 40%, or from 40% to 50%, or from 50% to 60%, or from 60% to 70%, or from 70% to 80%, or from 80% and 90%, or from 90% to 100%, or from 20% to 35%, or from 15% to 40%, or from 15% to 35%, and the CV of the diameter change upon being submerged in water at a temperature of 21° C.+/−1° C. along the length of the fiber is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%. Such long uniform RPFs can be made into filament yarns, spun yarns or blended yarns, and such filament yarns, spun yarns, or blended yarns are useful in textiles and garments such as skin knits or woven fabrics where transfer of moisture away from the skin is desired, such as active wear apparel. In some embodiments, these filament yarns, or spun yarns, or blended yarns can be constructed into plaited yarn or textile, or double knit textiles. In some embodiments, these textiles can be located in a position towards the outer surface of a textile and/or garment to allow the absorbed moisture to easily evaporate. Fiber diameter change can be directly measured using optical microscopy.

Two other moisture-related characteristics of fibers are moisture regain and moisture content, which measure the uptake of water vapor from the environment. In one type of measurement a sample is allowed to equilibrate in an environment with a known relative humidity (e.g., 60-70% relative humidity) and temperature (e.g., 20-25° C.), and then heated to drive out the water (e.g., at a temperature slightly above 100° C.). Using a tool, such as a thermogravimetric analysis (TGA) system, the initial conditioned mass (containing some water), the final dry mass, and the mass change can be measured over time. The moisture regain of the fiber is defined as the lost water mass divided by the dry mass. The moisture content of the RPF is defined as the lost water mass divided by the conditioned mass. In some embodiments, RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, wherein the mean or median properties of the fibers comprise a moisture regain or moisture content, when measured from equilibrium conditioned mass at 65% relative humidity environment at 22° C. and heated at 110° C. until approximately equilibrium dry mass is achieved, of greater than 1%, or greater than 2%, or greater than 3% or greater than 4%, or greater than 5%, or greater than 6%, or greater than 7%, or greater than 8%, or greater than 9%, or greater than 10%, or greater than 12%, or greater than 14%, or greater than 16%, or greater than 18%, or greater than 20%, or from 1% to 30%, or from 1% to 30%, or from 1% to 20%, or from 1% to 15%, or from 1% to 10%, or from 5% to 15%, or from 5% to 10%, and the CV of the moisture regain or moisture content along the length of the fiber is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%.

There are many different metrics by which to characterize the interaction between a fiber and water. One such method is measuring the hydrophilicity of the surface of the fiber, characterized by the contact angle with water. In some embodiments, the long uniform RPF when measured with a fiber tensiometer, have a median or mean tensiometer contact angle of less than 90 degrees, or less than 80 degrees, or less than 70 degrees, or less than 60 degrees, or between 60 and 90 degrees or 60 and 80 degrees, or from 60 and 70 degrees, or from 70 and 90 degrees, or from 70 and 80 degrees, or from 80 and 90 degrees when tested using a standard assay with a water-filled tensiometer, and the CV of the tensiometer contact angle along the length of the fiber is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%. Such long uniform RPFs can be made into yarns, and such yarns are useful in textiles which use fiber properties and yarn constructions used to pull moisture away from the skin in order to create more comfort for the wearer. In some embodiments, these filament yarns, or spun yarns, or blended yarns can be constructed into plaited yarn or textile, or double knit textiles. In some embodiments, these textiles can be located in a position towards the outer surface of a textile and/or garment to allow the absorbed moisture to easily evaporate.

In some embodiments, the long uniform RPFs have high moisture wicking properties. A standard method of measuring wicking rate is the AATCC test method 197-2011 for vertical wicking of textiles, and AATCC test method 198-2011 for horizontal wicking of textiles. In some embodiments, a plain weave 1/1 textile with warp density of 72 warps/cm and pick density of 40 picks/cm, comprising filament yarn, or spun yarn, or blended yarn, comprising long uniform RPFs, is tested using AATCC test method 197-2011, and has a median or mean horizontal wicking rate greater than 1 mm/s, or from 0.1 to 100 mm/s, or greater than 0.1 mm/s, or greater than 0.2 mm/s, or greater than 0.4 mm/s, or greater than 0.6 mm/s, or greater than 0.8 mm/s, or greater than 2 mm/s, or greater than 4 mm/s, or greater than 6 mm/s, or greater than 8 mm/s, or greater than 10 mm/s, or greater than 15 mm/s, or greater than 20 mm/s, or greater than 40 mm/s, or greater than 60 mm/s, or greater than 80 mm/s, or greater than 100 mm/s, or from 0.1 mm/s to 1 mm/s, or from 1 mm/s to 10 mm/s, or from 10 mm/s to 20 mm/s, or from 20 mm/s to 30 mm/s, or from 30 mm/s to 40 mm/s, or from 40 mm/s to 50 mm/s, or from 50 mm/s to 60 mm/s, or from 60 mm/s to 70 mm/s, or from 70 mm/s to 80 mm/s, or from 80 mm/s to 90 mm/s, or from 90 mm/s to 100 mm/s, and the CV of the horizontal wicking rate across the area of the textile is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%. Such filament yarns, or spun yarns, or blended yarns containing long uniform RPFs are useful in textiles and garments such as skin knits or woven fabrics where wicking of moisture away from the skin is desired, such as active wear apparel. In some embodiments, these filament yarns, or spun yarns, or blended yarns can be constructed into plaited yarn or textile, or double knit textiles. In some embodiments, these textiles are located in a position towards the outer surface of a textile and/or garment to allow the absorbed moisture to easily evaporate.

Combinations of Long Uniform RPF Properties

In different embodiments, fibers, yarns and textiles characteristics can be grouped together. For example, fibers can be engineered to have high moisture absorption and have high extensibility. In fact, all of the fibers, yarns and textiles properties discussed in this disclosure can be combined with each other. However, in some cases the quantification of the fibers, yarns or textiles property and the method by which the property is obtained, are both important, and may change which properties can be combined. For example, moisture absorption can be imparted to the fibers by increasing the ratio of poly-alanine to glycine-rich regions in the protein sequence, however, increasing the ratio of poly-alanine regions in the protein sequence tends to the make the fiber less extensible. Table 2 illustrates combinations of fibers, yarns and textiles properties that are not mutually exclusive (Y), and fibers properties that are mutually exclusive (N).

TABLE 2

Fibers, yarns and textiles properties, viable combinations

| | moisture absorption | wickability | antimicrobial | extensibility | tenacity | initial modulus | toughness | cross-section | linear density (or diameter) |
|---|---|---|---|---|---|---|---|---|---|
| moisture absorption | | Y | Y | Y | Y | Y | Y | Y | Y |
| wickability | | | Y | Y | Y | Y | Y | Y | Y |
| antimicrobial | | | | Y | Y | Y | Y | Y | Y |
| extensibility | | | | | Y | Y | Y | Y | Y |
| tenacity | | | | | | Y | Y | Y | Y |
| initial modulus | | | | | | | Y | Y | Y |
| toughness | | | | | | | | Y | Y |
| cross-section | | | | | | | | | Y |
| linear density (or diameter) | | | | | | | | | |

One example of a combination of physical, mechanical and moisture properties of long uniform RPFs is linear density, maximum tensile strength and diameter change upon being submerged in water. In some embodiments, the long uniform RPFs have a length greater than 20 m, or greater than 50 m, or greater than 100 m, or greater than 200 m, or greater than 300 m, or greater than 400 m, or greater than 500 m, or greater than 750 m, or greater than 1000 m, or greater than 1500 m, or greater than 2000 m, or greater than 5000 m, or greater than 10000 m, or from 20 to 2000 m, or from 50 to 2000 m, or from 100 to 2000 m, or from 200 to 2000 m, or from 500 to 2000 m, or from 20 to 5000 m, or from 50 to 5000 m, or from 100 to 5000 m, or from 200 to 5000 m, or from 500 to 5000 m, or from 20 to 10000 m, or from 50 to 10000 m, or from 100 to 10000 m, or from 200 to 10000 m, or from 500 to 10000 m, wherein the mean or median properties of the fibers comprise a linear density less than 10 dtex, or less than 5 dtex, or less than 3 dtex, or less than 2 dtex, or less than 1.5 dtex, or greater than 1.5 dtex, or greater than 1.7 dtex, or greater than 2 dtex, or from 1 to 15 dtex, or from 1 to 10 dtex, or from 1 to 5 dtex, or from 1 to 3 dtex, or from 1.5 to 2 dtex, or from 1.5 to 2.5 dtex, and a maximum tensile strength greater than 0.5 cN/tex, or greater than 1 cN/tex, or greater than 2 cN/tex, or greater than 4 cN/tex, or greater than 6 cN/tex, or greater than 7.7 cN/tex, or greater than 8 cN/tex, or a greater than 10 cN/tex, or greater than 15 cN/tex, or greater than 20 cN/tex, or greater than 25 cN/tex, or greater than 30 cN/tex, or greater than 40 cN/tex, or greater than 50 cN/tex, or greater than 60 cN/tex, or greater than 70 cN/tex, or greater than 80 cN/tex, or greater than 90 cN/tex, or greater than 100 cN/tex, or from 0.5 cN/tex to 120 cN/tex, or from 1 cN/tex to 120 cN/tex, or from 6 cN/tex to 120 cN/tex, or from 6 cN/tex to 50 cN/tex, or from 6 cN/tex to 30 cN/tex, or from 6 cN/tex to 20 cN/tex, and a diameter change upon being submerged in water at a temperature of 21° C.+/−1° C. of greater than 5%, or from 0.1% to 100%, or greater than 1%, or greater than 2%, or greater than 4%, or greater than 6%, or greater than 8%, or greater than 10%, or greater than 15%, or greater than 20%, or greater than 25%, or greater than 30%, or greater than 35%, or greater than 40%, or greater than 45%, or greater than 50%, or greater than 60%, or greater than 70%, or greater than 80%, or greater than 90%, or from 5% to 10%, or from 10% to 20%, or from 20% to 30%, or from 30% to 40%, or from 40% to 50%, or from 50% to 60%, or from 60% to 70%, or from 70% to 80%, or from 80% and 90%, or from 90% to 100%, or from 20% to 35%, or from 15% to 40%, or from 15% to 35%, and the CV of the linear density and/or the maximum tensile strength and/or diameter change upon being submerged in water at a temperature of 21° C.+/−1° C. along the length of the fiber is less than 50%, or less than 40%, or less than 30%, or less than 20%, or less than 15%, or less than 10%, or less than 5%, or from 0.1% to 50%, or from 0.1% to 40%, or from 0.1% to 30%, or from 0.1% to 20%, or from 0.1% to 15%, or from 0.1% to 10%, or from 1% to 50%, or from 1% to 40%, or from 1% to 30%, or from 1% to 20%, or from 1% to 15%, or from 1% to 10%.

Methods of Forming Recombinant Protein Fiber Yarns and Textiles

Individual RPFs are made into yarns to be used in textiles. There are different methods of forming yarns from ling uniform RPFs and there are different methods of forming textiles from yarns comprising long uniform RPFs, which produce yarns and textiles with different structures and properties.

Depending on the type of yarn desired, several filament yarn forming methods can be used to make filament yarns containing long uniform RPFs. These methods may include simple twisting of flat filament fibers using a silk throwing apparatus or continuous spinning. Textured filament yarns comprising long uniform RPFs can be further subjected to processes that arrange the straight filaments into crimped, coiled or looped filaments to create bulk, texture or stretch. Some examples of methods used for processing textured filament yarns comprising long uniform RPFs are air jet texturing, false twist texturing, or stuffer box texturing. Filament yarns may also be texturized during the spinning using false twist texturizing, air jet texturizing or stuffer box apparatus. Heating, chemically bonding or plying may also be employed.

In some embodiments, the yarns comprising long uniform RPFs are manufactured using a ring spinning apparatus. In some embodiments, the yarns comprising long uniform RPFs are manufactured using an open end spinning apparatus. In some embodiments, the yarns comprising long uniform RPFs are manufactured using an air jet spinning apparatus. In certain embodiments, twist is applied resulting in a twist angle optimized for desired mechanical, structural or other properties of the yarn. In certain embodiments, the twist applied to the inner core of the yarn has a different twist angle compared with the outer skin of the yarn. Throughout this disclosure "spun" yarns can refer to ring spun yarns, open end spun yarns, air-jet spun yarns, vortex spun yarns, or any other method of producing a yarn where the yarn comprises staple fibers.

In some embodiments, the blended yarn comprising long uniform RPFs and/or non-RPFs is manufactured by spinning. The structure of a spun yarn is influenced by the spinning methods parameters. The properties of the spun yarn are influenced by the structure of the yarn, as well as the constituent fibers. In embodiments, the blended yarn structure and the long uniform RPFs properties and the type of non-RPFs blended with the RPFs are all chosen to impart various characteristics to the resulting yarns. In some embodiments, the blended yarns are manufactured using a ring spinning apparatus. In some embodiments, the blended yarns are manufactured using an open end spinning apparatus. In some embodiments, the blended yarns are manufactured using an air-jet spinning apparatus. In many embodiments, twist is applied of a certain twist angle to optimize the mechanical properties of the blended yarn. In many embodiments, the twist applied to the inner core of the yarn has a different twist angle compared with the outer skin of the blended yarn.

In some embodiments, a method of making a spun yarn is employed, wherein a plurality of RPFs is provided, the fibers are cut into staple, the fibers are conveyed the fibers to a spinning apparatus, and twist is provided to spin the fibers into a yarn. In some embodiments, the spinning apparatus is a ring spinning apparatus. In some embodiments, the spinning apparatus is an open end spinning apparatus. In some embodiments, the spinning apparatus is an air jet spinning apparatus. In some embodiments, the fibers are carded prior to spinning. In some embodiments, the fibers are combed prior to spinning.

In some embodiments, a method of making a blended spun yarn is employed, wherein a plurality of long uniform RPFs and non-RPFs is provided, the fibers are cut into staple, the fibers are loaded in to a spinning apparatus, and twist is provided to spin the fibers into a yarn. In some embodiments, the spinning apparatus is a ring spinning apparatus. In some embodiments, the spinning apparatus is an open end spinning apparatus. In some embodiments, the spinning apparatus is an air jet spinning apparatus. In some embodiments, the fibers are carded prior to spinning. In some embodiments, the fibers are combed prior to spinning.

In some embodiments, the yarns comprising long uniform RPFs are manufactured into textiles, for example by weaving or knitting. In some embodiments, yarns containing long uniform RPFs are manufactured into textiles by knitting using a circular knitting apparatus, a warp knitting apparatus, a flat knitting apparatus, a one piece knitting apparatus, or a 3-D knitting apparatus. In some embodiments, yarns containing long uniform RPFs are manufactured into textiles by weaving using a plain weave loom, a dobby loom or a jacquard loom. In some embodiments, long uniform RPFs are manufactured into textiles using a 3d printing method. In some embodiments, long uniform RPFs or yarns containing long uniform RPFs are manufactured into non-woven textiles using techniques such as wet laying, spin bonding, stitch bonding, spunlacing (i.e., hydroentaglement), or needlepunching. In embodiments, the textile construction, the yarn structure and the long uniform RPFs properties are chosen to impart various characteristics to the resulting yarns and textiles.

EXAMPLES

Example 1: Recombinant Protein Fiber Spinning

Copolymers in this example were secreted from *Pichia pastoris* commonly used for the expression of recombinant DNA using published techniques, i.e., those described in WO2015042164 A2, at paragraphs 114-134. The copolymer polypeptide utilized for fiber spinning in this Example was SEQ ID NO. 1, concatenated 3 times, with a 3× FLAG sequence: GDYKDDDDKDYKDDDDKDYKDDDDK (SEQ ID NO: 98) bound to the C-terminal end of the polypeptide. The secreted proteins were purified and dried using standard techniques. The dried polypeptide powder was dissolved in a formic acid-based spinning solvent to generate a homogenous spin dope.

The RPFs in this example were spun by extruding the spin dope through a 125 μm diameter orifice with 1:1 ratio of length to diameter into a room temperature alcohol-based coagulation bath comprising 20% formic acid with a residence time of approximately 15 seconds. Fibers were pulled out of the coagulation bath under tension, and then drawn to three times their length, and subsequently allowed to dry. The volumetric flow rate out of spinneret was approximately 45 uL/min. The duration of the spinning event (i.e., spin run) was approximately 10 minutes. The volume of spin dope consumed in the spinning event was approximately 0.45 mL. The length of fibers produced in a single spinning event was approximately 200 m.

Example 2: Long Uniform Recombinant Protein Fibers Mechanical Properties

Figure 2:
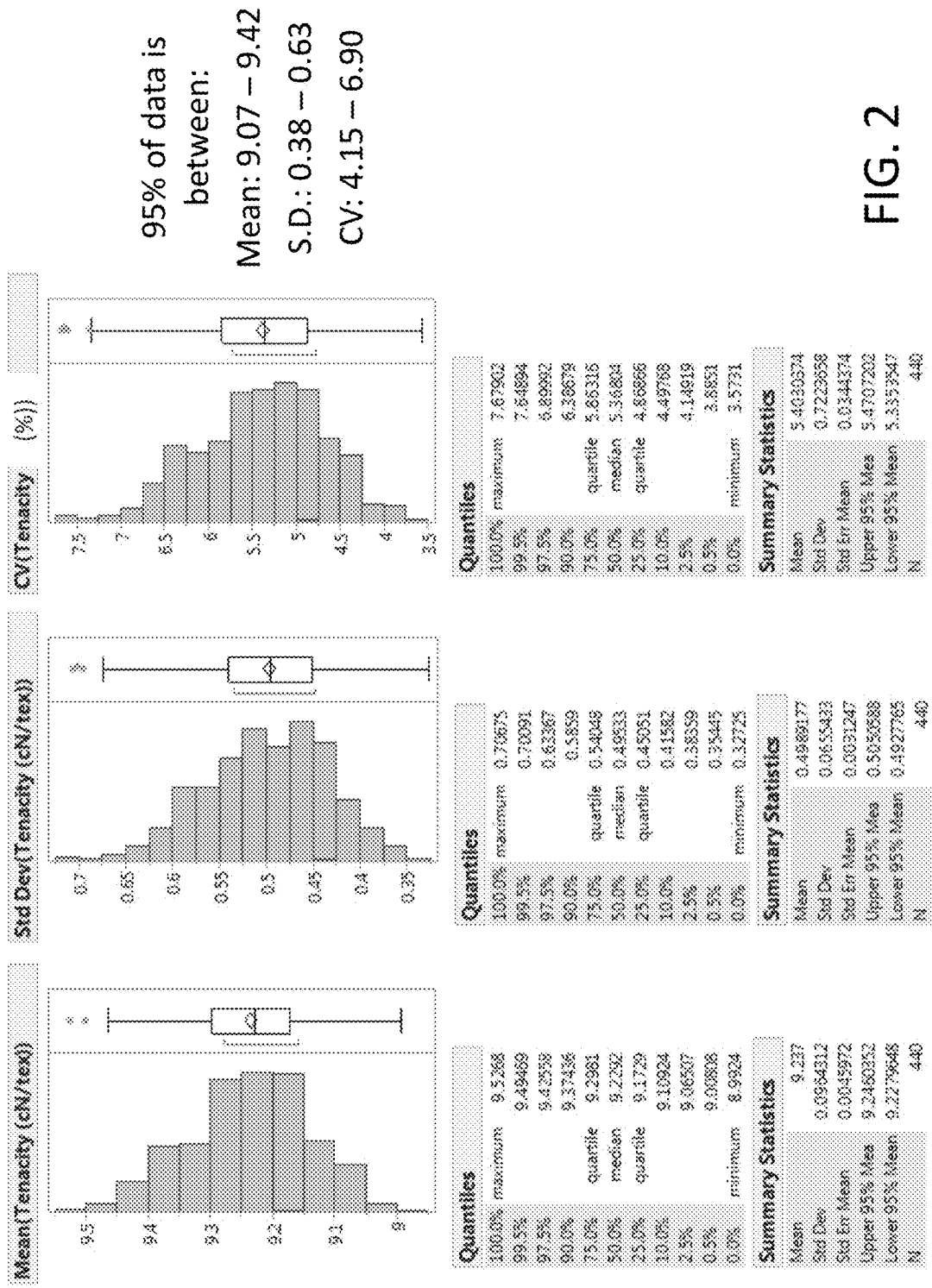
FIG. 2 shows maximum tensile strength measured from fibers of the present disclosure, in embodiments.
Figure 3:
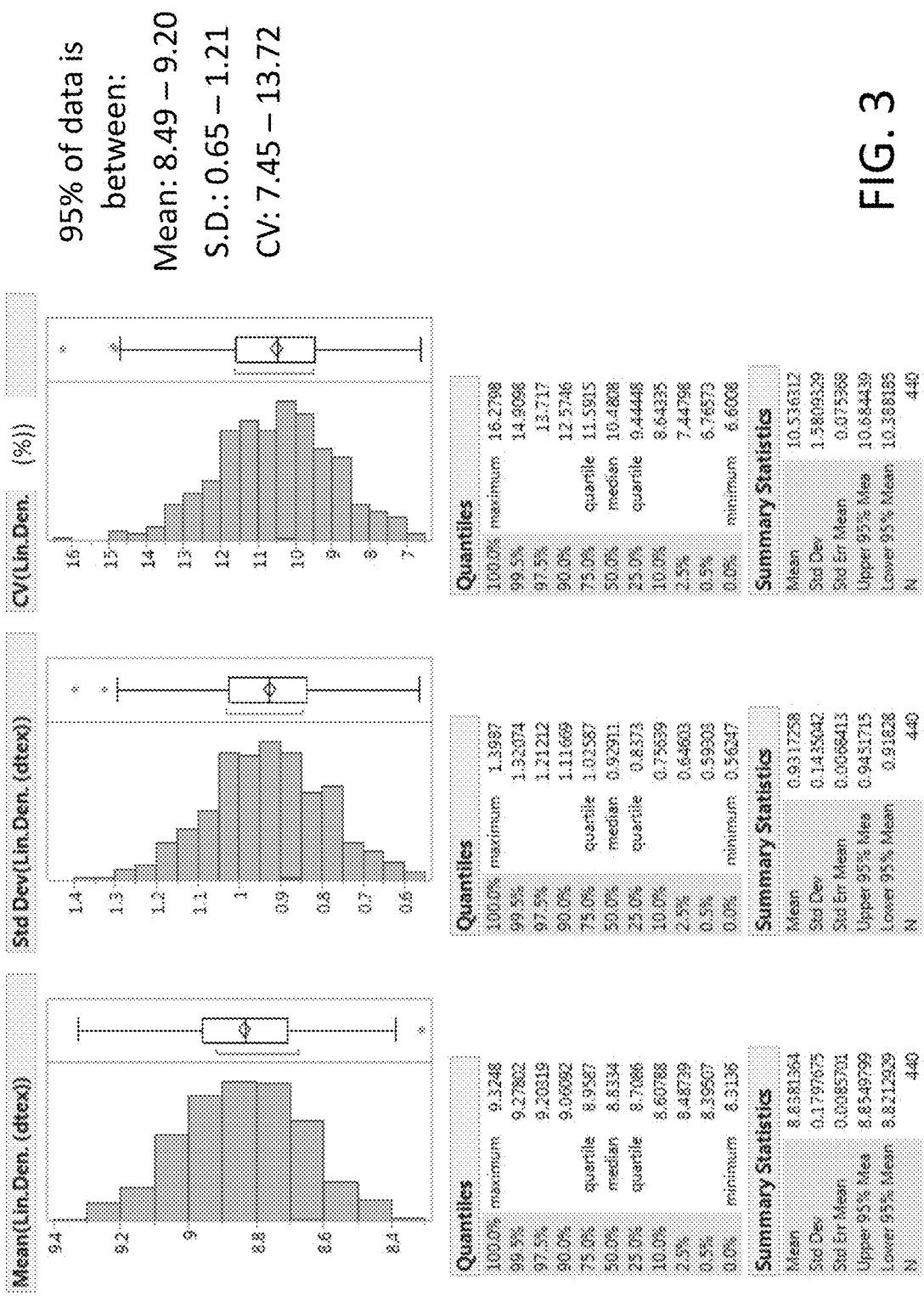
FIG. 3 shows linear density measured from fibers of the present disclosure, in embodiments.

FIGS. 2 and 3 show tenacity and linear density data from 1800 m of RPF. The fiber in this Example was produced by the methods described in Example 1. Two different batches of spin dopes were used, in 9 separate spin runs of 200 m each. 23-25 samples were collected at regular intervals along the length of the 200 m fiber from a given spin run and measured for tenacity and linear density.

To determine the mean, standard deviation and coefficient of variation (CV) for each parameter, a Monte Carlo method was used, where the data was randomly grouped into sets of 25 data points 440 different times. The resulting data was plotted in FIGS. 2 and 3. FIG. 2 shows the distribution of means, standard deviations and CVs of each group of 25 for maximum tenacity. FIG. 3 shows the distribution of means, standard deviations and CVs of each group of 25 for linear density.

Using this approach, the average mean for maximum tenacity was 9.24 cN/tex, the average standard deviation was 0.50 cN/tex, and the average CV was 5.40%. It can also be observed from the data that the mean maximum tenacity from all 440 randomized groups of 25 measurements was from 9 cN/tex to 9.5 cN/tex. Similarly, the standard deviation of the maximum tenacity for the 440 randomized groups of 25 measurements was from 0.3 cN/tex to 0.7 cN/tex, and the CV of the maximum tenacity for the 440 randomized groups of 25 measurements was from 3.5% to 7.7%.

Using the above approach, the average mean for linear density was 8.84 dtex, the average standard deviation was 0.93 dtex, and the average CV was 10.54%. It can also be observed from the data that the mean linear density from all 440 randomized groups of 25 measurements was from 8.3 dtex to 9.3 dtex. Similarly, the standard deviation of the linear density for the 440 randomized groups of 25 measurements was from 0.6 dtex to 1.4 dtex, and the CV of the linear density for the 440 randomized groups of 25 measurements was from 6.5% to 16%.

Stated another way, due to sampling statistics and depending on the groupings of the 25 data points within the 1800 m of fiber, the average measured parameters can vary. However, using proper statistics the values of the mean parameters can be determined to a high degree of confidence. For instance, for the long uniform RPF data in this Example, 95% of the time the CV for tenacity was from 4.15% and 6.90%, and 95% of the time the CV for the linear density was from 7.45% to 13.72%.

This Example illustrates that the process described in this disclosure to produce the long uniform fibers was robust and reproducible, since multiple spin dopes were used for the different spinning events, and the average CV for linear density (a physical property of the fibers) and the average CV for tenacity (a mechanical property of the fibers) were about 10.4% and 5.4%, respectively.

Example 3: Long Uniform Recombinant Protein Fibers Mechanical Properties

The spin dope in this Example was produced by the methods described in Example 1. The RPFs in this example were spun by extruding the spin dope through a 50-hole spinneret in which each orifice was 127 μm diameter with 1:1 ratio of length to diameter into a room temperature alcohol-based coagulation bath comprising 20% formic acid with a residence time of approximately 28 seconds. Fibers were pulled out of the coagulation bath under tension, and then drawn to four times their length in a pure alcohol wash bath. The fibers were subsequently passed through a 200° C. oven and collected onto a spool under tension. The volumetric flow rate out of spinneret was approximately 0.8 ml/min. The duration of the spinning event was approximately 30 minutes. The total volume of material consumed in the spinning event was approximately 23 mL.

Figure 4:
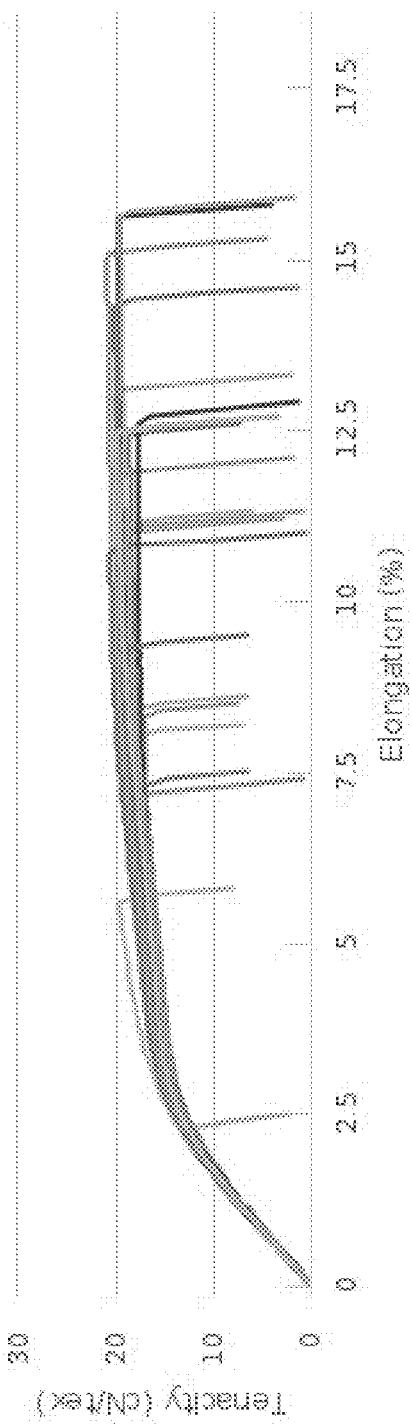
FIG. 4 shows stress-strain curves measured from fibers of the present disclosure, in embodiments.

FIG. 4 shows stress strain curves of 23 fibers with compositions described herein, and produced by the methods described above. The fibers in this Example have maximum tensile stress greater than 20 cN/tex, and the average of the maximum tensile stresses of the 23 fibers was about 18.6 cN/tex. This set of fibers was sampled from a 50-filament tow that was 800 m long, and therefore produced 40,000 m of fiber in a single spinning event. The maximum tensile stress ranges from about 17 to 21 cN/tex, and the standard deviation of the maximum tensile stress in this example was about 1.0 cN/tex. The average initial modulus of the 23 fibers was about 575 cN/tex, and the standard deviation in this example was about 6.7 cN/tex. The average maximum elongation of the 23 fibers was about 10.2%, and the standard deviation in this example was about 3.6%. The average linear density of the 23 fibers was about 3.1 dtex, and the standard deviation in this example was about 0.11 dtex.

For this specific spinning event, and the conditions and the batch of spin dope material used, the coefficient of variation of the maximum tensile strength for this set of fibers was about 5.4%, the coefficient of variation of the initial modulus for this set of fibers was about 1.2%, and the coefficient of variation of the linear density for this set of fibers was about 3.5%.

This Example illustrates that a long uniform RFP with tenacity above 20 cN/tex was produced using the methods described in this disclosure.

Example 4: Purity of Recombinant 18B Polypeptide Powder

Copolymers in this example were produced and dried into powder ("18B powder") as discussed above with respect to Example 1. Data characterizing the relative amounts of high, low and intermediate molecular weight impurities as compared with monomeric 18B and aggregate 18B (i.e., proteinaceous block copolymers) was collected using Size Exclusion Chromatography. 18B powder was dissolved in 5M Guanidine Thiocyanate and injected onto a Yarra SEC-3000 SEC-HPLC column to separate constituents on the basis of molecular weight. Refractive index was used as the detection modality. 18B aggregates, 18B monomer, low molecular weight (1-8 kDa) impurities, intermediate molecular weight impurities (8-50 kDa) and high molecular weight impurities (110-150 kDa) were quantified. Relevant composition was reported as mass % and area %. BSA was used as a general protein standard with the assumption that >90% of all proteins demonstrate dn/dc values (the response factor of refractive index) within ~7% of each other. Poly (ethylene oxide) was used as a retention time standard, and a BSA calibrator was used as a check standard to ensure consistent performance of the method.

Table 3 (below) lists the area % of the different components quantified using SEC and the mass % of 18B in its aggregate and monomeric forms. As shown, the overall purity by mass of the 18B powder was 59.86%

TABLE 3

| | Size Exclusion Chromatography | | |
|---|---|---|---|
| Source Ref | High MW Impurity [area %] | IMW Impurity [area %] | LMW Impurity [area %] |
| 148 | 1.98 | 31.73 | 6.10 |

| Source Ref | 18B Aggregate [area %] | 18B Aggregate [mass %] | 18B Monomer [area %] | 18B Monomer [mass %] | 18B Aggregate + Monomer [area %] | 18B Aggregate + Monomer [mass %] |
|---|---|---|---|---|---|---|
| 148 | 6.07 | 6.04 | 54.11 | 53.82 | 60.18 | 59.86 |

Example 5: Spin Dope Preparation and Rheology of the Spin Dopes

The 18B powder were dissolved in formic acid and mixed using a Thinky Planetary Centrifugal Mixer 400ARE-TWIN at 1600 RPM to generate spin dopes. Prior to dissolution, the 18B powder was baked to reduce the moisture content of the powder down to less than 4%.

A Malvern Kinexus Lab+ Rotational Rheometer was to measure the complex viscosity and the phase angle of the spin dopes. Parameters were set to a temperature of 22° C., a frequency of 100-0.1 Hz, and a strain of 1%. An interval of 3 points/decade was used to determine an average value for a given frequency.

The table below includes the concentration by weight of the 18B powder in the spin dope, the complex viscosity and the phase angle as measured at 10 Hz. Data was not collected for 125-FACU.

TABLE 4

18B Powder Concentration in Spin Dope, Complex Viscosity and Phase Angle

| Source ID | 18B Powder Concentration by weight [%] | Complex Viscosity [Pa s] | Phase Angle [o] |
|---|---|---|---|
| 144 | 36 | 42.67 | 65.26 |

Example 6: Drawing Conditions

The 18B protein powder referenced in Example 4 was wet-spun into fiber using traditional techniques. A spin dope was prepared using 67% formic acid (by weight) and 33% 18B powder (by weight). The spin dope was mixed using a FlackTek SpeedMixer DAC 600.2 VAC-LR vacuum mixer.

The spin dope was extruded directly into a coagulation bath comprised of 100% ethanol at room temperature through a spinneret that is 50 μm in diameter at a rate of 1.25 ml/minute to form a precursor fiber. Both the spinneret and the coagulation bath were maintained at room temperature. Precursor fiber is then collected on a set of uptake godets at a reel rate of 3.2 meters/minute. The precursor fiber was then drawn between the uptake godets and a heated godet spaced 81 inches apart. The reel rate of the heated godet was 19.8 meters/minute, providing a draw ratio of 6.19×. The drawn fiber was then drawn between the heated godet and a final godet that were spaced 139 inches apart. The uptake rate of the final godet was 22 meters/minute providing a draw ration of 1.12×.

Between the heated godet and the final godet, the drawn fiber was passed through a 40-inch tube furnace that was heated to 200° C. A lubricant comprising 200% proof ethanol at 99% by weight and Setol® was applied to the drawn, heat-treated fiber at a rate of 1.1 mL/minute. The fiber was then wound on a spool for further analysis.

Example 7: Long Uniform Recombinant Protein Fibers Mechanical Properties

Data characterizing tensile properties and linear density was collected from an approximately 700M spool (plus or minus 50M) of fiber produced in a single spin run according to the methods described in Examples 5 and 6. To produce the data, the fiber was divided into sixteen (16) segments of approximately 50 m each representing different regions of the spool. 11 of the 16 segments representing a random sample of the length of the spool were tested using a FAVIMAT fiber tensile test equipment model Favimat+ and Robot2 using 5 tows per segment and 4 filaments per tow to produce a total of 220 samples, from which 12 outliers were subtracted to produce 208 samples. Linear density was tested in accordance with ASTM D1577. Tensile properties were tested in accordance with ASTM D3822-14. Table 5 below lists the properties calculated the 208 samples taken from the 11 segments.

TABLE 5

Data collected from all Samples

| | Mean | Std Dev | Coefficient of Variance ("CV")% | Min | Max | N |
|---|---|---|---|---|---|---|
| Tenacity (cN/tex) | 12.75 | 1.69 | 13.28 | 7.96 | 18.14 | 208.00 |
| Linear. Den. (dtex) | 5.98 | 1.04 | 17.40 | 2.90 | 8.56 | 208.00 |
| Initial Modulus (cN/tex) | 488.88 | 22.99 | 4.70 | 400.97 | 571.33 | 208.00 |
| Elongation (%) | 24.88 | 10.12 | 40.70 | 2.78 | 46.69 | 208.00 |
| Elongation at Break (%) | 26.15 | 8.67 | 33.15 | 3.91 | 47.11 | 208.00 |
| Work of rupture (cN*cm) | 3.40 | 1.68 | 49.26 | 0.13 | 7.26 | 208.00 |
| Force at rupture (cN) | 7.62 | 1.73 | 22.71 | 3.09 | 12.56 | 208.00 |

TABLE 6

Data by segment

| | Tenacity (cN/tex) | | | Linear Den. (dtex) | | | Initial Modulus (cN/tex) | | | Elongation (%) | | |
|---|---|---|---|---|---|---|---|---|---|---|---|---|
| Segment | Mean | Std Dev | CV % | Mean | Std Dev | CV % | Mean | Std Dev | CV % | Mean | Std Dev | CV % |
| 1 | 12.66 | 1.71 | 13.51 | 5.92 | 0.94 | 15.79 | 492.24 | 21.47 | 4.36 | 25.27 | 10.03 | 39.68 |
| 2 | 12.38 | 2.01 | 16.27 | 6.00 | 1.40 | 23.36 | 483.22 | 23.08 | 4.78 | 27.23 | 11.33 | 41.59 |
| 4 | 13.02 | 1.48 | 11.40 | 5.34 | 1.26 | 23.49 | 494.08 | 22.81 | 4.62 | 23.99 | 5.68 | 23.67 |
| 6 | 12.52 | 1.39 | 11.11 | 5.87 | 0.84 | 14.28 | 483.86 | 24.33 | 5.03 | 26.42 | 8.15 | 30.84 |
| 8 | 12.48 | 1.20 | 9.59 | 6.45 | 1.06 | 16.48 | 487.68 | 14.89 | 3.05 | 23.45 | 11.62 | 49.55 |
| 9 | 12.93 | 1.51 | 11.69 | 6.22 | 0.88 | 14.12 | 498.16 | 15.20 | 3.05 | 20.73 | 13.79 | 66.52 |
| 11 | 13.17 | 1.43 | 10.84 | 5.84 | 0.82 | 13.98 | 501.40 | 16.81 | 3.35 | 21.90 | 8.48 | 38.72 |
| 12 | 14.11 | 1.99 | 14.07 | 6.11 | 1.04 | 17.00 | 507.46 | 29.76 | 5.86 | 24.74 | 7.29 | 29.45 |
| 14 | 12.70 | 1.84 | 14.47 | 5.98 | 1.16 | 19.40 | 477.68 | 24.57 | 5.14 | 28.33 | 8.07 | 28.49 |

TABLE 6-continued

Data by segment

| | Tenacity (cN/tex) | | | Linear Den. (dtex) | | | Initial Modulus (cN/tex) | | | Elongation (%) | | |
|---|---|---|---|---|---|---|---|---|---|---|---|---|
| Segment | Mean | Std Dev | CV % | Mean | Std Dev | CV % | Mean | Std Dev | CV % | Mean | Std Dev | CV % |
| 15 | 12.56 | 1.72 | 13.66 | 6.33 | 0.76 | 12.07 | 477.82 | 17.02 | 3.56 | 24.00 | 13.94 | 58.08 |
| 16 | 11.79 | 1.55 | 13.19 | 5.87 | 0.92 | 15.64 | 476.86 | 17.92 | 3.76 | 26.50 | 10.97 | 41.38 |

TABLE 7

Data by segment

| | Elongation at Break (%) | | | Work of rupture (cN*cm) | | | Force at rupture (cN) | | |
|---|---|---|---|---|---|---|---|---|---|
| Region | Mean | Std Dev | CV % | Mean | Std Dev | CV % | Mean | Std Dev | CV % |
| 1 | 25.62 | 9.88 | 38.59 | 3.28 | 1.36 | 41.43 | 7.46 | 1.46 | 19.55 |
| 2 | 27.93 | 10.58 | 37.90 | 3.65 | 1.99 | 54.57 | 7.49 | 2.21 | 29.46 |
| 4 | 24.30 | 5.66 | 23.28 | 2.92 | 0.99 | 33.81 | 6.91 | 1.64 | 23.76 |
| 6 | 26.72 | 8.08 | 30.25 | 3.43 | 1.37 | 39.88 | 7.36 | 1.53 | 20.74 |
| 8 | 25.51 | 8.92 | 34.98 | 3.57 | 2.04 | 57.02 | 8.08 | 1.72 | 21.31 |
| 9 | 26.65 | 8.29 | 31.13 | 3.08 | 2.35 | 76.32 | 8.06 | 1.62 | 20.07 |
| 11 | 22.68 | 7.57 | 33.39 | 3.05 | 1.29 | 42.28 | 7.68 | 1.38 | 17.94 |
| 12 | 25.00 | 7.28 | 29.13 | 3.87 | 1.67 | 43.11 | 8.66 | 2.13 | 24.61 |
| 14 | 28.63 | 8.09 | 28.26 | 3.84 | 1.63 | 42.35 | 7.52 | 1.63 | 21.68 |
| 15 | 25.88 | 12.15 | 46.93 | 3.40 | 2.10 | 61.74 | 7.96 | 1.61 | 20.19 |
| 16 | 28.53 | 7.67 | 26.90 | 3.32 | 1.57 | 47.18 | 6.94 | 1.64 | 23.65 |

Additional Considerations

The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the invention, which is set forth in the following claims.

What is claimed is:

1. A long uniform recombinant protein fiber, comprising: a continuous fiber length of at least 600 m, wherein the mean properties along the length of the fiber comprise:
   a tenacity greater than or equal to 12 cN/tex;
   a linear density less than or equal to 6 dtex;
   a coefficient of variation of tenacity less than 15%; and
   a coefficient of variation of linear density less than 20%,
   wherein the tenacity is measured using ASTM D3822-14, and the linear density is measured using ASTM D1577;
   wherein the recombinant protein fiber comprises a protein sequence comprising repeat units, wherein
   each repeat unit has at least 95% sequence identity to a sequence that comprises from 2 to 20 quasi-repeat units,
   each quasi-repeat unit comprising a polypeptide of {GGY-[GPG-$X_1$]$_{n1}$-GPS-(A)$_{n2}$} (SEQ ID NO: 111), wherein for each quasi-repeat unit: $X_1$ is independently selected from the group consisting of SGGQQ (SEQ ID NO: 100), GAGQQ (SEQ ID NO: 101), GQGPY (SEQ ID NO: 102), AGQQ (SEQ ID NO: 103), and SQ; n1 is from 4 to 8; and n2 is from 6 to 10.

2. The recombinant protein fiber of claim 1, wherein the length is at least 650 m.

3. The recombinant protein fiber of claim 1, wherein the tenacity has a coefficient of variation less than 10% along the length.

4. The recombinant protein fiber of claim 1, wherein the linear density has a coefficient of variation less than 15% along the length.

5. The recombinant protein fiber of claim 1, wherein the mean elongation at break is greater than 25% and the elongation at break has a coefficient of variation of less than 35% along the length.

6. The recombinant protein fiber of claim 1, wherein the mean initial modulus is greater than 480 cN/tex and the initial modulus has a coefficient of variation of less than 5% along the length.

7. The recombinant protein fiber of claim 1, wherein the mean elongation is greater than 24% and the elongation has a coefficient of variation of less than 45% along the length.

8. The recombinant protein fiber of claim 1, wherein the mean work of rupture is greater than 3 cN*cm and the work of rupture has a coefficient of variation of less than 50% along the length.

9. The recombinant protein fiber of claim 1, wherein the mean force at rupture is greater than 7 cN and the force at rupture has a coefficient of variation less than 25% along the length.

10. The recombinant protein fiber of claim 1, wherein the recombinant protein fiber is produced by wet spinning a dope comprising a recombinant protein powder dissolved in a spinning solution.

11. The recombinant protein fiber of claim 10, wherein the recombinant protein powder is less than 65% proteinaceous block copolymer by mass.

12. The recombinant protein fiber of claim 1, wherein n1 is from 4 to 5 for at least half of the quasi-repeat units.

13. The recombinant protein fiber of claim 1, wherein n2 is from 5 to 8 for at least half of the quasi-repeat units.

14. The recombinant protein fiber of claim 1, wherein the repeat unit comprises alanine-rich regions and glycine-rich regions, wherein:
   the alanine-rich regions form a plurality of nanocrystalline beta-sheets; and
   the glycine-rich regions form a plurality of beta-turn structures.

15. The recombinant protein fiber of claim 1, wherein the repeat unit comprises SEQ ID NO: 1.

16. The recombinant protein fiber of claim 1, wherein the linear density and the tenacity are measured using FAVIMAT fiber tensile test equipment model Favimat+ and Robot2.

17. A yarn comprising the recombinant protein fiber of claim 1, wherein the yarn is a filament yarn.

18. A textile comprising the yarn of claim 17, wherein the textile is a knitted textile.

19. The textile of claim 18, wherein the textile is selected from the group consisting of a circular-knitted textile, a flat-knitted textile, and a warp-knitted textiles.

20. A textile comprising the yarn of claim 17, wherein the textile is a woven textile.

21. The textile of claim 20, wherein the textile is selected from the group consisting of a plain weave textile, a dobby weave textile, and a jacquard weave textile.

22. A textile comprising the yarn of claim 17, wherein the textile is a non-woven textile.

23. The textile of claim 22, wherein the textile is selected from the group consisting of a needle punched textile, a spunlace textile, a wet-laid textile, a dry-laid textile, a melt-blown textile, and a 3-D printed non-woven textile.

24. A yarn comprising the recombinant protein fiber of claim 1, wherein the yarn is a spun yarn.

25. A yarn comprising the recombinant protein fiber of claim 1, wherein the yarn is a blended yarn.

* * * * *

SEQUENCE LISTING

```
<160> NUMBER OF SEQ ID NOS: 111

<210> SEQ ID NO 1
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
                20                  25                  30

Pro Gly Gly Ala Gly Gln Gln Gly Pro Gly Gly Gln Gly Pro Tyr Gly
            35                  40                  45

Pro Gly Ala Ala Ala Ala Ala Ala Ala Ala Gly Gly Tyr Gly Pro
        50                  55                  60

Gly Ala Gly Gln Gln Gly Pro Gly Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Gly Ser Gly Gly Gln Gln Gly Pro
            100                 105                 110

Gly Gly Gln Gly Pro Tyr Gly Pro Ser Ala Ala Ala Ala Ala Ala Ala
        115                 120                 125

Ala Ala Gly Gly Tyr Gly Pro Gly Ala Gly Gln Arg Ser Gln Gly Pro
130                 135                 140
```

Gly Gly Gln Gly Pro Tyr Gly Pro Gly Ala Gly Gln Gln Pro Gly
145                 150                 155                 160

Ser Gln Gly Pro Gly Ser Gly Gln Gln Gly Pro Gly Gln Gly
                165                 170                 175

Pro Tyr Gly Pro Ser Ala Ala Ala Ala Ala Ala Ala Gly Gly Tyr
            180                 185                 190

Gly Pro Gly Ala Gly Gln Gln Gly Pro Gly Ser Gln Gly Pro Gly Ser
        195                 200                 205

Gly Gly Gln Gln Gly Pro Gly Gly Gln Gly Pro Tyr Gly Pro Gly Ala
        210                 215                 220

Ala Ala Ala Ala Ala Val Gly Gly Tyr Gly Pro Gly Ala Gly Gln
225                 230                 235                 240

Gln Gly Pro Gly Ser Gln Gly Pro Gly Ser Gly Gly Gln Gln Gly Pro
            245                 250                 255

Gly Gly Gln Gly Pro Tyr Gly Pro Ser Ala Ala Ala Ala Ala Ala
            260                 265                 270

Ala Gly Gly Tyr Gly Pro Gly Ala Gly Gln Gln Gly Pro Gly Ser Gln
        275                 280                 285

Gly Pro Gly Ser Gly Gly Gln Gln Gly Pro Gly Gly Gln Gly Pro Tyr
        290                 295                 300

Gly Pro Ser Ala Ala Ala Ala Ala Ala Ala
305                 310                 315

<210> SEQ ID NO 2
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Gly Gln Gly Gly Arg Gly Gly Phe Gly Gly Leu Gly Ser Gln Gly
1               5                   10                  15

Ala Gly Gly Ala Gly Gln Gly Gly Ala Gly Ala Ala Ala Ala Ala
            20                  25                  30

Ala Ala Gly Gly Asp Gly Gly Ser Gly Leu Gly Gly Tyr Gly Ala Gly
        35                  40                  45

Arg Gly His Gly Val Gly Leu Gly Gly Ala Gly Ala Gly Ala Ala
50                  55                  60

Ser Ala Ala Ala Ala Gly Gly Gln Gly Gly Arg Gly Gly Phe Gly
65                  70                  75                  80

Gly Leu Gly Ser Gln Gly Ala Gly Gly Ala Gly Gln Gly Gly Ala Gly
            85                  90                  95

Ala Ala Ala Ala Ala Ala Ala Gly Gly Asp Gly Gly Ser Gly Leu
            100                 105                 110

Gly Gly Tyr Gly Ala Gly Arg Gly His Gly Ala Gly Leu Gly Gly Ala
        115                 120                 125

Gly Gly Ala Gly Ala Ala Ser Ala Ala Ala Ala Ala Gly Gly Gln Gly
        130                 135                 140

Gly Arg Gly Gly Phe Gly Gly Leu Gly Ser Gln Gly Ser Gly Gly Ala
145                 150                 155                 160

Gly Gln Gly Gly Ser Gly Ala Ala Ala Ala Ala Ala Ala Gly Gly
            165                 170                 175

Asp Gly Gly Ser Gly Leu Gly Gly Tyr Gly Ala Gly Arg Gly Tyr Gly

```
            180                 185                 190
Ala Gly Leu Gly Gly Ala Gly Gly Ala Gly Ala Ala Ser Ala Ala Ala
            195                 200                 205

Ala Ala Gly Gly Gln Gly Gly Arg Gly Gly Phe Gly Gly Leu Gly Ser
        210                 215                 220

Gln Gly Ala Gly Gly Ala Gly Gln Gly Gly Ser Gly Ala Ala Ala Ala
225                 230                 235                 240

Ala Ala Ala Ala Val Ala Asp Gly Gly Ser Gly Leu Gly Gly Tyr Gly
                245                 250                 255

Ala Gly Arg Gly Tyr Gly Ala Gly Leu Gly Gly Ala Gly Gly Ala Gly
            260                 265                 270

Ala Ala Ser Ala Ala Ala Ala Thr
            275                 280

<210> SEQ ID NO 3
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Ser Ala Pro Gln Gly Ala Gly Gly Pro Ala Pro Gln Gly Pro Ser
1               5                   10                  15

Gln Gln Gly Pro Val Ser Gln Gly Pro Tyr Gly Pro Gly Ala Ala Ala
            20                  25                  30

Ala Ala Ala Ala Gly Gly Tyr Gly Pro Gly Ala Gly Gln Gln Gly
        35                  40                  45

Pro Gly Ser Gln Gly Pro Gly Ser Gly Gly Gln Gly Pro Gly Ser
50                  55                  60

Gln Gly Pro Gly Ser Gly Gln Gln Gly Pro Gly Gly Gln Gly Pro
65                  70                  75                  80

Tyr Gly Pro Ser Ala Ala Ala Ala Ala Ala Ala Gly Gly Tyr
                85                  90                  95

Gly Pro Gly Ala Gly Gln Gln Gly Pro Gly Ser Gln Gly Pro Gly Ser
            100                 105                 110

Gly Gly Gln Gln Gly Pro Gly Gly Gln Gly Pro Tyr Gly Pro Gly Ala
        115                 120                 125

Ala Ala Ala Ala Ala Val Gly Gly Tyr Gly Pro Gly Ala Gly Gln
        130                 135                 140

Gln Gly Pro Gly Ser Gln Gly Pro Gly Ser Gly Gln Gln Gly Pro
145                 150                 155                 160

Gly Gly Gln Gly Pro Tyr Gly Pro Ser Ala Ala Ala Ala Ala Ala
                165                 170                 175

Ala Gly Gly Tyr Gly Pro Gly Ala Gly Gln Gln Gly Pro Gly Ser Gln
            180                 185                 190

Gly Pro Gly Ser Gly Gly Gln Gln Gly Pro Gly Gly Gln Gly Pro Tyr
        195                 200                 205

Gly Pro Ser Ala Ala Ala Ala Ala Ala Ala Gly Gly Tyr Gly Pro
        210                 215                 220

Gly Ala Gly Gln Gln Gly Pro Gly Ser Gly Gln Gln Gly Pro Gly
225                 230                 235                 240

Gly Gln Gly Pro Tyr Gly Ser Gly Gln Gln Gly Pro Gly Gly Ala Gly
                245                 250                 255
```

```
Gln Gln Gly Pro Gly Gly Gln Gly Pro Tyr Gly Pro Gly Ala Ala
            260                 265                 270
Ala Ala Ala Ala Ala Ala
            275

<210> SEQ ID NO 4
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Gly Tyr Gly Pro Gly Ala Gly Gln Gln Gly Pro Gly Ser Gly Gly
 1               5                  10                  15

Gln Gln Gly Pro Gly Gly Gln Gly Pro Tyr Gly Ser Gly Gln Gln Gly
            20                  25                  30

Pro Gly Gly Ala Gly Gln Gln Gly Pro Gly Gln Gly Pro Tyr Gly
            35                  40                  45

Pro Gly Ala Ala Ala Ala Ala Ala Ala Gly Gly Tyr Gly Pro
 50                  55                  60

Gly Ala Gly Gln Gln Gly Pro Gly Ala Gly Gln Gln Gly Pro Gly
 65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Gly Ser Gly Gly Gln Gln Gly Pro
            100                 105                 110

Gly Gly Gln Gly Pro Tyr Gly Pro Ser Ala Ala Ala Ala Ala Ala
            115                 120                 125

Ala Gly Gly Tyr Gly Pro Gly Ala Gly Gln Gln Gly Pro Gly Ser Gln
            130                 135                 140

Gly Pro Gly Ser Gly Gly Gln Gln Gly Pro Gly Gly Gln Gly Pro Tyr
145                 150                 155                 160

Gly Pro Ser Ala Ala Ala Ala Ala Ala Ala Gly Gly Tyr Gly Pro
                165                 170                 175

Gly Ala Gly Gln Gln Gly Pro Gly Ser Gly Gly Gln Gln Gly Pro Gly
            180                 185                 190

Gly Gln Gly Pro Tyr Gly Ser Gly Gln Gln Gly Pro Gly Gly Ala Gly
            195                 200                 205

Gln Gln Gly Pro Gly Gly Gln Gly Pro Tyr Gly Gly Tyr Gly Pro
            210                 215                 220

Gly Ala Gly Gln Gln Gly Pro Gly Ser Gln Gly Pro Gly Ser Gly Gly
225                 230                 235                 240

Gln Gln Gly Pro Gly Gly Gln Gly Pro Tyr Gly Pro Ser Ala Ala Ala
                245                 250                 255

Ala Ala Ala Ala Ala
            260

<210> SEQ ID NO 5
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

Gly Pro Gly Ala Arg Arg Gln Gly Pro Gly Ser Gln Gly Pro Gly Ser
1               5                   10                  15

Gly Gly Gln Gln Gly Pro Gly Gly Gln Gly Pro Tyr Gly Ser Gly Gln
            20                  25                  30

Gln Gly Pro Gly Gly Ala Gly Gln Gln Gly Pro Gly Gly Gln Gly Pro
            35                  40                  45

Tyr Gly Pro Gly Ala Ala Ala Ala Ala Ala Ala Ala Gly Gly Tyr
        50                  55                  60

Gly Pro Gly Ala Gly Gln Gln Gly Pro Gly Gly Ala Gly Gln Gln Gly
65                  70                  75                  80

Pro Gly Ser Gln Gly Pro Gly Gly Gln Gly Pro Tyr Gly Pro Gly Ala
            85                  90                  95

Gly Gln Gln Gly Pro Gly Ser Gln Gly Pro Gly Ser Gly Gly Gln Gln
            100                 105                 110

Gly Pro Gly Gly Gln Gly Pro Tyr Gly Pro Ser Ala Ala Ala Ala Ala
            115                 120                 125

Ala Ala Ala Ala Gly Gly Tyr Gly Pro Gly Ala Gly Gln Gln Gly Pro
        130                 135                 140

Gly Ser Gln Gly Pro Gly Ser Gly Gly Gln Gln Gly Pro Gly Gly Gln
145                 150                 155                 160

Gly Pro Tyr Gly Pro Gly Ala Ala Ala Ala Ala Ala Val Gly Gly
            165                 170                 175

Tyr Gly Pro Gly Ala Gly Gln Gln Gly Pro Gly Ser Gln Gly Pro Gly
            180                 185                 190

Ser Gly Gly Gln Gln Gly Pro Gly Gly Gln Gly Pro Tyr Gly Pro Ser
            195                 200                 205

Ala Ala Ala Ala Ala Ala Ala Ala Gly Gly Tyr Gly Pro Gly Ala Gly
            210                 215                 220

Gln Gln Gly Pro Gly Ser Gln Gly Pro Gly Ser Gly Gly Gln Gln Gly
225                 230                 235                 240

Pro Gly Gly Gln Gly Pro Tyr Gly Pro Ser Ala Ala Ala Ala Ala Ala
            245                 250                 255

Ala Ala

<210> SEQ ID NO 6
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Pro Gly Ala Arg Arg Gln Gly Pro Gly Ser Gln Gly Pro Gly Ser
1               5                   10                  15

Gly Gly Gln Gln Gly Pro Gly Gly Gln Gly Pro Tyr Gly Ser Gly Gln
            20                  25                  30

Gln Gly Pro Gly Gly Ala Gly Gln Gln Gly Pro Gly Gly Gln Gly Pro
            35                  40                  45

Tyr Gly Pro Gly Ala Ala Ala Ala Ala Ala Ala Ala Gly Gly Tyr
        50                  55                  60

Gly Pro Gly Ala Gly Gln Gln Gly Pro Gly Gly Ala Gly Gln Gln Gly
65                  70                  75                  80

Pro Gly Ser Gln Gly Pro Gly Gly Gln Gly Pro Tyr Gly Pro Gly Ala
            85                  90                  95

Gly Gln Gln Gly Pro Gly Ser Gln Gly Pro Gly Ser Gly Gly Gln Gln
            100                 105                 110

Gly Pro Gly Gly Gln Gly Pro Tyr Gly Pro Ser Ala Ala Ala Ala Ala
        115                 120                 125

Ala Ala Ala Gly Gly Tyr Gly Pro Gly Ala Gly Gln Gln Gly Pro Gly
    130                 135                 140

Ser Gln Gly Pro Gly Ser Gly Gly Gln Gln Gly Pro Gly Gly Gln Gly
145                 150                 155                 160

Pro Tyr Gly Pro Gly Ala Ala Ala Ala Ala Ala Val Gly Gly Tyr
                165                 170                 175

Gly Pro Gly Ala Gly Gln Gln Gly Pro Gly Ser Gln Gly Pro Gly Ser
        180                 185                 190

Gly Gly Gln Gln Gly Pro Gly Gly Gln Gly Pro Tyr Gly Pro Ser Ala
        195                 200                 205

Ala Ala Ala Ala Ala Ala Gly Gly Tyr Gly Pro Gly Ala Gly Gln
    210                 215                 220

Gln Gly Pro Gly Ser Gln Gly Pro Gly Ser Gly Gly Gln Gln Gly Pro
225                 230                 235                 240

Gly Gly Gln Gly Pro Tyr Gly Pro Ser Ala Ala Ala Ala Ala Ala
                245                 250                 255

Ala

<210> SEQ ID NO 7
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
            20                  25                  30

Pro Gly Gly Ala Gly Gln Gln Gly Pro Gly Gly Gln Gly Pro Tyr Gly
        35                  40                  45

Pro Gly Ala Ala Ala Ala Ala Ala Ala Ala Gly Gly Tyr Gly Pro
    50                  55                  60

Gly Ala Gly Gln Gln Gly Pro Gly Ala Gly Gln Gln Gly Pro Glu
65                  70                  75                  80

Gly Pro Gly Ser Gln Gly Pro Gly Ser Gly Gln Gln Gly Pro Gly
                85                  90                  95

Gly Gln Gly Pro Tyr Gly Pro Gly Ala Ala Ala Ala Ala Ala Val
            100                 105                 110

Gly Gly Tyr Gly Pro Gly Ala Gly Gln Gln Gly Pro Gly Ser Gln Gly
        115                 120                 125

Pro Gly Ser Gly Gly Gln Gln Gly Pro Gly Gly Gln Gly Pro Tyr Gly
    130                 135                 140

Pro Ser Ala Ala Ala Ala Ala Ala Ala Gly Gly Tyr Gly Pro Gly
145                 150                 155                 160

Ala Gly Gln Gln Gly Pro Gly Ser Gln Gly Pro Gly Ser Gly Gly Gln
                165                 170                 175

Gln Gly Pro Gly Gly Gln Gly Pro Tyr Gly Pro Ser Ala Ala Ala Ala
            180                 185                 190

```
Ala Ala Ala Ala Gly Gly Tyr Gly Pro Gly Ala Gly Gln Gln Gly Pro
            195                 200                 205

Gly Ser Gly Gly Gln Gln Gly Pro Gly Gly Gln Gly Pro Tyr Gly Ser
210                 215                 220

Gly Gln Gln Gly Pro Gly Ala Gly Gln Gln Gly Pro Gly Gly Gln
225                 230                 235                 240

Gly Pro Tyr Gly Pro Gly Ala Ala Ala Ala Ala Ala Ala Ala
            245                 250                 255

<210> SEQ ID NO 8
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Val Phe Ser Ala Gly Gln Gly Ala Thr Pro Trp Glu Asn Ser Gln
1               5                   10                  15

Leu Ala Glu Ser Phe Ile Ser Arg Phe Leu Arg Phe Ile Gly Gln Ser
            20                  25                  30

Gly Ala Phe Ser Pro Asn Gln Leu Asp Asp Met Ser Ser Ile Gly Asp
        35                  40                  45

Thr Leu Lys Thr Ala Ile Glu Lys Met Ala Gln Ser Arg Lys Ser Ser
50                  55                  60

Lys Ser Lys Leu Gln Ala Leu Asn Met Ala Phe Ala Ser Ser Met Ala
65                  70                  75                  80

Glu Ile Ala Val Ala Glu Gln Gly Gly Leu Ser Leu Glu Ala Lys Thr
                85                  90                  95

Asn Ala Ile Ala Ser Ala Leu Ser Ala Ala Phe Leu Glu Thr Thr Gly
            100                 105                 110

Tyr Val Asn Gln Gln Phe Val Asn Glu Ile Lys Thr Leu Ile Phe Met
        115                 120                 125

Ile Ala Gln Ala Ser Ser Asn Glu Ile Ser Gly Ser Ala Ala Ala Ala
130                 135                 140

Gly Gly Ser Ser Gly Gly Gly Gly Ser Gly Gln Gly Gly Tyr Gly
145                 150                 155                 160

Gln Gly Ala Tyr Ala Ser Ala Ser Ala Ala Ala Tyr Gly Ser Ala
            165                 170                 175

Pro Gln Gly Thr Gly Gly Pro Ala Ser Gln Gly Pro Ser Gln Gly
        180                 185                 190

Pro Val Ser Gln Pro Ser Tyr Gly Pro Ser Ala Thr Val Ala Val Thr
195                 200                 205

Ala Val Gly Gly Arg Pro Gln Gly Pro Ser Ala Pro Arg Gln Gln Gly
            210                 215                 220

Pro Ser Gln Gln Gly Pro Gly Gln Gln Gly Pro Gly Gly Arg Gly Pro
225                 230                 235                 240

Tyr Gly Pro Ser Ala Ala Ala Ala Ala Ala Ala Ala
            245                 250

<210> SEQ ID NO 9
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 9

```
Gly Ala Gly Ala Gly Ala Gly Ala Gly Ala Gly Ala Gly Ala Gly Ala
1               5                   10                  15
Gly Ser Gly Ala Ser Thr Ser Val Ser Thr Ser Ser Ser Ser Gly Ser
                20                  25                  30
Gly Ala Gly Ala Gly Ala Gly Ser Gly Ala Gly Ser Gly Ala Gly Ala
            35                  40                  45
Gly Ser Gly Ala Gly Ala Gly Ala Gly Ala Gly Gly Ala Gly Ala Gly
        50                  55                  60
Phe Gly Ser Gly Leu Gly Leu Gly Tyr Gly Val Gly Leu Ser Ser Ala
65                  70                  75                  80
Gln Ala Gln Ala Gln Ala Gln Ala Ala Ala Gln Ala Gln Ala Gln Ala
                85                  90                  95
Gln Ala Gln Ala Tyr Ala Ala Ala Gln Ala Gln Ala Gln Ala Gln Ala
            100                 105                 110
Gln Ala Gln Ala Ala Ala Ala Ala Ala Ala Ala Ala Ala Ala Gly Ala
        115                 120                 125
Gly Ala Gly Ala Gly Ala Gly Ala Gly Ala Gly Ala Gly Ala Gly Ser
    130                 135                 140
Gly Ala Ser Thr Ser Val Ser Thr Ser Ser Ser Gly Ser Gly Ala
145                 150                 155                 160
Gly Ala Gly Ala Gly Ser Gly Ala Gly Ser Gly Ala Gly Ala Gly Ser
                165                 170                 175
Gly Ala Gly Ala Gly Ala Gly Ala Gly Gly Ala Gly Ala Gly Phe Gly
            180                 185                 190
Ser Gly Leu Gly Leu Gly Tyr Gly Val Gly Leu Ser Ser Ala Gln Ala
        195                 200                 205
Gln Ala Gln Ala Gln Ala Ala Ala Gln Ala Gln Ala Gln Ala Gln Ala
    210                 215                 220
Gln Ala Tyr Ala Ala Ala Gln Ala Gln Ala Gln Ala Gln Ala Gln Ala
225                 230                 235                 240
Gln Ala Ala Ala Ala Ala Ala Ala Ala Ala Ala
                245                 250
```

<210> SEQ ID NO 10
<211> LENGTH: 252
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

```
Gly Ala Gly Ala Gly Ala Gly Ala Gly Ala Gly Ala Gly Ala Gly Ala
1               5                   10                  15
Gly Ser Gly Ala Ser Thr Ser Val Ser Thr Ser Ser Ser Ser Gly Ser
                20                  25                  30
Gly Ala Gly Ala Gly Ala Gly Ser Gly Ala Gly Ser Gly Ala Gly Ala
            35                  40                  45
Gly Ser Gly Ala Gly Ala Gly Ala Gly Ala Gly Gly Ala Gly Ala Ala
        50                  55                  60
Phe Gly Ser Gly Leu Gly Leu Gly Tyr Gly Val Gly Leu Ser Ser Ala
65                  70                  75                  80
Gln Ala Gln Ala Gln Ala Gln Ala Ala Ala Gln Ala Gln Ala Asp Ala
                85                  90                  95
```

```
Gln Ala Gln Ala Tyr Ala Ala Gln Ala Gln Ala Gln Ala
            100                 105                 110

Gln Ala Gln Ala Ala Ala Ala Ala Ala Ala Ala Gly Ala
            115                 120                 125

Gly Ala Gly Ala Gly Ala Gly Ser Gly Ala Gly Ala Gly Ser
130                 135                 140

Gly Ala Ser Thr Ser Val Ser Thr Ser Ser Ser Gly Ser Gly Ala
145                 150                 155                 160

Gly Ala Gly Ala Gly Ser Gly Ala Gly Ser Gly Ala Gly Ser
            165                 170                 175

Gly Ala Gly Ala Gly Ala Gly Ala Gly Gly Ala Gly Ala Gly Phe Gly
            180                 185                 190

Ser Gly Leu Gly Leu Gly Tyr Gly Val Gly Leu Ser Ser Ala Gln Ala
            195                 200                 205

Gln Ala Gln Ala Gln Ala Ala Gln Ala Gln Ala Asp Ala Gln Ala
            210                 215                 220

Gln Ala Tyr Ala Ala Ala Gln Ala Gln Ala Gln Ala Gln Ala
225                 230                 235                 240

Gln Ala Ala Ala Ala Ala Ala Ala Ala Ala Ala
            245                 250

<210> SEQ ID NO 11
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Ala Gly Ala Gly Ala Gly Ala Gly Ser Gly Ala Gly Ala Gly Ala
1               5                   10                  15

Gly Ser Gly Ala Ser Thr Ser Val Ser Thr Ser Ser Ser Gly Ser
            20                  25                  30

Gly Ala Gly Ala Gly Ala Gly Ser Gly Ala Gly Ser Gly Ala Gly Ala
            35                  40                  45

Gly Ser Gly Ala Gly Ala Gly Ala Gly Ala Gly Gly Ala Gly Ala Gly
            50                  55                  60

Phe Gly Ser Gly Leu Gly Leu Gly Tyr Gly Val Gly Leu Ser Ser Ala
65                  70                  75                  80

Gln Ala Gln Ala Gln Ser Ala Ala Ala Ala Arg Ala Gln Ala Asp Ala
            85                  90                  95

Gln Ala Gln Ala Tyr Ala Ala Gln Ala Gln Ala Gln Ala Gln Ala
            100                 105                 110

Gln Ala Gln Ala Ala Ala Ala Ala Ala Ala Ala Ala Gly Ala
            115                 120                 125

Gly Ala Gly Ala Gly Ala Gly Ala Gly Ala Gly Ala Gly Ser
130                 135                 140

Gly Ala Ser Thr Ser Val Ser Thr Ser Ser Ser Ala Ser Gly Ala
145                 150                 155                 160

Gly Ala Gly Ala Gly Ser Gly Ala Gly Ser Gly Ala Gly Ala Gly Ser
            165                 170                 175

Gly Ala Gly Ala Gly Ala Gly Ala Gly Gly Ala Gly Ala Gly Phe Gly
            180                 185                 190

Ser Gly Leu Gly Leu Gly Tyr Gly Val Gly Leu Ser Ser Ala Gln Ala
```

```
                195                 200                 205
Gln Ala Gln Ala Gln Ala Ala Gln Ala Gln Ala Gln Ala
        210                 215                 220
Gln Ala Leu Ala Ala Gln Ala Gln Ala Gln Ala Gln Ala
225                 230                 235                 240
Gln Ala Ala Ala Thr Ala Ala Ala Ala Ala
                245                 250

<210> SEQ ID NO 12
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Gly Tyr Gly Pro Gly Ala Gly Gln Gln Gly Pro Gly Gly Ala Gly
1               5                   10                  15
Gln Gln Gly Pro Gly Ser Gln Gly Pro Gly Gly Gln Gly Pro Tyr Gly
                20                  25                  30
Pro Gly Ala Gly Gln Gln Gly Pro Gly Ser Gln Gly Pro Gly Ser Gly
            35                  40                  45
Gly Gln Gln Gly Pro Gly Gln Gly Pro Tyr Gly Pro Ser Ala Ala
        50                  55                  60
Ala Ala Ala Ala Ala Ala Gly Gly Tyr Gly Pro Gly Ala Gly Gln Gln
65                  70                  75                  80
Gly Pro Gly Ser Gln Gly Pro Gly Ser Gly Gly Gln Gln Gly Pro Gly
                85                  90                  95
Ser Gln Gly Pro Gly Ser Gly Gly Gln Gln Gly Pro Gly Gly Gln Gly
            100                 105                 110
Pro Tyr Gly Pro Ser Ala Ala Ala Ala Ala Ala Ala Ala Gly Gly
        115                 120                 125
Tyr Gly Pro Gly Ala Gly Gln Gln Gly Pro Gly Ser Gln Gly Pro Gly
    130                 135                 140
Ser Gly Gly Gln Gln Gly Pro Gly Gly Gln Gly Pro Tyr Gly Pro Gly
145                 150                 155                 160
Ala Ala Ala Ala Ala Ala Val Gly Gly Tyr Gly Pro Gly Ala Gly
                165                 170                 175
Gln Gln Gly Pro Gly Ser Gln Gly Pro Gly Ser Gly Gly Gln Gln Gly
            180                 185                 190
Pro Gly Gly Gln Gly Pro Tyr Gly Pro Ser Ala Ala Ala Ala Ala
        195                 200                 205
Ala Ala Gly Gly Tyr Gly Pro Gly Ala Gly Gln Gln Gly Pro Gly Ser
    210                 215                 220
Gln Gly Pro Gly Ser Gly Gly Gln Gln Gly Pro Gly Gly Gln Gly Pro
225                 230                 235                 240
Tyr Gly Pro Ser Ala Ala Ala Ala Ala Ala Ala
                245                 250

<210> SEQ ID NO 13
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 13

Gly Gly Tyr Gly Pro Gly Ala Gly Gln Gln Gly Pro Gly Gly Ala Gly
1               5                   10                  15

Gln Gln Gly Pro Gly Ser Gln Gly Pro Gly Gly Gln Gly Pro Tyr Gly
            20                  25                  30

Pro Gly Ala Gly Gln Gln Gly Pro Gly Ser Gln Gly Pro Gly Ser Gly
        35                  40                  45

Gly Gln Gln Gly Pro Gly Gly Gln Gly Pro Tyr Gly Pro Ser Ala Ala
    50                  55                  60

Ala Ala Ala Ala Ala Ala Gly Gly Tyr Gly Pro Gly Ala Gly Gln Gln
65                  70                  75                  80

Gly Pro Gly Ser Gln Gly Pro Gly Ser Gly Gly Gln Gln Gly Pro Gly
                85                  90                  95

Ser Gln Gly Pro Gly Ser Gly Gly Gln Gln Gly Pro Gly Gly Gln Gly
            100                 105                 110

Pro Tyr Gly Pro Ser Ala Ala Ala Ala Ala Ala Ala Gly Gly Tyr
        115                 120                 125

Gly Pro Gly Ala Gly Gln Gln Gly Pro Gly Ser Gln Gly Pro Gly Ser
    130                 135                 140

Gly Gly Gln Gln Gly Pro Gly Gly Gln Gly Pro Tyr Gly Pro Gly Ala
145                 150                 155                 160

Ala Ala Ala Ala Ala Val Gly Gly Tyr Gly Pro Gly Ala Gly Gln
                165                 170                 175

Gln Gly Pro Gly Ser Gln Gly Pro Gly Ser Gly Gly Gln Gln Gly Pro
            180                 185                 190

Gly Gly Gln Gly Pro Tyr Gly Pro Ser Ala Ala Ala Ala Ala Ala
        195                 200                 205

Ala Gly Gly Tyr Gly Pro Gly Ala Gly Gln Gln Gly Pro Gly Ser Gln
    210                 215                 220

Gly Pro Gly Ser Gly Gly Gln Gln Gly Pro Gly Gly Gln Gly Pro Tyr
225                 230                 235                 240

Gly Pro Ser Ala Ala Ala Ala Ala Ala Ala
                245                 250

<210> SEQ ID NO 14
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly His Gln Gly Pro His Arg Lys Thr Pro Trp Glu Thr Pro Glu Met
1               5                   10                  15

Ala Glu Asn Phe Met Asn Asn Val Arg Glu Asn Leu Glu Ala Ser Arg
            20                  25                  30

Ile Phe Pro Asp Glu Leu Met Lys Asp Met Glu Ala Ile Thr Asn Thr
        35                  40                  45

Met Ile Ala Ala Val Asp Gly Leu Glu Ala Gln His Arg Ser Ser Tyr
    50                  55                  60

Ala Ser Leu Gln Ala Met Asn Thr Ala Phe Ala Ser Ser Met Ala Gln
65                  70                  75                  80

Leu Phe Ala Thr Glu Gln Asp Tyr Val Asp Thr Glu Val Ile Ala Gly
                85                  90                  95

```
Ala Ile Gly Lys Ala Tyr Gln Gln Ile Thr Gly Tyr Glu Asn Pro His
            100                 105                 110

Leu Ala Ser Glu Val Thr Arg Leu Ile Gln Leu Phe Arg Glu Glu Asp
        115                 120                 125

Asp Leu Glu Asn Glu Val Glu Ile Ser Phe Ala Asp Thr Asp Asn Ala
    130                 135                 140

Ile Ala Arg Ala Ala Gly Ala Ala Gly Ser Ala Ala Ser
145                 150                 155                 160

Ser Ser Ala Asp Ala Ser Ala Thr Ala Glu Gly Ala Ser Gly Asp Ser
                165                 170                 175

Gly Phe Leu Phe Ser Thr Gly Thr Phe Gly Arg Gly Gly Ala Gly Ala
            180                 185                 190

Gly Ala Gly Ala Ala Ala Ala Ser Ala Ala Ala Ser Ala Ala Ala
        195                 200                 205

Ala Gly Ala Glu Gly Asp Arg Gly Leu Phe Phe Ser Thr Gly Asp Phe
    210                 215                 220

Gly Arg Gly Gly Ala Gly Ala Gly Ala Gly Ala Ala Ala Ala Ser Ala
225                 230                 235                 240

Ala Ala Ala Ser Ala Ala Ala Ala
                245
```

<210> SEQ ID NO 15
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Gly Gly Ala Gln Lys His Pro Ser Gly Glu Tyr Ser Val Ala Thr Ala
1               5                   10                  15

Ser Ala Ala Ala Thr Ser Val Thr Ser Gly Gly Ala Pro Val Gly Lys
            20                  25                  30

Pro Gly Val Pro Ala Pro Ile Phe Tyr Pro Gln Gly Pro Leu Gln Gln
        35                  40                  45

Gly Pro Ala Pro Gly Pro Ser Asn Val Gln Pro Gly Thr Ser Gln Gln
    50                  55                  60

Gly Pro Ile Gly Gly Val Gly Glu Ser Asn Thr Phe Ser Ser Ser Phe
65                  70                  75                  80

Ala Ser Ala Leu Gly Gly Asn Arg Gly Phe Ser Gly Val Ile Ser Ser
                85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
        115                 120                 125

Tyr Asn Ser Ile Gly Ser Gly Ala Ser Ala Ser Ala Tyr Ala Gln Ala
    130                 135                 140

Phe Ala Arg Val Leu Tyr Pro Leu Leu Gln Gln Tyr Gly Leu Ser Ser
145                 150                 155                 160

Ser Ala Asp Ala Ser Ala Phe Ala Ser Ala Ile Ala Ser Ser Phe Ser
                165                 170                 175

Thr Gly Val Ala Gly Gln Gly Pro Ser Val Pro Tyr Val Gly Gln Gln
            180                 185                 190

Gln Pro Ser Ile Met Val Ser Ala Ala Ser Ala Ser Ala Ala Ala Ser
        195                 200                 205
```

Ala Ala Ala Val Gly Gly Pro Val Val Gln Gly Pro Tyr Asp Gly
        210                 215                 220

Gly Gln Pro Gln Gln Pro Asn Ile Ala Ala Ser Ala Ala Ala Ala
225                 230                 235                 240

Thr Ala Thr Ser Ser
            245

<210> SEQ ID NO 16
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Gly Gln Gly Gly Arg Gly Gly Phe Gly Gly Leu Gly Ser Gln Gly
1               5                   10                  15

Glu Gly Gly Ala Gly Gln Gly Gly Ala Gly Ala Ala Ala Ala Ala
            20                  25                  30

Ala Ala Gly Ala Asp Gly Gly Phe Gly Leu Gly Gly Tyr Gly Ala Gly
        35                  40                  45

Arg Gly Tyr Gly Ala Gly Leu Gly Gly Ala Gly Gly Ala Gly Ala Ala
    50                  55                  60

Ser Ala Ala Ala Ala Gly Gly Gln Gly Gly Arg Ser Gly Phe Gly
65                  70                  75                  80

Gly Leu Gly Ser Gln Gly Ala Gly Gly Ala Gln Gly Gly Ala Gly
                85                  90                  95

Ala Ala Ala Ala Ala Ala Ala Gly Ala Asp Gly Gly Ser Gly Leu
                100                 105                 110

Gly Gly Tyr Gly Ala Gly Arg Gly Tyr Gly Ala Ser Leu Gly Gly Ala
            115                 120                 125

Asp Gly Ala Gly Ala Ala Ser Ala Ala Ala Ala Gly Gly Gln Gly
        130                 135                 140

Gly Arg Gly Gly Phe Gly Gly Leu Gly Ser Gln Gly Ala Gly Gly Ala
145                 150                 155                 160

Gly Gln Gly Gly Ala Gly Ala Ala Ala Ala Ala Ala Ser Gly
                165                 170                 175

Asp Gly Gly Ser Gly Leu Gly Gly Tyr Gly Ala Gly Arg Gly Tyr Gly
            180                 185                 190

Ala Gly Leu Gly Gly Ala Gly Gly Ala Gly Ala Ala Ser Ala Ala Ala
        195                 200                 205

Ala Ala Gly Gly Glu Gly Gly Arg Gly Gly Phe Gly Gly Leu Gly Ser
    210                 215                 220

Gln Gly Ala Gly Gly Ala Gly Gln Gly Gly Ser Leu Ala Ala Ala
225                 230                 235                 240

Ala Ala Ala Ala

<210> SEQ ID NO 17
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Pro Gly Gly Tyr Gly Gly Pro Gly Gln Pro Gly Pro Gly Gln Gly
1               5                   10                  15

Gln Tyr Gly Pro Gly Pro Gly Gln Gln Gly Pro Arg Gln Gly Gly Gln
            20                  25                  30

Gln Gly Pro Ala Ser Ala Ala Ala Ala Ala Ala Ala Gly Pro Gly Gly
        35                  40                  45

Tyr Gly Gly Pro Gly Gln Gln Gly Pro Arg Gln Gln Gln Gln Gly
    50                  55                  60

Pro Ala Ser Ala Ala Ala Ala Ala Ala Ala Ala Gly Pro Arg
65                  70                  75                  80

Gly Tyr Gly Gly Pro Gly Gln Gln Gly Pro Val Gln Gly Gly Gln Gln
                85                  90                  95

Gly Pro Ala Ser Ala Ala Ala Ala Ala Ala Gly Val Gly Gly
            100                 105                 110

Tyr Gly Gly Pro Gly Gln Gln Gly Pro Gly Gln Gly Gln Tyr Gly Pro
            115                 120                 125

Gly Thr Gly Gln Gln Gly Gln Gly Pro Ser Gly Gln Gln Gly Pro Ala
        130                 135                 140

Gly Ala Ala Ala Ala Ala Gly Gly Ala Ala Gly Pro Gly Gly Tyr
145                 150                 155                 160

Gly Gly Pro Gly Gln Gln Gly Pro Gly Gln Gly Gln Tyr Gly Pro Gly
                165                 170                 175

Thr Gly Gln Gln Gly Gln Gly Pro Ser Gly Gln Gln Gly Pro Ala Gly
            180                 185                 190

Ala Ala Ala Ala Ala Ala Ala Ala Gly Pro Gly Gly Tyr Gly Gly
            195                 200                 205

Pro Gly Gln Gln Gly Pro Gly Gln Gly Gln Tyr Gly Pro Gly Ala Gly
    210                 215                 220

Gln Gln Gly Gln Gly Pro Gly Ser Gln Gln Gly Pro Ala Ser Ala Ala
225                 230                 235                 240

Ala Ala Ala Ala

<210> SEQ ID NO 18
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Ser Gly Ala Gly Gln Gly Thr Gly Ala Gly Ala Gly Ala Ala Ala
1               5                   10                  15

Ala Ala Ala Gly Ala Ala Gly Ser Gly Ala Gly Gln Gly Ala Gly Ser
            20                  25                  30

Gly Ala Gly Ala Ala Ala Ala Ala Ala Ser Ala Ala Gly Ala
        35                  40                  45

Gly Gln Gly Ala Gly Ser Gly Ser Gly Ala Gly Ala Ala Ala Ala Ala
    50                  55                  60

Ala Ala Ala Ala Gly Ala Gly Gln Gly Ala Gly Ser Gly Ser Gly Ala
65                  70                  75                  80

Gly Ala Ala Ala Ala Ala Ala Ala Ala Ala Ala Gln Gln Gln
                85                  90                  95

Gln Gln Gln Gln Ala Ala Ala Ala Ala Ala Ala Ala Ala Ala
            100                 105                 110

-continued

Ala Gly Ser Gly Gln Gly Ala Ser Phe Gly Val Thr Gln Gln Phe Gly
            115                 120                 125

Ala Pro Ser Gly Ala Ala Ser Ser Ala Ala Ala Ala Ala Ala Ala Ala
130                 135                 140

Ala Ala Ala Ala Ala Gly Ser Gly Ala Gly Gln Glu Ala Gly Thr Gly
145                 150                 155                 160

Ala Gly Ala Ala Ala Ala Ala Ala Ala Gly Ala Ala Gly Ser Gly
            165                 170                 175

Ala Gly Gln Gly Ala Gly Ser Gly Ala Gly Ala Ala Ala Ala Ala Ala
            180                 185                 190

Ala Ala Ala Ser Ala Ala Gly Ala Gly Gln Gly Ala Gly Ser Gly Ser
            195                 200                 205

Gly Ala Gly Ala Ala Ala Ala Ala Ala Ala Ala Ala Ala Ala Ala Gln
            210                 215                 220

Gln Gln Gln Gln Gln Ala Ala Ala Ala Ala Ala Ala Ala Ala
225                 230                 235                 240

Ala Ala Ala

<210> SEQ ID NO 19
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Gly Ala Gln Lys Gln Pro Ser Gly Glu Ser Ser Val Ala Thr Ala
1               5                   10                  15

Ser Ala Ala Ala Thr Ser Val Thr Ser Ala Gly Ala Pro Val Gly Lys
            20                  25                  30

Pro Gly Val Pro Ala Pro Ile Phe Tyr Pro Gln Gly Pro Leu Gln Gln
            35                  40                  45

Gly Pro Ala Pro Gly Pro Ser Tyr Val Gln Pro Ala Thr Ser Gln Gln
50                  55                  60

Gly Pro Ile Gly Gly Ala Gly Arg Ser Asn Ala Phe Ser Ser Ser Phe
65                  70                  75                  80

Ala Ser Ala Leu Ser Gly Asn Arg Gly Phe Ser Glu Val Ile Ser Ser
            85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Asn Ala Phe Ala Tyr Ala Gln Ala
            130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
            165                 170                 175

Ser Gly Ala Ala Gly Gln Gly Gln Ser Ile Pro Tyr Gly Gly Gln Gln
            180                 185                 190

Gln Pro Pro Met Thr Ile Ser Ala Ala Ser Ala Ser Ala Gly Ala Ser
            195                 200                 205

Ala Ala Ala Val Lys Gly Gly Gln Val Gly Gln Gly Pro Tyr Gly Gly
            210                 215                 220

Gln Gln Gln Ser Thr Ala Ala Ser Ala Ser Ala Ala Thr Thr Ala
225                 230                 235                 240

Thr Ala

<210> SEQ ID NO 20
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Ala Asp Gly Gly Ser Gly Leu Gly Gly Tyr Gly Ala Gly Arg Gly
1               5                   10                  15

Tyr Gly Ala Gly Leu Gly Gly Ala Asp Gly Ala Gly Ala Ala Ser Ala
            20                  25                  30

Ala Ala Ala Ala Gly Gly Gln Gly Gly Arg Gly Gly Phe Gly Arg Leu
        35                  40                  45

Gly Ser Gln Gly Ala Gly Ala Gly Gln Gly Ala Gly Ala Ala
    50                  55                  60

Ala Ala Val Ala Ala Ala Gly Gly Asp Gly Gly Ser Gly Leu Gly Gly
65                  70                  75                  80

Tyr Gly Ala Gly Arg Gly Tyr Gly Ala Gly Leu Gly Gly Ala Gly Gly
                85                  90                  95

Ala Gly Ala Ala Ser Ala Ala Ala Ala Gly Gly Gln Gly Gly Arg
            100                 105                 110

Gly Gly Phe Gly Gly Leu Gly Ser Gln Gly Ala Gly Ala Gly Gln
        115                 120                 125

Gly Gly Ala Gly Ala Ala Ser Gly Asp Gly Gly Ser Gly Leu Gly
    130                 135                 140

Gly Tyr Gly Ala Gly Arg Gly Tyr Gly Ala Gly Leu Gly Gly Ala Asp
145                 150                 155                 160

Gly Ala Gly Ala Ala Ser Ala Ala Ser Ala Ala Gly Gly Gln Gly Gly
                165                 170                 175

Arg Gly Gly Phe Gly Gly Leu Gly Ser Gln Gly Ala Gly Ala Gly
            180                 185                 190

Gln Gly Gly Ala Gly Ala Ala Ala Ala Ala Thr Ala Gly Gly Asp
        195                 200                 205

Gly Gly Ser Gly Leu Gly Gly Tyr Gly Ala Gly Arg Gly Tyr Gly Ala
    210                 215                 220

Gly Leu Gly Gly Ala Gly Gly Ala Gly Ala Ala Ser Ala Ala Ala Ala
225                 230                 235                 240

Ala

<210> SEQ ID NO 21
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Ala Gly Ala Gly Gln Gly Gly Arg Gly Gly Tyr Gly Gln Gly Gly
1               5                   10                  15

Phe Gly Gly Gln Gly Ser Gly Ala Gly Ala Gly Ala Ser Ala Ala Ala
            20                  25                  30

Gly Ala Gly Ala Gly Gln Gly Gly Arg Gly Gly Tyr Gly Gln Gly Gly
        35                  40                  45

Phe Gly Gly Gln Gly Ser Gly Ala Gly Ala Gly Ser Ala Ala Ala
    50                  55                  60

Gly Ala Gly Ala Gly Gln Gly Gly Arg Gly Gly Tyr Gly Gln Gly Gly
65                  70                  75                  80

Phe Gly Gly Gln Gly Ser Gly Ala Gly Ala Gly Ser Ala Ala Ala
                85                  90                  95

Ala Ala Gly Ala Gly Gln Gly Gly Arg Gly Gly Tyr Gly Gln Gly Gly
            100                 105                 110

Leu Gly Gly Ser Gly Ser Gly Ala Gly Ala Gly Ala Gly Ala Ala Ala
            115                 120                 125

Ala Ala Ala Ala Gly Ala Gly Gly Tyr Gly Gln Gly Gly Leu Gly Gly
            130                 135                 140

Tyr Gly Gln Gly Ala Gly Ala Gly Gln Gly Gly Leu Gly Gly Tyr Gly
145                 150                 155                 160

Ser Gly Ala Gly Ala Gly Ala Ser Ala Ala Ala Ala Gly Ala Gly
                165                 170                 175

Gly Ala Gly Gln Gly Gly Leu Gly Gly Tyr Gly Gln Gly Ala Gly Ala
            180                 185                 190

Gly Gln Gly Gly Leu Gly Gly Tyr Gly Ser Gly Ala Gly Ala Gly Ala
            195                 200                 205

Ala Ala Ala Ala Ala Gly Ala Gly Gly Ser Gly Gln Gly Gly Leu
            210                 215                 220

Gly Gly Tyr Gly Ser Gly Gly Ala Gly Ala Ser Ala Ala Ala
225                 230                 235                 240

Ala

<210> SEQ ID NO 22
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Ala Tyr Ala Tyr Ala Tyr Ala Ile Ala Asn Ala Phe Ala Ser Ile
1               5                   10                  15

Leu Ala Asn Thr Gly Leu Leu Ser Val Ser Ser Ala Ala Ser Val Ala
                20                  25                  30

Ser Ser Val Ala Ser Ala Ile Ala Thr Ser Val Ser Ser Ser Ser Ala
            35                  40                  45

Ala Ala Ala Ser Ala Ser Ala Ala Ala Ala Ser Ala Gly Ala
        50                  55                  60

Ser Ala Ala Ser Ser Ala Ser Ala Ser Ser Ala Ser Ala Ala Ala
65                  70                  75                  80

Gly Ala Gly Ala Gly Ala Gly Ala Gly Ala Ser Gly Ala Ser Gly Ala
                85                  90                  95

Ala Gly Gly Ser Gly Gly Phe Gly Leu Ser Ser Gly Phe Gly Ala Gly
            100                 105                 110

Ile Gly Gly Leu Gly Gly Tyr Pro Ser Gly Ala Leu Gly Gly Leu Gly
            115                 120                 125

Ile Pro Ser Gly Leu Leu Ser Ser Gly Leu Leu Ser Pro Ala Ala Asn
            130                 135                 140

-continued

Gln Arg Ile Ala Ser Leu Ile Pro Leu Ile Leu Ser Ala Ile Ser Pro
145                 150                 155                 160

Asn Gly Val Asn Phe Gly Val Ile Gly Ser Asn Ile Ala Ser Leu Ala
                165                 170                 175

Ser Gln Ile Ser Gln Ser Gly Gly Ile Ala Ala Ser Gln Ala Phe
            180                 185                 190

Thr Gln Ala Leu Leu Glu Leu Val Ala Ala Phe Ile Gln Val Leu Ser
        195                 200                 205

Ser Ala Gln Ile Gly Ala Val Ser Ser Ser Ala Ser Ala Gly Ala
    210                 215                 220

Thr Ala Asn Ala Phe Ala Gln Ser Leu Ser Ser Ala Phe Ala Gly
225                 230                 235

<210> SEQ ID NO 23
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Ala Ala Gln Lys Gln Pro Ser Gly Glu Ser Ser Val Ala Thr Ala
1               5                   10                  15

Ser Ala Ala Ala Thr Ser Val Thr Ser Gly Gly Ala Pro Val Gly Lys
                20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
        50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
        115                 120                 125

Tyr Asn Ser Ile Gly Ser Gly Ala Asn Ala Phe Ala Tyr Ala Gln Ala
    130                 135                 140

Phe Ala Arg Val Leu Tyr Pro Leu Val Arg Gln Tyr Gly Leu Ser Ser
145                 150                 155                 160

Ser Gly Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Gln Pro Pro
            180                 185                 190

Val Thr Ile Ser Ala Ala Ser Ala Gly Ala Ser Ala Ala Ala
        195                 200                 205

Val Gly Gly Gly Gln Val Gly Gln Gly Pro Tyr Gly Gly Gln Gln Gln
    210                 215                 220

Ser Thr Ala Ala Ser Ala Ser Ala Ala Ala Thr Ala Thr Ser
225                 230                 235

<210> SEQ ID NO 24
<211> LENGTH: 239
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 24

```
Gly Ala Ala Gln Lys Gln Pro Ser Gly Glu Ser Ser Val Ala Thr Ala
1               5                   10                  15

Ser Ala Ala Ala Thr Ser Val Thr Ser Gly Gly Ala Pro Val Gly Lys
            20                  25                  30

Pro Gly Val Pro Ala Pro Ile Phe Tyr Pro Gln Gly Pro Leu Gln Gln
        35                  40                  45

Gly Pro Ala Pro Gly Pro Ser Asn Val Gln Pro Gly Thr Ser Gln Gln
    50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
        115                 120                 125

Tyr Asn Ser Ile Gly Ser Gly Ala Asn Ala Phe Ala Tyr Ala Gln Ala
    130                 135                 140

Phe Ala Arg Val Leu Tyr Pro Leu Val Arg Gln Tyr Gly Leu Ser Ser
145                 150                 155                 160

Ser Gly Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Gln Pro Pro
            180                 185                 190

Val Thr Ile Ser Ala Ala Ser Ala Ser Ala Gly Ala Ser Ala Ala Ala
        195                 200                 205

Val Gly Gly Gly Gln Val Gly Gln Gly Pro Tyr Gly Gly Gln Gln Gln
    210                 215                 220

Ser Thr Ala Ala Ser Ala Ser Ala Ala Ala Thr Ala Thr Ser
225                 230                 235
```

<210> SEQ ID NO 25
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Gly Ala Ala Gln Lys Gln Pro Ser Gly Glu Ser Ser Val Ala Thr Ala
1               5                   10                  15

Ser Ala Ala Ala Thr Ser Val Thr Ser Gly Gly Ala Pro Val Gly Lys
            20                  25                  30

Pro Gly Val Pro Ala Pro Ile Phe Tyr Pro Gln Gly Pro Leu Gln Gln
        35                  40                  45

Gly Pro Ala Pro Gly Pro Ser Asn Val Gln Pro Gly Thr Ser Gln Gln
    50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
```

```
                        85                  90                  95
Ala Ser Ala Thr Ala Val Ala Ser Ala Phe Gln Lys Gly Leu Ala Pro
                    100                 105                 110

Tyr Gly Thr Ala Phe Ala Leu Ser Ala Ala Ser Ala Ala Ala Asp Ala
                    115                 120                 125

Tyr Asn Ser Ile Gly Ser Gly Ala Asn Ala Phe Ala Tyr Ala Gln Ala
                    130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
                    165                 170                 175

Ser Gly Thr Ser Gly Gln Gly Pro Ser Ile Gly Gln Gln Gln Pro Pro
                    180                 185                 190

Val Thr Ile Ser Ala Ala Ser Ala Ser Ala Gly Ala Ser Ala Ala Ala
                    195                 200                 205

Val Gly Gly Gly Gln Val Gly Gln Gly Pro Tyr Gly Gly Gln Gln Gln
                    210                 215                 220

Ser Thr Ala Ala Ser Ala Ser Ala Ala Ala Thr Ala Thr Ser
225                 230                 235

<210> SEQ ID NO 26
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Gly Ala Gln Lys Gln Pro Ser Gly Glu Ser Ser Val Ala Thr Ala
1               5                   10                  15

Ser Ala Ala Ala Thr Ser Val Thr Ser Ala Gly Ala Pro Val Gly Lys
                    20                  25                  30

Pro Gly Val Pro Ala Pro Ile Phe Tyr Pro Gln Gly Pro Leu Gln Gln
                    35                  40                  45

Gly Pro Ala Pro Gly Pro Ser Asn Val Gln Pro Gly Thr Ser Gln Gln
                    50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                    85                  90                  95

Ala Ser Ala Thr Ala Val Ala Ser Ala Phe Gln Lys Gly Leu Ala Pro
                    100                 105                 110

Tyr Gly Thr Ala Phe Ala Leu Ser Ala Ala Ser Ala Ala Ala Asp Ala
                    115                 120                 125

Tyr Asn Ser Ile Gly Ser Gly Ala Asn Ala Phe Ala Tyr Ala Gln Ala
                    130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
                    165                 170                 175

Ser Gly Thr Ser Gly Gln Gly Pro Ser Asn Gly Gln Gln Gln Pro Pro
                    180                 185                 190

Val Thr Ile Ser Ala Ala Ser Ala Ser Ala Gly Ala Ser Ala Ala Ala
                    195                 200                 205
```

Val Gly Gly Gln Val Ser Gln Gly Pro Tyr Gly Gln Gln Gln
    210                 215                 220

Ser Thr Ala Ala Ser Ala Ser Ala Ala Ala Thr Ala Thr Ser
225                 230                 235

<210> SEQ ID NO 27
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Gly Ala Gln Lys Gln Pro Ser Gly Glu Ser Ser Val Ala Thr Ala
1               5                   10                  15

Ser Ala Ala Ala Thr Ser Val Thr Ser Ala Gly Ala Pro Gly Gly Lys
                20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
        50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
        115                 120                 125

Tyr Asn Ser Ile Gly Ser Gly Ala Asn Ala Phe Ala Tyr Ala Gln Ala
    130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Pro Pro
            180                 185                 190

Val Thr Ile Ser Ala Ala Ser Ala Ser Ala Gly Ala Ser Ala Ala Ala
        195                 200                 205

Val Gly Gly Gln Val Gly Gln Gly Pro Tyr Gly Gly Gln Gln Gln
    210                 215                 220

Ser Thr Ala Ala Ser Ala Ser Ala Ala Ala Thr Ala Thr Ser
225                 230                 235

<210> SEQ ID NO 28
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Pro Gly Gly Tyr Gly Gly Pro Gly Gln Gln Gly Pro Gly Gln Gly
1               5                   10                  15

Gln Gln Gln Gly Pro Ala Ser Ala Ala Ala Ala Ala Ala Ala Gly
                20                  25                  30

-continued

Pro Gly Gly Tyr Gly Gly Pro Gly Gln Gln Gly Pro Gly Gln Gly Gln
                35                  40                  45
Gln Gln Gly Pro Ala Ser Ala Ala Ala Ala Ala Ala Ala Ala Ala Gly
    50                  55                  60
Pro Gly Gly Tyr Gly Gly Pro Gly Gln Gln Arg Pro Gly Gln Ala Gln
65                  70                  75                  80
Tyr Gly Arg Gly Thr Gly Gln Gln Gln Gly Pro Gly Ala Gln Gln
                85                  90                  95
Gly Pro Ala Ser Ala Ala Ala Ala Ala Ala Gly Ala Gly Leu Tyr
                100                 105                 110
Gly Gly Pro Gly Gln Gln Gly Pro Gly Gln Gln Gln Gln Gly Pro
            115                 120                 125
Ala Ser Ala Ala Ala Ala Ala Ala Ala Ala Ala Gly Pro Gly
        130                 135                 140
Gly Tyr Gly Gly Pro Gly Gln Gln Gly Pro Gly Gln Ala Gln Gln Gln
145                 150                 155                 160
Gly Pro Ala Ser Ala Ala Ala Ala Ala Ala Gly Pro Gly Gly Tyr
                165                 170                 175
Ser Gly Pro Gly Gln Gln Gly Pro Gly Gln Ala Gln Gln Gln Gly Pro
            180                 185                 190
Ala Ser Ala Ala Ala Ala Ala Ala Ala Gly Pro Gly Gly Tyr
                195                 200                 205
Gly Gly Pro Gly Gln Gln Gly Pro Gly Gln Gly Gln Gln Gly Pro
210                 215                 220
Ala Ser Ala Ala Ala Ala Ala Ala Thr Ala Ala
225                 230                 235

<210> SEQ ID NO 29
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Ala Gly Gly Asp Gly Gly Leu Phe Leu Ser Ser Gly Asp Phe Gly
1               5                   10                  15
Arg Gly Gly Ala Gly Ala Gly Ala Gly Ala Ala Ala Ser Ala Ala
                20                  25                  30
Ala Ala Ser Ser Ala Ala Ala Gly Ala Arg Gly Gly Ser Gly Phe Gly
            35                  40                  45
Val Gly Thr Gly Gly Phe Gly Arg Gly Gly Ala Gly Asp Gly Ala Ser
    50                  55                  60
Ala Ala Ala Ala Ser Ala Ala Ala Ser Ala Ala Ala Gly Ala
65                  70                  75                  80
Gly Gly Asp Ser Gly Leu Phe Leu Ser Ser Gly Asp Phe Gly Arg Gly
                85                  90                  95
Gly Ala Gly Ala Gly Ala Gly Ala Ala Ala Ser Ala Ala Ala Ala
                100                 105                 110
Ser Ala Ala Ala Ala Gly Thr Gly Gly Val Gly Leu Phe Leu Ser
            115                 120                 125
Ser Gly Asp Phe Gly Arg Gly Gly Ala Gly Ala Gly Ala Ala
        130                 135                 140
Ala Ala Ser Ala Ala Ala Ala Ser Ser Ala Ala Ala Gly Ala Arg Gly
145                 150                 155                 160

```
Gly Ser Gly Phe Gly Val Thr Gly Gly Phe Arg Gly Gly Pro
                165                 170                 175

Gly Ala Gly Thr Gly Ala Ala Ala Ser Ala Ala Ala Ser Ala
            180                 185                 190

Ala Ala Ala Gly Ala Gly Gly Asp Ser Gly Leu Phe Leu Ser Ser Glu
            195                 200                 205

Asp Phe Gly Arg Gly Gly Ala Gly Ala Gly Thr Gly Ala Ala Ala
210                 215                 220

Ser Ala Ala Ala Ala Ser Ala Ala Ala Ala
225                 230
```

<210> SEQ ID NO 30
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Gly Ala Gly Arg Gly Tyr Gly Gly Gly Tyr Gly Gly Ala Ala Ala
1               5                   10                  15

Gly Ala Gly Ala Gly Ala Gly Ala Gly Arg Gly Tyr Gly Gly Gly Tyr
            20                  25                  30

Gly Gly Gly Ala Gly Ser Gly Ala Ser Gly Ala Gly Ala Gly Gly
            35                  40                  45

Gly Ser Gly Tyr Gly Arg Gly Ala Gly Ala Gly Ala Gly Ala
50                  55                  60

Ala Ala Ala Ala Gly Ala Gly Ala Gly Ala Gly Tyr Gly Gly
65                  70                  75                  80

Gly Ala Gly Ala Gly Ala Gly Ala Ser Ala Ala Gly Ala Gly Ala
            85                  90                  95

Gly Ala Gly Gly Ala Gly Gly Tyr Gly Gly Tyr Gly Gly Ala
            100                 105                 110

Gly Ala Gly Ala Gly Ala Gly Ala Ala Ala Ala Ala Gly Ala Gly Ala
            115                 120                 125

Gly Ala Gly Ala Gly Arg Gly Tyr Gly Gly Gly Phe Gly Gly Ala
            130                 135                 140

Gly Ser Gly Ala Gly Ala Gly Ala Gly Ala Gly Gly Ser Gly Tyr
145                 150                 155                 160

Gly Arg Gly Ala Gly Gly Tyr Gly Gly Tyr Gly Gly Gly Ala Gly
            165                 170                 175

Thr Gly Ala Gly Ala Ala Ala Thr Gly Ala Gly Ala Gly Ala Gly
            180                 185                 190

Ala Gly Arg Gly Tyr Gly Gly Gly Tyr Gly Gly Ala Gly Ala Gly
            195                 200                 205

Ala Gly Ala Gly Ala Gly Ala Gly Gly Gly Ser Gly Tyr Gly Arg Gly
            210                 215                 220

Ala Gly Ala Gly Ala Ser Val Ala Ala
225                 230
```

<210> SEQ ID NO 31
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Gly Ala Leu Gly Gln Gly Ala Ser Val Trp Ser Ser Pro Gln Met Ala
1               5                   10                  15

Glu Asn Phe Met Asn Gly Phe Ser Met Ala Leu Ser Gln Ala Gly Ala
            20                  25                  30

Phe Ser Gly Gln Glu Met Lys Asp Phe Asp Asp Val Arg Asp Ile Met
        35                  40                  45

Asn Ser Ala Met Asp Lys Met Ile Arg Ser Gly Lys Ser Gly Arg Gly
    50                  55                  60

Ala Met Arg Ala Met Asn Ala Ala Phe Gly Ser Ala Ile Ala Glu Ile
65                  70                  75                  80

Val Ala Ala Asn Gly Gly Lys Glu Tyr Gln Ile Gly Ala Val Leu Asp
                85                  90                  95

Ala Val Thr Asn Thr Leu Leu Gln Leu Thr Gly Asn Ala Asp Asn Gly
            100                 105                 110

Phe Leu Asn Glu Ile Ser Arg Leu Ile Thr Leu Phe Ser Ser Val Glu
        115                 120                 125

Ala Asn Asp Val Ser Ala Ser Ala Gly Ala Asp Ala Ser Gly Ser Ser
    130                 135                 140

Gly Pro Val Gly Gly Tyr Ser Ser Gly Ala Gly Ala Val Gly Gln
145                 150                 155                 160

Gly Thr Ala Gln Ala Val Gly Tyr Gly Gly Ala Gln Gly Val Ala
                165                 170                 175

Ser Ser Ala Ala Ala Gly Ala Thr Asn Tyr Ala Gln Gly Val Ser Thr
            180                 185                 190

Gly Ser Thr Gln Asn Val Ala Thr Ser Thr Val Thr Thr Thr Thr Asn
        195                 200                 205

Val Ala Gly Ser Thr Ala Thr Gly Tyr Asn Thr Gly Tyr Gly Ile Gly
    210                 215                 220

Ala Ala Ala Gly Ala Ala Ala
225                 230

<210> SEQ ID NO 32
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Gly Gln Gly Gly Gln Gly Gly Tyr Asp Gly Leu Gly Ser Gln Gly
1               5                   10                  15

Ala Gly Gln Gly Gly Tyr Gly Gln Gly Gly Ala Ala Ala Ala Ala Ala
            20                  25                  30

Ala Ala Ser Gly Ala Gly Ser Ala Gln Arg Gly Gly Leu Gly Ala Gly
        35                  40                  45

Gly Ala Gly Gln Gly Tyr Gly Ala Gly Ser Gly Gly Gln Gly Gly Ala
    50                  55                  60

Gly Gln Gly Gly Ala Ala Ala Thr Ala Ala Ala Gly Gly Gln Gly
65                  70                  75                  80

Gly Gly Gln Gly Gly Tyr Gly Gly Leu Gly Ser Gln Gly Ser Gly Gln
                85                  90                  95

Gly Gly Tyr Gly Gln Gly Gly Ala Ala Ala Ala Ala Ala Ala Ala Ser

```
                100                 105                 110
Gly Asp Gly Gly Ala Gly Gln Glu Gly Leu Gly Ala Gly Gly Ala Gly
            115                 120                 125

Gln Gly Tyr Gly Ala Gly Leu Gly Gly Gln Gly Gly Ala Gly Gln Gly
        130                 135                 140

Gly Ala Ala Ala Ala Ala Ala Ala Ala Gly Gly Gln Gly Gly Gly Gln
145                 150                 155                 160

Gly Gly Tyr Gly Gly Leu Gly Ser Gln Gly Ala Gly Gln Gly Gly Tyr
                165                 170                 175

Gly Gln Gly Gly Ala Ala Ala Ala Ala Ala Ala Ser Gly Ala Gly
            180                 185                 190

Gly Ala Gly Gln Gly Gly Leu Gly Ala Ala Gly Gln Gly Tyr
        195                 200                 205

Gly Ala Gly Ser Gly Gly Gln Gly Gly Ala Gly Gln Gly Gly Ala Ala
        210                 215                 220

Ala Ala Ala Ala Ala Ala Ala
225                 230

<210> SEQ ID NO 33
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Gly Gln Gly Gly Gln Gly Gly Tyr Gly Gly Leu Gly Ser Gln Gly
1               5                   10                  15

Ala Gly Gln Gly Gly Tyr Gly Gln Gly Gly Val Ala Ala Ala Ala
            20                  25                  30

Ala Ala Ser Gly Ala Gly Gly Ala Gly Arg Gly Gly Leu Gly Ala Gly
        35                  40                  45

Gly Ala Gly Gln Glu Tyr Gly Ala Val Ser Gly Gly Gln Gly Gly Ala
    50                  55                  60

Gly Gln Gly Gly Glu Ala Ala Ala Ala Ala Ala Ala Gly Gly Gln
65                  70                  75                  80

Gly Gly Gln Gly Gly Tyr Gly Gly Leu Gly Ser Gln Gly Ala Gly Gln
                85                  90                  95

Gly Gly Tyr Gly Gln Gly Gly Ala Ala Ala Ala Ala Ala Ala Ser
            100                 105                 110

Gly Ala Gly Gly Ala Arg Arg Gly Gly Leu Gly Ala Gly Gly Ala Gly
        115                 120                 125

Gln Gly Tyr Gly Ala Gly Leu Gly Gly Gln Gly Gly Ala Gly Gln Gly
    130                 135                 140

Ser Ala Ser Ala Ala Ala Ala Ala Ala Gly Gly Gln Gly Gly Gln
145                 150                 155                 160

Gly Gly Tyr Gly Gly Leu Gly Ser Gln Gly Ser Gly Gly Tyr
                165                 170                 175

Gly Gln Gly Gly Ala Ala Ala Ala Ala Ala Ala Ser Gly Ala Gly
            180                 185                 190

Gly Ala Gly Arg Gly Ser Leu Gly Ala Gly Gly Ala Gly Gln Gly Tyr
        195                 200                 205

Gly Ala Gly Leu Gly Gly Gln Gly Gly Ala Gly Gln Gly Gly Ala Ala
    210                 215                 220
```

Ala Ala Ala Ser Ala Ala Ala
225                 230

<210> SEQ ID NO 34
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Pro Gly Gly Tyr Gly Gly Pro Gly Gln Gln Gly Pro Gly Gln Gly
1               5                   10                  15

Gln Tyr Gly Pro Gly Thr Gly Gln Gln Gly Gly Pro Gly Gly Gln
            20                  25                  30

Gln Gly Pro Val Gly Ala Ala Ala Ala Ala Ala Ala Val Ser Ser
            35                  40                  45

Gly Gly Tyr Gly Ser Gln Gly Ala Gly Gln Gly Gln Gln Gly Ser
50                      55                  60

Gly Gln Arg Gly Pro Ala Ala Gly Pro Gly Gly Tyr Ser Gly Pro
65              70                  75                  80

Gly Gln Gln Gly Pro Gly Gln Gly Gln Gln Gly Pro Ala Ser Ala
                85                  90                  95

Ala Ala Ala Ala Ala Ala Ala Gly Pro Gly Gly Tyr Gly Gly Ser
            100                 105                 110

Gly Gln Gln Gly Pro Gly Gln Gly Arg Gly Thr Gly Gln Gln Gly Gln
            115                 120                 125

Gly Pro Gly Gly Gln Gln Gly Pro Ala Ser Ala Ala Ala Ala Ala
            130                 135                 140

Ala Gly Pro Gly Gly Tyr Gly Gly Pro Gly Gln Gln Gly Pro Gly Gln
145             150                 155                 160

Gly Gln Tyr Gly Pro Gly Thr Gly Gln Gln Gly Gln Gly Pro Ala Ser
                165                 170                 175

Ala Ala Ala Ala Ala Ala Gly Pro Gly Gly Tyr Gly Gly Pro Gly
            180                 185                 190

Gln Gln Gly Pro Gly Gln Gly Gln Tyr Gly Pro Gly Thr Gly Gln Gln
            195                 200                 205

Gly Gln Gly Pro Gly Gly Gln Gln Gly Pro Gly Gly Ala Ser Ala Ala
        210                 215                 220

Ala Ala Ala Ala Ala
225

<210> SEQ ID NO 35
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
            20                  25                  30

Pro Gly Gly Ala Gly Gln Gln Gly Pro Gly Gly Gln Gly Pro Tyr Gly
            35                  40                  45

```
Pro Gly Ala Ala Ala Ala Ala Ala Ala Gly Gly Tyr Gly Pro
    50                  55                  60

Gly Ala Gly Gln Gln Gly Pro Gly Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Gly Ser Gly Gln Gln Gly Pro
            100                 105                 110

Gly Gly Gln Gly Pro Tyr Gly Pro Ser Ala Ala Ala Ala Ala Ala
            115                 120                 125

Ala Ala Gly Gly Tyr Gly Pro Gly Ala Gly Gln Arg Ser Gln Gly Pro
130                 135                 140

Gly Gly Gln Gly Pro Tyr Gly Pro Gly Ala Gly Gln Gln Gly Pro Gly
145                 150                 155                 160

Ser Gln Gly Pro Gly Ser Gly Gln Gln Gly Pro Gly Gly Gln Gly
                165                 170                 175

Pro Tyr Gly Pro Ser Ala Ala Ala Ala Ala Ala Gly Pro Gly
        180                 185                 190

Ala Gly Arg Gln Gly Pro Gly Ser Gln Gly Pro Gly Ser Gly Gln
            195                 200                 205

Gln Gly Pro Gly Gly Gln Gly Pro Tyr Gly Pro Ser Ala Ala Ala
    210                 215                 220

Ala Ala Ala Ala
225

<210> SEQ ID NO 36
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Gln Gly Gly Gln Gly Gly Gln Gly Gly Leu Gly Gln Gly Gly Tyr
1               5                   10                  15

Gly Gln Gly Ala Gly Ser Ser Ala Ala Ala Ala Ala Ala Ala Ala Ala
                20                  25                  30

Ala Ala Ala Ala Ala Gly Arg Gly Gln Gly Gly Tyr Gly Gln Gly Ser
            35                  40                  45

Gly Gly Asn Ala Ala Ala Ala Ala Ala Ala Ala Ala Ala Ala Ala Ser
        50                  55                  60

Gly Gln Gly Ser Gln Gly Gln Gly Gln Gln Gly Gly Tyr
65                  70                  75                  80

Gly Gln Gly Ala Gly Ser Ser Ala Ala Ala Ala Ala Ala Ala Ala Ala
                85                  90                  95

Ala Ala Ala Ala Ser Gly Arg Gly Gln Gly Gly Tyr Gly Gln Gly Ala
            100                 105                 110

Gly Gly Asn Ala Ala Ala Ala Ala Ala Ala Ala Ala Ala Ala Ala Ala
        115                 120                 125

Ala Gly Gln Gly Gly Gln Gly Gly Tyr Gly Gly Leu Gly Gln Gly Gly
130                 135                 140

Tyr Gly Gln Gly Ala Gly Ser Ser Ala Ala Ala Ala Ala Ala Ala Ala
145                 150                 155                 160

Ala Ala Ala Ala Gly Gly Gln Gly Gly Gln Gly Gln Gly Gly Tyr Gly
                165                 170                 175
```

```
Gln Gly Ser Gly Gly Ser Ala Ala Ala Ala Ala Ala Ala Ala
                180                 185                 190

Ala Ala Ala Ala Ala Gly Arg Gly Gln Gly Gly Tyr Gly Gln Gly Ser
            195                 200                 205

Gly Gly Asn Ala Ala Ala Ala Ala Ala Ala Ala Ala Ala Ala
        210                 215                 220

Ala
225

<210> SEQ ID NO 37
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Arg Gly Pro Gly Gly Tyr Gly Pro Gly Gln Gln Gly Pro Gly Gly
1               5                   10                  15

Pro Gly Ala Ala Ala Ala Ala Ala Gly Pro Gly Gly Tyr Gly Pro Gly
            20                  25                  30

Gly Tyr Gly Pro Gly Gln Gln Gly Pro Gly Gly Pro Gly Ala Ala Ala
        35                  40                  45

Ala Ala Ala Ala Gly Arg Gly Pro Gly Gly Tyr Gly Pro Gly Gln Gln
    50                  55                  60

Gly Pro Gly Gln Gln Gly Pro Gly Gly Ser Gly Ala Ala Ala Ala Ala
65                  70                  75                  80

Ala Gly Arg Gly Pro Gly Gly Tyr Gly Pro Gly Gln Gln Gly Pro Gly
                85                  90                  95

Gly Pro Gly Ala Ala Ala Ala Ala Ala Gly Pro Gly Gly Tyr Gly Pro
            100                 105                 110

Gly Gln Gln Gly Pro Gly Ala Ala Ala Ala Ala Ala Ala Gly Arg
        115                 120                 125

Gly Pro Gly Gly Tyr Gly Pro Gly Gln Gln Gly Pro Gly Gly Pro Gly
    130                 135                 140

Ala Ala Ala Ala Ala Ala Gly Arg Gly Pro Gly Gly Tyr Gly Pro
145                 150                 155                 160

Gly Gln Gln Gly Pro Gly Gln Gln Gly Pro Gly Gly Ser Gly Ala Ala
                165                 170                 175

Ala Ala Ala Ala Gly Arg Gly Pro Gly Gly Tyr Gly Pro Gly Gln Gln
            180                 185                 190

Gly Pro Gly Gly Pro Gly Ala Ala Ala Ala Ala Ala Gly Pro Gly Gly
        195                 200                 205

Tyr Gly Pro Gly Gln Gln Gly Pro Gly Ala Ala Ala Ala Ala Ala
    210                 215                 220

Ala
225

<210> SEQ ID NO 38
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38
```

```
Gly Arg Gly Pro Gly Tyr Gly Pro Gly Gln Gln Gly Pro Gly Gly
1               5                   10                  15

Ser Gly Ala Ala Ala Ala Ala Gly Arg Gly Pro Gly Gly Tyr Gly
            20                  25                  30

Pro Gly Gln Gln Gly Pro Gly Gly Pro Gly Ala Ala Ala Ala Ala
            35                  40                  45

Gly Pro Gly Gly Tyr Gly Pro Gly Gln Gln Gly Thr Gly Ala Ala
    50                  55                  60

Ala Ala Ala Ala Gly Ser Gly Ala Gly Gly Tyr Gly Pro Gly Gln Gln
65                  70                  75                  80

Gly Pro Gly Gly Pro Gly Ala Ala Ala Ala Ala Gly Pro Gly Gly
                85                  90                  95

Tyr Gly Pro Gly Gln Gln Gly Pro Gly Ala Ala Ala Ala Ala Ala
            100                 105                 110

Gly Ser Gly Pro Gly Gly Tyr Gly Pro Gly Gln Gln Gly Pro Gly Gly
            115                 120                 125

Ser Ser Ala Ala Ala Ala Ala Gly Pro Gly Arg Tyr Gly Pro Gly
    130                 135                 140

Gln Gln Gly Pro Gly Ala Ala Ala Ala Ser Ala Gly Arg Gly Pro
145                 150                 155                 160

Gly Gly Tyr Gly Pro Gly Gln Gln Gly Pro Gly Pro Gly Ala Ala
            165                 170                 175

Ala Ala Ala Ala Gly Pro Gly Gly Tyr Gly Pro Gly Gln Gln Gly Pro
            180                 185                 190

Gly Ala Ala Ala Ala Ala Ala Gly Ser Gly Pro Gly Gly Tyr Gly
            195                 200                 205

Pro Gly Gln Gln Gly Pro Gly Gly Pro Gly Ala Ala Ala Ala Ala
            210                 215                 220

Ala
225

<210> SEQ ID NO 39
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Ala Ala Ala Thr Ala Gly Ala Gly Ala Ser Val Ala Gly Gly Tyr
1               5                   10                  15

Gly Gly Gly Ala Gly Ala Ala Gly Ala Gly Ala Gly Gly Tyr Gly
            20                  25                  30

Gly Gly Tyr Gly Ala Val Ala Gly Ser Gly Ala Gly Ala Ala Ala
            35                  40                  45

Ala Ser Ser Gly Ala Gly Gly Ala Ala Gly Tyr Gly Arg Gly Tyr Gly
50                  55                  60

Ala Gly Ser Gly Ala Gly Ala Gly Thr Val Ala Ala Tyr Gly
65                  70                  75                  80

Gly Ala Gly Gly Val Ala Thr Ser Ser Ser Ala Thr Ala Ser Gly
            85                  90                  95

Ser Arg Ile Val Thr Ser Gly Gly Tyr Gly Tyr Gly Thr Ser Ala Ala
            100                 105                 110

Ala Gly Ala Gly Val Ala Ala Gly Ser Tyr Ala Gly Ala Val Asn Arg
```

```
            115                 120                 125
Leu Ser Ser Ala Glu Ala Ala Ser Arg Val Ser Asn Ile Ala Ala
    130                 135                 140

Ile Ala Ser Gly Gly Ala Ser Ala Leu Pro Ser Val Ile Ser Asn Ile
145                 150                 155                 160

Tyr Ser Gly Val Val Ala Ser Gly Val Ser Ser Asn Glu Ala Leu Ile
                165                 170                 175

Gln Ala Leu Leu Glu Leu Leu Ser Ala Leu Val His Val Leu Ser Ser
            180                 185                 190

Ala Ser Ile Gly Asn Val Ser Ser Val Gly Val Asp Ser Thr Leu Asn
            195                 200                 205

Val Val Gln Asp Ser Val Gly Gln Tyr Val Gly
            210                 215

<210> SEQ ID NO 40
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Gly Gln Gly Gly Phe Ser Gly Gln Gly Gln Gly Gly Phe Gly Pro
1               5                   10                  15

Gly Ala Gly Ser Ser Ala Ala Ala Ala Ala Ala Ala Ala Ala Ala Ala
                20                  25                  30

Arg Gln Gly Gly Gln Gly Gln Gly Gly Phe Gly Gln Gly Ala Gly Gly
            35                  40                  45

Asn Ala Ala Ala Ala Ala Ala Ala Ala Ala Ala Ala Ala Ala Ala Gln
        50                  55                  60

Gln Gly Gly Gln Gly Gly Phe Ser Gly Arg Gly Gln Gly Gly Phe Gly
65              70                  75                  80

Pro Gly Ala Gly Ser Ser Ala Ala Ala Ala Ala Gly Gln Gly Gly
                85                  90                  95

Gln Gly Gln Gly Gly Phe Gly Gln Gly Ala Gly Gly Asn Ala Ala Ala
            100                 105                 110

Ala Ala Ala Ala Ala Ala Ala Ala Ala Ala Ala Gly Gln Gly Gly
        115                 120                 125

Gln Gly Arg Gly Gly Phe Gly Gln Gly Ala Gly Gly Asn Ala Ala Ala
        130                 135                 140

Ala Ala Ala Ala Ala Ala Ala Ala Ala Ala Gln Gln Gly Gly
145                 150                 155                 160

Gln Gly Gly Phe Gly Gly Arg Gly Gln Gly Gly Phe Gly Pro Gly Ala
                165                 170                 175

Gly Ser Ser Ala Ala Ala Ala Ala Gly Gln Gly Gly Gln Gly Arg
            180                 185                 190

Gly Gly Phe Gly Gln Gly Ala Gly Gly Asn Ala Ala Ala Ala Ser Ala
        195                 200                 205

Ala Ala Ala Ala Ser Ala Ala Ala Ala Gly Gln
        210                 215

<210> SEQ ID NO 41
<211> LENGTH: 218
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 41

Gly Gly Tyr Gly Pro Gly Ala Gly Gln Gln Gly Pro Gly Ala Gly
1               5                   10                  15

Gln Gln Gly Pro Gly Ser Gln Gly Pro Gly Gly Ala Gly Gln Gln Gly
            20                  25                  30

Pro Gly Gly Gln Gly Pro Tyr Gly Pro Gly Ala Ala Ala Ala Ala
            35                  40                  45

Ala Val Gly Gly Tyr Gly Pro Gly Ala Gly Gln Gln Gly Pro Gly Ser
50                      55                  60

Gln Gly Pro Gly Ser Gly Gln Gln Gly Pro Gly Gln Gly Pro
65              70                  75                  80

Tyr Gly Pro Ser Ala Ala Ala Ala Ala Ala Ala Gly Gly Tyr Gly
                85                  90                  95

Pro Gly Ala Gly Gln Gln Gly Pro Gly Ser Gln Gly Pro Gly Ser Gly
            100                 105                 110

Gly Gln Gln Gly Pro Gly Gly Leu Gly Pro Tyr Gly Pro Ser Ala Ala
            115                 120                 125

Ala Ala Ala Ala Ala Gly Gly Tyr Gly Pro Gly Ala Gly Gln Gln
    130                 135                 140

Gly Pro Gly Ser Gln Gly Pro Gly Ser Gly Gln Gln Arg Pro Gly
145                 150                 155                 160

Gly Leu Gly Pro Tyr Gly Pro Ser Ala Ala Ala Ala Ala Ala Ala
                165                 170                 175

Gly Gly Tyr Gly Pro Gly Ala Gly Gln Gln Gly Pro Gly Ser Gln Gly
                180                 185                 190

Pro Gly Ser Gly Gln Gln Arg Pro Gly Gly Leu Gly Pro Tyr Gly
            195                 200                 205

Pro Ser Ala Ala Ala Ala Ala Ala Ala
            210                 215

<210> SEQ ID NO 42
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Ala Gly Ala Gly Gly Gly Tyr Gly Gly Tyr Ser Ala Gly Gly
1               5                   10                  15

Gly Ala Gly Ala Gly Ser Gly Ala Ala Ala Gly Ala Gly Ala Gly Arg
            20                  25                  30

Gly Gly Ala Gly Gly Tyr Ser Ala Gly Ala Gly Thr Gly Ala Gly Ala
            35                  40                  45

Ala Ala Gly Ala Gly Thr Ala Gly Gly Tyr Ser Gly Tyr Gly Ala
50                      55                  60

Gly Ala Ser Ser Ser Ala Gly Ser Ser Phe Ile Ser Ser Ser Met
65              70                  75                  80

Ser Ser Ser Gln Ala Thr Gly Tyr Ser Ser Ser Gly Tyr Gly Gly
                85                  90                  95

Gly Ala Ala Ser Ala Ala Ala Gly Ala Gly Ala Ala Ala Gly Gly Tyr
            100                 105                 110

Gly Gly Gly Tyr Gly Ala Gly Ala Gly Ala Ala Ala Ser
            115                 120                 125

Gly Ala Thr Gly Arg Val Ala Asn Ser Leu Gly Ala Met Ala Ser Gly
            130                 135                 140

Gly Ile Asn Ala Leu Pro Gly Val Phe Ser Asn Ile Phe Ser Gln Val
145                 150                 155                 160

Ser Ala Ala Ser Gly Ala Ser Gly Ala Val Leu Val Gln Ala
            165                 170                 175

Leu Thr Glu Val Ile Ala Leu Leu Leu His Ile Leu Ser Ser Ala Ser
            180                 185                 190

Ile Gly Asn Val Ser Ser Gln Gly Leu Glu Gly Ser Met Ala Ile Ala
            195                 200                 205

Gln Gln Ala Ile Gly Ala Tyr Ala Gly
            210                 215

<210> SEQ ID NO 43
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Ala Gly Ala Gly Gly Ala Gly Gly Tyr Ala Gln Gly Tyr Gly Ala
1               5                   10                  15

Gly Ala Gly Ala Gly Ala Gly Ala Thr Gly Ala Gly Gly Ala Gly
            20                  25                  30

Gly Tyr Gly Gln Gly Tyr Gly Ala Ser Gly Ala Gly Ala Gly Gly
            35                  40                  45

Ala Gly Gly Tyr Gly Ala Gly Ala Gly Ala Gly Ala Gly Ala Gly Asp
            50                  55                  60

Ala Ser Gly Tyr Gly Gln Gly Tyr Gly Asp Gly Ala Gly Ala Gly Ala
65                  70                  75                  80

Gly Ala Ala Ala Ala Ala Gly Ala Ala Ala Gly Ala Arg Gly Ala Gly
            85                  90                  95

Gly Tyr Gly Gly Gly Ala Gly Ala Gly Ala Gly Ala Gly Ala Gly Ala
            100                 105                 110

Ala Gly Gly Tyr Gly Gln Gly Tyr Gly Ala Gly Ala Gly Glu Gly Ala
            115                 120                 125

Gly Ala Gly Ala Gly Ala Gly Ala Val Ala Gly Ala Gly Ala Ala Ala
            130                 135                 140

Ala Ala Gly Ala Gly Ala Gly Ala Gly Ala Glu Gly Tyr Gly Ala
145                 150                 155                 160

Gly Ala Gly Ala Gly Gly Ala Gly Gly Tyr Gly Gln Ser Tyr Gly Asp
            165                 170                 175

Gly Ala Ala Ala Ala Ala Gly Ser Gly Ala Gly Ala Gly Gly Ser Gly
            180                 185                 190

Gly Tyr Gly Ala Gly Ala Gly Ala Gly Ser Gly Ala Gly Ala Ala Gly
            195                 200                 205

Gly Tyr Gly Gly Gly Ala Gly Ala
            210                 215

<210> SEQ ID NO 44
<211> LENGTH: 216
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 44

Gly Pro Gly Gly Tyr Gly Pro Gly Gln Gln Gly Pro Gly Gly Tyr Gly
1               5                   10                  15

Pro Gly Gln Gln Gly Pro Gly Arg Tyr Gly Pro Gly Gln Gln Gly Pro
                20                  25                  30

Ser Gly Pro Gly Ser Ala Ala Ala Ala Ala Gly Ser Gly Gln Gln
            35                  40                  45

Gly Pro Gly Gly Tyr Gly Pro Arg Gln Gln Gly Pro Gly Gly Tyr Gly
        50                  55                  60

Gln Gly Gln Gly Pro Ser Gly Pro Gly Ser Ala Ala Ala Ser
65                  70                  75                  80

Ala Ala Ala Ser Ala Glu Ser Gly Gln Gln Gly Pro Gly Gly Tyr Gly
                85                  90                  95

Pro Gly Gln Gln Gly Pro Gly Gly Tyr Gly Pro Gly Gln Gln Gly Pro
                100                 105                 110

Gly Gly Tyr Gly Pro Gly Gln Gln Gly Pro Ser Gly Pro Gly Ser Ala
            115                 120                 125

Ala Ala Ala Ala Ala Ala Ser Gly Pro Gly Gln Gln Gly Pro Gly
        130                 135                 140

Gly Tyr Gly Pro Gly Gln Gln Gly Pro Gly Gly Tyr Gly Pro Gly Gln
145                 150                 155                 160

Gln Gly Pro Ser Gly Pro Gly Ser Ala Ala Ala Ala Ala Ala Ala
                165                 170                 175

Ser Gly Pro Gly Gln Gln Gly Pro Gly Gly Tyr Gly Pro Gly Gln Gln
                180                 185                 190

Gly Pro Gly Gly Tyr Gly Pro Gly Gln Gln Gly Leu Ser Gly Pro Gly
            195                 200                 205

Ser Ala Ala Ala Ala Ala Ala Ala
        210                 215

<210> SEQ ID NO 45
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Arg Gly Pro Gly Gly Tyr Gly Gln Gly Gln Gln Gly Pro Gly Gly
1               5                   10                  15

Pro Gly Ala Ala Ala Ala Ala Ala Gly Pro Gly Tyr Gly Pro Gly
                20                  25                  30

Gln Gln Gly Pro Gly Ala Ala Ala Ala Ala Ala Gly Ser Gly Pro
            35                  40                  45

Gly Gly Tyr Gly Pro Gly Gln Gln Pro Gly Arg Ser Gly Ala Ala
        50                  55                  60

Ala Ala Ala Ala Ala Gly Arg Gly Pro Gly Gly Tyr Gly Pro Gly
65                  70                  75                  80

Gln Gln Gly Pro Gly Gly Pro Gly Ala Ala Ala Ala Ala Gly Pro
                85                  90                  95

Gly Gly Tyr Gly Pro Gly Gln Gln Gly Pro Gly Ala Ala Ala Ala Ala
            100                 105                 110
```

-continued

Ser Ala Gly Arg Gly Pro Gly Tyr Gly Pro Gly Gln Gln Gly Pro
        115                 120                 125

Gly Gly Ser Gly Ala Ala Ala Ala Ala Gly Arg Gly Pro Gly Gly
    130                 135                 140

Tyr Gly Pro Gly Gln Gln Gly Pro Gly Pro Gly Ala Ala Ala Ala
145                 150                 155                 160

Ala Ala Ala Gly Arg Gly Pro Gly Gly Tyr Gly Pro Gly Gln Gln Gly
            165                 170                 175

Pro Gly Gln Gln Gly Pro Gly Gly Ser Gly Ala Ala Ala Ala Ala
            180                 185                 190

Gly Arg Gly Pro Gly Gly Tyr Gly Pro Gly Gln Gln Gly Pro Gly Gly
        195                 200                 205

Pro Gly Ala Ala Ala Ala Ala Ala
        210                 215

<210> SEQ ID NO 46
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Val Gly Ala Gly Gly Glu Gly Gly Tyr Asp Gln Gly Tyr Gly Ala
1               5                   10                  15

Gly Ala Gly Ala Gly Ser Gly Gly Ala Gly Gly Ala Gly Gly Tyr
            20                  25                  30

Gly Gly Gly Ala Gly Ala Gly Ser Gly Gly Gly Ala Gly Ala Gly
        35                  40                  45

Gly Tyr Gly Gly Gly Ala Gly Ala Gly Ala Gly Ala Gly Gly
    50                  55                  60

Ala Gly Gly Tyr Gly Gly Gly Ala Gly Ala Gly Thr Gly Ala Arg Ala
65                  70                  75                  80

Gly Ala Gly Gly Val Gly Gly Tyr Gly Gln Ser Tyr Gly Ala Gly Ala
            85                  90                  95

Ser Ala Ala Ala Gly Ala Gly Val Gly Ala Gly Gly Ala Gly Ala Gly
            100                 105                 110

Gly Ala Gly Gly Tyr Gly Gln Gly Tyr Gly Ala Gly Ala Gly Ile Gly
        115                 120                 125

Ala Gly Asp Ala Gly Gly Tyr Gly Gly Gly Ala Gly Ala Gly Ala Ser
    130                 135                 140

Ala Gly Ala Gly Gly Tyr Gly Gly Gly Ala Gly Ala Gly Ala Gly Gly
145                 150                 155                 160

Val Gly Gly Tyr Gly Lys Gly Tyr Gly Ala Gly Ser Gly Ala Gly Ala
            165                 170                 175

Ala Ala Ala Ala Gly Ala Gly Ala Gly Ser Ala Gly Gly Tyr Gly Arg
        180                 185                 190

Gly Asp Gly Ala Gly Ala Gly Gly Ala Ser Gly Tyr Gly Gln Gly Tyr
    195                 200                 205

Gly Ala Gly Ala Ala Ala
        210

<210> SEQ ID NO 47
<211> LENGTH: 212
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 47

Gly Tyr Gly Ala Gly Ala Gly Arg Gly Tyr Gly Ala Gly Ala Gly Ala
1               5                   10                  15

Gly Ala Gly Ala Val Ala Ala Ser Gly Ala Gly Ala Gly Ala Gly Tyr
            20                  25                  30

Gly Ala Gly Ala Gly Ala Gly Ala Gly Ala Gly Tyr Gly Ala Gly Ala
        35                  40                  45

Gly Arg Gly Tyr Gly Ala Gly Ala Gly Ala Gly Ala Gly Ser Gly Ala
    50                  55                  60

Ala Ser Gly Ala Gly Ala Gly Ala Gly Tyr Gly Ala Gly Ala Gly Ala
65                  70                  75                  80

Gly Ala Gly Tyr Gly Ala Gly Ala Gly Ser Gly Tyr Gly Thr Gly Ala
                85                  90                  95

Gly Ala Gly Ala Gly Ala Ala Ala Ala Gly Gly Ala Gly Ala Gly Ala
            100                 105                 110

Gly Tyr Gly Ala Gly Ala Gly Arg Gly Tyr Gly Ala Gly Ala Gly Ala
        115                 120                 125

Gly Ala Ala Ser Gly Ala Gly Ala Gly Ala Gly Ala Gly Ala Ala Ser
    130                 135                 140

Gly Ala Gly Ala Gly Ser Gly Tyr Gly Ala Gly Ala Ala Ala Ala Gly
145                 150                 155                 160

Gly Ala Gly Ala Gly Ala Gly Gly Gly Tyr Gly Ala Gly Ala Gly Arg
                165                 170                 175

Gly Tyr Gly Ala Gly Ala Gly Ala Gly Ala Gly Ala Gly Ser Gly Ser
            180                 185                 190

Gly Ser Ala Ala Gly Tyr Gly Gln Gly Tyr Gly Ser Gly Ser Gly Ala
        195                 200                 205

Gly Ala Ala Ala
    210

<210> SEQ ID NO 48
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Gln Gly Thr Asp Ser Ser Ala Ser Ser Val Ser Thr Ser Thr Ser
1               5                   10                  15

Val Ser Ser Ser Ala Thr Gly Pro Asp Thr Gly Tyr Pro Val Gly Tyr
            20                  25                  30

Tyr Gly Ala Gly Gln Ala Glu Ala Ala Ser Ala Ala Ala Ala Ala Ala
        35                  40                  45

Ala Ala Ser Ala Ala Glu Ala Ala Thr Ile Ala Gly Leu Gly Tyr Gly
    50                  55                  60

Arg Gln Gly Gln Gly Thr Asp Ser Ser Ala Ser Ser Val Ser Thr Ser
65                  70                  75                  80

Thr Ser Val Ser Ser Ser Ala Thr Gly Pro Asp Met Gly Tyr Pro Val
                85                  90                  95

Gly Asn Tyr Gly Ala Gly Gln Ala Glu Ala Ala Ala Ser Ala Ala Ala
```

```
                  100                 105                 110

Ala Ala Ala Ala Ser Ala Ala Glu Ala Ala Thr Ile Ala Ser Leu Gly
            115                 120                 125

Tyr Gly Arg Gln Gly Gln Gly Thr Asp Ser Ser Ala Ser Ser Val Ser
        130                 135                 140

Thr Ser Thr Ser Val Ser Ser Ser Ala Thr Gly Pro Gly Ser Arg Tyr
145                 150                 155                 160

Pro Val Arg Asp Tyr Gly Ala Asp Gln Ala Glu Ala Ala Ala Ser Ala
                165                 170                 175

Ala Ala Ala Ala Ala Ala Ala Ser Ala Ala Glu Glu Ile Ala Ser
            180                 185                 190

Leu Gly Tyr Gly Arg Gln
        195

<210> SEQ ID NO 49
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Gln Gly Thr Asp Ser Val Ala Ser Ser Ala Ser Ser Ser Ala Ser
1               5                   10                  15

Ala Ser Ser Ser Ala Thr Gly Pro Asp Thr Gly Tyr Pro Val Gly Tyr
            20                  25                  30

Tyr Gly Ala Gly Gln Ala Glu Ala Ala Ala Ser Ala Ala Ala Ala Ala
        35                  40                  45

Ala Ala Ser Ala Ala Glu Ala Ala Thr Ile Ala Gly Leu Gly Tyr Gly
    50                  55                  60

Arg Gln Gly Gln Gly Thr Asp Ser Ser Ala Ser Ser Val Ser Thr Ser
65                  70                  75                  80

Thr Ser Val Ser Ser Ser Ala Thr Gly Pro Gly Ser Arg Tyr Pro Val
                85                  90                  95

Arg Asp Tyr Gly Ala Asp Gln Ala Glu Ala Ala Ala Ser Ala Thr Ala
            100                 105                 110

Ala Ala Ala Ala Ala Ala Ser Ala Ala Glu Glu Ile Ala Ser Leu Gly
        115                 120                 125

Tyr Gly Arg Gln Gly Gln Gly Thr Asp Ser Val Ala Ser Ser Ala Ser
    130                 135                 140

Ser Ser Ala Ser Ala Ser Ser Ser Ala Thr Gly Pro Asp Thr Gly Tyr
145                 150                 155                 160

Pro Val Gly Tyr Tyr Gly Ala Gly Gln Ala Glu Ala Ala Ala Ser Ala
                165                 170                 175

Ala Ala Ala Ala Ala Ser Ala Ala Glu Ala Ala Thr Ile Ala Gly
            180                 185                 190

Leu Gly Tyr Gly Arg Gln
        195

<210> SEQ ID NO 50
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 50

Gly Gln Gly Gly Gln Gly Gly Tyr Gly Gly Leu Gly Gln Gly Gly Tyr
1               5                   10                  15

Gly Gln Gly Ala Gly Ser Ser Ala Ala Ala Ala Ala Ala Ala Ala Ala
            20                  25                  30

Ala Ala Ala Ala Gly Gly Gln Gly Gly Gln Gly Gln Gly Arg Tyr Gly
        35                  40                  45

Gln Gly Ala Gly Ser Ser Ala Ala Ala Ala Ala Ala Ala Ala Ala Ala
    50                  55                  60

Ala Ala Ala Ala Gly Arg Gly Gln Gly Tyr Gly Gln Gly Ser Gly
65                  70                  75                  80

Gly Asn Ala Ala Ala Ala Ala Ala Ala Ala Ala Ala Ala Ala Ser Gly
                85                  90                  95

Gln Gly Ser Gln Gly Gly Gln Gly Gly Gln Gly Gln Gly Gly Tyr Gly
            100                 105                 110

Gln Gly Ala Gly Ser Ser Ala Ala Ala Ala Ala Ala Ala Ala Ala Ala
            115                 120                 125

Ala Ala Ala Ser Gly Arg Gly Gln Gly Gly Tyr Gly Gln Gly Ala Gly
        130                 135                 140

Gly Asn Ala Ala Ala Ala Ala Ala Ala Ala Ala Ala Ala Ala Ala Ala
145                 150                 155                 160

Gly Gln Gly Gly Gln Gly Gly Tyr Gly Gly Leu Gly Gln Gly Gly Tyr
                165                 170                 175

Gly Gln Gly Ala Gly Ser Ser Ala Ala Ala Ala Ala Ala Ala Ala Ala
            180                 185                 190

Ala Ala Ala
        195

<210> SEQ ID NO 51
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Gly Leu Gly Gly Gln Gly Gly Leu Gly Gly Leu Gly Ser Gln Gly
1               5                   10                  15

Ala Gly Leu Gly Gly Tyr Gly Gln Gly Gly Ala Gly Gln Gly Gly Ala
            20                  25                  30

Ala Ala Ala Ala Ala Ala Ala Gly Gly Leu Gly Gly Gln Gly Gly Arg
        35                  40                  45

Gly Gly Leu Gly Ser Gln Gly Ala Gly Gln Gly Gly Tyr Gly Gln Gly
    50                  55                  60

Gly Ala Gly Gln Gly Gly Ala Ala Ala Ala Ala Ala Ala Gly Gly
65                  70                  75                  80

Leu Gly Gly Gln Gly Gly Leu Gly Ala Leu Gly Ser Gln Gly Ala Gly
                85                  90                  95

Gln Gly Gly Ala Gly Gln Gly Gly Tyr Gly Gln Gly Gly Ala Ala Ala
            100                 105                 110

Ala Ala Ala Gly Gly Leu Gly Gly Gln Gly Gly Leu Gly Gly Leu Gly
        115                 120                 125

Ser Gln Gly Ala Gly Gln Gly Gly Tyr Gly Gln Gly Gly Ala Gly Gln
    130                 135                 140
```

```
Gly Gly Ala Ala Ala Ala Ala Ala Gly Leu Gly Gly Gln
145                 150                 155                 160

Gly Gly Leu Gly Gly Leu Gly Ser Gln Gly Ala Gly Pro Gly Gly Tyr
            165                 170                 175

Gly Gln Gly Gly Ala Gly Gln Gly Gly Ala Ala Ala Ala Ala Ala
            180                 185                 190

Ala

<210> SEQ ID NO 52
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Gly Gln Gly Arg Gly Gly Phe Gly Gln Gly Ala Gly Gly Asn Ala
1               5                   10                  15

Ala Ala Ala Ala Ala Ala Ala Ala Ala Ala Ala Ala Ala Gln Gln Val
                20                  25                  30

Gly Gln Phe Gly Phe Gly Gly Arg Gly Gln Gly Gly Phe Gly Pro Phe
            35                  40                  45

Ala Gly Ser Ser Ala Ala Ala Ala Ala Ala Ser Ala Ala Ala Gly
            50                  55                  60

Gln Gly Gln Gly Gln Gly Gly Phe Gly Gln Gly Ala Gly Gly Asn
65                  70                  75                  80

Ala Ala Ala Ala Ala Ala Ala Ala Ala Ala Ala Arg Gln Gly Gly
                85                  90                  95

Gln Gly Gln Gly Gly Phe Ser Gln Gly Ala Gly Gly Asn Ala Ala Ala
            100                 105                 110

Ala Ala Ala Ala Ala Ala Ala Ala Ala Ala Gln Gln Gly Gly
            115                 120                 125

Gln Gly Gly Phe Gly Gly Arg Gly Gln Gly Gly Phe Gly Pro Gly Ala
            130                 135                 140

Gly Ser Ser Ala Ala Ala Ala Ala Ala Thr Ala Ala Ala Gly Gln
145                 150                 155                 160

Gly Gly Gln Gly Arg Gly Gly Phe Gly Gln Gly Ala Gly Ser Asn Ala
            165                 170                 175

Ala Ala Ala Ala Ala Ala Ala Ala Ala Ala Ala Ala Gly Gln
            180                 185                 190

<210> SEQ ID NO 53
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Gly Gln Gly Gly Gln Gly Gly Tyr Gly Gly Leu Gly Ser Gln Gly
1               5                   10                  15

Ala Gly Gln Gly Gly Tyr Gly Ala Gly Gln Gly Ala Ala Ala Ala Ala
                20                  25                  30

Ala Ala Ala Gly Gly Ala Gly Gly Ala Gly Arg Gly Gly Leu Gly Ala
            35                  40                  45

Gly Gly Ala Gly Gln Gly Tyr Gly Ala Gly Leu Gly Gly Gln Gly Gly
```

```
Ala Gly Gln Ala Ala Ala Ala Ala Ala Gly Gly Ala Gly Gly Ala
 65                  70                  75                  80

Arg Gln Gly Gly Leu Gly Ala Gly Ala Gly Gln Gly Tyr Gly Ala
                 85                  90                  95

Gly Leu Gly Gly Gln Gly Gly Ala Gln Gly Gly Ala Ala Ala Ala
                100                 105                 110

Ala Ala Ala Ala Gly Gly Gln Gly Gly Gln Gly Gly Tyr Gly Gly Leu
            115                 120                 125

Gly Ser Gln Gly Ala Gly Gln Gly Gly Tyr Gly Ala Gly Gln Gly Gly
        130                 135                 140

Ala Ala Ala Ala Ala Ala Ala Gly Gln Gly Gly Gln Gly Gly
145                 150                 155                 160

Tyr Gly Gly Leu Gly Ser Gln Gly Ala Gly Gln Gly Gly Tyr Gly Gly
                165                 170                 175

Arg Gln Gly Gly Ala Gly Ala Ala Ala Ala Ala Ala Ala
            180                 185                 190

<210> SEQ ID NO 54
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Gly Ala Gly Gln Arg Gly Tyr Gly Gly Leu Gly Asn Gln Gly Ala
1               5                   10                  15

Gly Arg Gly Gly Leu Gly Gly Gln Gly Ala Gly Ala Ala Ala Ala Ala
            20                  25                  30

Ala Ala Gly Gly Ala Gly Gln Gly Gly Tyr Gly Gly Leu Gly Asn Gln
        35                  40                  45

Gly Ala Gly Arg Gly Gly Gln Gly Ala Ala Ala Ala Ala Gly Gly Ala
 50                  55                  60

Gly Gln Gly Gly Tyr Gly Gly Leu Gly Ser Gln Gly Ala Gly Arg Gly
 65                  70                  75                  80

Gly Gln Gly Ala Gly Ala Ala Ala Ala Ala Val Gly Ala Gly Gln
                85                  90                  95

Glu Gly Ile Arg Gly Gln Gly Ala Gln Gly Gly Tyr Gly Gly Leu
                100                 105                 110

Gly Ser Gln Gly Ser Gly Arg Gly Gly Leu Gly Gly Gln Gly Ala Gly
            115                 120                 125

Ala Ala Ala Ala Ala Ala Gly Gly Ala Gly Gln Gly Gly Leu Gly Gly
        130                 135                 140

Gln Gly Ala Gly Gln Gly Ala Gly Ala Ala Ala Ala Ala Gly Gly
145                 150                 155                 160

Val Arg Gln Gly Gly Tyr Gly Gly Leu Gly Ser Gln Gly Ala Gly Arg
                165                 170                 175

Gly Gly Gln Gly Ala Gly Ala Ala Ala Ala Ala
            180                 185

<210> SEQ ID NO 55
<211> LENGTH: 186
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 55

```
Gly Gly Ala Gly Gln Gly Gly Leu Gly Gly Gln Gly Ala Gln Gly
1               5                   10                  15

Ala Gly Ala Ser Ala Ala Ala Gly Gly Ala Gly Gln Gly Gly Tyr
            20                  25                  30

Gly Gly Leu Gly Ser Gln Gly Ala Gly Arg Gly Gly Glu Gly Ala Gly
        35                  40                  45

Ala Ala Ala Ala Ala Ala Gly Gly Ala Gly Gln Gly Gly Tyr Gly Gly
    50                  55                  60

Leu Gly Gly Gln Gly Ala Gly Gln Gly Gly Tyr Gly Gly Leu Gly Ser
65                  70                  75                  80

Gln Gly Ala Gly Arg Gly Gly Leu Gly Gly Gln Gly Ala Gly Ala Ala
            85                  90                  95

Ala Ala Gly Gly Ala Gly Gln Gly Gly Leu Gly Gly Gln Gly Ala Gly
            100                 105                 110

Gln Gly Ala Gly Ala Ala Ala Ala Ala Gly Gly Ala Gly Gln Gly
        115                 120                 125

Gly Tyr Gly Gly Leu Gly Ser Gln Gly Ala Gly Arg Gly Gly Leu Gly
    130                 135                 140

Gly Gln Gly Ala Gly Ala Val Ala Ala Ala Ala Ala Gly Gly Ala Gly
145                 150                 155                 160

Gln Gly Gly Tyr Gly Gly Leu Gly Ser Gln Gly Ala Gly Arg Gly Gly
                165                 170                 175

Gln Gly Ala Gly Ala Ala Ala Ala Ala
            180                 185
```

<210> SEQ ID NO 56
<211> LENGTH: 182
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

```
Gly Ala Gly Ala Gly Ala Gly Ala Gly Ser Gly Ala Gly Ala Ala Gly
1               5                   10                  15

Gly Tyr Gly Gly Gly Ala Gly Ala Gly Val Gly Ala Gly Gly Ala Gly
            20                  25                  30

Gly Tyr Asp Gln Gly Tyr Gly Ala Gly Ala Gly Ala Gly Ser Gly Ala
        35                  40                  45

Gly Ala Gly Gly Ala Gly Gly Tyr Gly Gly Ala Gly Ala Gly Ala
    50                  55                  60

Asp Ala Gly Ala Gly Gly Ala Gly Gly Tyr Gly Gly Ala Gly Ala
65                  70                  75                  80

Gly Ala Gly Ala Arg Ala Gly Ala Gly Val Gly Gly Tyr Gly Gln
            85                  90                  95

Ser Tyr Gly Ala Gly Ala Gly Ala Gly Ala Gly Val Gly Ala Gly Gly
            100                 105                 110

Ala Gly Ala Gly Gly Ala Asp Gly Tyr Gly Gln Gly Tyr Gly Ala Gly
        115                 120                 125

Ala Gly Thr Gly Ala Gly Asp Ala Gly Gly Tyr Gly Gly Gly Ala Gly
    130                 135                 140
```

Ala Gly Ala Ser Ala Gly Ala Gly Gly Tyr Gly Gly Ala Gly Ala
145                 150                 155                 160

Gly Gly Val Gly Val Tyr Gly Lys Gly Tyr Gly Ser Gly Ser Gly Ala
                165                 170                 175

Gly Ala Ala Ala Ala Ala
            180

<210> SEQ ID NO 57
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Gly Ala Gly Gly Tyr Gly Val Gly Gln Gly Tyr Gly Ala Gly Ala
1               5                   10                  15

Gly Ala Gly Ala Ala Gly Ala Gly Ala Gly Ala Gly Ala Gly Gly Tyr
            20                  25                  30

Gly Ala Gly Gln Gly Tyr Gly Ala Gly Ala Gly Val Gly Ala Ala Ala
        35                  40                  45

Ala Ala Gly Ala Gly Ala Gly Val Gly Gly Ala Gly Gly Tyr Gly Arg
    50                  55                  60

Gly Ala Gly Ala Gly Ala Gly Ala Gly Ala Ala Ala Gly Ala
65                  70                  75                  80

Gly Ala Gly Ala Ala Gly Ala Gly Ala Gly Ala Gly Gly Tyr
            85                  90                  95

Gly Ala Gly Gln Gly Tyr Gly Ala Gly Ala Gly Val Gly Ala Ala Ala
        100                 105                 110

Ala Ala Gly Ala Gly Ala Gly Val Gly Gly Ala Gly Tyr Gly Arg
    115                 120                 125

Gly Ala Gly Ala Gly Ala Gly Ala Gly Ala Gly Gly Tyr
130                 135                 140

Gly Arg Gly Ala Gly Ala Gly Ala Gly Ala Gly Ala Gly Gly
145                 150                 155                 160

Ala Gly Gly Tyr Gly Ala Gly Gln Gly Tyr Gly Ala Gly Ala Gly Ala
                165                 170                 175

Gly Ala Ala Ala Ala Ala
            180

<210> SEQ ID NO 58
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Glu Ala Phe Ser Ala Ser Ser Ala Ser Ala Val Val Phe Glu
1               5                   10                  15

Ser Ala Gly Pro Gly Glu Glu Ala Gly Ser Ser Gly Asp Gly Ala Ser
            20                  25                  30

Ala Ala Ala Ser Ala Ala Ala Ala Gly Ala Gly Ser Gly Arg Arg
        35                  40                  45

Gly Pro Gly Gly Ala Arg Ser Arg Gly Gly Ala Gly Ala Gly Ala Gly
    50                  55                  60

```
Ala Gly Ser Gly Val Gly Tyr Gly Ser Gly Ser Gly Ala Gly Ala
 65                  70                  75                  80

Gly Ala Gly Ala Gly Ala Gly Ala Gly Gly Glu Gly Gly Phe Gly Glu
                 85                  90                  95

Gly Gln Gly Tyr Gly Ala Gly Ala Gly Ala Gly Phe Gly Ser Gly Ala
            100                 105                 110

Gly Ala Gly Ala Gly Ala Gly Ser Gly Ala Gly Ala Gly Glu Gly Val
            115                 120                 125

Gly Ser Gly Ala Gly Ala Gly Ala Gly Ala Gly Phe Gly Val Gly Ala
            130                 135                 140

Gly Ala Gly Ala Gly Ala Gly Ala Gly Phe Gly Ser Gly Ala Gly Ala
145                 150                 155                 160

Gly Ser Gly Ala Gly Ala Gly Tyr Gly Ala Gly Arg Ala Gly Gly Arg
            165                 170                 175

Gly Arg Gly Gly Arg Gly
            180

<210> SEQ ID NO 59
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Glu Ala Phe Ser Ala Ser Ser Ala Ser Ser Ala Val Val Phe Glu
 1               5                  10                  15

Ser Ala Gly Pro Gly Glu Glu Ala Gly Ser Ser Gly Gly Gly Ala Ser
                20                  25                  30

Ala Ala Ala Ser Ala Ala Ala Ala Ala Gly Ala Gly Ser Gly Arg Arg
            35                  40                  45

Gly Pro Gly Gly Ala Arg Ser Arg Gly Gly Ala Gly Ala Gly Ala Gly
        50                  55                  60

Ala Gly Ser Gly Val Gly Gly Tyr Gly Ser Gly Ser Gly Ala Gly Ala
 65                  70                  75                  80

Gly Ala Gly Ala Gly Ala Gly Ala Gly Gly Glu Gly Gly Phe Gly Glu
                 85                  90                  95

Gly Gln Gly Tyr Gly Ala Gly Ala Gly Ala Gly Phe Gly Ser Gly Ala
            100                 105                 110

Gly Ala Gly Ala Gly Ala Gly Ser Gly Ala Gly Ala Gly Glu Gly Val
            115                 120                 125

Gly Ser Gly Ala Gly Ala Gly Ala Gly Ala Gly Phe Gly Val Gly Ala
            130                 135                 140

Gly Ala Gly Ala Gly Ala Gly Ala Gly Phe Gly Ser Gly Ala Gly Ala
145                 150                 155                 160

Gly Ser Gly Ala Gly Ala Gly Tyr Gly Ala Gly Arg Ala Gly Gly Arg
            165                 170                 175

Gly Arg Gly Gly Arg Gly
            180

<210> SEQ ID NO 60
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 60

Gly Asn Gly Leu Gly Gln Ala Leu Leu Ala Asn Gly Val Leu Asn Ser
1               5                   10                  15

Gly Asn Tyr Leu Gln Leu Ala Asn Ser Leu Ala Tyr Ser Phe Gly Ser
            20                  25                  30

Ser Leu Ser Gln Tyr Ser Ser Ala Ala Gly Ala Ser Ala Ala Gly
        35                  40                  45

Ala Ala Ser Gly Ala Ala Gly Ala Gly Ala Ala Ser Ser Gly
    50                  55                  60

Gly Ser Ser Gly Ser Ala Ser Ser Ser Thr Thr Thr Thr Thr Thr Thr
65                  70                  75                  80

Ser Thr Ser Ala Ala Ala Ala Ala Ala Ala Ala Ala Ala Ala Ser
                85                  90                  95

Ala Ala Ala Ser Thr Ser Ala Ser Ala Ser Ala Ser Ala Ser
            100                 105                 110

Ala Ser Ala Phe Ser Gln Thr Phe Val Gln Thr Val Leu Gln Ser Ala
            115                 120                 125

Ala Phe Gly Ser Tyr Phe Gly Gly Asn Leu Ser Leu Gln Ser Ala Gln
    130                 135                 140

Ala Ala Ala Ser Ala Ala Ala Gln Ala Ala Ala Gln Gln Ile Gly Leu
145                 150                 155                 160

Gly Ser Tyr Gly Tyr Ala Leu Ala Asn Ala Val Ala Ser Ala Phe Ala
                165                 170                 175

Ser Ala Gly Ala Asn Ala
            180

<210> SEQ ID NO 61
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Asn Gly Leu Gly Gln Ala Leu Leu Ala Asn Gly Val Leu Asn Ser
1               5                   10                  15

Gly Asn Tyr Leu Gln Leu Ala Asn Ser Leu Ala Tyr Ser Phe Gly Ser
            20                  25                  30

Ser Leu Ser Gln Tyr Ser Ser Ala Ala Gly Ala Ser Ala Ala Gly
        35                  40                  45

Ala Ala Ser Gly Ala Ala Gly Ala Gly Ala Ala Ser Ser Gly
    50                  55                  60

Gly Ser Ser Gly Ser Ala Ser Ser Ser Thr Thr Thr Thr Thr Thr Thr
65                  70                  75                  80

Ser Thr Ser Ala Ala Ala Ala Ala Ala Ala Ala Ala Ala Ala Ser
                85                  90                  95

Ala Ala Ala Ser Thr Ser Ala Ser Ala Ser Ala Ser Ala Ser
            100                 105                 110

Ala Ser Ala Phe Ser Gln Thr Phe Val Gln Thr Val Leu Gln Ser Ala
            115                 120                 125

Ala Phe Gly Ser Tyr Phe Gly Gly Asn Leu Ser Leu Gln Ser Ala Gln
    130                 135                 140

Ala Ala Ala Ser Ala Ala Ala Gln Ala Ala Ala Gln Gln Ile Gly Leu
145                 150                 155                 160

Gly Ser Tyr Gly Tyr Ala Leu Ala Asn Ala Val Ala Ser Ala Phe Ala
                165                 170                 175

Ser Ala Gly Ala Asn Ala
            180

<210> SEQ ID NO 62
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Asn Gly Leu Gly Gln Ala Leu Leu Ala Asn Gly Val Leu Asn Ser
1               5                   10                  15

Gly Asn Tyr Leu Gln Leu Ala Asn Ser Leu Ala Tyr Ser Phe Gly Ser
            20                  25                  30

Ser Leu Ser Gln Tyr Ser Ser Ala Ala Gly Ala Ser Ala Ala Gly
        35                  40                  45

Ala Ala Ser Gly Ala Ala Gly Ala Gly Ala Gly Ala Ala Ser Ser Gly
50                  55                  60

Gly Ser Ser Gly Ser Ala Ser Ser Ser Thr Thr Thr Thr Thr Thr Thr
65                  70                  75                  80

Ser Thr Ser Ala Ala Ala Ala Ala Ala Ala Ala Ala Ala Ala Ala Ser
                85                  90                  95

Ala Ala Ala Ser Thr Ser Ala Ser Ala Ser Ala Ser Ala Ser Ala Ser
                100                 105                 110

Ala Ser Ala Phe Ser Gln Thr Phe Val Gln Thr Val Leu Gln Ser Ala
                115                 120                 125

Ala Phe Gly Ser Tyr Phe Gly Gly Asn Leu Ser Leu Gln Ser Ala Gln
            130                 135                 140

Ala Ala Ala Ser Ala Ala Ala Gln Ala Ala Ala Gln Gln Ile Gly Leu
145                 150                 155                 160

Gly Ser Tyr Gly Tyr Ala Leu Ala Asn Ala Val Ala Ser Ala Phe Ala
                165                 170                 175

Ser Ala Gly Ala Asn Ala
            180

<210> SEQ ID NO 63
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Ala Ser Gly Ala Gly Gln Gly Gln Gly Tyr Gly Gln Gln Gly Gln
1               5                   10                  15

Gly Gly Ser Ser Ala Ala Ala Ala Ala Ala Ala Ala Ala Ala Ala Ala
            20                  25                  30

Ala Ala Ala Gln Gly Gln Gly Gln Tyr Gly Gln Gln Gly Gln Gly Gly
        35                  40                  45

Ser Ala Ala Ala Ala Ala Ala Ala Ala Ala Gly Ala Ser Gly Ala
        50                  55                  60

Gly Gln Gly Gln Gly Tyr Gly Gln Gln Gly Gln Gly Ser Ala Ala Ala
65                  70                  75                  80

Ala Ala Ala Ala Ala Ala Gly Ala Ser Gly Ala Gly Gln Gly Gln
                85                  90                  95

Gly Tyr Gly Gln Gln Gly Gln Gly Gly Ser Ser Ala Ala Ala Ala
                100                 105                 110

Ala Ala Ala Ala Ala Ala Ala Ala Ala Ala Gln Gly Gln Gly Tyr
            115                 120                 125

Gly Gln Gln Gly Gln Gly Ser Ala Ala Ala Ala Ala Ala Ala Ala
            130                 135                 140

Gly Ala Ser Gly Ala Gly Gln Gly Gln Gly Tyr Gly Gln Gln Gly Gln
145                 150                 155                 160

Gly Gly Ser Ser Ala Ala Ala Ala Ala Ala Ala Ala Ala Ala
            165                 170                 175

Ala Ala Ala Ala
        180

<210> SEQ ID NO 64
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Arg Gly Gln Gly Gly Tyr Gly Gln Gly Ser Gly Gly Asn Ala Ala
1               5                   10                  15

Ala Ala Ala Ala Ala Gly Gln Gly Gly Phe Gly Gly Gln Glu Gly Asn
            20                  25                  30

Gly Gln Gly Ala Gly Ser Ala Ala Ala Ala Ala Ala Ala Ala Ala
        35                  40                  45

Ala Ala Gly Gly Ser Gly Gln Gly Arg Tyr Gly Gly Arg Gly Gln Gly
50                  55                  60

Gly Tyr Gly Gln Gly Ala Gly Ala Ala Ser Ala Ala Ala Ala Ala
65                  70                  75                  80

Ala Ala Ala Ala Ala Gly Gln Gly Gly Phe Gly Gly Gln Glu Gly Asn
                85                  90                  95

Gly Gln Gly Ala Gly Ser Ala Ala Ala Ala Ala Ala Ala Ala Ala
            100                 105                 110

Ala Ala Gly Gly Ser Gly Gln Gly Gly Tyr Gly Gly Arg Gly Gln Gly
        115                 120                 125

Gly Tyr Gly Gln Gly Ala Gly Ala Ala Ala Ala Ala Ala Ala
            130                 135                 140

Ala Ala Ala Ala Ala Gly Gln Gly Gly Gln Gly Gly Phe Gly Ser Gln
145                 150                 155                 160

Gly Gly Asn Gly Gln Gly Ala Gly Ser Ala Ala Ala Ala Ala Ala
                165                 170                 175

Ala Ala Ala

<210> SEQ ID NO 65
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Gly Gln Asn Thr Pro Trp Ser Ser Thr Glu Leu Ala Asp Ala Phe Ile
1               5                   10                  15

Asn Ala Phe Met Asn Glu Ala Gly Arg Thr Gly Ala Phe Thr Ala Asp
            20                  25                  30

Gln Leu Asp Asp Met Ser Thr Ile Gly Asp Thr Ile Lys Thr Ala Met
        35                  40                  45

Asp Lys Met Ala Arg Ser Asn Lys Ser Ser Lys Gly Lys Leu Gln Ala
50                  55                  60

Leu Asn Met Ala Phe Ala Ser Ser Met Ala Glu Ile Ala Ala Val Glu
65                  70                  75                  80

Gln Gly Gly Leu Ser Val Asp Ala Lys Thr Asn Ala Ile Ala Asp Ser
                85                  90                  95

Leu Asn Ser Ala Phe Tyr Gln Thr Thr Gly Ala Ala Asn Pro Gln Phe
                100                 105                 110

Val Asn Glu Ile Arg Ser Leu Ile Asn Met Phe Ala Gln Ser Ser Ala
            115                 120                 125

Asn Glu Val Ser Tyr Gly Gly Tyr Gly Gly Gln Ser Ala Gly Ala
            130                 135                 140

Ala Ala Ser Ala Ala Ala Gly Gly Gly Gln Gly Gly Tyr Gly
145                 150                 155                 160

Asn Leu Gly Gly Gln Gly Ala Gly Ala Ala Ala Ala Ala Ser
                165                 170                 175

Ala Ala
```

<210> SEQ ID NO 66
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Gly Gln Asn Thr Pro Trp Ser Ser Thr Glu Leu Ala Asp Ala Phe Ile
1               5                   10                  15

Asn Ala Phe Leu Asn Glu Ala Gly Arg Thr Gly Ala Phe Thr Ala Asp
            20                  25                  30

Gln Leu Asp Asp Met Ser Thr Ile Gly Asp Thr Leu Lys Thr Ala Met
        35                  40                  45

Asp Lys Met Ala Arg Ser Asn Lys Ser Ser Gln Ser Lys Leu Gln Ala
50                  55                  60

Leu Asn Met Ala Phe Ala Ser Ser Met Ala Glu Ile Ala Ala Val Glu
65                  70                  75                  80

Gln Gly Gly Leu Ser Val Ala Glu Lys Thr Asn Ala Ile Ala Asp Ser
                85                  90                  95

Leu Asn Ser Ala Phe Tyr Gln Thr Thr Gly Ala Val Asn Val Gln Phe
                100                 105                 110

Val Asn Glu Ile Arg Ser Leu Ile Ser Met Phe Ala Gln Ala Ser Ala
            115                 120                 125

Asn Glu Val Ser Tyr Gly Gly Tyr Gly Gly Gln Gly Gly Gln
            130                 135                 140

Ser Ala Gly Ala Ala Ala Ala Ala Ser Ala Gly Ala Gln Gly
145                 150                 155                 160

Gly Tyr Gly Gly Leu Gly Gly Gln Gly Ala Gly Ser Ala Ala Ala Ala
                165                 170                 175
```

Ala Ala

<210> SEQ ID NO 67
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gly Gly Gln Gly Gly Gln Gly Gly Tyr Gly Gly Leu Gly Ser Gln Gly
1               5                   10                  15

Ala Gly Gln Gly Gly Tyr Gly Gln Gly Gly Ala Ala Ala Ala Ala Ala
            20                  25                  30

Ser Ala Gly Gly Gln Gly Gly Gln Gly Gly Tyr Gly Gly Leu Gly Ser
        35                  40                  45

Gln Gly Ala Gly Gln Gly Gly Tyr Gly Gly Gly Ala Phe Ser Gly Gln
    50                  55                  60

Gln Gly Gly Ala Ala Ser Val Ala Thr Ala Ser Ala Ala Ala Ser Arg
65                  70                  75                  80

Leu Ser Ser Pro Gly Ala Ala Ser Arg Val Ser Ser Ala Val Thr Ser
                85                  90                  95

Leu Val Ser Ser Gly Gly Pro Thr Asn Ser Ala Ala Leu Ser Asn Thr
            100                 105                 110

Ile Ser Asn Val Val Ser Gln Ile Ser Ser Ser Asn Pro Gly Leu Ser
        115                 120                 125

Gly Cys Asp Val Leu Val Gln Ala Leu Leu Glu Ile Val Ser Ala Leu
    130                 135                 140

Val His Ile Leu Gly Ser Ala Asn Ile Gly Gln Val Asn Ser Ser Gly
145                 150                 155                 160

Val Gly Arg Ser Ala Ser Ile Val Gly Gln Ser Ile Asn Gln Ala Phe
                165                 170                 175

Ser

<210> SEQ ID NO 68
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Gly Ala Gly Gln Gly Gly Tyr Gly Gly Leu Gly Gly Gln Gly Ala
1               5                   10                  15

Gly Ala Ala Ala Ala Ala Gly Gly Ala Gly Gln Gly Gly Tyr Gly
            20                  25                  30

Gly Gln Gly Ala Gly Gln Gly Ala Ala Ala Ala Ala Ser Gly Ala
        35                  40                  45

Gly Gln Gly Gly Tyr Glu Gly Pro Gly Ala Gly Gln Gly Ala Gly Ala
    50                  55                  60

Ala Ala Ala Ala Gly Gly Ala Gly Gln Gly Gly Tyr Gly Gly Leu
65                  70                  75                  80

Gly Gly Gln Gly Ala Gly Gln Gly Ala Gly Ala Ala Ala Ala Ala
                85                  90                  95

Gly Gly Ala Gly Gln Gly Gly Tyr Gly Gly Leu Gly Gly Gln Gly Ala
            100                 105                 110

```
Gly Gln Gly Ala Gly Ala Ala Ala Ala Ala Gly Gly Ala Gly Gln
        115                 120                 125

Gly Gly Tyr Gly Gly Gln Gly Ala Gly Gln Gly Ala Ala Ala Ala
        130                 135                 140

Ala Gly Gly Ala Gly Gln Gly Gly Tyr Gly Gly Leu Gly Ser Gly Gln
145                 150                 155                 160

Gly Gly Tyr Gly Arg Gln Gly Ala Gly Ala Ala Ala Ala Ala Ala
                165                 170                 175

Ala
```

<210> SEQ ID NO 69
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Gly Ala Ser Ser Ala Ala Ala Ala Ala Ala Thr Ala Thr Ser Gly
1               5                   10                  15

Gly Ala Pro Gly Gly Tyr Gly Gly Tyr Gly Pro Gly Ile Gly Ala
            20                  25                  30

Phe Val Pro Ala Ser Thr Thr Gly Thr Gly Ser Gly Ser Gly Ser Gly
        35                  40                  45

Ala Gly Ala Ala Gly Ser Gly Gly Leu Gly Gly Leu Gly Ser Ser Gly
50                  55                  60

Gly Ser Gly Gly Leu Gly Gly Asn Gly Gly Ser Gly Ala Ser Ala
65                  70                  75                  80

Ala Ala Ser Ala Ala Ala Ser Ser Ser Pro Gly Ser Gly Gly Tyr
            85                  90                  95

Gly Pro Gly Gln Gly Val Gly Ser Gly Ser Gly Ser Gly Ala Ala Gly
        100                 105                 110

Gly Ser Gly Thr Gly Ser Gly Ala Gly Gly Pro Gly Ser Gly Gly Tyr
        115                 120                 125

Gly Gly Pro Gln Phe Phe Ala Ser Ala Tyr Gly Gly Gln Gly Leu Leu
        130                 135                 140

Gly Thr Ser Gly Tyr Gly Asn Gly Gln Gly Gly Ala Ser Gly Thr Gly
145                 150                 155                 160

Ser Gly Gly Val Gly Gly Ser Gly Ser Gly Ala Gly Ser Asn Ser
                165                 170                 175
```

<210> SEQ ID NO 70
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Gly Gln Pro Ile Trp Thr Asn Pro Asn Ala Ala Met Thr Met Thr Asn
1               5                   10                  15

Asn Leu Val Gln Cys Ala Ser Arg Ser Gly Val Leu Thr Ala Asp Gln
            20                  25                  30

Met Asp Asp Met Gly Met Met Ala Asp Ser Val Asn Ser Gln Met Gln
        35                  40                  45
```

Lys Met Gly Pro Asn Pro Pro Gln His Arg Leu Arg Ala Met Asn Thr
 50                  55                  60

Ala Met Ala Ala Glu Val Ala Glu Val Val Ala Thr Ser Pro Pro Gln
 65                  70                  75                  80

Ser Tyr Ser Ala Val Leu Asn Thr Ile Gly Ala Cys Leu Arg Glu Ser
                 85                  90                  95

Met Met Gln Ala Thr Gly Ser Val Asp Asn Ala Phe Thr Asn Glu Val
             100                 105                 110

Met Gln Leu Val Lys Met Leu Ser Ala Asp Ser Ala Asn Glu Val Ser
         115                 120                 125

Thr Ala Ser Ala Ser Gly Ala Ser Tyr Ala Thr Ser Thr Ser Ser Ala
130                 135                 140

Val Ser Ser Ser Gln Ala Thr Gly Tyr Ser Thr Ala Ala Gly Tyr Gly
145                 150                 155                 160

Asn Ala Ala Gly Ala Gly Ala Gly Ala Ala Ala Val Ser
                165                 170

<210> SEQ ID NO 71
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Gln Lys Ile Trp Thr Asn Pro Asp Ala Ala Met Ala Met Thr Asn
1               5                   10                  15

Asn Leu Val Gln Cys Ala Gly Arg Ser Gly Ala Leu Thr Ala Asp Gln
                 20                  25                  30

Met Asp Asp Leu Gly Met Val Ser Asp Ser Val Asn Ser Gln Val Arg
             35                  40                  45

Lys Met Gly Ala Asn Ala Pro Pro His Lys Ile Lys Ala Met Ser Thr
 50                  55                  60

Ala Val Ala Ala Gly Val Ala Glu Val Val Ala Ser Ser Pro Pro Gln
 65                  70                  75                  80

Ser Tyr Ser Ala Val Leu Asn Thr Ile Gly Gly Cys Leu Arg Glu Ser
                 85                  90                  95

Met Met Gln Val Thr Gly Ser Val Asp Asn Thr Phe Thr Thr Glu Met
             100                 105                 110

Met Gln Met Val Asn Met Phe Ala Ala Asp Asn Ala Asn Glu Val Ser
         115                 120                 125

Ala Ser Ala Ser Gly Ser Gly Ala Ser Tyr Ala Thr Gly Thr Ser Ser
130                 135                 140

Ala Val Ser Thr Ser Gln Ala Thr Gly Tyr Ser Thr Ala Gly Gly Tyr
145                 150                 155                 160

Gly Thr Ala Ala Gly Ala Gly Ala Gly Ala Ala Ala Ala
                165                 170

<210> SEQ ID NO 72
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Gly Ser Gly Tyr Gly Ala Gly Ala Gly Ala Gly Ser Gly Tyr
1               5                   10                  15
Gly Ala Gly Ala Gly Ala Gly Ser Gly Tyr Gly Ala Gly Ala
            20                  25                  30
Gly Ala Gly Ser Gly Tyr Val Ala Gly Ala Gly Ala Gly Ala
            35                  40                  45
Gly Ser Gly Tyr Gly Ala Gly Ala Gly Ala Gly Ser Ser Tyr
        50                  55                  60
Ser Ala Gly Ala Gly Ala Gly Ala Gly Ser Gly Tyr Gly Ala Gly Ser
65                  70                  75                  80
Ser Ala Ser Ala Gly Ser Ala Val Ser Thr Gln Thr Val Ser Ser Ser
                85                  90                  95
Ala Thr Thr Ser Ser Gln Ser Ala Ala Ala Ala Thr Gly Ala Ala Tyr
            100                 105                 110
Gly Thr Arg Ala Ser Thr Gly Ser Gly Ala Ser Ala Gly Ala Ala Ala
            115                 120                 125
Ser Gly Ala Gly Ala Gly Tyr Gly Gly Gln Ala Gly Tyr Gly Gln Gly
            130                 135                 140
Gly Gly Ala Ala Ala Tyr Arg Ala Gly Ala Gly Ser Gln Ala Ala Tyr
145                 150                 155                 160
Gly Gln Gly Ala Ser Gly Ser Ser Gly Ala Ala Ala Ala
                165                 170

<210> SEQ ID NO 73
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Gly Gln Gly Gly Arg Gly Gly Phe Gly Gly Leu Ser Ser Gln Gly
1               5                   10                  15
Ala Gly Gly Ala Gly Gln Gly Gly Ser Gly Ala Ala Ala Ala Ala Ala
            20                  25                  30
Ala Ala Gly Gly Asp Gly Gly Ser Gly Leu Gly Asp Tyr Gly Ala Gly
            35                  40                  45
Arg Gly Tyr Gly Ala Gly Leu Gly Gly Ala Gly Ala Gly Val Ala
        50                  55                  60
Ser Ala Ala Ala Ser Ala Ala Ala Ser Arg Leu Ser Ser Pro Ser Ala
65                  70                  75                  80
Ala Ser Arg Val Ser Ser Ala Val Thr Ser Leu Ile Ser Gly Gly
                85                  90                  95
Pro Thr Asn Pro Ala Ala Leu Ser Asn Thr Phe Ser Asn Val Val Tyr
            100                 105                 110
Gln Ile Ser Val Ser Ser Pro Gly Leu Ser Gly Cys Asp Val Leu Ile
            115                 120                 125
Gln Ala Leu Leu Glu Leu Val Ser Ala Leu Val His Ile Leu Gly Ser
            130                 135                 140
Ala Ile Ile Gly Gln Val Asn Ser Ser Ala Ala Gly Glu Ser Ala Ser
145                 150                 155                 160
Leu Val Gly Gln Ser Val Tyr Gln Ala Phe Ser
                165                 170

<210> SEQ ID NO 74
```

<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Val Gly Gln Ala Ala Thr Pro Trp Glu Asn Ser Gln Leu Ala Glu
1               5                   10                  15

Asp Phe Ile Asn Ser Phe Leu Arg Phe Ile Ala Gln Ser Gly Ala Phe
            20                  25                  30

Ser Pro Asn Gln Leu Asp Asp Met Ser Ser Ile Gly Asp Thr Leu Lys
        35                  40                  45

Thr Ala Ile Glu Lys Met Ala Gln Ser Arg Lys Ser Ser Lys Ser Lys
    50                  55                  60

Leu Gln Ala Leu Asn Met Ala Phe Ala Ser Ser Met Ala Glu Ile Ala
65                  70                  75                  80

Val Ala Glu Gln Gly Gly Leu Ser Leu Glu Ala Lys Thr Asn Ala Ile
                85                  90                  95

Ala Asn Ala Leu Ala Ser Ala Phe Leu Glu Thr Thr Gly Phe Val Asn
            100                 105                 110

Gln Gln Phe Val Ser Glu Ile Lys Ser Leu Ile Tyr Met Ile Ala Gln
        115                 120                 125

Ala Ser Ser Asn Glu Ile Ser Gly Ser Ala Ala Ala Gly Gly Gly
    130                 135                 140

Ser Gly Gly Gly Gly Ser Gly Gln Gly Tyr Gly Gln Gly Ala
145                 150                 155                 160

Ser Ala Ser Ala Ser Ala Ala Ala Ala
                165

<210> SEQ ID NO 75
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Gly Gly Asp Gly Tyr Gly Gln Gly Tyr Gly Asn Gln Arg Gly
1               5                   10                  15

Val Gly Ser Tyr Gly Gln Gly Ala Gly Ala Gly Ala Ala Thr Ser
            20                  25                  30

Ala Ala Gly Gly Ala Gly Ser Gly Arg Gly Gly Tyr Gly Glu Gln Gly
        35                  40                  45

Gly Leu Gly Gly Tyr Gly Gln Gly Ala Gly Ala Gly Ala Ala Ser Thr
    50                  55                  60

Ala Ala Gly Gly Gly Asp Gly Tyr Gly Gln Gly Tyr Gly Asn Gln
65                  70                  75                  80

Gly Gly Arg Gly Ser Tyr Gly Gln Ser Gly Ala Gly Ala Gly Ala
                85                  90                  95

Ala Val Ala Ala Ala Gly Gly Ala Val Ser Gly Gln Gly Gly Tyr
            100                 105                 110

Asp Gly Glu Gly Gly Gln Gly Gly Tyr Gly Gln Gly Ser Gly Ala Gly
        115                 120                 125

Ala Ala Val Ala Ala Ala Ser Gly Gly Thr Gly Ala Gly Gln Gly Gly
    130                 135                 140

Tyr Gly Ser Gln Gly Ser Gln Ala Gly Tyr Gly Gln Gly Ala Gly Phe
145                 150                 155                 160

Arg Ala Ala Ala Thr Ala Ala Ala
                165

<210> SEQ ID NO 76
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Ala Gly Ala Gly Tyr Gly Gly Gln Val Gly Tyr Gly Gln Gly Ala
1               5                   10                  15

Gly Ala Ser Ala Gly Ala Ala Ala Gly Ala Gly Ala Gly Tyr Gly
            20                  25                  30

Gly Gln Ala Gly Tyr Gly Gln Gly Ala Gly Ser Ala Gly Ala Ala
        35                  40                  45

Ala Ala Gly Ala Gly Ala Gly Arg Gln Ala Gly Tyr Gly Gln Gly Ala
    50                  55                  60

Gly Ala Ser Ala Arg Ala Ala Ala Gly Ala Gly Thr Gly Tyr Gly
65                  70                  75                  80

Gln Gly Ala Gly Ala Ser Ala Gly Ala Ala Ala Gly Ala Gly Ala
                85                  90                  95

Gly Ser Gln Val Gly Tyr Gly Gln Gly Ala Gly Ser Ser Gly Ala
            100                 105                 110

Ala Ala Ala Gly Ala Gly Ala Gly Tyr Gly Gly Gln Val Gly Tyr
        115                 120                 125

Glu Gln Gly Ala Gly Ala Ser Ala Gly Ala Glu Ala Ala Ser Ser
    130                 135                 140

Ala Gly Ala Gly Tyr Gly Gly Gln Ala Gly Tyr Gly Gln Gly Ala Gly
145                 150                 155                 160

Ala Ser Ala Gly Ala Ala Ala Ala
                165

<210> SEQ ID NO 77
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gly Gly Ala Gly Gln Gly Gly Tyr Gly Gly Leu Gly Gly Gln Gly Ala
1               5                   10                  15

Gly Gln Gly Gly Leu Gly Gly Gln Arg Ala Gly Ala Ala Ala Ala
            20                  25                  30

Ala Gly Gly Ala Gly Gln Gly Gly Tyr Gly Gly Leu Gly Ser Gln Gly
    35                  40                  45

Ala Gly Arg Gly Gly Tyr Gly Gly Val Gly Ser Gly Ala Ser Ala Ala
    50                  55                  60

Ser Ala Ala Ala Ser Arg Leu Ser Ser Pro Glu Ala Ser Ser Arg Val
65                  70                  75                  80

Ser Ser Ala Val Ser Asn Leu Val Ser Ser Gly Pro Thr Asn Ser Ala
                85                  90                  95

-continued

```
Ala Leu Ser Ser Thr Ile Ser Asn Val Val Ser Gln Ile Ser Ala Ser
                100                 105                 110

Asn Pro Gly Leu Ser Gly Cys Asp Val Leu Val Gln Ala Leu Leu Glu
            115                 120                 125

Val Val Ser Ala Leu Ile Gln Ile Leu Gly Ser Ser Ser Ile Gly Gln
    130                 135                 140

Val Asn Tyr Gly Thr Ala Gly Gln Ala Ala Gln Ile Val Gly Gln Ser
145                 150                 155                 160

Val Tyr Gln Ala Leu Gly
                165

<210> SEQ ID NO 78
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Gly Tyr Gly Pro Gly Ser Gly Gln Gln Gly Pro Gly Gly Ala Gly
1               5                   10                  15

Gln Gln Gly Pro Gly Gly Gln Gly Pro Tyr Gly Pro Gly Ser Ser Ser
            20                  25                  30

Ala Ala Ala Val Gly Gly Tyr Gly Pro Ser Ser Gly Leu Gln Gly Pro
        35                  40                  45

Ala Gly Gln Gly Pro Tyr Gly Pro Gly Ala Ala Ala Ser Ala Ala Ala
    50                  55                  60

Ala Ala Gly Ala Ser Arg Leu Ser Ser Pro Gln Ala Ser Ser Arg Val
65                  70                  75                  80

Ser Ser Ala Val Ser Ser Leu Val Ser Ser Gly Pro Thr Asn Ser Ala
                85                  90                  95

Ala Leu Thr Asn Thr Ile Ser Ser Val Val Ser Gln Ile Ser Ala Ser
                100                 105                 110

Asn Pro Gly Leu Ser Gly Cys Asp Val Leu Ile Gln Ala Leu Leu Glu
            115                 120                 125

Ile Val Ser Ala Leu Val His Ile Leu Gly Tyr Ser Ser Ile Gly Gln
    130                 135                 140

Ile Asn Tyr Asp Ala Ala Ala Gln Tyr Ala Ser Leu Val Gly Gln Ser
145                 150                 155                 160

Val Ala Gln Ala Leu Ala
                165

<210> SEQ ID NO 79
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gly Gly Ala Gly Ala Gly Gln Gly Ser Tyr Gly Gly Gln Gly Gly Tyr
1               5                   10                  15

Gly Gln Gly Gly Ala Gly Ala Ala Thr Ala Thr Ala Ala Ala Ala Gly
            20                  25                  30

Gly Ala Gly Ser Gly Gln Gly Gly Tyr Gly Gly Gln Gly Gly Leu Gly
        35                  40                  45
```

```
Gly Tyr Gly Gln Gly Ala Gly Ala Ala Ala Ala Ala Ala
        50                  55                  60

Ala Ala Gly Gly Ala Gly Ala Gly Gln Gly Gly Tyr Gly Gly Gln Gly
 65                  70                  75                  80

Gly Gln Gly Gly Tyr Gly Gln Gly Ala Gly Ala Gly Ala Ala Ala Ala
                 85                  90                  95

Ala Ala Gly Gly Ala Gly Ala Gly Gln Gly Gly Tyr Gly Gly Gln Gly
            100                 105                 110

Gly Tyr Gly Gln Gly Gly Ala Gly Ala Ala Ala Ala Ala Ala
            115                 120                 125

Ala Ser Gly Gly Ser Gly Ser Gly Gln Gly Gly Tyr Gly Gly Gln Gly
            130                 135                 140

Gly Leu Gly Gly Tyr Gly Gln Gly Ala Gly Ala Gly Ala Gly Ala Ala
145                 150                 155                 160

Ala Ser Ala Ala Ala Ala
            165

<210> SEQ ID NO 80
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Gln Gly Gly Gln Gly Gly Tyr Gly Arg Gln Ser Gln Gly Ala Gly
 1                   5                  10                  15

Ser Ala Ala Ala Ala Ala Ala Ala Ala Ala Ala Ala Ala Ala Ala Gly
                20                  25                  30

Ser Gly Gln Gly Gly Tyr Gly Gly Gln Gly Gln Gly Gly Tyr Gly Gln
                35                  40                  45

Ser Ser Ala Ser Ala Ser Ala Ala Ala Ser Ala Ala Ser Thr Val Ala
            50                  55                  60

Asn Ser Val Ser Arg Leu Ser Ser Pro Ser Ala Val Ser Arg Val Ser
 65                  70                  75                  80

Ser Ala Val Ser Ser Leu Val Ser Asn Gly Gln Val Asn Met Ala Ala
                85                  90                  95

Leu Pro Asn Ile Ile Ser Asn Ile Ser Ser Val Ser Ala Ser Ala
            100                 105                 110

Pro Gly Ala Ser Gly Cys Glu Val Ile Val Gln Ala Leu Leu Glu Val
            115                 120                 125

Ile Thr Ala Leu Val Gln Ile Val Ser Ser Ser Val Gly Tyr Ile
            130                 135                 140

Asn Pro Ser Ala Val Asn Gln Ile Thr Asn Val Val Ala Asn Ala Met
145                 150                 155                 160

Ala Gln Val Met Gly
            165

<210> SEQ ID NO 81
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81
```

Gly Gly Ala Gly Gln Gly Gly Tyr Gly Gly Leu Gly Gly Gln Gly Ser
1               5                   10                  15

Gly Ala Ala Ala Ala Gly Thr Gly Gln Gly Gly Tyr Gly Ser Leu Gly
                20                  25                  30

Gly Gln Gly Ala Gly Ala Ala Gly Ala Ala Ala Ala Val Gly Gly
            35                  40                  45

Ala Gly Gln Gly Gly Tyr Gly Gly Val Gly Ser Ala Ala Ala Ser Ala
        50                  55                  60

Ala Ala Ser Arg Leu Ser Ser Pro Glu Ala Ser Ser Arg Val Ser Ser
65                  70                  75                  80

Ala Val Ser Asn Leu Val Ser Ser Gly Pro Thr Asn Ser Ala Ala Leu
                85                  90                  95

Ser Asn Thr Ile Ser Asn Val Val Ser Gln Ile Ser Ser Ser Asn Pro
                100                 105                 110

Gly Leu Ser Gly Cys Asp Val Leu Val Gln Ala Leu Leu Glu Val Val
                115                 120                 125

Ser Ala Leu Ile His Ile Leu Gly Ser Ser Ser Ile Gly Gln Val Asn
130                 135                 140

Tyr Gly Ser Ala Gly Gln Ala Thr Gln Ile Val Gly Gln Ser Val Tyr
145                 150                 155                 160

Gln Ala Leu Gly

<210> SEQ ID NO 82
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Ala Gly Ala Gly Gly Ala Gly Gly Tyr Gly Ala Gly Gln Gly Tyr
1               5                   10                  15

Gly Ala Gly Ala Gly Ala Gly Ala Ala Ala Gly Ala Gly Ala Gly Gly
                20                  25                  30

Ala Arg Gly Tyr Gly Ala Arg Gln Gly Tyr Gly Ser Gly Ala Gly Ala
            35                  40                  45

Gly Ala Gly Ala Arg Ala Gly Ala Gly Gly Tyr Gly Arg Gly Ala
        50                  55                  60

Gly Ala Gly Ala Ala Ala Ser Gly Ala Gly Ala Gly Gly Tyr Gly
65                  70                  75                  80

Ala Gly Gln Gly Tyr Gly Ala Gly Ala Gly Ala Val Ala Ser Ala Ala
                85                  90                  95

Ala Gly Ala Gly Ser Gly Ala Gly Gly Ala Gly Gly Tyr Gly Arg Gly
                100                 105                 110

Ala Gly Ala Val Ala Gly Ala Gly Ala Gly Ala Gly Gly Tyr Gly
                115                 120                 125

Ala Gly Ala Gly Ala Ala Ala Gly Val Gly Ala Gly Gly Ser Gly Gly
            130                 135                 140

Tyr Gly Gly Arg Gln Gly Gly Tyr Ser Ala Gly Ala Gly Ala Gly Ala
145                 150                 155                 160

Ala Ala Ala Ala

<210> SEQ ID NO 83
<211> LENGTH: 163

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gly Gln Gly Gly Gln Gly Gly Tyr Gly Gly Leu Gly Gln Gly Gly Tyr
1               5                   10                  15

Gly Gln Gly Ala Gly Ser Ser Ala Ala Ala Ala Ala Ala Ala Ala Ala
            20                  25                  30

Ala Ala Gly Arg Gly Gln Gly Gly Tyr Gly Gln Gly Ser Gly Gly Asn
        35                  40                  45

Ala Ala Ala Ala Ala Ala Ala Ala Ala Ala Ala Ala Ser Gly Gln Gly
    50                  55                  60

Gly Gln Gly Gly Gln Gly Gly Gln Gly Gly Tyr Gly Gln Gly
65                  70                  75                  80

Ala Gly Ser Ser Ala Ala Ala Ala Ala Ala Ala Ala Ala Ala Ala Ala
                85                  90                  95

Ala Ala Ala Gly Arg Gly Gln Gly Gly Tyr Gly Gln Gly Ala Gly Gly
            100                 105                 110

Asn Ala Ala Ala Ala Ala Ala Ala Ala Ala Ala Ala Ser Gly Gln
        115                 120                 125

Gly Gly Gln Gly Gly Gln Gly Gly Gln Gly Gly Tyr Gly Gln
    130                 135                 140

Gly Ala Gly Ser Ser Ala Ala Ala Ala Ala Ala Ala Ala Ala Ala
145                 150                 155                 160

Ala Ala Ala

<210> SEQ ID NO 84
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Gly Tyr Gly Pro Gly Ser Gly Gln Gln Gly Pro Gly Gln Gln Gly
1               5                   10                  15

Pro Gly Gln Gln Gly Pro Gly Gln Gln Gly Pro Tyr Gly Ala Gly Ala
            20                  25                  30

Ser Ala Ala Ala Ala Ala Ala Gly Gly Tyr Gly Pro Gly Ser Gly Gln
        35                  40                  45

Gln Gly Pro Gly Val Arg Val Ala Ala Pro Val Ala Ser Ala Ala Ala
    50                  55                  60

Ser Arg Leu Ser Ser Ala Ala Ser Ser Arg Val Ser Ser Ala Val
65                  70                  75                  80

Ser Ser Leu Val Ser Ser Gly Pro Thr Thr Pro Ala Ala Leu Ser Asn
                85                  90                  95

Thr Ile Ser Ser Ala Val Ser Gln Ile Ser Ala Ser Asn Pro Gly Leu
            100                 105                 110

Ser Gly Cys Asp Val Leu Val Gln Ala Leu Leu Glu Val Val Ser Ala
        115                 120                 125

Leu Val His Ile Leu Gly Ser Ser Ser Val Gly Gln Ile Asn Tyr Gly
    130                 135                 140

Ala Ser Ala Gln Tyr Ala Gln Met Val Gly Gln Ser Val Thr Gln Ala
```

-continued 145          150          155          160

Leu Val

<210> SEQ ID NO 85
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gly Ala Gly Ala Gly Gly Ala Gly Tyr Gly Arg Gly Ala Gly Ala Gly
1               5                   10                  15

Ala Gly Ala Ala Ala Gly Ala Gly Ala Gly Ala Ala Ala Gly Ala Gly
                20                  25                  30

Ala Gly Ala Gly Gly Tyr Gly Gly Gln Gly Gly Tyr Gly Ala Gly Ala
                35                  40                  45

Gly Ala Gly Ala Ala Ala Ala Gly Ala Gly Ala Gly Gly Ala Ala
        50                  55                  60

Gly Tyr Ser Arg Gly Gly Arg Ala Gly Ala Ala Gly Ala Gly Ala Gly
65                  70                  75                  80

Ala Ala Ala Gly Ala Gly Ala Gly Ala Gly Gly Tyr Gly Gly Gln Gly
                85                  90                  95

Gly Tyr Gly Ala Gly Ala Gly Ala Gly Ala Ala Ala Ala Gly Ala
                100                 105                 110

Gly Ser Gly Gly Ala Gly Gly Tyr Gly Arg Gly Ala Gly Ala Gly Ala
        115                 120                 125

Ala Ala Gly Ala Gly Ala Ala Gly Ala Gly Ala Gly Ala Gly Gly
    130                 135                 140

Tyr Gly Gly Gln Gly Gly Tyr Gly Ala Gly Ala Gly Ala Ala Ala Ala
145                 150                 155                 160

Ala

<210> SEQ ID NO 86
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Ala Gly Ala Gly Arg Gly Gly Tyr Gly Arg Gly Ala Gly Ala Gly
1               5                   10                  15

Gly Tyr Gly Gly Gln Gly Gly Tyr Gly Ala Gly Ala Gly Ala Gly Ala
                20                  25                  30

Ala Ala Ala Ala Gly Ala Gly Ala Gly Tyr Gly Asp Lys Glu Ile
        35                  40                  45

Ala Cys Trp Ser Arg Cys Arg Tyr Thr Val Ala Ser Thr Thr Ser Arg
    50                  55                  60

Leu Ser Ser Ala Glu Ala Ser Ser Arg Ile Ser Ser Ala Ala Ser Thr
65                  70                  75                  80

Leu Val Ser Gly Gly Tyr Leu Asn Thr Ala Ala Leu Pro Ser Val Ile
                85                  90                  95

Ser Asp Leu Phe Ala Gln Val Gly Ala Ser Ser Pro Gly Val Ser Asp
                100                 105                 110

Ser Glu Val Leu Ile Gln Val Leu Glu Ile Val Ser Ser Leu Ile
            115                 120                 125

His Ile Leu Ser Ser Ser Val Gly Gln Val Asp Phe Ser Ser Val
            130                 135                 140

Gly Ser Ser Ala Ala Val Gly Gln Ser Met Gln Val Val Met Gly
145                 150                 155                 160

<210> SEQ ID NO 87
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gly Ala Gly Ala Gly Ala Gly Gly Ala Gly Tyr Gly Arg Gly Ala
1               5                   10                  15

Gly Ala Gly Ala Gly Ala Gly Ala Gly Ala Ala Gly Gln Gly Tyr
            20                  25                  30

Gly Ser Gly Ala Gly Ala Gly Ala Gly Ser Ala Gly Gly Ala Gly
            35                  40                  45

Ser Tyr Gly Arg Gly Ala Gly Ala Gly Ala Ala Ala Ser Gly Ala
        50                  55                  60

Gly Ala Gly Gly Tyr Gly Ala Gly Gln Gly Tyr Gly Ala Gly Ala Gly
65                  70                  75                  80

Ala Val Ala Ser Ala Ala Gly Ala Gly Ser Gly Ala Gly Gly Ala
                85                  90                  95

Gly Gly Tyr Gly Arg Gly Ala Val Ala Gly Ser Gly Ala Gly Ala Gly
                100                 105                 110

Ala Gly Ala Gly Gly Ala Gly Tyr Gly Ala Gly Ala Gly Ala Gly
            115                 120                 125

Ala Ala Ala Gly Ala Val Ala Gly Gly Ser Gly Gly Tyr Gly Gly Arg
            130                 135                 140

Gln Gly Gly Tyr Ser Ala Gly Ala Gly Ala Gly Ala Ala Ala Ala
145                 150                 155                 160

<210> SEQ ID NO 88
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gly Pro Gly Gly Tyr Gly Pro Val Gln Gln Gly Pro Ser Gly Pro Gly
1               5                   10                  15

Ser Ala Ala Gly Pro Gly Gly Tyr Gly Pro Ala Gln Gln Gly Pro Ala
            20                  25                  30

Arg Tyr Gly Pro Gly Ser Ala Ala Ala Ala Ala Ala Gly Ser
            35                  40                  45

Ala Gly Tyr Gly Pro Gly Pro Gln Ala Ser Ala Ala Ala Ser Arg Leu
        50                  55                  60

Ala Ser Pro Asp Ser Gly Ala Arg Val Ala Ser Ala Val Ser Asn Leu
65                  70                  75                  80

Val Ser Ser Gly Pro Thr Ser Ser Ala Ala Leu Ser Ser Val Ile Ser
                85                  90                  95

-continued

```
Asn Ala Val Ser Gln Ile Gly Ala Ser Asn Pro Gly Leu Ser Gly Cys
                100                 105                 110

Asp Val Leu Ile Gln Ala Leu Leu Glu Ile Val Ser Ala Cys Val Thr
            115                 120                 125

Ile Leu Ser Ser Ser Ile Gly Gln Val Asn Tyr Gly Ala Ala Ser
        130                 135                 140

Gln Phe Ala Gln Val Val Gly Gln Ser Val Leu Ser Ala Phe Ser
145                 150                 155

<210> SEQ ID NO 89
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gly Thr Gly Gly Val Gly Gly Leu Phe Leu Ser Ser Gly Asp Phe Gly
1               5                   10                  15

Arg Gly Gly Ala Gly Ala Gly Ala Gly Ala Ala Ala Ser Ala Ala
            20                  25                  30

Ala Ala Ser Ser Ala Ala Ala Gly Ala Arg Gly Gly Ser Gly Phe Gly
        35                  40                  45

Val Gly Thr Gly Gly Phe Gly Arg Gly Gly Ala Gly Ala Gly Thr Gly
    50                  55                  60

Ala Ala Ala Ala Ser Ala Ala Ala Ser Ala Ala Ala Ala Gly Ala
65                  70                  75                  80

Gly Gly Asp Gly Gly Leu Phe Leu Ser Ser Gly Asp Phe Gly Arg Gly
                85                  90                  95

Gly Ala Gly Ala Gly Ala Gly Ala Ala Ala Ser Ala Ala Ala Ala
            100                 105                 110

Ser Ser Ala Ala Ala Gly Ala Arg Gly Gly Ser Gly Phe Gly Val Gly
        115                 120                 125

Thr Gly Gly Phe Gly Arg Gly Gly Ala Gly Asp Gly Ala Ser Ala Ala
    130                 135                 140

Ala Ala Ser Ala Ala Ala Ala Ser Ala Ala Ala Ala
145                 150                 155

<210> SEQ ID NO 90
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gly Gly Tyr Gly Pro Gly Ala Gly Gln Gln Gly Pro Gly Gly Ala Gly
1               5                   10                  15

Gln Gln Gly Pro Gly Gly Gln Gly Pro Tyr Gly Pro Ser Val Ala Ala
            20                  25                  30

Ala Ala Ser Ala Ala Gly Gly Tyr Gly Pro Gly Ala Gly Gln Gln Gly
        35                  40                  45

Pro Val Ala Ser Ala Ala Val Ser Arg Leu Ser Ser Pro Gln Ala Ser
    50                  55                  60

Ser Arg Val Ser Ser Ala Val Ser Ser Leu Val Ser Ser Gly Pro Thr
65                  70                  75                  80
```

```
Asn Pro Ala Ala Leu Ser Asn Ala Met Ser Ser Val Ser Gln Val
                85                  90                  95

Ser Ala Ser Asn Pro Gly Leu Ser Gly Cys Asp Val Leu Val Gln Ala
            100                 105                 110

Leu Leu Glu Ile Val Ser Ala Leu Val His Ile Leu Gly Ser Ser Ser
        115                 120                 125

Ile Gly Gln Ile Asn Tyr Ala Ala Ser Ser Gln Tyr Ala Gln Met Val
    130                 135                 140

Gly Gln Ser Val Ala Gln Ala Leu Ala
145                 150
```

<210> SEQ ID NO 91
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Gly Gly Ala Gly Gln Gly Gly Tyr Gly Gly Leu Gly Ser Gln Gly Ala
1               5                   10                  15

Gly Arg Gly Gly Tyr Gly Gly Gln Gly Ala Gly Ala Ala Ala Ala Ala
            20                  25                  30

Thr Gly Gly Ala Gly Gln Gly Gly Tyr Gly Gly Val Gly Ser Gly Ala
        35                  40                  45

Ser Ala Ala Ser Ala Ala Ala Ser Arg Leu Ser Ser Pro Gln Ala Ser
    50                  55                  60

Ser Arg Val Ser Ser Ala Val Ser Asn Leu Val Ala Ser Gly Pro Thr
65                  70                  75                  80

Asn Ser Ala Ala Leu Ser Ser Thr Ile Ser Asn Ala Val Ser Gln Ile
                85                  90                  95

Gly Ala Ser Asn Pro Gly Leu Ser Gly Cys Asp Val Leu Ile Gln Ala
            100                 105                 110

Leu Leu Glu Val Val Ser Ala Leu Ile His Ile Leu Gly Ser Ser Ser
        115                 120                 125

Ile Gly Gln Val Asn Tyr Gly Ser Ala Gly Gln Ala Thr Gln Ile Val
    130                 135                 140

Gly Gln Ser Val Tyr Gln Ala Leu Gly
145                 150
```

<210> SEQ ID NO 92
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Gly Gly Ala Gly Gln Gly Gly Tyr Gly Gly Leu Gly Ser Gln Gly Ala
1               5                   10                  15

Gly Arg Gly Gly Tyr Gly Gly Gln Gly Ala Gly Ala Ala Val Ala Ala
            20                  25                  30

Ile Gly Gly Val Gly Gln Gly Gly Tyr Gly Gly Val Gly Ser Gly Ala
        35                  40                  45

Ser Ala Ala Ser Ala Ala Ala Ser Arg Leu Ser Ser Pro Glu Ala Ser
    50                  55                  60
```

```
Ser Arg Val Ser Ser Ala Val Ser Asn Leu Val Ser Ser Gly Pro Thr
 65                  70                  75                  80

Asn Ser Ala Ala Leu Ser Ser Thr Ile Ser Asn Val Val Ser Gln Ile
                 85                  90                  95

Gly Ala Ser Asn Pro Gly Leu Ser Gly Cys Asp Val Leu Ile Gln Ala
            100                 105                 110

Leu Leu Glu Val Val Ser Ala Leu Val His Ile Leu Gly Ser Ser Ser
        115                 120                 125

Ile Gly Gln Val Asn Tyr Gly Ser Ala Gly Gln Ala Thr Gln Ile Val
    130                 135                 140

Gly Gln Ser Val Tyr Gln Ala Leu Gly
145                 150

<210> SEQ ID NO 93
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gly Ala Ser Gly Gly Tyr Gly Gly Gly Ala Gly Glu Gly Ala Gly Ala
1               5                   10                  15

Ala Ala Ala Ala Gly Ala Gly Ala Gly Gly Ala Gly Gly Tyr Gly Gly
            20                  25                  30

Gly Ala Gly Ser Gly Ala Gly Ala Val Ala Arg Ala Gly Ala Gly Gly
        35                  40                  45

Ala Gly Gly Tyr Gly Ser Gly Ile Gly Gly Gly Tyr Gly Ser Gly Ala
    50                  55                  60

Gly Ala Ala Ala Gly Ala Gly Ala Gly Gly Ala Tyr Gly Gly
 65                  70                  75                  80

Gly Tyr Gly Thr Gly Ala Gly Ala Gly Ala Arg Gly Ala Asp Ser Ala
                 85                  90                  95

Gly Ala Ala Ala Gly Tyr Gly Gly Gly Val Gly Thr Gly Thr Gly Ser
            100                 105                 110

Ser Ala Gly Tyr Gly Arg Gly Ala Gly Ala Gly Ala Gly Ala Gly Ala
        115                 120                 125

Ala Ala Gly Ser Gly Ala Gly Ala Ala Gly Gly Tyr Gly Gly Gly Tyr
    130                 135                 140

Gly Ala Gly Ala Gly Ala Gly Ala
145                 150

<210> SEQ ID NO 94
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gly Ala Gly Ser Gly Gln Gly Gly Tyr Gly Gly Gln Gly Gly Leu Gly
1               5                   10                  15

Gly Tyr Gly Gln Gly Ala Gly Ala Gly Ala Ala Gly Ala Ser Gly
            20                  25                  30

Ser Gly Ser Gly Gly Ala Gly Gln Gly Gly Leu Gly Gly Tyr Gly Gln
        35                  40                  45
```

Gly Ala Gly Ala Gly Ala Ala Ala Ala Ala Gly Ala Ser Gly Ala
            50                  55                  60

Gly Gln Gly Gly Phe Gly Pro Tyr Gly Ser Tyr Gln Ser Ser Thr
65                  70                  75                  80

Ser Tyr Ser Val Thr Ser Gln Gly Ala Ala Gly Leu Gly Gly Tyr
                85                  90                  95

Gly Gln Gly Ser Gly Ala Gly Ala Ala Ala Gly Ala Ala Gly Gln
            100                 105                 110

Gly Gly Gln Gly Gly Tyr Gly Gln Ala Gly Ala Gly Ala Gly Ala
            115                 120                 125

Gly Ala Gly Gln Gly Gly Leu Gly Gly Tyr Gly Gln Gly Ala Gly Ser
130                 135                 140

Ser Ala Ala Ser Ala Ala Ala Ala
145                 150

<210> SEQ ID NO 95
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Gly Ala Gly Gln Gly Gly Tyr Gly Gly Leu Gly Gly Gln Gly Val
1               5                   10                  15

Gly Arg Gly Gly Leu Gly Gly Gln Gly Ala Gly Ala Ala Ala Ala Gly
            20                  25                  30

Gly Ala Gly Gln Gly Gly Tyr Gly Gly Val Gly Ser Gly Ala Ser Ala
            35                  40                  45

Ala Ser Ala Ala Ala Ser Arg Leu Ser Ser Pro Gln Ala Ser Ser Arg
    50                  55                  60

Leu Ser Ser Ala Val Ser Asn Leu Val Ala Thr Gly Pro Thr Asn Ser
65                  70                  75                  80

Ala Ala Leu Ser Ser Thr Ile Ser Asn Val Val Ser Gln Ile Gly Ala
                85                  90                  95

Ser Asn Pro Gly Leu Ser Gly Cys Asp Val Leu Ile Gln Ala Leu Leu
            100                 105                 110

Glu Val Val Ser Ala Leu Ile Gln Ile Leu Gly Ser Ser Ser Ile Gly
            115                 120                 125

Gln Val Asn Tyr Gly Ser Ala Gly Gln Ala Thr Gln Ile Val Gly Gln
            130                 135                 140

Ser Val Tyr Gln Ala Leu Gly
145                 150

<210> SEQ ID NO 96
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gly Ala Gly Ser Gly Gly Ala Gly Gly Tyr Gly Arg Gly Ala Gly Ala
1               5                   10                  15

Gly Ala Gly Ala Ala Ala Gly Ala Gly Ala Gly Ser Tyr Gly
            20                  25                  30

Gly Gln Gly Gly Tyr Gly Ala Gly Ala Gly Ala Ala Ala
            35                  40                  45

Ala Gly Ala Gly Ala Gly Ala Gly Gly Tyr Gly Arg Gly Ala Gly Ala
 50                  55                  60

Gly Ala Gly Ala Gly Ala Gly Ala Ala Ala Arg Ala Gly Ala Gly Ala
 65                  70                  75                  80

Gly Gly Ala Gly Tyr Gly Gly Gln Gly Tyr Gly Ala Gly Ala
                85                  90                  95

Ala Gly Ala Ala Ala Ala Gly Ala Gly Ala Gly Ala Gly Gly
            100                 105                 110

Tyr Gly Arg Gly Ala Gly Ala Gly Ala Gly Ala Ala Gly Ala Gly
            115                 120                 125

Ala Gly Ala Gly Gly Tyr Gly Gly Gln Ser Gly Tyr Gly Ala Gly Ala
            130                 135                 140

Gly Ala Ala Ala Ala Ala
145                 150

<210> SEQ ID NO 97
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gly Ala Ser Gly Ala Gly Gln Gly Gln Gly Tyr Gly Gln Gln Gly Gln
1               5                   10                  15

Gly Gly Ser Ser Ala Ala Ala Ala Ala Ala Ala Ala Ala Gln
            20                  25                  30

Gly Gln Gly Gln Gly Tyr Gly Gln Gly Gln Gly Tyr Gly Gln Gln
            35                  40                  45

Gly Gln Gly Gly Ser Ser Ala Ala Ala Ala Ala Ala Ala Ala
 50                  55                  60

Ala Ala Ala Gln Gly Gln Gly Gln Gly Tyr Gly Gln Gln Gly Gln Gly
 65                  70                  75                  80

Ser Ala Ala Ala Ala Ala Ala Ala Gly Ala Ser Gly Ala Gly
            85                  90                  95

Gln Gly Gln Gly Tyr Gly Gln Gln Gly Gln Gly Gly Ser Ser Ala Ala
            100                 105                 110

Ala Ala Ala Ala Ala Ala Ala Ala Ala Ala Gln Gly Gln
            115                 120                 125

Gly Tyr Gly Gln Gln Gly Gln Gly Ser Ala Ala Ala Ala Ala
            130                 135                 140

Ala Ala Ala Ala Ala Ala
145                 150

<210> SEQ ID NO 98
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Asp Tyr Lys Asp Asp Asp Asp Lys Asp Tyr Lys Asp Asp Asp Asp
1               5                   10                  15

Lys Asp Tyr Lys Asp Asp Asp Asp Lys
            20                  25

<210> SEQ ID NO 99
<211> LENGTH: 1800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (71)..(90)
<223> OTHER INFORMATION: This region may encompass 6-20 residues
<220> FEATURE:
<221> NAME/KEY: MISC_FEATURE
<222> LOCATION: (97)..(101)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (105)..(109)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (113)..(117)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (121)..(125)

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (129)..(133)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (137)..(141)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (145)..(149)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (153)..(157)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (94)..(157)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (161)..(180)
<223> OTHER INFORMATION: This region may encompass 6-20 residues
<220> FEATURE:
<221> NAME/KEY: MISC_FEATURE
<222> LOCATION: (187)..(191)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (195)..(199)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (203)..(207)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (211)..(215)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (219)..(223)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (227)..(231)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (235)..(239)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (243)..(247)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (184)..(247)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
```

```
<221> NAME/KEY: MISC_FEATURE
<222> LOCATION: (251)..(270)
<223> OTHER INFORMATION: This region may encompass 6-20 residues
<220> FEATURE:
<221> NAME/KEY: MISC_FEATURE
<222> LOCATION: (277)..(281)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (285)..(289)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (293)..(297)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (301)..(305)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (309)..(313)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (317)..(321)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (325)..(329)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (333)..(337)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (274)..(337)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (341)..(360)
<223> OTHER INFORMATION: This region may encompass 6-20 residues
<220> FEATURE:
<221> NAME/KEY: MISC_FEATURE
<222> LOCATION: (367)..(371)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (375)..(379)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (383)..(387)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (391)..(395)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (399)..(403)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (407)..(411)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (415)..(419)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (423)..(427)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (364)..(427)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (431)..(450)
<223> OTHER INFORMATION: This region may encompass 6-20 residues
<220> FEATURE:
<221> NAME/KEY: MISC_FEATURE
<222> LOCATION: (457)..(461)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (465)..(469)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (473)..(477)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (481)..(485)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (489)..(493)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (497)..(501)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (505)..(509)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (513)..(517)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (454)..(517)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (521)..(540)
<223> OTHER INFORMATION: This region may encompass 6-20 residues
<220> FEATURE:
<221> NAME/KEY: MISC_FEATURE
<222> LOCATION: (547)..(551)
<223> OTHER INFORMATION: This region may encompass "SGGQQ," "GAGQQ,"
      "GQGPY," "AGQQ" or "SQ," wherein some positions may be absent
```

```
-continued

<220> FEATURE:
<221> NAME/KEY: MISC_FEATURE
<222> LOCATION: (555)..(559)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (563)..(567)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (571)..(575)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (579)..(583)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (587)..(591)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (595)..(599)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (603)..(607)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (544)..(607)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (611)..(630)
<223> OTHER INFORMATION: This region may encompass 6-20 residues
<220> FEATURE:
<221> NAME/KEY: MISC_FEATURE
<222> LOCATION: (637)..(641)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (645)..(649)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (653)..(657)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (661)..(665)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (669)..(673)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (677)..(681)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (685)..(689)
<223> OTHER INFORMATION: This region may encompass "SGGQQ," "GAGQQ,"
```

```
      "GQGPY," "AGQQ" or "SQ," wherein some positions may be absent
<220> FEATURE:
<221> NAME/KEY: MISC_FEATURE
<222> LOCATION: (693)..(697)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (634)..(697)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (701)..(720)
<223> OTHER INFORMATION: This region may encompass 6-20 residues
<220> FEATURE:
<221> NAME/KEY: MISC_FEATURE
<222> LOCATION: (727)..(731)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (735)..(739)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (743)..(747)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (751)..(755)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (759)..(763)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (767)..(771)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (775)..(779)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (783)..(787)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (724)..(787)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (791)..(810)
<223> OTHER INFORMATION: This region may encompass 6-20 residues
<220> FEATURE:
<221> NAME/KEY: MISC_FEATURE
<222> LOCATION: (817)..(821)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (825)..(829)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (833)..(837)
```

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (841)..(845)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (849)..(853)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (857)..(861)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (865)..(869)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (873)..(877)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (814)..(877)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (881)..(900)
<223> OTHER INFORMATION: This region may encompass 6-20 residues
<220> FEATURE:
<221> NAME/KEY: MISC_FEATURE
<222> LOCATION: (907)..(911)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (915)..(919)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (923)..(927)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (931)..(935)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (939)..(943)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (947)..(951)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (955)..(959)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (963)..(967)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (904)..(967)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (971)..(990)
<223> OTHER INFORMATION: This region may encompass 6-20 residues
<220> FEATURE:
<221> NAME/KEY: MISC_FEATURE
<222> LOCATION: (997)..(1001)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1005)..(1009)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1013)..(1017)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1021)..(1025)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1029)..(1033)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1037)..(1041)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1045)..(1049)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1053)..(1057)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (994)..(1057)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1061)..(1080)
<223> OTHER INFORMATION: This region may encompass 6-20 residues
<220> FEATURE:
<221> NAME/KEY: MISC_FEATURE
<222> LOCATION: (1087)..(1091)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1095)..(1099)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1103)..(1107)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1111)..(1115)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (1119)..(1123)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1127)..(1131)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1135)..(1139)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1143)..(1147)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1084)..(1147)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1151)..(1170)
<223> OTHER INFORMATION: This region may encompass 6-20 residues
<220> FEATURE:
<221> NAME/KEY: MISC_FEATURE
<222> LOCATION: (1177)..(1181)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1185)..(1189)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1193)..(1197)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1201)..(1205)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1209)..(1213)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1217)..(1221)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1225)..(1229)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1233)..(1237)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1174)..(1237)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1241)..(1260)
<223> OTHER INFORMATION: This region may encompass 6-20 residues
```

```
<220> FEATURE:
<221> NAME/KEY: MISC_FEATURE
<222> LOCATION: (1267)..(1271)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1275)..(1279)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1283)..(1287)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1291)..(1295)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1299)..(1303)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1307)..(1311)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1315)..(1319)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1323)..(1327)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1264)..(1327)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1331)..(1350)
<223> OTHER INFORMATION: This region may encompass 6-20 residues
<220> FEATURE:
<221> NAME/KEY: MISC_FEATURE
<222> LOCATION: (1357)..(1361)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1365)..(1369)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1373)..(1377)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1381)..(1385)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1389)..(1393)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1397)..(1401)
<223> OTHER INFORMATION: This region may encompass "SGGQQ," "GAGQQ,"
```

-continued

```
      "GQGPY," "AGQQ" or "SQ," wherein some positions may be absent
<220> FEATURE:
<221> NAME/KEY: MISC_FEATURE
<222> LOCATION: (1405)..(1409)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1413)..(1417)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1354)..(1417)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1421)..(1440)
<223> OTHER INFORMATION: This region may encompass 6-20 residues
<220> FEATURE:
<221> NAME/KEY: MISC_FEATURE
<222> LOCATION: (1447)..(1451)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1455)..(1459)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1463)..(1467)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1471)..(1475)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1479)..(1483)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1487)..(1491)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1495)..(1499)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1503)..(1507)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1444)..(1507)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1511)..(1530)
<223> OTHER INFORMATION: This region may encompass 6-20 residues
<220> FEATURE:
<221> NAME/KEY: MISC_FEATURE
<222> LOCATION: (1537)..(1541)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1545)..(1549)
```

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1553)..(1557)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1561)..(1565)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1569)..(1573)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1577)..(1581)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1585)..(1589)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1593)..(1597)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1534)..(1597)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1601)..(1620)
<223> OTHER INFORMATION: This region may encompass 6-20 residues
<220> FEATURE:
<221> NAME/KEY: MISC_FEATURE
<222> LOCATION: (1627)..(1631)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1635)..(1639)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1643)..(1647)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1651)..(1655)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1659)..(1663)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1667)..(1671)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1675)..(1679)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (1683)..(1687)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1624)..(1687)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1691)..(1710)
<223> OTHER INFORMATION: This region may encompass 6-20 residues
<220> FEATURE:
<221> NAME/KEY: MISC_FEATURE
<222> LOCATION: (1717)..(1721)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1725)..(1729)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1733)..(1737)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1741)..(1745)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1749)..(1753)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1757)..(1761)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1765)..(1769)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1773)..(1777)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1714)..(1777)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1781)..(1800)
<223> OTHER INFORMATION: This region may encompass 6-20 residues
<220> FEATURE:
<221> NAME/KEY: MISC_FEATURE
<222> LOCATION: (1)..(1800)
<223> OTHER INFORMATION: This sequence may encompass 2-20 "GGY-[GPG-
      X1]n1-GPS-(A)n2" repeating units, wherein X1 is "SGGQQ,"
      "GAGQQ," "GQGPY," "AGQQ" or "SQ," n1 is 4-8 and n2 is 6-20 and some
      positions may be absent

<400> SEQUENCE: 99

Gly Gly Tyr Gly Pro Gly Xaa Xaa Xaa Xaa Xaa Gly Pro Gly Xaa Xaa
1               5                   10                  15

Xaa Xaa Xaa Gly Pro Gly Xaa Xaa Xaa Xaa Gly Pro Gly Xaa Xaa
            20                  25                  30
```

-continued

```
Xaa Xaa Xaa Gly Pro Gly Xaa Xaa Xaa Xaa Gly Pro Gly Xaa Xaa
            35                  40                  45

Xaa Xaa Xaa Gly Pro Gly Xaa Xaa Xaa Xaa Gly Pro Gly Xaa Xaa
            50                  55                  60

Xaa Xaa Xaa Gly Pro Ser Ala Ala Ala Ala Ala Ala Ala Ala Ala
65                  70                  75                  80

Ala Ala Ala Ala Ala Ala Ala Ala Gly Gly Tyr Gly Pro Gly
                85                  90                  95

Xaa Xaa Xaa Xaa Xaa Gly Pro Gly Xaa Xaa Xaa Xaa Gly Pro Gly
                100                 105                 110

Xaa Xaa Xaa Xaa Xaa Gly Pro Gly Xaa Xaa Xaa Xaa Gly Pro Gly
            115                 120                 125

Xaa Xaa Xaa Xaa Xaa Gly Pro Gly Xaa Xaa Xaa Xaa Gly Pro Gly
            130                 135                 140

Xaa Xaa Xaa Xaa Xaa Gly Pro Gly Xaa Xaa Xaa Xaa Gly Pro Ser
145                 150                 155                 160

Ala Ala Ala Ala Ala Ala Ala Ala Ala Ala Ala Ala Ala Ala Ala
                165                 170                 175

Ala Ala Ala Ala Gly Gly Tyr Gly Pro Gly Xaa Xaa Xaa Xaa Gly
            180                 185                 190

Pro Gly Xaa Xaa Xaa Xaa Gly Pro Gly Xaa Xaa Xaa Xaa Xaa Gly
        195                 200                 205

Pro Gly Xaa Xaa Xaa Xaa Xaa Gly Pro Gly Xaa Xaa Xaa Xaa Gly
        210                 215                 220

Pro Gly Xaa Xaa Xaa Xaa Xaa Gly Pro Gly Xaa Xaa Xaa Xaa Gly
225                 230                 235                 240

Pro Gly Xaa Xaa Xaa Xaa Xaa Gly Pro Ser Ala Ala Ala Ala Ala
            245                 250                 255

Ala Ala Ala Ala Ala Ala Ala Ala Ala Ala Ala Ala Ala Gly Gly
                260                 265                 270

Tyr Gly Pro Gly Xaa Xaa Xaa Xaa Xaa Gly Pro Gly Xaa Xaa Xaa
            275                 280                 285

Xaa Gly Pro Gly Xaa Xaa Xaa Xaa Xaa Gly Pro Gly Xaa Xaa Xaa Xaa
290                 295                 300

Xaa Gly Pro Gly Xaa Xaa Xaa Xaa Xaa Gly Pro Gly Xaa Xaa Xaa Xaa
305                 310                 315                 320

Xaa Gly Pro Gly Xaa Xaa Xaa Xaa Xaa Gly Pro Gly Xaa Xaa Xaa Xaa
                325                 330                 335

Xaa Gly Pro Ser Ala Ala Ala Ala Ala Ala Ala Ala Ala Ala
            340                 345                 350

Ala Ala Ala Ala Ala Ala Ala Gly Gly Tyr Gly Pro Gly Xaa Xaa
            355                 360                 365

Xaa Xaa Xaa Gly Pro Gly Xaa Xaa Xaa Xaa Gly Pro Gly Xaa Xaa
            370                 375                 380

Xaa Xaa Xaa Gly Pro Gly Xaa Xaa Xaa Xaa Gly Pro Gly Xaa Xaa
385                 390                 395                 400

Xaa Xaa Xaa Gly Pro Gly Xaa Xaa Xaa Xaa Gly Pro Gly Xaa Xaa
                405                 410                 415

Xaa Xaa Xaa Gly Pro Gly Xaa Xaa Xaa Xaa Gly Pro Ser Ala Ala
            420                 425                 430

Ala Ala Ala Ala Ala Ala Ala Ala Ala Ala Ala Ala Ala Ala Ala
            435                 440                 445

Ala Ala Gly Gly Tyr Gly Pro Gly Xaa Xaa Xaa Xaa Xaa Gly Pro Gly
```

```
            450                 455                 460
Xaa Xaa Xaa Xaa Xaa Gly Pro Gly Xaa Xaa Xaa Xaa Gly Pro Gly
465                 470                 475                 480

Xaa Xaa Xaa Xaa Xaa Gly Pro Gly Xaa Xaa Xaa Xaa Gly Pro Gly
                485                 490                 495

Xaa Xaa Xaa Xaa Xaa Gly Pro Gly Xaa Xaa Xaa Xaa Gly Pro Gly
            500                 505                 510

Xaa Xaa Xaa Xaa Xaa Gly Pro Ser Ala Ala Ala Ala Ala Ala Ala
        515                 520                 525

Ala Ala Ala Ala Ala Ala Ala Ala Ala Ala Gly Gly Tyr Gly
    530                 535                 540

Pro Gly Xaa Xaa Xaa Xaa Xaa Gly Pro Gly Xaa Xaa Xaa Xaa Gly
545                 550                 555                 560

Pro Gly Xaa Xaa Xaa Xaa Xaa Gly Pro Gly Xaa Xaa Xaa Xaa Gly
                565                 570                 575

Pro Gly Xaa Xaa Xaa Xaa Xaa Gly Pro Gly Xaa Xaa Xaa Xaa Gly
            580                 585                 590

Pro Gly Xaa Xaa Xaa Xaa Xaa Gly Pro Gly Xaa Xaa Xaa Xaa Gly
        595                 600                 605

Pro Ser Ala Ala Ala Ala Ala Ala Ala Ala Ala Ala Ala Ala
    610                 615                 620

Ala Ala Ala Ala Ala Ala Gly Gly Tyr Gly Pro Gly Xaa Xaa Xaa
625                 630                 635                 640

Xaa Gly Pro Gly Xaa Xaa Xaa Xaa Xaa Gly Pro Gly Xaa Xaa Xaa
                645                 650                 655

Xaa Gly Pro Gly Xaa Xaa Xaa Xaa Xaa Gly Pro Gly Xaa Xaa Xaa
            660                 665                 670

Xaa Gly Pro Gly Xaa Xaa Xaa Xaa Xaa Gly Pro Gly Xaa Xaa Xaa
        675                 680                 685

Xaa Gly Pro Gly Xaa Xaa Xaa Xaa Xaa Gly Pro Ser Ala Ala Ala Ala
    690                 695                 700

Ala Ala Ala Ala Ala Ala Ala Ala Ala Ala Ala Ala Ala Ala Ala
705                 710                 715                 720

Gly Gly Tyr Gly Pro Gly Xaa Xaa Xaa Xaa Gly Pro Gly Xaa Xaa
                725                 730                 735

Xaa Xaa Xaa Gly Pro Gly Xaa Xaa Xaa Xaa Xaa Gly Pro Gly Xaa Xaa
            740                 745                 750

Xaa Xaa Xaa Gly Pro Gly Xaa Xaa Xaa Xaa Xaa Gly Pro Gly Xaa Xaa
        755                 760                 765

Xaa Xaa Xaa Gly Pro Gly Xaa Xaa Xaa Xaa Xaa Gly Pro Gly Xaa Xaa
    770                 775                 780

Xaa Xaa Xaa Gly Pro Ser Ala Ala Ala Ala Ala Ala Ala Ala Ala
785                 790                 795                 800

Ala Ala Ala Ala Ala Ala Ala Ala Ala Gly Gly Tyr Gly Pro Gly
                805                 810                 815

Xaa Xaa Xaa Xaa Xaa Gly Pro Gly Xaa Xaa Xaa Xaa Gly Pro Gly
            820                 825                 830

Xaa Xaa Xaa Xaa Xaa Gly Pro Gly Xaa Xaa Xaa Xaa Gly Pro Gly
        835                 840                 845

Xaa Xaa Xaa Xaa Xaa Gly Pro Gly Xaa Xaa Xaa Xaa Gly Pro Gly
    850                 855                 860

Xaa Xaa Xaa Xaa Xaa Gly Pro Gly Xaa Xaa Xaa Xaa Gly Pro Ser
865                 870                 875                 880
```

-continued

Ala Ala Ala Ala Ala Ala Ala Ala Ala Ala Ala Ala
            885                 890                 895

Ala Ala Ala Ala Gly Gly Tyr Gly Pro Gly Xaa Xaa Xaa Xaa Gly
        900                 905                 910

Pro Gly Xaa Xaa Xaa Xaa Xaa Gly Pro Gly Xaa Xaa Xaa Xaa Gly
        915                 920                 925

Pro Gly Xaa Xaa Xaa Xaa Xaa Gly Pro Gly Xaa Xaa Xaa Xaa Gly
        930                 935                 940

Pro Gly Xaa Xaa Xaa Xaa Xaa Gly Pro Gly Xaa Xaa Xaa Xaa Gly
945                 950                 955                 960

Pro Gly Xaa Xaa Xaa Xaa Xaa Gly Pro Ser Ala Ala Ala Ala Ala
            965                 970                 975

Ala Ala Ala Ala Ala Ala Ala Ala Ala Ala Ala Ala Ala Gly Gly
            980                 985                 990

Tyr Gly Pro Gly Xaa Xaa Xaa Xaa Xaa Gly Pro Gly Xaa Xaa Xaa Xaa
        995                 1000                1005

Xaa Gly Pro Gly Xaa Xaa Xaa Xaa Xaa Gly Pro Gly Xaa Xaa Xaa
    1010                1015                1020

Xaa Xaa Gly Pro Gly Xaa Xaa Xaa Xaa Xaa Gly Pro Gly Xaa
    1025                1030                1035

Xaa Xaa Xaa Gly Pro Gly Xaa Xaa Xaa Xaa Xaa Gly Pro Gly Xaa
    1040                1045                1050

Xaa Xaa Xaa Xaa Gly Pro Ser Ala Ala Ala Ala Ala Ala Ala
    1055                1060                1065

Ala Ala Ala Ala Ala Ala Ala Ala Ala Ala Ala Gly Gly Tyr
    1070                1075                1080

Gly Pro Gly Xaa Xaa Xaa Xaa Xaa Gly Pro Gly Xaa Xaa Xaa Xaa
    1085                1090                1095

Xaa Gly Pro Gly Xaa Xaa Xaa Xaa Xaa Gly Pro Gly Xaa Xaa Xaa
    1100                1105                1110

Xaa Xaa Gly Pro Gly Xaa Xaa Xaa Xaa Xaa Gly Pro Gly Xaa Xaa
    1115                1120                1125

Xaa Xaa Xaa Gly Pro Gly Xaa Xaa Xaa Xaa Xaa Gly Pro Gly Xaa
    1130                1135                1140

Xaa Xaa Xaa Xaa Gly Pro Ser Ala Ala Ala Ala Ala Ala Ala
    1145                1150                1155

Ala Ala Ala Ala Ala Ala Ala Ala Ala Ala Ala Gly Gly Tyr
    1160                1165                1170

Gly Pro Gly Xaa Xaa Xaa Xaa Xaa Gly Pro Gly Xaa Xaa Xaa Xaa
    1175                1180                1185

Xaa Gly Pro Gly Xaa Xaa Xaa Xaa Xaa Gly Pro Gly Xaa Xaa Xaa
    1190                1195                1200

Xaa Xaa Gly Pro Gly Xaa Xaa Xaa Xaa Xaa Gly Pro Gly Xaa Xaa
    1205                1210                1215

Xaa Xaa Xaa Gly Pro Gly Xaa Xaa Xaa Xaa Xaa Gly Pro Gly Xaa
    1220                1225                1230

Xaa Xaa Xaa Xaa Gly Pro Ser Ala Ala Ala Ala Ala Ala Ala
    1235                1240                1245

Ala Ala Ala Ala Ala Ala Ala Ala Ala Ala Ala Gly Gly Tyr
    1250                1255                1260

Gly Pro Gly Xaa Xaa Xaa Xaa Xaa Gly Pro Gly Xaa Xaa Xaa Xaa
    1265                1270                1275

-continued

```
Xaa Gly Pro Gly Xaa Xaa Xaa Xaa Gly Pro Gly Xaa Xaa Xaa
    1280            1285            1290

Xaa Xaa Gly Pro Gly Xaa Xaa Xaa Xaa Xaa Gly Pro Gly Xaa Xaa
    1295            1300            1305

Xaa Xaa Xaa Gly Pro Gly Xaa Xaa Xaa Xaa Gly Pro Gly Xaa
    1310            1315            1320

Xaa Xaa Xaa Xaa Gly Pro Ser Ala Ala Ala Ala Ala Ala Ala
    1325            1330            1335

Ala Ala Ala Ala Ala Ala Ala Ala Ala Ala Ala Gly Gly Tyr
    1340            1345            1350

Gly Pro Gly Xaa Xaa Xaa Xaa Gly Pro Gly Xaa Xaa Xaa Xaa
    1355            1360            1365

Xaa Gly Pro Gly Xaa Xaa Xaa Xaa Xaa Gly Pro Gly Xaa Xaa Xaa
    1370            1375            1380

Xaa Xaa Gly Pro Gly Xaa Xaa Xaa Xaa Xaa Gly Pro Gly Xaa Xaa
    1385            1390            1395

Xaa Xaa Xaa Gly Pro Gly Xaa Xaa Xaa Xaa Gly Pro Gly Xaa
    1400            1405            1410

Xaa Xaa Xaa Xaa Gly Pro Ser Ala Ala Ala Ala Ala Ala Ala
    1415            1420            1425

Ala Ala Ala Ala Ala Ala Ala Ala Ala Ala Ala Gly Gly Tyr
    1430            1435            1440

Gly Pro Gly Xaa Xaa Xaa Xaa Gly Pro Gly Xaa Xaa Xaa Xaa
    1445            1450            1455

Xaa Gly Pro Gly Xaa Xaa Xaa Xaa Xaa Gly Pro Gly Xaa Xaa Xaa
    1460            1465            1470

Xaa Xaa Gly Pro Gly Xaa Xaa Xaa Xaa Xaa Gly Pro Gly Xaa Xaa
    1475            1480            1485

Xaa Xaa Xaa Gly Pro Gly Xaa Xaa Xaa Xaa Gly Pro Gly Xaa
    1490            1495            1500

Xaa Xaa Xaa Xaa Gly Pro Ser Ala Ala Ala Ala Ala Ala Ala
    1505            1510            1515

Ala Ala Ala Ala Ala Ala Ala Ala Ala Ala Ala Gly Gly Tyr
    1520            1525            1530

Gly Pro Gly Xaa Xaa Xaa Xaa Gly Pro Gly Xaa Xaa Xaa Xaa
    1535            1540            1545

Xaa Gly Pro Gly Xaa Xaa Xaa Xaa Xaa Gly Pro Gly Xaa Xaa Xaa
    1550            1555            1560

Xaa Xaa Gly Pro Gly Xaa Xaa Xaa Xaa Xaa Gly Pro Gly Xaa Xaa
    1565            1570            1575

Xaa Xaa Xaa Gly Pro Gly Xaa Xaa Xaa Xaa Gly Pro Gly Xaa
    1580            1585            1590

Xaa Xaa Xaa Xaa Gly Pro Ser Ala Ala Ala Ala Ala Ala Ala
    1595            1600            1605

Ala Ala Ala Ala Ala Ala Ala Ala Ala Ala Ala Gly Gly Tyr
    1610            1615            1620

Gly Pro Gly Xaa Xaa Xaa Xaa Gly Pro Gly Xaa Xaa Xaa Xaa
    1625            1630            1635

Xaa Gly Pro Gly Xaa Xaa Xaa Xaa Xaa Gly Pro Gly Xaa Xaa Xaa
    1640            1645            1650

Xaa Xaa Gly Pro Gly Xaa Xaa Xaa Xaa Xaa Gly Pro Gly Xaa Xaa
    1655            1660            1665

Xaa Xaa Xaa Gly Pro Gly Xaa Xaa Xaa Xaa Xaa Gly Pro Gly Xaa
```

```
                    1670                1675                1680

Xaa Xaa  Xaa Xaa Gly Pro Ser  Ala Ala Ala Ala  Ala Ala Ala
         1685                1690                1695

Ala Ala  Ala Ala Ala Ala Ala  Ala Ala Ala Ala  Gly Gly Tyr
1700                1705                1710

Gly Pro  Gly Xaa Xaa Xaa Xaa  Xaa Gly Pro Gly  Xaa Xaa Xaa
         1715                1720                1725

Xaa Gly  Pro Gly Xaa Xaa Xaa  Xaa Xaa Gly Pro  Gly Xaa Xaa Xaa
         1730                1735                1740

Xaa Xaa  Gly Pro Gly Xaa Xaa  Xaa Xaa Xaa Gly  Pro Gly Xaa Xaa
         1745                1750                1755

Xaa Xaa  Xaa Gly Pro Gly Xaa  Xaa Xaa Xaa Xaa  Gly Pro Gly Xaa
         1760                1765                1770

Xaa Xaa  Xaa Xaa Gly Pro Ser  Ala Ala Ala Ala  Ala Ala Ala
         1775                1780                1785

Ala Ala  Ala Ala Ala Ala Ala  Ala Ala Ala Ala
1790                1795                1800

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Gly Gln Gln
1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ala Gly Gln Gln
1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gln Gly Pro Tyr
1               5

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103
```

Ala Gly Gln Gln
1

<210> SEQ ID NO 104
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 "GPG-X1"
      repeating units, wherein X1 is "SGGQQ," "GAGQQ," "GQGPY," "AGQQ"
      or "SQ," and some positions may be absent

<400> SEQUENCE: 104

Gly Gly Tyr Gly Pro Gly Xaa Xaa Xaa Xaa Xaa Gly Pro Gly Xaa Xaa
1               5                   10                  15

Xaa Xaa Xaa Gly Pro Gly Xaa Xaa Xaa Xaa Xaa Gly Pro Gly Xaa Xaa
            20                  25                  30

Xaa Xaa Xaa Gly Pro Gly Xaa Xaa Xaa Xaa Xaa Gly Pro Gly Xaa Xaa
        35                  40                  45

Xaa Xaa Xaa Gly Pro Gly Xaa Xaa Xaa Xaa Xaa Gly Pro Gly Xaa Xaa
    50                  55                  60

Xaa Xaa Xaa Gly Pro Ser
65                  70

<210> SEQ ID NO 105
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 6-20 residues

<400> SEQUENCE: 105

Ala Ala Ala Ala Ala Ala Ala Ala Ala Ala Ala Ala Ala Ala Ala Ala
1               5                   10                  15

Ala Ala Ala Ala
            20

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 106

Gly Pro Gly Gly Xaa
1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Pro Gly Gln Gln
1               5

<210> SEQ ID NO 108
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 "GPG-X1"
      repeating units, wherein X1 is "SGGQQ," "GAGQQ," "GQGPY," "AGQQ"
      or "SQ," and some positions may be absent
<220> FEATURE:
<221> NAME/KEY: MISC_FEATURE
<222> LOCATION: (71)..(90)
<223> OTHER INFORMATION: This region may encompass 6-20 residues

<400> SEQUENCE: 108

Gly Gly Tyr Gly Pro Gly Xaa Xaa Xaa Xaa Gly Pro Gly Xaa Xaa
1               5                   10                  15

Xaa Xaa Xaa Gly Pro Gly Xaa Xaa Xaa Xaa Gly Pro Gly Xaa Xaa
            20                  25                  30

Xaa Xaa Xaa Gly Pro Gly Xaa Xaa Xaa Xaa Gly Pro Gly Xaa Xaa
            35                  40                  45

Xaa Xaa Xaa Gly Pro Gly Xaa Xaa Xaa Xaa Gly Pro Gly Xaa Xaa
            50                  55                  60

Xaa Xaa Xaa Gly Pro Ser Ala Ala Ala Ala Ala Ala Ala Ala
65              70                  75                  80

Ala Ala Ala Ala Ala Ala Ala Ala Ala Ala
                85                  90

<210> SEQ ID NO 109
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (4)..(8)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (12)..(16)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (20)..(24)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (28)..(32)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (36)..(40)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (44)..(48)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (52)..(56)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (60)..(64)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1)..(64)
<223> OTHER INFORMATION: This region may encompass 4-8 "GPG-X1"
      repeating units, wherein X1 is "SGGQQ," "GAGQQ," "GQGPY," "AGQQ"
      or "SQ," and some positions may be absent

<400> SEQUENCE: 109

Gly Pro Gly Xaa Xaa Xaa Xaa Xaa Gly Pro Gly Xaa Xaa Xaa Xaa Xaa
1               5                   10                  15

Gly Pro Gly Xaa Xaa Xaa Xaa Xaa Gly Pro Gly Xaa Xaa Xaa Xaa Xaa
            20                  25                  30

Gly Pro Gly Xaa Xaa Xaa Xaa Xaa Gly Pro Gly Xaa Xaa Xaa Xaa Xaa
        35                  40                  45

Gly Pro Gly Xaa Xaa Xaa Xaa Xaa Gly Pro Gly Xaa Xaa Xaa Xaa Xaa
    50                  55                  60

<210> SEQ ID NO 110
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(23)
<223> OTHER INFORMATION: This region may encompass 6-20 residues

<400> SEQUENCE: 110

Gly Pro Ser Ala Ala Ala Ala Ala Ala Ala Ala Ala Ala Ala Ala Ala
1               5                   10                  15

Ala Ala Ala Ala Ala Ala Ala
            20

<210> SEQ ID NO 111
<211> LENGTH: 1600
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (71)..(80)
<223> OTHER INFORMATION: This region may encompass 6-10 residues
<220> FEATURE:
<221> NAME/KEY: MISC_FEATURE
<222> LOCATION: (87)..(91)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (95)..(99)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (103)..(107)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (111)..(115)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (119)..(123)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (127)..(131)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (135)..(139)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (143)..(147)
<223> OTHER INFORMATION: This region may encompass "SGGQQ," "GAGQQ,"
      "GQGPY," "AGQQ" or "SQ," wherein some positions may be absent
```

-continued

```
<220> FEATURE:
<221> NAME/KEY: MISC_FEATURE
<222> LOCATION: (84)..(147)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (151)..(160)
<223> OTHER INFORMATION: This region may encompass 6-10 residues
<220> FEATURE:
<221> NAME/KEY: MISC_FEATURE
<222> LOCATION: (167)..(171)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (175)..(179)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (183)..(187)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (191)..(195)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (199)..(203)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (207)..(211)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (215)..(219)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (223)..(227)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (164)..(227)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (231)..(240)
<223> OTHER INFORMATION: This region may encompass 6-10 residues
<220> FEATURE:
<221> NAME/KEY: MISC_FEATURE
<222> LOCATION: (247)..(251)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (255)..(259)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (263)..(267)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (271)..(275)
<223> OTHER INFORMATION: This region may encompass "SGGQQ," "GAGQQ,"
```

```
        "GQGPY," "AGQQ" or "SQ," wherein some positions may be absent
<220> FEATURE:
<221> NAME/KEY: MISC_FEATURE
<222> LOCATION: (279)..(283)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (287)..(291)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (295)..(299)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (303)..(307)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (244)..(307)
<223> OTHER INFORMATION: This region may encompass 4-8 repeating
        "GPG-X1" repeating units, wherein X1 is "SGGQQ," "GAGQQ,"
        "GQGPY," "AGQQ" or "SQ," and some positions may be absent
<220> FEATURE:
<221> NAME/KEY: MISC_FEATURE
<222> LOCATION: (311)..(320)
<223> OTHER INFORMATION: This region may encompass 6-10 residues
<220> FEATURE:
<221> NAME/KEY: MISC_FEATURE
<222> LOCATION: (327)..(331)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (335)..(339)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (343)..(347)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (351)..(355)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (359)..(363)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (367)..(371)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (375)..(379)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (383)..(387)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (324)..(387)
<223> OTHER INFORMATION: This region may encompass 4-8 repeating
        "GPG-X1" repeating units, wherein X1 is "SGGQQ," "GAGQQ,"
        "GQGPY," "AGQQ" or "SQ," and some positions may be absent
<220> FEATURE:
<221> NAME/KEY: MISC_FEATURE
```

```
<222> LOCATION: (391)..(400)
<223> OTHER INFORMATION: This region may encompass 6-10 residues
<220> FEATURE:
<221> NAME/KEY: MISC_FEATURE
<222> LOCATION: (407)..(411)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (415)..(419)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (423)..(427)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (431)..(435)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (439)..(443)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (447)..(451)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (455)..(459)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (463)..(467)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (404)..(467)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (471)..(480)
<223> OTHER INFORMATION: This region may encompass 6-10 residues
<220> FEATURE:
<221> NAME/KEY: MISC_FEATURE
<222> LOCATION: (487)..(491)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (495)..(499)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (503)..(507)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (511)..(515)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (519)..(523)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (527)..(531)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (535)..(539)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (543)..(547)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (484)..(547)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (551)..(560)
<223> OTHER INFORMATION: This region may encompass 6-10 residues
<220> FEATURE:
<221> NAME/KEY: MISC_FEATURE
<222> LOCATION: (567)..(571)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (575)..(579)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (583)..(587)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (591)..(595)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (599)..(603)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (607)..(611)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (615)..(619)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (623)..(627)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (564)..(627)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (631)..(640)
<223> OTHER INFORMATION: This region may encompass 6-10 residues
<220> FEATURE:
<221> NAME/KEY: MISC_FEATURE
<222> LOCATION: (647)..(651)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (655)..(659)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (663)..(667)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (671)..(675)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (679)..(683)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (687)..(691)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (695)..(699)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (703)..(707)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (644)..(707)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (711)..(720)
<223> OTHER INFORMATION: This region may encompass 6-10 residues
<220> FEATURE:
<221> NAME/KEY: MISC_FEATURE
<222> LOCATION: (727)..(731)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (735)..(739)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (743)..(747)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (751)..(755)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (759)..(763)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (767)..(771)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (775)..(779)
<223> OTHER INFORMATION: This region may encompass "SGGQQ," "GAGQQ,"
      "GQGPY," "AGQQ" or "SQ," wherein some positions may be absent
```

-continued

```
<220> FEATURE:
<221> NAME/KEY: MISC_FEATURE
<222> LOCATION: (783)..(787)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (724)..(787)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (791)..(800)
<223> OTHER INFORMATION: This region may encompass 6-10 residues
<220> FEATURE:
<221> NAME/KEY: MISC_FEATURE
<222> LOCATION: (807)..(811)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (815)..(819)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (823)..(827)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (831)..(835)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (839)..(843)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (847)..(851)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (855)..(859)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (863)..(867)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (804)..(867)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (871)..(880)
<223> OTHER INFORMATION: This region may encompass 6-10 residues
<220> FEATURE:
<221> NAME/KEY: MISC_FEATURE
<222> LOCATION: (887)..(891)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (895)..(899)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (903)..(907)
<223> OTHER INFORMATION: This region may encompass "SGGQQ," "GAGQQ,"
```

```
        "GQGPY," "AGQQ" or "SQ," wherein some positions may be absent
<220> FEATURE:
<221> NAME/KEY: MISC_FEATURE
<222> LOCATION: (911)..(915)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (919)..(923)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (927)..(931)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (935)..(939)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (943)..(947)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (884)..(947)
<223> OTHER INFORMATION: This region may encompass 4-8 repeating
        "GPG-X1" repeating units, wherein X1 is "SGGQQ," "GAGQQ,"
        "GQGPY," "AGQQ" or "SQ," and some positions may be absent
<220> FEATURE:
<221> NAME/KEY: MISC_FEATURE
<222> LOCATION: (951)..(960)
<223> OTHER INFORMATION: This region may encompass 6-10 residues
<220> FEATURE:
<221> NAME/KEY: MISC_FEATURE
<222> LOCATION: (967)..(971)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (975)..(979)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (983)..(987)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (991)..(995)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (999)..(1003)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1007)..(1011)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1015)..(1019)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (1023)..(1027)
<223> OTHER INFORMATION: This region may encompass "SGGQQ," "GAGQQ,"
        "GQGPY," "AGQQ" or "SQ," wherein some positions may be absent
<220> FEATURE:
<221> NAME/KEY: MISC_FEATURE
<222> LOCATION: (964)..(1027)
```

```
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1031)..(1040)
<223> OTHER INFORMATION: This region may encompass 6-10 residues
<220> FEATURE:
<221> NAME/KEY: MISC_FEATURE
<222> LOCATION: (1047)..(1051)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1055)..(1059)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1063)..(1067)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1071)..(1075)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1079)..(1083)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1087)..(1091)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1095)..(1099)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1103)..(1107)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1044)..(1107)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1111)..(1120)
<223> OTHER INFORMATION: This region may encompass 6-10 residues
<220> FEATURE:
<221> NAME/KEY: MISC_FEATURE
<222> LOCATION: (1127)..(1131)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1135)..(1139)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1143)..(1147)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1151)..(1155)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (1159)..(1163)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1167)..(1171)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1175)..(1179)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1183)..(1187)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1124)..(1187)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1191)..(1200)
<223> OTHER INFORMATION: This region may encompass 6-10 residues
<220> FEATURE:
<221> NAME/KEY: MISC_FEATURE
<222> LOCATION: (1207)..(1211)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1215)..(1219)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1223)..(1227)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1231)..(1235)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1239)..(1243)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1247)..(1251)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1255)..(1259)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1263)..(1267)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1204)..(1267)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1271)..(1280)
<223> OTHER INFORMATION: This region may encompass 6-10 residues
<220> FEATURE:
```

-continued

```
<221> NAME/KEY: MISC_FEATURE
<222> LOCATION: (1287)..(1291)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1295)..(1299)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1303)..(1307)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1311)..(1315)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1319)..(1323)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1327)..(1331)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1335)..(1339)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1343)..(1347)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1284)..(1347)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1351)..(1360)
<223> OTHER INFORMATION: This region may encompass 6-10 residues
<220> FEATURE:
<221> NAME/KEY: MISC_FEATURE
<222> LOCATION: (1367)..(1371)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1375)..(1379)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1383)..(1387)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1391)..(1395)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1399)..(1403)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1407)..(1411)
<223> OTHER INFORMATION: This region may encompass "SGGQQ," "GAGQQ,"
      "GQGPY," "AGQQ" or "SQ," wherein some positions may be absent
```

```
<220> FEATURE:
<221> NAME/KEY: MISC_FEATURE
<222> LOCATION: (1415)..(1419)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1423)..(1427)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1364)..(1427)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1431)..(1440)
<223> OTHER INFORMATION: This region may encompass 6-10 residues
<220> FEATURE:
<221> NAME/KEY: MISC_FEATURE
<222> LOCATION: (1447)..(1451)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1455)..(1459)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1463)..(1467)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1471)..(1475)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1479)..(1483)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1487)..(1491)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1495)..(1499)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1503)..(1507)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1444)..(1507)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1511)..(1520)
<223> OTHER INFORMATION: This region may encompass 6-10 residues
<220> FEATURE:
<221> NAME/KEY: MISC_FEATURE
<222> LOCATION: (1527)..(1531)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1535)..(1539)
<223> OTHER INFORMATION: This region may encompass "SGGQQ," "GAGQQ,"
```

```
                "GQGPY," "AGQQ" or "SQ," wherein some positions may be absent
<220> FEATURE:
<221> NAME/KEY: MISC_FEATURE
<222> LOCATION: (1543)..(1547)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1551)..(1555)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1559)..(1563)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1567)..(1571)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1575)..(1579)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1583)..(1587)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1524)..(1587)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1591)..(1600)
<223> OTHER INFORMATION: This region may encompass 6-10 residues
<220> FEATURE:
<221> NAME/KEY: MISC_FEATURE
<222> LOCATION: (1)..(1600)
<223> OTHER INFORMATION: This sequence may encompass 2-20 "GGY-[GPG-
      X1]n1-GPS-(A)n2" repeating units, wherein X1 is "SGGQQ," "GAGQQ,"
      "GQGPY," "AGQQ" or "SQ," n1 is 4-8 and n2 is 6-10 and some
      positions may be absent

<400> SEQUENCE: 111

Gly Gly Tyr Gly Pro Gly Xaa Xaa Xaa Xaa Gly Pro Gly Xaa Xaa
1               5                   10                  15

Xaa Xaa Xaa Gly Pro Gly Xaa Xaa Xaa Xaa Gly Pro Gly Xaa Xaa
            20                  25                  30

Xaa Xaa Xaa Gly Pro Gly Xaa Xaa Xaa Xaa Gly Pro Gly Xaa Xaa
        35                  40                  45

Xaa Xaa Xaa Gly Pro Gly Xaa Xaa Xaa Xaa Gly Pro Gly Xaa Xaa
    50                  55                  60

Xaa Xaa Xaa Gly Pro Ser Ala Ala Ala Ala Ala Ala Ala Ala Ala
65                  70                  75                  80

Gly Gly Tyr Gly Pro Gly Xaa Xaa Xaa Xaa Gly Pro Gly Xaa Xaa
                85                  90                  95

Xaa Xaa Xaa Gly Pro Gly Xaa Xaa Xaa Xaa Gly Pro Gly Xaa Xaa
            100                 105                 110

Xaa Xaa Xaa Gly Pro Gly Xaa Xaa Xaa Xaa Gly Pro Gly Xaa Xaa
        115                 120                 125

Xaa Xaa Xaa Gly Pro Gly Xaa Xaa Xaa Xaa Gly Pro Gly Xaa Xaa
    130                 135                 140

Xaa Xaa Xaa Gly Pro Ser Ala Ala Ala Ala Ala Ala Ala Ala Ala
```

-continued

```
            145                 150                 155                 160
Gly Gly Tyr Gly Pro Gly Xaa Xaa Xaa Xaa Gly Pro Gly Xaa Xaa
                    165                 170                 175

Xaa Xaa Xaa Gly Pro Gly Xaa Xaa Xaa Xaa Gly Pro Gly Xaa Xaa
            180                 185                 190

Xaa Xaa Xaa Gly Pro Gly Xaa Xaa Xaa Xaa Gly Pro Gly Xaa Xaa
            195                 200                 205

Xaa Xaa Xaa Gly Pro Gly Xaa Xaa Xaa Xaa Gly Pro Gly Xaa Xaa
            210                 215                 220

Xaa Xaa Xaa Gly Pro Ser Ala Ala Ala Ala Ala Ala Ala Ala Ala
225                 230                 235                 240

Gly Gly Tyr Gly Pro Gly Xaa Xaa Xaa Xaa Gly Pro Gly Xaa Xaa
                    245                 250                 255

Xaa Xaa Xaa Gly Pro Gly Xaa Xaa Xaa Xaa Gly Pro Gly Xaa Xaa
            260                 265                 270

Xaa Xaa Xaa Gly Pro Gly Xaa Xaa Xaa Xaa Gly Pro Gly Xaa Xaa
            275                 280                 285

Xaa Xaa Xaa Gly Pro Gly Xaa Xaa Xaa Xaa Gly Pro Gly Xaa Xaa
            290                 295                 300

Xaa Xaa Xaa Gly Pro Ser Ala Ala Ala Ala Ala Ala Ala Ala Ala
305                 310                 315                 320

Gly Gly Tyr Gly Pro Gly Xaa Xaa Xaa Xaa Gly Pro Gly Xaa Xaa
                    325                 330                 335

Xaa Xaa Xaa Gly Pro Gly Xaa Xaa Xaa Xaa Gly Pro Gly Xaa Xaa
            340                 345                 350

Xaa Xaa Xaa Gly Pro Gly Xaa Xaa Xaa Xaa Gly Pro Gly Xaa Xaa
            355                 360                 365

Xaa Xaa Xaa Gly Pro Gly Xaa Xaa Xaa Xaa Gly Pro Gly Xaa Xaa
            370                 375                 380

Xaa Xaa Xaa Gly Pro Ser Ala Ala Ala Ala Ala Ala Ala Ala Ala
385                 390                 395                 400

Gly Gly Tyr Gly Pro Gly Xaa Xaa Xaa Xaa Gly Pro Gly Xaa Xaa
                    405                 410                 415

Xaa Xaa Xaa Gly Pro Gly Xaa Xaa Xaa Xaa Gly Pro Gly Xaa Xaa
            420                 425                 430

Xaa Xaa Xaa Gly Pro Gly Xaa Xaa Xaa Xaa Gly Pro Gly Xaa Xaa
            435                 440                 445

Xaa Xaa Xaa Gly Pro Gly Xaa Xaa Xaa Xaa Gly Pro Gly Xaa Xaa
            450                 455                 460

Xaa Xaa Xaa Gly Pro Ser Ala Ala Ala Ala Ala Ala Ala Ala Ala
465                 470                 475                 480

Gly Gly Tyr Gly Pro Gly Xaa Xaa Xaa Xaa Gly Pro Gly Xaa Xaa
                    485                 490                 495

Xaa Xaa Xaa Gly Pro Gly Xaa Xaa Xaa Xaa Gly Pro Gly Xaa Xaa
            500                 505                 510

Xaa Xaa Xaa Gly Pro Gly Xaa Xaa Xaa Xaa Gly Pro Gly Xaa Xaa
            515                 520                 525

Xaa Xaa Xaa Gly Pro Gly Xaa Xaa Xaa Xaa Gly Pro Gly Xaa Xaa
            530                 535                 540

Xaa Xaa Xaa Gly Pro Ser Ala Ala Ala Ala Ala Ala Ala Ala Ala
545                 550                 555                 560

Gly Gly Tyr Gly Pro Gly Xaa Xaa Xaa Xaa Gly Pro Gly Xaa Xaa
                    565                 570                 575
```

Xaa Xaa Xaa Gly Pro Gly Xaa Xaa Xaa Xaa Gly Pro Gly Xaa Xaa
            580                 585                 590

Xaa Xaa Xaa Gly Pro Gly Xaa Xaa Xaa Xaa Gly Pro Gly Xaa Xaa
            595                 600                 605

Xaa Xaa Xaa Gly Pro Gly Xaa Xaa Xaa Xaa Gly Pro Gly Xaa Xaa
            610                 615                 620

Xaa Xaa Xaa Gly Pro Ser Ala Ala Ala Ala Ala Ala Ala Ala Ala
625                 630                 635                 640

Gly Gly Tyr Gly Pro Gly Xaa Xaa Xaa Xaa Gly Pro Gly Xaa Xaa
            645                 650                 655

Xaa Xaa Xaa Gly Pro Gly Xaa Xaa Xaa Xaa Gly Pro Gly Xaa Xaa
            660                 665                 670

Xaa Xaa Xaa Gly Pro Gly Xaa Xaa Xaa Xaa Gly Pro Gly Xaa Xaa
            675                 680                 685

Xaa Xaa Xaa Gly Pro Gly Xaa Xaa Xaa Xaa Gly Pro Gly Xaa Xaa
            690                 695                 700

Xaa Xaa Xaa Gly Pro Ser Ala Ala Ala Ala Ala Ala Ala Ala Ala
705                 710                 715                 720

Gly Gly Tyr Gly Pro Gly Xaa Xaa Xaa Xaa Gly Pro Gly Xaa Xaa
            725                 730                 735

Xaa Xaa Xaa Gly Pro Gly Xaa Xaa Xaa Xaa Gly Pro Gly Xaa Xaa
            740                 745                 750

Xaa Xaa Xaa Gly Pro Gly Xaa Xaa Xaa Xaa Gly Pro Gly Xaa Xaa
            755                 760                 765

Xaa Xaa Xaa Gly Pro Gly Xaa Xaa Xaa Xaa Gly Pro Gly Xaa Xaa
            770                 775                 780

Xaa Xaa Xaa Gly Pro Ser Ala Ala Ala Ala Ala Ala Ala Ala Ala
785                 790                 795                 800

Gly Gly Tyr Gly Pro Gly Xaa Xaa Xaa Xaa Gly Pro Gly Xaa Xaa
            805                 810                 815

Xaa Xaa Xaa Gly Pro Gly Xaa Xaa Xaa Xaa Gly Pro Gly Xaa Xaa
            820                 825                 830

Xaa Xaa Xaa Gly Pro Gly Xaa Xaa Xaa Xaa Gly Pro Gly Xaa Xaa
            835                 840                 845

Xaa Xaa Xaa Gly Pro Gly Xaa Xaa Xaa Xaa Gly Pro Gly Xaa Xaa
            850                 855                 860

Xaa Xaa Xaa Gly Pro Ser Ala Ala Ala Ala Ala Ala Ala Ala Ala
865                 870                 875                 880

Gly Gly Tyr Gly Pro Gly Xaa Xaa Xaa Xaa Gly Pro Gly Xaa Xaa
            885                 890                 895

Xaa Xaa Xaa Gly Pro Gly Xaa Xaa Xaa Xaa Gly Pro Gly Xaa Xaa
            900                 905                 910

Xaa Xaa Xaa Gly Pro Gly Xaa Xaa Xaa Xaa Gly Pro Gly Xaa Xaa
            915                 920                 925

Xaa Xaa Xaa Gly Pro Gly Xaa Xaa Xaa Xaa Gly Pro Gly Xaa Xaa
            930                 935                 940

Xaa Xaa Xaa Gly Pro Ser Ala Ala Ala Ala Ala Ala Ala Ala Ala
945                 950                 955                 960

Gly Gly Tyr Gly Pro Gly Xaa Xaa Xaa Xaa Gly Pro Gly Xaa Xaa
            965                 970                 975

Xaa Xaa Xaa Gly Pro Gly Xaa Xaa Xaa Xaa Gly Pro Gly Xaa Xaa
            980                 985                 990

Xaa Xaa Xaa Gly Pro Gly Xaa Xaa  Xaa Xaa Xaa Gly Pro  Gly Xaa Xaa
        995              1000                  1005

Xaa Xaa  Xaa Gly Pro Gly Xaa  Xaa Xaa Xaa Gly  Pro Gly Xaa
    1010             1015                 1020

Xaa Xaa  Xaa Xaa Gly Pro Ser  Ala Ala Ala Ala  Ala Ala Ala
    1025             1030                 1035

Ala Ala  Gly Gly Tyr Gly Pro  Gly Xaa Xaa Xaa  Xaa Gly Pro
    1040             1045                 1050

Gly Xaa  Xaa Xaa Xaa Xaa Gly  Pro Gly Xaa Xaa  Xaa Xaa Gly
    1055             1060                 1065

Pro Gly  Xaa Xaa Xaa Xaa Xaa  Gly Pro Gly Xaa  Xaa Xaa Xaa
    1070             1075                 1080

Gly Pro  Gly Xaa Xaa Xaa Xaa  Xaa Gly Pro Gly  Xaa Xaa Xaa
    1085             1090                 1095

Xaa Gly  Pro Gly Xaa Xaa Xaa  Xaa Xaa Gly Pro  Ser Ala Ala Ala
    1100             1105                 1110

Ala Ala  Ala Ala Ala Ala Ala  Gly Gly Tyr Gly  Pro Gly Xaa Xaa
    1115             1120                 1125

Xaa Xaa  Xaa Gly Pro Gly Xaa  Xaa Xaa Xaa Gly  Pro Gly Xaa
    1130             1135                 1140

Xaa Xaa  Xaa Xaa Gly Pro Gly  Xaa Xaa Xaa Xaa  Gly Pro Gly
    1145             1150                 1155

Xaa Xaa  Xaa Xaa Xaa Gly Pro  Gly Xaa Xaa Xaa  Xaa Gly Pro
    1160             1165                 1170

Gly Xaa  Xaa Xaa Xaa Xaa Gly  Pro Gly Xaa Xaa  Xaa Xaa Gly
    1175             1180                 1185

Pro Ser  Ala Ala Ala Ala Ala  Ala Ala Ala Ala  Gly Gly Tyr
    1190             1195                 1200

Gly Pro  Gly Xaa Xaa Xaa Xaa  Xaa Gly Pro Gly  Xaa Xaa Xaa Xaa
    1205             1210                 1215

Xaa Gly  Pro Gly Xaa Xaa Xaa  Xaa Xaa Gly Pro  Gly Xaa Xaa Xaa
    1220             1225                 1230

Xaa Xaa  Gly Pro Gly Xaa Xaa  Xaa Xaa Xaa Gly  Pro Gly Xaa Xaa
    1235             1240                 1245

Xaa Xaa  Xaa Gly Pro Gly Xaa  Xaa Xaa Xaa Gly  Pro Gly Xaa
    1250             1255                 1260

Xaa Xaa  Xaa Xaa Gly Pro Ser  Ala Ala Ala Ala  Ala Ala Ala
    1265             1270                 1275

Ala Ala  Gly Gly Tyr Gly Pro  Gly Xaa Xaa Xaa  Xaa Xaa Gly Pro
    1280             1285                 1290

Gly Xaa  Xaa Xaa Xaa Xaa Gly  Pro Gly Xaa Xaa  Xaa Xaa Xaa Gly
    1295             1300                 1305

Pro Gly  Xaa Xaa Xaa Xaa Xaa  Gly Pro Gly Xaa  Xaa Xaa Xaa
    1310             1315                 1320

Gly Pro  Gly Xaa Xaa Xaa Xaa  Xaa Gly Pro Gly  Xaa Xaa Xaa
    1325             1330                 1335

Xaa Gly  Pro Gly Xaa Xaa Xaa  Xaa Xaa Gly Pro  Ser Ala Ala Ala
    1340             1345                 1350

Ala Ala  Ala Ala Ala Ala Ala  Gly Gly Tyr Gly  Pro Gly Xaa Xaa
    1355             1360                 1365

Xaa Xaa  Xaa Gly Pro Gly Xaa  Xaa Xaa Xaa Gly  Pro Gly Xaa
    1370             1375                 1380

Xaa Xaa  Xaa Xaa Gly Pro Gly  Xaa Xaa Xaa Xaa Xaa  Gly Pro Gly

-continued

```
           1385                1390                1395
Xaa Xaa Xaa Xaa Xaa Gly Pro Gly Xaa Xaa Xaa Xaa Gly Pro
           1400                1405                1410

Gly Xaa Xaa Xaa Xaa Xaa Gly Pro Gly Xaa Xaa Xaa Xaa Xaa Gly
           1415                1420                1425

Pro Ser Ala Ala Ala Ala Ala Ala Ala Ala Ala Gly Gly Tyr
           1430                1435                1440

Gly Pro Gly Xaa Xaa Xaa Xaa Xaa Gly Pro Gly Xaa Xaa Xaa Xaa
           1445                1450                1455

Xaa Gly Pro Gly Xaa Xaa Xaa Xaa Xaa Gly Pro Gly Xaa Xaa Xaa
           1460                1465                1470

Xaa Xaa Gly Pro Gly Xaa Xaa Xaa Xaa Xaa Gly Pro Gly Xaa Xaa
           1475                1480                1485

Xaa Xaa Xaa Gly Pro Gly Xaa Xaa Xaa Xaa Xaa Gly Pro Gly Xaa
           1490                1495                1500

Xaa Xaa Xaa Xaa Gly Pro Ser Ala Ala Ala Ala Ala Ala Ala Ala
           1505                1510                1515

Ala Ala Gly Gly Tyr Gly Pro Gly Xaa Xaa Xaa Xaa Xaa Gly Pro
           1520                1525                1530

Gly Xaa Xaa Xaa Xaa Xaa Gly Pro Gly Xaa Xaa Xaa Xaa Xaa Gly
           1535                1540                1545

Pro Gly Xaa Xaa Xaa Xaa Xaa Gly Pro Gly Xaa Xaa Xaa Xaa Xaa
           1550                1555                1560

Gly Pro Gly Xaa Xaa Xaa Xaa Xaa Gly Pro Gly Xaa Xaa Xaa Xaa
           1565                1570                1575

Xaa Gly Pro Gly Xaa Xaa Xaa Xaa Xaa Gly Pro Ser Ala Ala Ala
           1580                1585                1590

Ala Ala Ala Ala Ala Ala Ala
           1595                1600
```